(12) United States Patent
Bougueleret

(10) Patent No.: US 7,432,367 B2
(45) Date of Patent: *Oct. 7, 2008

(54) NUCLEIC ACID ENCODING A RETINOBLASTOMA BINDING PROTEIN (RBP-7) AND POLYMORPHIC MARKERS ASSOCIATED WITH SAID NUCLEIC ACID

(75) Inventor: Lydie Bougueleret, Petit-Lancy (CH)

(73) Assignee: Serono Genetics Institute, S.A., Evry (FR)

( * ) Notice: Subject to any disclaimer, the term of this patent is extended or adjusted under 35 U.S.C. 154(b) by 367 days.

This patent is subject to a terminal disclaimer.

(21) Appl. No.: 11/132,838

(22) Filed: May 19, 2005

(65) Prior Publication Data

US 2005/0221371 A1    Oct. 6, 2005

Related U.S. Application Data

(60) Continuation of application No. 10/071,179, filed on Mar. 19, 2002, now Pat. No. 6,908,988, which is a division of application No. 09/345,882, filed on Jun. 30, 1999, now Pat. No. 6,399,373.

(60) Provisional application No. 60/111,909, filed on Dec. 10, 1998, provisional application No. 60/091,315, filed on Jun. 30, 1998.

(51) Int. Cl.
C07H 21/04    (2006.01)

(52) U.S. Cl. .......................... 536/24.31; 435/6
(58) Field of Classification Search ........................ None
See application file for complete search history.

(56) References Cited

U.S. PATENT DOCUMENTS

| 5,650,287 | A | 7/1997 | Nevins et al. |
| 5,795,714 | A | 8/1998 | Cantor et al. |
| 6,399,373 | B1 * | 6/2002 | Bougueleret ................ 435/330 |
| 2003/0170647 | A1 | 9/2003 | Bougueleret |

FOREIGN PATENT DOCUMENTS

| WO | WO 93/06168 A1 | 9/1992 |
| WO | WO 93/23539 | 5/1993 |
| WO | WO 94/12521 | 6/1994 |
| WO | WO 95/17198 A1 | 12/1994 |
| WO | WO 95/05392 | 2/1995 |
| WO | WO 96/25494 | 8/1996 |
| WO | WO 96/28568 | 9/1996 |
| WO | WO 99/04265 | 1/1999 |

OTHER PUBLICATIONS

Annotated ESTs from GenBank, pp. 1-19, (2004).
Adams, M.D. et al., "Initial assessment of human gene diversity and expression patterns based upon 83 million nucleotides of cDNA sequence", *Nature*, 1995, vol. 377, (6547 Suppl), pp. 3-174, Accession No. AA296993.
Berendsen, Herman, "A Glimpse of the Holy Grail?", *Science*, 1998, vol. 282, pp. 642-643.
Cao, J. et al., "RBP1L1, a Retinoblastoma-Binding Protein-Related Gene Encoding an Antigenic Epitope Abundantly Expressed in Human Carcinomas and Normal Testis", *J. Natl Cancer Inst.*, 2001, vol. 93, No. 15, pp. 1159-1165.
Fattaey, A., et al., "Characterization of the retinoblastoma binding proteins RBP1 and RBP2", *Oncogene*, 1993, vol. 8, pp. 3149-3156, Pub: MacMillan Press, Ltd.
Galperin, M. et al., "Who's your neighbor? New Computational approaches for functional genomics", *Nature Biotechnology*, 2000, vol. 18, pp. 609-613.
Helin, K. et al., "A cDNA Encoding a pRB-Binding Protein with Properties of the Transcription Factor E2F", *Cell*, 1992, vol. 70, pp. 337-350.
Hillier L. et al., "Generation and Analysis of 280,000 human expressed sequence tags", *Genome Res.*, 1996, vol. 6, No. 9, pp. 807-828, Accession No. T61718.
Hillier L. et al., "Generation and Analysis of 280,000 human expressed sequence tags", *Genome Res.*, 1996, vol. 6, No. 9, pp. 807-828, Accession No. AA082927.
Hillier L. et al., "The WashU-Merck EST Project", Unpublished—*EMBL Sequence Database*, Apr. 12, 1995, Accession No. R14337.
Hillier L. et al., "The WashU-Merck EST Project", Unpublished—*EMBL Sequence Database*, Apr. 24, 1995, Accession No. R27405.
Hillier L. et al., "The WashU-Merck EST Project", Unpublished—*EMBL Sequence Database*, May 22, 1995, Accession No. R40663.
Hillier L. et al., "The WashU-Merck EST Project", Unpublished—*EMBL Sequence Database*, May 22, 1995, Accession No. R44970.

(Continued)

*Primary Examiner*—James S Ketter
(74) *Attorney, Agent, or Firm*—Saliwanchik, Lloyd & Salwanchik

(57) ABSTRACT

The present invention is directed to a polynucleotide comprising open reading frames defining a coding region encoding a retinoblastoma binding protein (RBP-7) as well as regulatory regions located both at the 5' end and the 3' end of said coding region. The present invention also pertains to a polynucleotide carrying the natural regulation signals of the RBP-7 gene which is useful in order to express a heterologous nucleic acid in host cells or host organisms as well as functionally active regulatory polynucleotides derived from said regulatory region. The invention also concerns polypeptides encoded by the coding region of the RBP-7 gene. The invention also deals with antibodies directed specifically against such polypeptides that are useful as diagnostic reagents. The invention also comprises genetic markers, namely biallelic markers, that are means that may be useful for the diagnosis of diseases related to an alteration in the regulation or in the coding regions of the RBP-7 gene and for the prognosis/diagnosis of an eventual treatment with therapeutic agents, especially agents acting on pathologies involving abnormal cell proliferation and/or abnormal cell differentiation.

15 Claims, 2 Drawing Sheets

OTHER PUBLICATIONS

Hillier L. et al., "The WashU-Merck EST Project", Unpublished—*EMBL Sequence Database*, Jun. 23, 1995, Accession No. H08612.

Hillier L. et al., "The WashU-Merck EST Project", Unpublished—*EMBL Sequence Database*, Aug. 16, 1995, Accession No. H38607.

Hillier L. et al., "The WashU-Merck EST Project", Unpublished—*EMBL Sequence Database*, Aug. 16, 1995, Accession No. H39516.

Hillier L. et al., "The WashU-Merck EST Project", Unpublished—*EMBL Sequence Database*, Oct. 10, 1996, Accession No. W37603.

Hillier L. et al., "The WashU-Merck EST Project", Unpublished—*EMBL Sequence Database*, Oct. 15, 1996, Accession No. W67770.

Hillier L. et al., "The WashU-Merck EST Project", Unpublished—*EMBL Sequence Database*, Oct. 15, 1996, Accession No. W67771.

Hillier L. et al., "The WashU-Merck EST Project", Unpublished—*EMBL Sequence Database*, Oct. 17, 1996, Accession No. W84531.

Hillier L. et al., "The WashU-Merck EST Project", Unpublished—*EMBL Sequence Database*, May 22, 1996, Accession No. W44777.

Hillier L. et al., "The WashU-Merck EST Project", Unpublished—*EMBL Sequence Database*, Jun. 16, 1996, XP002121367, Accession No. W67771.

Hillier L. et al., "The WashU-Merck EST Project", Unpublished—*EMBL Sequence Database*, Apr. 29, 1997, XP002021368, Accession No. AA399016.

Hillier L. et al., "The WashU-Merck EST Project", Unpublished—*EMBL Sequence Database*, May 16, 1997, Accession No. AA399016.

Hillier L. et al., "The WashU-Merck EST Project", Unpublished—*EMBL Sequence Database*, Aug. 8, 1997, Accession No. AA479433.

Hillier L. et al., "The WashU-NCI human EST Project", Unpublished—*EMBL Sequence Database*, Mar. 9, 1998, Accession No. AA167428.

Hillier L. et al., "The WashU-NCI human EST Project",, Unpublished—*EMBL Sequence Database*, Mar. 9, 1998, Accession No. AA169631.

Kaelin, W. et al., "Expression Cloning of a cDNA Encoding a Retinoblastoma-Binding Protein with E2F-like Properties", *Cell*, 1992, vol. 70, pp. 351-364, Pub: Cell Press.

Neuman, E. et al., "Structure and Partial Genomic Sequence of the Human *E2F1* gene", *Gene*, 1996, 173:163-169, Pub: Elsevier Science B.V.

Otterson, G. et al., "Alternative splicing of the *RBP1* gene clusters in an internal exon that encodes potential phosphorylation sites", *Oncogene*, 1993, vol. 8, pp. 949-957, Pub: MacMillan Press Ltd.

Qlan, Y. et al., "A retinoblastoma-binding protein related to a negative regulator of Ras in yeast", *Nature*, 1993, vol. 364, pp. 648-652.

Sakai, Y. et al., "cDNA Sequence and Chromosomal Localization of Novel Human Protein, RBQ-1 (RBBP6), That Binds to the Retinoblastoma Gene Product", *Genomics*, vol. 30, pp. 98-101 (1995), Pub: Academic Press, Inc.

Smith, D.R., "Sequencing of Human Chromosome 10", *Genome Therapeutics Corporation* (Submitted), Dec. 4, 1998, Accession No. AC006107.

Takahashi, T. et al., "Cytotoxic T lymphocytes that recognize decameric peptide sequences of retinoblastoma binding protein 1 (RBP-1) associated with human breast cancer", *British Journal of Cancer*, 1999, vol. 2, pp. 342-349, Pub: Cancer Research Campaign.

Unknown, "National Cancer Institute, Cancer Genome Anatomy Project (CGAP), Tumor Gene Index", Unpublished—*EMBL Sequence Database*, Aug. 13, 1997, Accession No. AA262427.

Unknown, "National Cancer Institute, Cancer Genome Anatomy Project (CGAP), Tumor Gene Index", Unpublished—*EMBL Sequence Database*, Aug. 15, 1997, Accession No. AA279595.

Unknown, "National Cancer Institute, Cancer Genome Anatomy Project (CGAP), Tumor Gene Index", Unpublished—*EMBL Sequence Database*, Aug. 15, 1997, Accession No. AA485189.

Unknown, "National Cancer Institute, Cancer Genome Anatomy Project (CGAP), Tumor Gene Index", Unpublished—*EMBL Sequence Database*, Jan. 29, 1998, Accession No. AA772654.

Unknown, "National Cancer Institute, Cancer Genome Anatomy Project (CGAP), Tumor Gene Index", Unpublished—*EMBL Sequence Database*, Apr. 7, 1998, Accession No. AA830588.

Unknown, "National Cancer Institute, Cancer Genome Anatomy Project (CGAP), Tumor Gene Index", Unpublished—*EMBL Sequence Database*, Dec. 31, 1998, Accession No. AA772654.

Accession No. H38848, Aug. 16, 1995.
Accession No. AAR33389, first entry Jul. 15, 1993.
Accession No. H38848, Feb. 16, 1995.
Accession No. H22266, Jul. 6, 1995.
Accession No. H22303, Jul. 6, 1995.
Accession No. H43964, Jul. 31, 1995.
Accession No. W84569, Oct. 17, 1996.
Accession No. AA713956, Jan. 22, 1998.
Accession No. R20183, Apr. 17, 1995.
Accession No. AA249450, Mar. 11, 1997.

Fleischer, T. C. et al. "Identification and Characterization of Three New Components of the mSin3A Corepressor Complex", *Molecular and Cellular Biology*, May 2003, pp. 3456-3467, vol. 23, No. 10.

UniProtKB/TrEMBL Accession No. Q86XU1, Jun. 2003.
UniProtKB/SwissProt Accession No. Q96ST3, Mar. 2004.

* cited by examiner

SEQUENCE LISTING

```
<160> NUMBER OF SEQ ID NOS: 140

<210> SEQ ID NO 1
<211> LENGTH: 162450
<212> TYPE: DNA
<213> ORGANISM: Homo sapiens
<220> FEATURE:
<221> NAME/KEY: allele
<222> LOCATION: 72794
<223> OTHER INFORMATION: 5-124-273  :  polymorphic  base  A  or  G
<220> FEATURE:
<221> NAME/KEY: allele
<222> LOCATION: 88073
<223> OTHER INFORMATION: 5-127-261  :  polymorphic  base  A  or  C
<220> FEATURE:
<221> NAME/KEY: allele
```

```
<222> LOCATION: 90842
<223> OTHER INFORMATION: 99-1437-325  :  polymorphic  base  A  or  G
<220> FEATURE:
<221> NAME/KEY: allele
<222> LOCATION: 93714
<223> OTHER INFORMATION: 5-128-60  :  polymorphic  base  deletion  of GT
<220> FEATURE:
<221> NAME/KEY: allele
<222> LOCATION: 97122
<223> OTHER INFORMATION: 99-1442-224  :  polymorphic  base  G  or  T
<220> FEATURE:
<221> NAME/KEY: allele
<222> LOCATION: 97152
<223> OTHER INFORMATION: 5-129-144  :  polymorphic  base  deletion  of T
<220> FEATURE:
<221> NAME/KEY: allele
<222> LOCATION: 99098
<223> OTHER INFORMATION: 5-130-257  :  polymorphic  base  A  or  G
<220> FEATURE:
<221> NAME/KEY: allele
<222> LOCATION: 99117
<223> OTHER INFORMATION: 5-130-276  :  polymorphic  base  A  or  G
<220> FEATURE:
<221> NAME/KEY: allele
<222> LOCATION: 103806
<223> OTHER INFORMATION: 5-131-395  :  polymorphic  base  A  or  T
<220> FEATURE:
<221> NAME/KEY: allele
<222> LOCATION: 106940
<223> OTHER INFORMATION: 5-133-375  :  polymorphic  base  insertion of A
<220> FEATURE:
<221> NAME/KEY: allele
<222> LOCATION: 108106
<223> OTHER INFORMATION: 5-135-155  :  polymorphic  base  insertion of A
<220> FEATURE:
<221> NAME/KEY: allele
<222> LOCATION: 108149
<223> OTHER INFORMATION: 5-135-198  :  polymorphic base insertion of GTTT
<220> FEATURE:
<221> NAME/KEY: allele
<222> LOCATION: 108308
<223> OTHER INFORMATION: 5-135-357  :  polymorphic  base  A  or  G
<220> FEATURE:
<221> NAME/KEY: allele
<222> LOCATION: 108471
<223> OTHER INFORMATION: 5-136-174  :  polymorphic  base  C  or  T
<220> FEATURE:
<221> NAME/KEY: allele
<222> LOCATION: 134134
<223> OTHER INFORMATION: 5-140-120  :  polymorphic  base  C  or  T
<220> FEATURE:
<221> NAME/KEY: allele
<222> LOCATION: 134362
<223> OTHER INFORMATION: 5-140-348  :  polymorphic  base  insertion  of A
<220> FEATURE:
<221> NAME/KEY: allele
<222> LOCATION: 134374
<223> OTHER INFORMATION: 5-140-361  :  polymorphic  base insertion of CA
<220> FEATURE:
<221> NAME/KEY: allele
<222> LOCATION: 146328
<223> OTHER INFORMATION: 5-143-84  :  polymorphic  base  A  or  G
<220> FEATURE:
<221> NAME/KEY: allele
<222> LOCATION: 146345
<223> OTHER INFORMATION: 5-143-101  :  polymorphic  base  A  or  C
<220> FEATURE:
<221> NAME/KEY: allele
<222> LOCATION: 150329
<223> OTHER INFORMATION: 5-145-24  :  polymorphic  base  A  or  G
<220> FEATURE:
<221> NAME/KEY: allele
<222> LOCATION: 160031
<223> OTHER INFORMATION: 5-148-352  :  polymorphic  base  G  or  T
<220> FEATURE:
<221> NAME/KEY: allele
<222> LOCATION: 72771..72817
<223> OTHER INFORMATION: polymorphic fragment 5-124-273 SEQ ID30
<220> FEATURE:
```

-continued

```
<221> NAME/KEY: allele
<222> LOCATION: 72771..72817
<223> OTHER INFORMATION: polymorphic fragment 5-124-273 SEQ ID51
<220> FEATURE:
<221> NAME/KEY: allele
<222> LOCATION: 88050..88096
<223> OTHER INFORMATION: polymorphic fragment 5-127-261 SEQ ID31
<220> FEATURE:
<221> NAME/KEY: allele
<222> LOCATION: 88050..88096
<223> OTHER INFORMATION: polymorphic fragment 5-127-261 SEQ ID52
<220> FEATURE:
<221> NAME/KEY: allele
<222> LOCATION: 90819..90865
<223> OTHER INFORMATION: complement polymorphic fragment 99-1437-325
      SEQ ID49
<220> FEATURE:
<221> NAME/KEY: allele
<222> LOCATION: 90819..90865
<223> OTHER INFORMATION: complement polymorphic fragment 99-1437-325
      SEQ ID70
<220> FEATURE:
<221> NAME/KEY: allele
<222> LOCATION: 93690..93736
<223> OTHER INFORMATION: polymorphic fragment 5-128-60 SEQ ID32
<220> FEATURE:
<221> NAME/KEY: allele
<222> LOCATION: 93690..93736
<223> OTHER INFORMATION: polymorphic fragment 5-128-60 SEQ ID53
<220> FEATURE:
<221> NAME/KEY: allele
<222> LOCATION: 97099..97145
<223> OTHER INFORMATION: polymorphic fragment 99-1442-224 SEQ ID50
<220> FEATURE:
<221> NAME/KEY: allele
<222> LOCATION: 97099..97145
<223> OTHER INFORMATION: polymorphic fragment 99-1442-224 SEQ ID71
<220> FEATURE:
<221> NAME/KEY: allele
<222> LOCATION: 97130..97177
<223> OTHER INFORMATION: polymorphic fragment 5-129-144 SEQ ID33
<220> FEATURE:
<221> NAME/KEY: allele
<222> LOCATION: 97130..97177
<223> OTHER INFORMATION: polymorphic fragment 5-129-144 SEQ ID54
<220> FEATURE:
<221> NAME/KEY: allele
<222> LOCATION: 99075..99121
<223> OTHER INFORMATION: polymorphic fragment 5-130-257 SEQ ID34
<220> FEATURE:
<221> NAME/KEY: allele
<222> LOCATION: 99075..99121
<223> OTHER INFORMATION: polymorphic fragment 5-130-257 SEQ ID55
<220> FEATURE:
<221> NAME/KEY: allele
<222> LOCATION: 99094..99140
<223> OTHER INFORMATION: polymorphic fragment 5-130-276 SEQ ID35
<220> FEATURE:
<221> NAME/KEY: allele
<222> LOCATION: 99094..99140
<223> OTHER INFORMATION: polymorphic fragment 5-130-276 SEQ ID56
<220> FEATURE:
<221> NAME/KEY: allele
<222> LOCATION: 103783..103828
<223> OTHER INFORMATION: polymorphic fragment 5-131-395 SEQ ID36
<220> FEATURE:
<221> NAME/KEY: allele
<222> LOCATION: 103783..103828
<223> OTHER INFORMATION: polymorphic fragment 5-131-395 SEQ ID57
<220> FEATURE:
<221> NAME/KEY: allele
<222> LOCATION: 106918..106966
<223> OTHER INFORMATION: polymorphic fragment 5-133-375 SEQ ID37
<220> FEATURE:
<221> NAME/KEY: allele
<222> LOCATION: 106918..106966
<223> OTHER INFORMATION: polymorphic fragment 5-133-375 SEQ ID58
<220> FEATURE:
<221> NAME/KEY: allele
```

```
<222> LOCATION: 108084..108130
<223> OTHER INFORMATION: polymorphic fragment 5-135-155 SEQ ID38
<220> FEATURE:
<221> NAME/KEY: allele
<222> LOCATION: 108084..108130
<223> OTHER INFORMATION: polymorphic fragment 5-135-155 SEQ ID59
<220> FEATURE:
<221> NAME/KEY: allele
<222> LOCATION: 108127..108177
<223> OTHER INFORMATION: polymorphic fragment 5-135-198 SEQ ID39
<220> FEATURE:
<221> NAME/KEY: allele
<222> LOCATION: 108127..108177
<223> OTHER INFORMATION: polymorphic fragment 5-135-198 SEQ ID60
<220> FEATURE:
<221> NAME/KEY: allele
<222> LOCATION: 108285..108331
<223> OTHER INFORMATION: polymorphic fragment 5-135-357 SEQ ID40
<220> FEATURE:
<221> NAME/KEY: allele
<222> LOCATION: 108285..108331
<223> OTHER INFORMATION: polymorphic fragment 5-135-357 SEQ ID61
<220> FEATURE:
<221> NAME/KEY: allele
<222> LOCATION: 108448..108494
<223> OTHER INFORMATION: polymorphic fragment 5-136-174 SEQ ID41
<220> FEATURE:
<221> NAME/KEY: allele
<222> LOCATION: 108448..108494
<223> OTHER INFORMATION: polymorphic fragment 5-136-174 SEQ ID62
<220> FEATURE:
<221> NAME/KEY: allele
<222> LOCATION: 134111..134157
<223> OTHER INFORMATION: polymorphic fragment 5-140-120 SEQ ID42
<220> FEATURE:
<221> NAME/KEY: allele
<222> LOCATION: 134111..134157
<223> OTHER INFORMATION: polymorphic fragment 5-140-120 SEQ ID63
<220> FEATURE:
<221> NAME/KEY: allele
<222> LOCATION: 134340..134386
<223> OTHER INFORMATION: polymorphic fragment 5-140-348 SEQ ID43
<220> FEATURE:
<221> NAME/KEY: allele
<222> LOCATION: 134340..134386
<223> OTHER INFORMATION: polymorphic fragment 5-140-348 SEQ ID64
<220> FEATURE:
<221> NAME/KEY: allele
<222> LOCATION: 134352..134397
<223> OTHER INFORMATION: polymorphic fragment 5-140-361 SEQ ID44
<220> FEATURE:
<221> NAME/KEY: allele
<222> LOCATION: 134352..134397
<223> OTHER INFORMATION: polymorphic fragment 5-140-361 SEQ ID65
<220> FEATURE:
<221> NAME/KEY: allele
<222> LOCATION: 146305..146351
<223> OTHER INFORMATION: polymorphic fragment 5-143-84 SEQ ID46
<220> FEATURE:
<221> NAME/KEY: allele
<222> LOCATION: 146305..146351
<223> OTHER INFORMATION: polymorphic fragment 5-143-84 SEQ ID67
<220> FEATURE:
<221> NAME/KEY: allele
<222> LOCATION: 146322..146368
<223> OTHER INFORMATION: polymorphic fragment 5-143-101 SEQ ID45
<220> FEATURE:
<221> NAME/KEY: allele
<222> LOCATION: 146322..146368
<223> OTHER INFORMATION: polymorphic fragment 5-143-101 SEQ ID66
<220> FEATURE:
<221> NAME/KEY: allele
<222> LOCATION: 150306..150352
<223> OTHER INFORMATION: polymorphic fragment 5-145-24 SEQ ID47
<220> FEATURE:
<221> NAME/KEY: allele
<222> LOCATION: 150306..150352
<223> OTHER INFORMATION: polymorphic fragment 5-145-24 SEQ ID68
<220> FEATURE:
```

```
<221> NAME/KEY: allele
<222> LOCATION: 160008..160054
<223> OTHER INFORMATION: polymorphic fragment 5-148-352 SEQ ID48
<220> FEATURE:
<221> NAME/KEY: allele
<222> LOCATION: 160008..160054
<223> OTHER INFORMATION: polymorphic fragment 5-148-352 SEQ ID69
<220> FEATURE:
<221> NAME/KEY: exon
<222> LOCATION: 274..665
<223> OTHER INFORMATION: exon1
<220> FEATURE:
<221> NAME/KEY: exon
<222> LOCATION: 1466..1520
<223> OTHER INFORMATION: exon2
<220> FEATURE:
<221> NAME/KEY: exon
<222> LOCATION: 67593..67703
<223> OTHER INFORMATION: exon3
<220> FEATURE:
<221> NAME/KEY: exon
<222> LOCATION: 71119..71184
<223> OTHER INFORMATION: exon4
<220> FEATURE:
<221> NAME/KEY: exon
<222> LOCATION: 72599..72689
<223> OTHER INFORMATION: exon5
<220> FEATURE:
<221> NAME/KEY: exon
<222> LOCATION: 75544..75623
<223> OTHER INFORMATION: exon6
<220> FEATURE:
<221> NAME/KEY: exon
<222> LOCATION: 81842..81933
<223> OTHER INFORMATION: exon7
<220> FEATURE:
<221> NAME/KEY: exon
<222> LOCATION: 87902..88040
<223> OTHER INFORMATION: exon8
<220> FEATURE:
<221> NAME/KEY: exon
<222> LOCATION: 93857..93936
<223> OTHER INFORMATION: exon9
<220> FEATURE:
<221> NAME/KEY: exon
<222> LOCATION: 97159..97235
<223> OTHER INFORMATION: exon10
<220> FEATURE:
<221> NAME/KEY: exon
<222> LOCATION: 98963..99117
<223> OTHER INFORMATION: exon11
<220> FEATURE:
<221> NAME/KEY: exon
<222> LOCATION: 103570..103642
<223> OTHER INFORMATION: exon12
<220> FEATURE:
<221> NAME/KEY: exon
<222> LOCATION: 105085..105179
<223> OTHER INFORMATION: exon13
<220> FEATURE:
<221> NAME/KEY: exon
<222> LOCATION: 106683..106780
<223> OTHER INFORMATION: exon14
<220> FEATURE:
<221> NAME/KEY: exon
<222> LOCATION: 107799..108042
<223> OTHER INFORMATION: exon15
<220> FEATURE:
<221> NAME/KEY: exon
<222> LOCATION: 108376..108551
<223> OTHER INFORMATION: exon16
<220> FEATURE:
<221> NAME/KEY: exon
<222> LOCATION: 114336..114593
<223> OTHER INFORMATION: exon17
<220> FEATURE:
<221> NAME/KEY: exon
<222> LOCATION: 132247..132331
<223> OTHER INFORMATION: exon18
```

```
<220> FEATURE:
<221> NAME/KEY: exon
<222> LOCATION: 134151..134349
<223> OTHER INFORMATION: exon19
<220> FEATURE:
<221> NAME/KEY: exon
<222> LOCATION: 145566..146774
<223> OTHER INFORMATION: exon20
<220> FEATURE:
<221> NAME/KEY: exon
<222> LOCATION: 150447..150560
<223> OTHER INFORMATION: exon21
<220> FEATURE:
<221> NAME/KEY: exon
<222> LOCATION: 152960..153175
<223> OTHER INFORMATION: exon22
<220> FEATURE:
<221> NAME/KEY: exon
<222> LOCATION: 155591..155737
<223> OTHER INFORMATION: exon23
<220> FEATURE:
<221> NAME/KEY: exon
<222> LOCATION: 159702..161451
<223> OTHER INFORMATION: exon24
<220> FEATURE:
<221> NAME/KEY: misc_feature
<222> LOCATION: 114564..114593
<223> OTHER INFORMATION: homology with EST in ref embl:AA082927
<220> FEATURE:
<221> NAME/KEY: misc_feature
<222> LOCATION: 132247..132331
<223> OTHER INFORMATION: homology with EST in ref embl:AA082927
<220> FEATURE:
<221> NAME/KEY: misc_feature
<222> LOCATION: 134151..134265
<223> OTHER INFORMATION: homology with EST in ref embl:AA082927
<220> FEATURE:
<221> NAME/KEY: misc_feature
<222> LOCATION: 161029..161452
<223> OTHER INFORMATION: complement homology with EST in ref
      embl:AA167428
<220> FEATURE:
<221> NAME/KEY: misc_feature
<222> LOCATION: 146630..146774
<223> OTHER INFORMATION: complement homology with EST in ref
      embl:AA169631
<220> FEATURE:
<221> NAME/KEY: misc_feature
<222> LOCATION: 150447..150541
<223> OTHER INFORMATION: complement homology with EST in ref
      embl:AA169631
<220> FEATURE:
<221> NAME/KEY: misc_feature
<222> LOCATION: 81890..81933
<223> OTHER INFORMATION: complement homology with EST in ref
      embl:AA262427
<220> FEATURE:
<221> NAME/KEY: misc_feature
<222> LOCATION: 87902..88040
<223> OTHER INFORMATION: complement homology with EST in ref
      embl:AA262427
<220> FEATURE:
<221> NAME/KEY: misc_feature
<222> LOCATION: 93857..93936
<223> OTHER INFORMATION: complement homology with EST in ref
      embl:AA262427
<220> FEATURE:
<221> NAME/KEY: misc_feature
<222> LOCATION: 97159..97235
<223> OTHER INFORMATION: complement homology with EST in ref
      embl:AA262427
<220> FEATURE:
<221> NAME/KEY: misc_feature
<222> LOCATION: 98963..99082
<223> OTHER INFORMATION: complement homology with EST in ref
      embl:AA262427
<220> FEATURE:
<221> NAME/KEY: misc_feature
<222> LOCATION: 146333..146732
```

```
<223> OTHER INFORMATION: homology with EST in ref embl:AA279595
<220> FEATURE:
<221> NAME/KEY: misc_feature
<222> LOCATION: 108393..108551
<223> OTHER INFORMATION: homology with EST in ref embl:AA296993
<220> FEATURE:
<221> NAME/KEY: misc_feature
<222> LOCATION: 114336..114417
<223> OTHER INFORMATION: homology with EST in ref embl:AA296993
<220> FEATURE:
<221> NAME/KEY: misc_feature
<222> LOCATION: 159726..160245
<223> OTHER INFORMATION: homology with EST in ref embl:AA399016
<220> FEATURE:
<221> NAME/KEY: misc_feature
<222> LOCATION: 159977..160465
<223> OTHER INFORMATION: homology with EST in ref embl:AA479433
<220> FEATURE:
<221> NAME/KEY: misc_feature
<222> LOCATION: 103582..103642
<223> OTHER INFORMATION: complement homology with EST in ref
      embl:AA485189
<220> FEATURE:
<221> NAME/KEY: misc_feature
<222> LOCATION: 105085..105179
<223> OTHER INFORMATION: complement homology with EST in ref
      embl:AA485189
<220> FEATURE:
<221> NAME/KEY: misc_feature
<222> LOCATION: 106683..106780
<223> OTHER INFORMATION: complement homology with EST in ref
      embl:AA485189
<220> FEATURE:
<221> NAME/KEY: misc_feature
<222> LOCATION: 107799..107896
<223> OTHER INFORMATION: complement homology with EST in ref
      embl:AA485189
<220> FEATURE:
<221> NAME/KEY: misc_feature
<222> LOCATION: 152960..153175
<223> OTHER INFORMATION: homology with EST in ref embl:H08612
<220> FEATURE:
<221> NAME/KEY: misc_feature
<222> LOCATION: 155591..155737
<223> OTHER INFORMATION: homology with EST in ref embl:H08612
<220> FEATURE:
<221> NAME/KEY: misc_feature
<222> LOCATION: 159702..159723
<223> OTHER INFORMATION: homology with EST in ref embl:H08612
<220> FEATURE:
<221> NAME/KEY: misc_feature
<222> LOCATION: 134197..134349
<223> OTHER INFORMATION: complement homology with EST in ref
      embl:H38607
<220> FEATURE:
<221> NAME/KEY: misc_feature
<222> LOCATION: 145566..145841
<223> OTHER INFORMATION: complement homology with EST in ref
      embl:H38607
<220> FEATURE:
<221> NAME/KEY: misc_feature
<222> LOCATION: 67608..67703
<223> OTHER INFORMATION: complement homology with EST in ref
      embl:H39516
<220> FEATURE:
<221> NAME/KEY: misc_feature
<222> LOCATION: 71119..71184
<223> OTHER INFORMATION: complement homology with EST in ref
      embl:H39516
<220> FEATURE:
<221> NAME/KEY: misc_feature
<222> LOCATION: 72599..72689
<223> OTHER INFORMATION: complement homology with EST in ref
      embl:H39516
<220> FEATURE:
<221> NAME/KEY: misc_feature
<222> LOCATION: 75544..75623
<223> OTHER INFORMATION: complement homology with EST in ref
      embl:H39516
```

```
<220> FEATURE:
<221> NAME/KEY: misc_feature
<222> LOCATION: 81842..81933
<223> OTHER INFORMATION: complement homology with EST in ref
      embl:H39516
<220> FEATURE:
<221> NAME/KEY: misc_feature
<222> LOCATION: 114492..114592
<223> OTHER INFORMATION: homology with EST in ref embl:T61718
<220> FEATURE:
<221> NAME/KEY: misc_feature
<222> LOCATION: 103434..103744
<223> OTHER INFORMATION: homology with EST in ref embl:R14337
<220> FEATURE:
<221> NAME/KEY: misc_feature
<222> LOCATION: 103189..103447
<223> OTHER INFORMATION: homology with EST in ref embl:R27405
<220> FEATURE:
<221> NAME/KEY: misc_feature
<222> LOCATION: 104304..104653
<223> OTHER INFORMATION: complement homology with EST in ref
      embl:R40663
<220> FEATURE:
<221> NAME/KEY: misc_feature
<222> LOCATION: 83020..83405
<223> OTHER INFORMATION: homology with EST in ref embl:R44970
<220> FEATURE:
<221> NAME/KEY: misc_feature
<222> LOCATION: 1466..1520
<223> OTHER INFORMATION: complement homology with EST in ref
      embl:W37603
<220> FEATURE:
<221> NAME/KEY: misc_feature
<222> LOCATION: 67593..67703
<223> OTHER INFORMATION: complement homology with EST in ref
      embl:W37603
<220> FEATURE:
<221> NAME/KEY: misc_feature
<222> LOCATION: 71119..71184
<223> OTHER INFORMATION: complement homology with EST in ref
      embl:W37603
<220> FEATURE:
<221> NAME/KEY: misc_feature
<222> LOCATION: 72599..72689
<223> OTHER INFORMATION: complement homology with EST in ref
      embl:W37603
<220> FEATURE:
<221> NAME/KEY: misc_feature
<222> LOCATION: 75544..75623
<223> OTHER INFORMATION: complement homology with EST in ref
      embl:W37603
<220> FEATURE:
<221> NAME/KEY: misc_feature
<222> LOCATION: 81842..81861
<223> OTHER INFORMATION: complement homology with EST in ref
      embl:W37603
<220> FEATURE:
<221> NAME/KEY: misc_feature
<222> LOCATION: 75590..75623
<223> OTHER INFORMATION: complement homology with EST in ref
      embl:W67770
<220> FEATURE:
<221> NAME/KEY: misc_feature
<222> LOCATION: 81842..81933
<223> OTHER INFORMATION: complement homology with EST in ref
      embl:W67770
<220> FEATURE:
<221> NAME/KEY: misc_feature
<222> LOCATION: 87902..88040
<223> OTHER INFORMATION: complement homology with EST in ref
      embl:W67770
<220> FEATURE:
<221> NAME/KEY: misc_feature
<222> LOCATION: 93857..93936
<223> OTHER INFORMATION: complement homology with EST in ref
      embl:W67770
<220> FEATURE:
<221> NAME/KEY: misc_feature
<222> LOCATION: 97159..97235
```

```
<223> OTHER INFORMATION: complement homology with EST in ref
      embl:W67770
<220> FEATURE:
<221> NAME/KEY: misc_feature
<222> LOCATION: 98963..99085
<223> OTHER INFORMATION: complement homology with EST in ref
      embl:W67770
<220> FEATURE:
<221> NAME/KEY: misc_feature
<222> LOCATION: 482..665
<223> OTHER INFORMATION: homology with EST in ref embl:W84531
<220> FEATURE:
<221> NAME/KEY: misc_feature
<222> LOCATION: 1466..1520
<223> OTHER INFORMATION: homology with EST in ref embl:W84531
<220> FEATURE:
<221> NAME/KEY: misc_feature
<222> LOCATION: 67593..67703
<223> OTHER INFORMATION: homology with EST in ref embl:W84531
<220> FEATURE:
<221> NAME/KEY: misc_feature
<222> LOCATION: 71119..71184
<223> OTHER INFORMATION: homology with EST in ref embl:W84531
<220> FEATURE:
<221> NAME/KEY: misc_feature
<222> LOCATION: 72599..72689
<223> OTHER INFORMATION: homology with EST in ref embl:W84531
<220> FEATURE:
<221> NAME/KEY: misc_feature
<222> LOCATION: 75544..75623
<223> OTHER INFORMATION: homology with EST in ref embl:W84531
<220> FEATURE:
<221> NAME/KEY: misc_feature
<222> LOCATION: 81842..81917
<223> OTHER INFORMATION: homology with EST in ref embl:W84531
<220> FEATURE:
<221> NAME/KEY: primer_bind
<222> LOCATION: 313..330
<223> OTHER INFORMATION: upstream amplification primer 5-199
<220> FEATURE:
<221> NAME/KEY: primer_bind
<222> LOCATION: 732..751
<223> OTHER INFORMATION: downstream amplification primer 5-199,
      complement
<220> FEATURE:
<221> NAME/KEY: primer_bind
<222> LOCATION: 1282..1299
<223> OTHER INFORMATION: upstream amplification primer 5-200
<220> FEATURE:
<221> NAME/KEY: primer_bind
<222> LOCATION: 1682..1699
<223> OTHER INFORMATION: downstream amplification primer 5-200,
      complement
<220> FEATURE:
<221> NAME/KEY: primer_bind
<222> LOCATION: 67531..67549
<223> OTHER INFORMATION: upstream amplification primer 5-122
<220> FEATURE:
<221> NAME/KEY: primer_bind
<222> LOCATION: 67810..67830
<223> OTHER INFORMATION: downstream amplification primer 5-122,
      complement
<220> FEATURE:
<221> NAME/KEY: primer_bind
<222> LOCATION: 70927..70945
<223> OTHER INFORMATION: upstream amplification primer 5-123
<220> FEATURE:
<221> NAME/KEY: primer_bind
<222> LOCATION: 71257..71276
<223> OTHER INFORMATION: downstream amplification primer 5-123,
      complement
<220> FEATURE:
<221> NAME/KEY: primer_bind
<222> LOCATION: 71613..71631
<223> OTHER INFORMATION: upstream amplification primer 99-1439
<220> FEATURE:
<221> NAME/KEY: primer_bind
<222> LOCATION: 72043..72060
<223> OTHER INFORMATION: downstream amplification primer 99-1439,
```

```
            complement
<220> FEATURE:
<221> NAME/KEY: primer_bind
<222> LOCATION: 75390..75409
<223> OTHER INFORMATION: upstream amplification primer 5-125
<220> FEATURE:
<221> NAME/KEY: primer_bind
<222> LOCATION: 75795..75814
<223> OTHER INFORMATION: downstream amplification primer 5-125,
      complement
<220> FEATURE:
<221> NAME/KEY: primer_bind
<222> LOCATION: 77544..77563
<223> OTHER INFORMATION: upstream amplification primer 99-1444
<220> FEATURE:
<221> NAME/KEY: primer_bind
<222> LOCATION: 77926..77943
<223> OTHER INFORMATION: downstream amplification primer 99-1444,
      complement
<220> FEATURE:
<221> NAME/KEY: primer_bind
<222> LOCATION: 81708..81726
<223> OTHER INFORMATION: upstream amplification primer 5-126
<220> FEATURE:
<221> NAME/KEY: primer_bind
<222> LOCATION: 82108..82127
<223> OTHER INFORMATION: downstream amplification primer 5-126,
      complement
<220> FEATURE:
<221> NAME/KEY: primer_bind
<222> LOCATION: 105046..105065
<223> OTHER INFORMATION: upstream amplification primer 5-132
<220> FEATURE:
<221> NAME/KEY: primer_bind
<222> LOCATION: 105326..105345
<223> OTHER INFORMATION: downstream amplification primer 5-132,
      complement
<220> FEATURE:
<221> NAME/KEY: primer_bind
<222> LOCATION: 104751..104770
<223> OTHER INFORMATION: downstream amplification primer 99-1451
<220> FEATURE:
<221> NAME/KEY: primer_bind
<222> LOCATION: 105297..105316
<223> OTHER INFORMATION: upstream amplification primer 99-1451,
      complement
<220> FEATURE:
<221> NAME/KEY: primer_bind
<222> LOCATION: 107691..107710
<223> OTHER INFORMATION: upstream amplification primer 5-134
<220> FEATURE:
<221> NAME/KEY: primer_bind
<222> LOCATION: 108091..108110
<223> OTHER INFORMATION: downstream amplification primer 5-134,
      complement
<220> FEATURE:
<221> NAME/KEY: primer_bind
<222> LOCATION: 114296..114315
<223> OTHER INFORMATION: upstream amplification primer 5-137
<220> FEATURE:
<221> NAME/KEY: primer_bind
<222> LOCATION: 114698..114716
<223> OTHER INFORMATION: downstream amplification primer 5-137,
      complement
<220> FEATURE:
<221> NAME/KEY: primer_bind
<222> LOCATION: 114327..114345
<223> OTHER INFORMATION: upstream amplification primer 5-138
<220> FEATURE:
<221> NAME/KEY: primer_bind
<222> LOCATION: 114735..114753
<223> OTHER INFORMATION: downstream amplification primer 5-138,
      complement
<220> FEATURE:
<221> NAME/KEY: primer_bind
<222> LOCATION: 132101..132118
<223> OTHER INFORMATION: upstream amplification primer 5-139
<220> FEATURE:
<221> NAME/KEY: primer_bind
```

```
<222> LOCATION: 132504..132521
<223> OTHER INFORMATION: downstream amplification primer 5-139,
      complement
<220> FEATURE:
<221> NAME/KEY: primer_bind
<222> LOCATION: 145522..145541
<223> OTHER INFORMATION: upstream amplification primer 5-141
<220> FEATURE:
<221> NAME/KEY: primer_bind
<222> LOCATION: 145923..145942
<223> OTHER INFORMATION: downstream amplification primer 5-141,
      complement
<220> FEATURE:
<221> NAME/KEY: primer_bind
<222> LOCATION: 145866..145884
<223> OTHER INFORMATION: upstream amplification primer 5-142
<220> FEATURE:
<221> NAME/KEY: primer_bind
<222> LOCATION: 146266..146285
<223> OTHER INFORMATION: downstream amplification primer 5-142,
      complement
<220> FEATURE:
<221> NAME/KEY: primer_bind
<222> LOCATION: 145956..145976
<223> OTHER INFORMATION: downstream amplification primer 99-1445
<220> FEATURE:
<221> NAME/KEY: primer_bind
<222> LOCATION: 146399..146418
<223> OTHER INFORMATION: upstream amplification primer 99-1445,
      complement
<220> FEATURE:
<221> NAME/KEY: primer_bind
<222> LOCATION: 146529..146547
<223> OTHER INFORMATION: upstream amplification primer 5-144
<220> FEATURE:
<221> NAME/KEY: primer_bind
<222> LOCATION: 146955..146972
<223> OTHER INFORMATION: downstream amplification primer 5-144,
      complement
<220> FEATURE:
<221> NAME/KEY: primer_bind
<222> LOCATION: 152763..152780
<223> OTHER INFORMATION: upstream amplification primer 5-146
<220> FEATURE:
<221> NAME/KEY: primer_bind
<222> LOCATION: 153164..153182
<223> OTHER INFORMATION: downstream amplification primer 5-146,
      complement
<220> FEATURE:
<221> NAME/KEY: primer_bind
<222> LOCATION: 155404..155422
<223> OTHER INFORMATION: upstream amplification primer 5-147
<220> FEATURE:
<221> NAME/KEY: primer_bind
<222> LOCATION: 155706..155726
<223> OTHER INFORMATION: downstream amplification primer 5-147,
      complement
<220> FEATURE:
<221> NAME/KEY: primer_bind
<222> LOCATION: 160043..160060
<223> OTHER INFORMATION: upstream amplification primer 5-149
<220> FEATURE:
<221> NAME/KEY: primer_bind
<222> LOCATION: 160445..160462
<223> OTHER INFORMATION: downstream amplification primer 5-149,
      complement
<220> FEATURE:
<221> NAME/KEY: primer_bind
<222> LOCATION: 160361..160378
<223> OTHER INFORMATION: upstream amplification primer 5-150
<220> FEATURE:
<221> NAME/KEY: primer_bind
<222> LOCATION: 160770..160788
<223> OTHER INFORMATION: downstream amplification primer 5-150,
      complement
<220> FEATURE:
<221> NAME/KEY: primer_bind
<222> LOCATION: 160742..160759
<223> OTHER INFORMATION: upstream amplification primer 5-151
```

```
<220> FEATURE:
<221> NAME/KEY: primer_bind
<222> LOCATION: 161147..161165
<223> OTHER INFORMATION: downstream amplification primer 5-151,
      complement
<220> FEATURE:
<221> NAME/KEY: primer_bind
<222> LOCATION: 161127..161144
<223> OTHER INFORMATION: upstream amplification primer 5-152
<220> FEATURE:
<221> NAME/KEY: primer_bind
<222> LOCATION: 161530..161547
<223> OTHER INFORMATION: downstream amplification primer 5-152,
      complement
<220> FEATURE:
<221> NAME/KEY: primer_bind
<222> LOCATION: 161217..161235
<223> OTHER INFORMATION: upstream amplification primer 5-153
<220> FEATURE:
<221> NAME/KEY: primer_bind
<222> LOCATION: 161617..161636
<223> OTHER INFORMATION: downstream amplification primer 5-153,
      complement

<400> SEQUENCE: 1
ccccagagta tggactttat ttcccagaaa gccttgaggc gtaactttct gtttccatag      60
aactggtggg aaaatggcgt cgttgtttgt atccagggac aataggaac agtgtatagg     120 cgggttctaa agaactttaa ccaatccaag gtcgtctaag aggccatccg ggaaagaggt     180
aggggagggg gggaaaaaaa atctagggga ggggagaaag ggggggaacc tagagtcggt     240
gggggggaag cgatgtttgc ccgtcagtcg agtccggagt gaggagctcg gtcgccgaag     300
cggagggaga ctcttgagct tcatcttgcc gccgccacgg ccaccgcctg gacctttgcc     360
cggagggagc tgcagagggt ccatcgccgc cgtcctctgg agggcagcgc gattgggggc     420
ccggacctcc agtccggggg ggattttcg tcgtccccct ccccccaacc agggagcccg     480
agcggccgcc aaacaaaggt accagtcgcc gccgcgggag gaggaggagc cggagcctct     540
gcctcagcag ccgctggacc cgccgcccct tcttccccat tctccccgg gcctgctggt     600 tttgggggg agaaggagag aggggactct ggacgtgcca gggtcagatc tcgcctccga     660
ggaaggtagg gatattttct ggggctttcg tggtctccta aggggttct tttgggagtc     720 gctgggcccg gccaaggagc agaggaagat cgccggtggtg gtccctgcgg cgcccgaatt     780
cggggcctcg gcctcccggg aacccccacc ccccgcagcc gctgtgtccg agccgcccc      840 tggctgggcg gccgcacact cagcggttta gcggccgcgg tcggggcccc gggcagggtg     900
ggggccgttc cgcctccggg gccctcggcc ctcacgttgt cccgcggcg gggccagatg     960 ttgatctcgc tcccacttgt cgggtctgag cccggaacgg gacgtgggca ggggctctgt    1020
ggcgggccgg tcctgccgc ggcccacagg ccctcctggc ccctcggtgg ccccggccg      1080 gcctctcgct cggacgcggc gcgtgggggc gcggattcgc tcggccgggc gccgaggccc    1140
taggggagag cggccggccc tgcgccggac gcgggcttg ttgtgagttt cttctctgac    1200
agaaatggcg tcattgtcgt agacgggaaa ctccgtcggg tctcgacaat ggggacggga    1260
agctgccgag ctgtgtaggt ggttgggttt gcggggatgg cggggccgga gggagccccg    1320
agtcggcgtg tgatggttcg ggggctggcg cctggttgcg gctctttctt cggggttcgg    1380
acgtcgctcg cttctttccc tccgcctccg ccagtgcaga ggggctcctg tggtgttgac    1440
tgggtgtctt ttgtttcccc tccaggtgca gctgaacctg gtgtttaga ggataccttg     1500 gtcccagagt catcatgaag gtaagattgc ctgcggaaaa cgaatctctg ggttatcga    1560 attcaggaag taggaggttt cgacgaggtc gtcgtgtggg gcttccgagt tttgcagagg    1620
```

```
aaggtgtgtt tggtgacttg gtgaccgagc ccttccccag agagaccggg gtcagctggc   1680
gggctttgct gtggagttgg aggcagttat aggatgtctc aactgaagat gattctccca   1740
tattgaacat ctcttttgt agggaatgag aggaataacg gcatgaatta aagtgtttta   1800
aaaggtaaaa taaaaagcaa gtcaggtaat ctgaccctag aaactgaact gtattgtggt   1860
tctatcagtt acactgatga aagagaatct tatttattgt gtgaacagta ctgtaaaatt   1920
ttagcagaaa actctttgac tcgtcacaaa ataatttaa ttgaaagatt taaaaagaga   1980 attttttgtga ttttttacac aattcagaga taccagttgt ttcttgtatt tccagtgact   2040
tggggttata tggtttattt ttctttattg atctggttgg tctgtaaata agtcagaggc   2100
tctgttgcat tatgatgtgt ggaaaactga tggccaggtt cctcttagat gtcaatatgt   2160
taactgagtg gagaataggg tcaaaaaatt tgcttaattg ttggaagaaa tgataacgat   2220
aaaaatacag gtattttgt tacttgagag aatatgtata tgaatgctgt ctttttttt   2280 tttaaacaca tgctagaata aaaccttaga tttttgaaaa gtctggattc aactggtgga   2340
acttagacac tagcttgatt ttttcatcca ttacaaattc agaagtgctt gaaaagggta   2400
gagtgttcac aagtgtagaa atgcaacaga tagcatgtta gaatatcaac gttgtctact   2460
tttgacagtt cctttgaact atttaaaaaa atatttcact tgtcctcaga atcaagactg   2520
ctttgacaat tttgcatcca aattaaaatt tgtaatactt gtggttgtag aaggtaaaag   2580
ctgtggctac ttaaatcttg gtctactata cagagtaatt aagtttagtc taatttttt   2640 aaggttttct ctttgagttt gggatgctgt aaactacctg aaacagttta ttcctatctc   2700
atttcatgaa gcatagacat gtttcaggaa tgaatccctt ttgttagtca caaatcctag   2760
ctataactct catcacctgt gtaaaacagt ggtgaaagtg catttattag gtaactcgta   2820
tatgtacctt gatgttgggt gagaatttct taagaaaagt tttggtttga gtaagaaata   2880
ataagttcag aagccgaata aataaaaggt ttagtttgga gtaaatgtaa tgtgtcacat   2940
ttcccagtgt tgtagtgctt gtcacttctt aggtgctcta taaatgtttg gttaaaagaa   3000
atgtagttaa gttgaaagtc tgagattaaa atgttttttt tcttcctttc gtttccttt   3060 ttttttaag tagtctgttt aaaaaaatga aagtatgttg gaaactttag ccttaaaagt   3120
ttcttggtaa tactagccaa atgcaaattt tttggtatct ttttagaaat actaatttta   3180
agtgctcagc attacattct actgcatttt ttaaaaggt gcttttaacg ttaaaaggaa   3240
aaagttacta aaataaattt ctaacttcat acaagtactt cctgttatta taagtatagc   3300
aaatctcaga gaatttgcta gtaattatta gtactaaaaa cttagcttat ttcttacaac   3360
tttatttctt atgtgataaa agatgagaag cttcttgtaa tttgtatttt gctttagcaa   3420
aaattgcaat tcagaatcta tttaatgttg agtgtattag gcctaaattt tgtttctttt   3480
tctgtgtgtt cccaatttct ttcgttcttt tttattttc tttttgatat agagtctcac   3540
tatttcaccc tggctggcac gatctgtaac tgctgcctcc tgggctcaaa taatcctccc   3600
acctcagcct cctgagtagc tgggactaca ggcacacctg ctaattttt gtagttttg   3660 tagagatgag gttttgccgt gttgcccagg ctggtgtcga acttctgggc tcaggtgact   3720
ctcccgcctt agcctcccaa agtgctggga ttacaggcga gagtcaccgt gcctggtgta   3780
atttctgtat tacgatgatc attgagctac agaaggtttt atgccattta ttggatctta   3840
ccaaacatat ttgtacttgg gagcaagctt ttaagtttga attgtctgtt gtattaacga   3900
caacaaatct ttaaatttta ttaagtgaca gtttattgag gtgattgaaa gttagattat   3960
```

```
gtagtaatac ttttaggtg ttgttttaaa gttgaagtgt tgtatgtttt agcagttttc    4020
ccatgtacta cctttaagaa tttatgtaaa caaatacatt cccattactg tctaatatat    4080
gctatgttac ttttttcaca gtatgttttt gaggaatatg attcgtaata cataaggaat    4140
ttgtgctgta acatagatcg tgatgttggt gttatgttga atttattttt catgctcttg    4200
atagactttt aaaaatcagt ggtgccggct gggcatggtg gctcacgcct gtaatcacag    4260
cactttggga ggccgaggta ggaggatcac ctgaggtcaa gggagtttga gaccagcctg    4320
gccagcgtag taaaccctg tctcttctaa aaatacaaaa ttagctgggc atggtggcac    4380
acacctgtaa tcccagctat tcggaaggct gaggcaggag aactgcttga acccaggagg    4440
cggaggttgc agtgagctga ggttgcgcca ctgaactcca gcctggcgaa aaagtgaaa     4500 ctctctctct caaaaaaaaa aaactaaata aaataaaata aaaatcagca gtaccacatt    4560
ataaggaggt ggtagattat taaagtttgt aaataattcc aagacttatt tttattatgt    4620
caggttgatt tttacttttt ttttttaaga cggactttg ctcttgttgc ccaggccgga     4680
gtgcagtggt gcgatctcgg ctcactgcaa cctctgcctc ccaggttcaa gcagttctcc    4740
tgcctcagcc tcctgagtaa ctggaattat aggcatgcac catcatgccg gctaattttt    4800
gtgcttttag tagagacaag gtttctccat attggtcagg ctggtctcga actcctgacc    4860
tcaggtgatc tgcccgcctc ggcctcccaa agtgctggga ttacaggcgt gagccactgc    4920
gcccggccga ttttactttt ttttaaactc aaacttttt ttcctgtatc tatattgtac     4980
atgttattaa cgtctttat tacgtagcag taaattttca attaaaatgg ctggttggg      5040 ctggatatac cagaatcttt agaggaggaa tgatttagat gattatactt tggcgggcat    5100
ggtggctcat gcttgtaatc ccagtacttt gggaggctga ggtgggtgga ttacttgagg    5160
ttgggagttc aagaccagcc tggccaaagt gatgaaaacc ccgtctctac taaaagtata    5220
aaaaaattag ctgggcatgg tggcgcatgc ctgtattccc agctactcag gagactgagg    5280
taggatcgct tgaacctagg aggtggaggt tgcagtgagt cgagatggca ccactgcact    5340
ccagcttggg tgacagggag accccatttc aggaaaaaaa aaaaaaaaag gtggttatat    5400
ttagaatcca cgtagattga attttccaga tgtacttttc tttcttcaac aatgattggc    5460
ttaggccaca tgaaaaaata atggattgat tacaaattcc cttttttaat gcccgtgtg     5520 tgtgtacatg ttctctctct ctctccccct acctctacct ttgtttgtct ccctatccac    5580
tctgtcagtt cgttcccccc tctctgttct tttccttccc cctcttcctt ctgtctcacc    5640
cctttcataa gtcattcatt taacaacaac ccgtttcata tatcaggtaa tatagaatga    5700
aggtgggtga ggcatctgac ctgctttcag ggagcccaca gtgtagcaga agatgcagat    5760
aaataaagca aaactcctag catatctatt tatgagtatt ccaacataaa ataattgtag    5820
gaaatgctat gagaggacag aagaggacag ctaaatcaga gagctatgga aagttttctg    5880
gtggagttga catctaagct gagtgcgaag gcttttgcta ggcaaagaag ggagaaaaag    5940
tttttcagat agaggataac gtactggaaa atgaacgaaa caaggtgaag tatctggaaa    6000
ctgtaagtaa tttggtgtga ctgaattaac ttaaagcatg atatgtttgg gtaggaataa    6060
aagggcagtg gtgggagatg aagctgagtg agggagtcga aaattttctt ggccaggcat    6120
ggtgtctcac acctgtaatc ccagcacttt gggaggttga ggcaggtgga tcacctgagt    6180
tctataccag cctggccaac atggtgaaac cctgtttcta ctaaaaatac aaaattagca    6240
gggcatggtg gtgtgagcct gtaatgccag ctattaggga ggctgaggca gaagaatagc    6300
ttgaacacgg gaggtggagg ttacagtgag ccgagatcat gccattgcac tccagcctgg    6360
```

```
gtgacaagag caatactctg tctcaaaaaa aaaaaaattt tttcttgaaa actacatgga    6420
accattgaaa gttgttgaga attgcttgaa cccaggagct ggaggttgcg gtgagctgag    6480
atcaggccac tgcaaaaaca aggggagagc tgaatgtaag gatggaaatt ccaggtaaga    6540
agtccaagtg gaaatgaat aagggcctga actaatgcat tggaagtgga gcagagagga    6600
tagatctgag ccttttttgaa gtagaattca gggccgggca cagtggctca cacctgtaat    6660
cccagcactt tgggaggctg aggtgggtgg atcatgaggt caggagattg agaccatcct    6720
ggctaacaca gtgaaacccc gtctctacta aaaaaataca aaaaatagaa attagccagg    6780
cttggtagcg ggcgcctgta ggacgctgag gcaggagaat ggtgcgaacc tgggaggcgg    6840
agcttgcagt gagccgagat cacgccactg cactccagcc tgggcgacag agcaagagtc    6900
tgtcttaaaa gaagtagaat tcaggaccta gtaactcatc ctggggtagg aagaagatgg    6960
aggttttttt cttaggaaat tagatagatg ttactgtcat ttgaagcatg ctgtcattgg    7020
acctgctagt taagatgtaa gagtaagtag gtaggatgaa gtcagaggct tggttaatct    7080
ggtgtgaatg ttaacctcat atctatgata tttgaaggga tttaagatcc ataacatggc    7140
aaattttgtg ctataaattt gtggtccttt agatgaatag gtaatcttgt aaaatactaa    7200
catgttttct gtccaaattg ctaaatcttt gtttattgta attaaaaaaa atactaggtg    7260
agtacctatg tcactgaaga atgttttttgc caagtcagcc agtgaattca gtcattgaac    7320
acattgtgta ctttccttgt accggacatt gttctgggtt ttgaggatgc agcagtgaat    7380
agaacaagag ttcttaccct cgtggagttt actttctact atggtggaca cacgttaaga    7440
aaaaaaataa tgctaagtgc tttgaagaga aatgatacgg aatcagaata agaggttaga    7500
gtgacagagg gtgggttact ttagattagg tgataatgga gggccttttc gagatgacat    7560
ttaagtgtgc tgtgaaacaa gtgatagagt gagccattca ggtttctggg ggaggagcat    7620
tccctgcaga aaacaagtgc aaataccctg agatggagtg tgcttggcat gtttgagtgt    7680
gatacattta aggaacatta aggccatcag ggctggagtg gtaggagagg aggtcagaga    7740
gggtcacaaa gggccagtac aattgtaggg cctatagga catggtaagg acttgagtaa    7800
aatctgaatg tgttaggaac cctttgaagg gtgttgagtg aagtgatgtg ataaacattt    7860
tcaaaaatgt ttgactgctg ggtagtgaac acatcatggg ttcgaacaga tcatgggaac    7920
acaagagtgg aagtagggag atcagtcaga aggctgtcaa gctagtcctg gggagagatg    7980
gtggtgagga gaaatagtag tatttgggaat atatttgaag atggggatga ttggatttca    8040
atggattggg tgtgaaggga aaattctact tactgcaact tgcacatgta tgtcctccca    8100
caagtgccct ccctccttttt cttttgagac ggagcctctc tctgttgcct aggctggagt    8160
gcagtgatgt gatctcggct cactgcagcc tctgtctccc gagtttaagt aattctcttg    8220
ccccagactc ccctgtagct gggattacag gcacctgcca ccacgcctgg ctaattttttt    8280 ttgtattttt tgtttttttt ttttagacg gagtttcgct cgttacccag gttggagtgc    8340
aatggcacga tctcggctca ctgcaacctc tgcctcccag gttcaagcga ttctcctgcc    8400
tcagcctccc aagtagctgg gactacaggc atgtgccacc atgtctggct aatttttgta    8460 ttttttagtag agacggggtt tcaccatgtt ggccaggctg gtctcaaact cctgaccttg    8520
ttatccacct gcctcggcct cccagagtgc tgggattaca ggtgtgagtc acctcgcccg    8580
gccttttttt ttgtgttttt agtagcaatg gggtttcacc atgttggcca ggatggttct    8640
gaactcctga ccttaagtga tccgcccgcc ttggcctccc aaagtgtgag ccactgcacc    8700
```

```
tggccgtcct ccctttttt aaaaagtct ttttgctgtg attagttggt agatgggatt    8760
cttggaactg agtatgacca tgaaggcatt gtcaaatctt agccttctca gtgagcagtg    8820
aacattgagt tgagcaatcc tttcacttgt tttttaatt aaaaaaaatg agatataatt    8880
cacataccat aaaattcacc cttttatttt attttttttg agacatggcc acagtctgtt    8940
gcccaggcag gagtgtagtg gcgcaatcac agctcactgc agccttgatc ttcagtgggc    9000
tcatgtgatc ctgcttcaac ctcccaggta gctgggacca gaggtgcacg gcaccatgcc    9060
cagctaactt ttaaatttc tgtggaggtc tcactgtgtt gcccaggctg gtcttgaact    9120
cctgggctca aatgatcctc ccatcttggc ctaccaaagt gttgggatta caggcatgag    9180
ccaccgcgcc tcaccaaatt cacctttta aagtgttcat aaatttctag tattttcaca    9240
agtttgtgca tccatcacta ctatcttttg aaaacttttt tgttaatttc ttttgtttgt    9300 tttttagag atgaggtctt gctgtgttac ctaggctggc cttgaactct gtggtcaag    9360 tgatctttcc ccctcaactt cctgagtagc tgagacttca ggcacgttac ttatccctag    9420
ctatctgtca ctgctattta actccagaac atttccaaat tcccaacaag aaacttctta    9480
tccattagca gtcattcact gttctccctt tcttttatcc ctccagtaac taatctaaat    9540 ttttttttg agaagagttt tgattctgtc acccaggctg gagtgcagtg gctcgaccat    9600
ggctcactgc agcatcgacc tcctgggttc aagcgatctt cctgcctcca gctcccaagt    9660
agatgggatt acaggtgtgc gccaccatgc ccagcaaatt ttggaatttt ttgtagtagt    9720
gaagtctcac tatgttccct agcctggtct ggaactcctg agctcaagtg atcctcttgc    9780
attggccccc aaagtgctgg gattacaaga ttcagacact gagcttagca tttactttct    9840
gtctataagg atttgcgtat tctgggcatt ttctgttaac ggaatcctgt aatacatatg    9900 tggcctttt gtgtctgatt tcttttactt cccataagtg aaagaagtag caagtgttga    9960
ccaggcgcga tggctcacgc ctgtaatccc agcactttgg gaagccgatg tgggtggatc   10020
acgatgtcag gagttcaaga ccagcctggc caagatggtg aaacccccatc tgtactaaat   10080 aaaaaaatta gccgggtgtg gtggtgggcg cctgtaatcc cagctactca ggaggctgag   10140
gcagagaatt gcttgaacct gggaggcaaa ggttgcagtg agctgcgatg cgccactgc   10200 actccagcct aggtgtcaga tcaagactcc gtctcaaaaa aaaaaaaaa aaaaaaaaa   10260 aggagtagca agtgttaata ctatgctctt ttttattgct gaataatagt ccatcttatg   10320
aagatacgac attttgtcag tctacttatt tggaggacat gtgggttatt tctgctttt   10380 tgcttattgt gagtaatgct gctatgagca tttgtatgta agtttctgtg cgaacatgta   10440
tttttaattc tcttgggtcc tgggagtgga cctttcagtt cttagggtac taatattacc   10500
tgtgtgataa cctggggagt gctgagtatt taacttcatg tattttgtgt tgtggcaagt   10560
ggccaccaag gagttggaca tttaaaaaat taattcaata tttattgaat acttattatg   10620
tattggtctc tgttctagtc agttggaata tgtcagggaa caaaacaggt agaaattcct   10680
ggctctttgg atctcttagg agtacaggaa actctggtat tcaaggtttc cgtagaaaat   10740
aatgtgcttt tagaaatcat aatttcgtt ctaaaattgg agacagcatt cagatttggg   10800
gaagaaaaaa atgagtttat ggaagtatat aaacagttta ctagaaaata aaaagcaggt   10860
ctactaaggt cagcatagac aaactatctt catgttcacc ttaccatagt ggctgttatt   10920
ttaagctggt taatagaagc aagggacata atgaaagagt caaaaaggga aagttttaa   10980 aacaatactt ggcttactct gagcatagtt tccccttcc ttaattaacg cttgctcata   11040
tattactcag aaagtccaag tgtaggcttc agaggagagg agccatagat agctttcatc   11100
```

```
agattcttga tgaaacccac agtacaaatg ttaagaaaca cagctctgtg gtatcatctg   11160
ttgactgatc tgctgctaat ctatttaata ggaagagttg tttctatatc cttctacttt   11220
taccattaaa gaaaaagtaa tcaactagtc actgttcatt ttattttcaa atttattttt   11280
gcttaaatca ttgcagaatc agaaaaaaat ttttattata ttgtttctga aatgttaaca   11340
tttaggtgaa atgcttaatc aggttgagta tcacttacct gaaatgcttg ggaccagaaa   11400
tatttgggat tttttcagat tttggaatat ttgcatttat atgcttagta tttgaacatc   11460
ccaaatctga aaatccaaaa tgttccagtg agcatttccc tttggtgtaa catgaacact   11520
gaaaaagttt cagttttttgt agcatttctg atttttttgtg ttttacgtat gtatatgtat   11580
atctgtatct tgtttttttg tttggttgtt tgagacagaa tcttgctctg tcacccaggc   11640
tggagtgcag tggtgcgatc tcagctcact gcaacactcg gctcccggat tcaaacgatt   11700
cttctccctc agcctcccaa gtagctggga ttacaggcgc ctgccaccac acctggctaa   11760
tttttgtatt tttagtacag acgaggtttc gccatgttgg ccaggctggt ctctcgaact   11820
ccagacctca ggtgatcctc ctgcctcagc ctcccaaagt gctggaatta taggcatcag   11880
ccaccgtgcc cagccttata taaatatatt attatttttt tgagacgaag tcttgctgtg   11940
tcgcccaggc tggagtgcag tagtgcgatc ttggcttact gcagcctctg gctcctgggt   12000
tcaagtgatt ctcctgcctc agcttccaga gtagttggga ttacaggcgt gtgccacaac   12060
acctggctaa ttttttgtat tttagtgga gacgaggctt caccatgttg gccaggctgg   12120
tctcgaactc ctgacctcaa gtgatccgcc cgcctcagcc ttccaaagtg ctggaattac   12180
aggtgtgagc cactgcaccc cacttatttt tgagttaggg atactcaatg tgaattgctt   12240
gaaatgttta cctcgttgaa ttcctaagaa gaatttgaat ttttttaaatt tataactagc   12300 ctttgatcca tggaaacatt ttataaaata atttccaaaa taatttcctg gaaatctgga   12360
attgtagtct gtagcaaatt gggattattt attaatttaa tttaatttaa tttatgagat   12420
cagagtcttg gtatgttgcg ttggctggtc tcgaactcct aggcttgagt gatccttctg   12480
cctcagcctc tctagtggct ggaactgtaa gtgcacacca ccatggcaca ttggatatta   12540
tttatgaaac tatttattac aaatgttagt atatgcttac tcttacccttt tgcatattca   12600 attatttact ctaatcgggt tatctaaggc aagaatagta tctaactgtg aataaccaga   12660
tatgcttagc tttaggatac agttagacgt aagtatagaa ttcaacatcc ctgtaactaa   12720
tgtctttcca gattaatgtt agtgttgata gtaaggtggt agaacgggct aattctctgg   12780
gccattatta ctgatttata aggtagaaaa tagggtgtat cactttaaag ttacaaattt   12840
acatttataa ggaagaaaat agggtatatc acttttaagt tacaaattta cctgtcatca   12900
attaagagaa taataattag gcagtaggtt tataccatta aaatgtgtga gattacttac   12960
actatatctt ggacagtggg acagataatt tattttttttg gagacatagc cttgttctgc   13020
ggcccaggtt ggagtgcggt ggcgcaatca tagctcactg cagcctccag ctcctgggct   13080
caagtgatct tcctacctca gtcacccaag tagctgagac tacaaataat gcacaccacc   13140
atgcctcgct aaattttttt gtattttgg tagagacggg gtctccttat cttgcccagg   13200
ctagtcttga actcttgagc tcaggtgatc ctcccacctt ggcctcccaa atgttgggat   13260
ttacagatgt gagccaccaa gcctggcctg gacaatggga cagatacttt atatgtgac   13320 ttttctcatt taagccattt ttctctagtt tatagataaa ttttttggcaa tgtgacaact   13380 agaatatctg aaatcctata taaaagttct attaatgcta tctgctaatt gataaccttt   13440
```

```
tgatttcagg gtataattgc ttatgagaac atagtcattg ataactttag taagtttcat   13500
tgaacatcat attttaacaa tgcacttcaa tagcaaatga agattataaa ctaaaacctt   13560
tgagcaagtg gtatttaaag aaaggattta ctttatattg atagccaaaa taatgtatat   13620
accgaaatat atataaatac gtatttataa acatatttta ctgatagtaa aatgttatat   13680
atattgttat atatcattta agataattta tatgtaaatt aaatataaac cagatttctt   13740
tattccagga accttgctgt tgtttctaac ctttcttttc ctgctactta gtgatgcaga   13800
agcttttctt ggtaaatcta cttgtcccct ctcttaattt actgcttgaa tatgactgtg   13860
aaaactgtct ttgtttaaag tgcccagtaa acattgtagc ttcatgatta agagcatatg   13920
gcttggaaag tcagtggtct tatttccagt ccttttatg tcctttactt ggctgctgag    13980
gtttgggtaa agttactgtt tttgaaatga agtaaacat cagtttcaat ttttgtaaaa     14040
tgagaataat aacagctacc ttgtaaagtt gtgtaaatat gaaatgaaat accatattta   14100
aaatgcttta cactgtgctt ggcatagttc tgagcagtta gtacgtggca gttgtattat   14160
tagaggaagc ctgtcttgtt tttttttaaa taagctgata gagtgaggat tcttttaatc   14220
aagactgttt gggattgaat tgccactcct gcttaccaga gtgtaggcag tttttcttaa   14280
actttccaag aagactggtg tcctcatcta aaatacgaaa tgcttacagt aattgcctca   14340
tggggttgtt tgggtgact aaatgtagta ggatttacta catagtaagt tctcaataca    14400
ttgtagctat tattattagt tcggtagaaa gaatgtgcag attcttatga gtttaagtag   14460
gctttcgggg agatagattg actctggtct tttaaaagtt aattttgaag ttgcagtttt   14520
gtgattaagc cttaaatctg ttattctttc cttctgaaat ccttaaaaac agaatgttta   14580
gtagaaggtg ataaccagat ttctttattc caagaactct ttgctctcat gtctaacctt   14640
tattttcctg gtacttactg atgcagaagc ttctcttagt aaatataata catctcctct   14700
ctcctaattt gctcccgtct ttccttgtaa gggaaaagta aattttactt ccaagcctag   14760
agggttattt atggattagg tgaactactg aagatactta ttttctggat aagcatccat   14820
ctgtatagcc ttttatgtat ggcaaaaatt gttttcattt cttgatcaga atactgttct   14880
gatgtggtgt agtcagccac ctgaagctga tctagcatgg gcagcctagg caggtagggc   14940
gaatgactgt aggagccctg ctaaacccga gtctctactc cagagaggag ttaaaaaaag   15000
ctgaacaagc ctgaacacgg aggagccact attgctgtca aagttaagtg aagcagcttg   15060
gcttatgtct atttcagaat aaaaaaaaaa aattcaactt aggcatgcac ggtgggtcat   15120
gcccgtaatc ctagcacttt gggcgtttga ggctggcaga ttacttgagg tcaggagttt   15180
gagaccagcc tggccaacat ggtgaaacct tgtctctact gaaaatataa aaattagcca   15240
ggcatggtgg tatgcctgtt tgggaggctg atgcaggaga atctcttgaa cccgggaagt   15300
ggaaattgca gtaagctgag atcgcaccac tgcactccag cctaggtgat agaatgagac   15360
tgcatctcaa aaattcaact tttcacattt tcagttttat cttgataagg atacctcatc   15420
aaagaaccct tttcttttct tttcttttct ttttcttgaa gcagaatctt gctgtgcatc   15480
ccaggctgga gtgcagtggt gcaatcttgg ctcagtgcaa cctccgcctc ctaggttcaa   15540
acgattcttg tgcctcagcc tctgagtag ctaggactac aggcatgcgc caccatgctc    15600
ggctaatttt tgtatttta gtagagatgg gttttgtaa tgttacctag ggtggtctca     15660
aactcccgag ctcaggtgat cgcctgcctt ggcttctcaa agtgctagga ttacaggtgg   15720
gagccaccac gcccagcccc atttctgttt tttttaatct gaatattctt tgctaaagtg   15780
ttgttgtttt ttttaaaggc aagccagaga gcttttggca tttagtaagt cacctattcg   15840
```

```
tgctttgctc taacttggag aaatattttt ctaaactagt tcttctagca aaattaaaga    15900
aatttttatt atgaaagcaa taaagatttt ctgtaaacat taaaaattac atagtagtat    15960
tcagtggaca gtagaagtct tacttcctgg taacttgatt caacagtttt tgggtgtatt    16020
cttccacacc ttttctttg cacatatgaa tcaaacatga gtatttattt tgttatgttt    16080
gactgtattg aaatgggctt atgctatgca tattgttcgt aatttctttt tcttttcttt    16140
tctttgagac ggactgtcgc tctgtcacca gactagagtg tggtggcacg atcttggcta    16200
actgcaacct ctgcctcccg ggttcaagca gttctcctgc ctcagcctcc tgagtagctg    16260
gaactacagg tgcgcgccac cacgcccagc taattttgt atttttagta gacagggttt    16320
caccatgttg gccaggctgg tcttgatctc ttgagctcgt gatttgcctg cctcggcctc    16380
ccaaagtgct gggattacag acgtgagcca ccatgcctgg cccataattt tcttttacat    16440
tcttctatat cagtacatat tacacaagtc tgtgtcattc ttcttgatgg ctttagtaag    16500
attttatttg cattcaacat gttatttttt ctacaaccaa ataatttata tagggcaccg    16560
gtatgtttct ttaagttttg caggtatgta gcagtgctta gtattcagta ggtactgttt    16620
ttgtttgttt gtttgtttgt tttgttttt gttttgaga cagggtcttg ctctgttgcc     16680
caggctggag tgcagtggca cagtcttggc tcactgcaac ctctgcctcc cgggttcaag    16740
agattctcat gtttctgcct cccaagtagc tgggactaca gtcccgtgcc atcacaccca    16800
gctaattttt gtatttttat tagagacagg ttttgccac gttggccagg ctggtctcaa     16860
actcctgacc tcaagtgatc tgcctgcctc gacctcccaa agtacaggtg tgagccactg    16920
tgcctggcct tcagtaagta ttgttaactt atttggatgc ctagtactag taggtggcaa    16980
atagtcccag tacctattat atatacaaag cttcttatag tcctatgaat tattattatt    17040
attattatta ttattattat tattattatt attgttttga cagggtct tgctctgtca      17100 cccaggctgg agtgcacagt acaatcacgg ctcactgtag ccttgacctt ctgggctcaa    17160
gcgatcctcc cacctcagcc tctcgagtag ttgggactac aggtgtgggt caccataggt    17220 tgattttta tattttctag atgggggtc tcactatgtt gcctaggctg gtcttgaact       17280
cttgccctgt gaattattgc agccaccaac tgttaaatat cattgcatga cattgttact    17340
aaaaggtaat ctatgaggat tagtgaggga gcatccctgt gctatatggc tggttctaaa    17400
aaagcttatg ctgttctttg ggatccctgt tagcattgat tagacaggtt aattttgggg    17460
gccgggtgcg gtggcttata cctgtaatcc cagcagtttg gtaggctgat atgggtggat    17520
tacttgaacc caggagtttg agaccagcat ggacaatgtg gcaaaaccct gcttctacaa    17580
aaaagtttta aaatagccag gagtggtggc ctgtgactgt atttccagct actcaggaag    17640
ttgaggctgg gaggattgct tgaacccagg atgtcaagtc tgcagtggag ctgtgattgc    17700
agccactgta ctccagccta ggtgacagag caagaccccg ttttaaaaac aaaatcaaaa    17760
acacgttaat tttggaatgg atctctatag gaagtgtccc cagcatatgc tcaaagtcag    17820
aatatatagt ttataaggaa ttctttaacc gtacagttat atggcacatt acgttttaa     17880 agttccataa tcattagtta tatctaataa catccctttg aggcaggtca gcaacatttt    17940
tcccttttta tggtcgaaga agcaggtgta aagatgttga gtgatttgcc cacaggcaca    18000
cattaaactg atcacagagc ctgttctttt gttagtaaac tgaaccatgc tgcctctcta    18060
ctagttatta taaataaata ataaagttgt tgccatttag tgcttttg atggctttat      18120 tgaatagtaa gtgtagttta caaaccttt gcctacttac tttgttgaaa aagttttaaa     18180
```

```
tttagaattt acttgtatca tggtatgaaa cattttatg taaatttccc tgtttcttt    18240
tttttatttt tttttattga tcattcttgg gtgtttctca cagaggggga tttggcaggg   18300
tcataggaca atagtggagg gaaggtcagc agataaacaa gtgaacaaag gtctctggtt   18360
ttcctaggca gaggaccctg tggccttccg cagtgtttgt gtccctgggt acttgagatt   18420
agggagtggt gatgactctt aaggagcatg ctgccttcaa gcatctgttt aacaaagcac   18480
atcttgcacc tcccttaatc catttaaccc tgagtggaca cagcacatgt ttcagagagc   18540
acagggttgg gggtaagtaa ggtcacagat caacaggatc ccaaggccga agaatttttc   18600
ttagtacaga acaaaaggaa aagtctccca tgtctacttc tttctacaca gacacggcaa   18660
ccatctgatt tctcaatctt ttccccacct ttccccccctt tctattccac aaaaccgcca   18720
ttgtcatcat ggcccgttct caatgagctg ttgggtacac ctcccagacg gggtggcggg   18780
cgggcagagg ggctcctcac ttcccagtag gggtggccgg gcagaggcgc ccctcacctc   18840
ccggacgggg cggctgaccg ggcgggggc tgaccccccc acctccctcc cggacggggc   18900
ggctggccgg gcagaggggc tcctcacttt ccagtagggg cggccgggca gaggcgcccc   18960
ttacctcccg gatggggcgg ctggccgggc gggggctga ccccccccacc tccctcccgg   19020
acgggtggct gccgggcaga gacgctcctc acttcccaga cggggtggtt gccggcggga   19080
ggggctcctc acttctcaga tggggcggct gccgggcgga ggggctcctc acttctcaga   19140
tggggcggct gccgggcgga ggggctcctc acttctcaga tggggcggtt gccaggtgga   19200
gggtctcccc acttctcaga cggggcggcc gggcagagac gctcctcacc tcccagacgg   19260
ggtcacggcc gggcagaggc gctcctcaca tcccagacgg ggcggcgggg cagaggtgct   19320
ccccacatct cagacaatgg gcggccgggc agagacgctc ctcacttcct agatgggatg   19380
gcggccggga agaggcgctc ctcacttcct agatgggatg gcggccgggc agagacgctc   19440
gtcactttcc agactgggca gccaggcaga ggggctcctc acgtcccaga cgatgggcgg   19500
ccaggcagag acgctcctca cttcccagat ggggtggcag ccgggcagag gctgcactct   19560
cggcactttg ggaggccaag gcaggtggct gggaggtgga ggttgtagcg agccgagatc   19620
acgccactgc actccagcct gggcaccatt gagcactgag tgaaccagac tccgtctgca   19680
atcccggcac ctcgggaggc tgaggctggc ggatcactcg cggttaggag ctggagacca   19740
gcccggccaa cacagcgaag ccccgtctcc accaaaaaaa tacaaaaacc agtcaggcgt   19800
ggcagcgcgc acctgcaatc gcgggcactc ggcaggctga ggcaggagaa tcaggcaggg   19860
aggttgcagt gagctgagat ggcagcagta cagtccagct tcggctcggc atcagaggga   19920
gaccgtggaa agagagggag agggagaccg tggggagagg gatagggaga gggagggga   19980
gggggagggg agccctgtt tcttaaaaat tagaaaaat caggctggga gcggtggctc    20040
atgcctgtaa tcccagcact ttgggaggcc aaggtgggcg aatcacttga agtcaggagg   20100
agttcatgac cagcctggcc aacacagcga aaccctgtct ctactaaaaa tacaatacaa   20160
aaattagctg tgcatggtag catgtgcttc tggtcccagc tactcaggcg ctgagacagg   20220
agaagtgcct gaacctggga ggcggaggtt gcagtgagct gagatcaggt cactgcactc   20280
tagcctgggc gacagagcaa gatgcaagac tctgtccccc tccaaaaaaa aaaaaaaaa   20340
aaaaattaga agaaatcata tgaaaaaaca taaaaatgaa cgacagtgga cttagttctt   20400
ctgggagaac tttgctagct tgaaaattag tgtcaagctg gacaggtggc ttgtgcctgt   20460
aattccagct acttgggagg ctgagacagg aggagcttga gccaggagc tcaaggctgc    20520
agtgagcctt gattgcacca ctagattcca gcctgggcga cagagcgaga ctctatctct   20580
```

```
aaaagaaagg aaaattagta ttataaatta gaaaattaga ggctttgtac aaagctttga   20640
agagttaata ttttaaagta ggagaaaaat gaatcctctg gttatattgc cacaagtaat   20700
tttgcgttga aacactgtgg cccatatagc ctgaagagac tttgaaaggt catttgagcc   20760
cttgagttca gaacctatct cttctgccaa gtgatgacac agaatatgat ctagctcaga   20820
aaagttttac aatctgggtg gtttgtctct cttttctct ctctcttttt ctttggctga    20880
agaatcttta gaacagtcaa ccttctctta aattgcaagt ttcctttggc catttgaaac   20940
attttctttt tttcttttct ttttcctttt tcttttttg taaagagaca gggcctagct    21000
ctgtcactta gactggaatt tagcggtgtg atcataattc actgtagccg tgaactcctg   21060
gattcaaggg atcttcccat ctcagtctct tgagtagctg ggaatacagg cttgcgccac   21120
cacattcagc taagtttttt attttttgt agtgctgtgg cctcactgtg tttcccaggt    21180
tggtcttgaa ctcctggcct caagtgacct tcccttgttg gcctcccaaa gcactgggat   21240
tacagacatc agccactgca cccagccaga cattttctat ttacttgtat ggacttaatt   21300
ctgtctatcc cattccccct tcccccatta aatttttttt tctctgtaat ttgtaggtac   21360
aagttctttc tctcactgaa aagctttcca attgtagttt ttctgcattg atggaggtag   21420
tgaaggggag gttcaggtaa tttacaacta ttgtaaacag tttttatttg gcatggtaca   21480
gtgtctaatg cctgtaatcc cagcactttg ggaggctgag gcgggaaaa ttgcaagttt    21540
actttgagtt tgagactagc ccggccaaca tcgcgaaacc ctgtctctac caaaaataca   21600
aaaaattag ccgggtgtgg tggtgcacac ctgaaatccc agctgttctg gaagctgagg    21660
cgtgagaatc gcttgaatcc gggaggtgaa agttgtagtg agctgaggtc acaccactgc   21720
actccagcct gggcgacaga gggagagact ctgtcttaaa aaaagagatt ttatttaagg   21780
gatcatacag agccctaaaa ttatatattc acatttggaa tgttaagcag atgctttgac   21840
atgatatatt ataaatctgt aataataaat agtagttaat cctcatatac tttagtaatt   21900
agcacagtcc aattttttt ttttttgaga tggagtctca ctctgttgcc caggctggag    21960
tgcagtggta tgatctcggc tcactgcagc ctctgccttc catgttcaag tgattctcct   22020
ggctcagcct cccgagtaac tgggactaca ggtgtgtgcc accacgcctg gctaattttt   22080
tgtatttta gtagagacgg ggtttcactg tcttagccag gatggtctcg atcttctgac    22140
cttgtgatct gcctgtctca gcctcccaaa gtgagccacc gtgcccagcc agcacaatct   22200
tattttttag taggcatgta atttctaaat ttgtctttat tgctaaagta acatcccatt   22260
tatctcaaac taactgtcat cagtcttgtc ttgttctgaa atagcattaa aatatttatc   22320
acaccagcct ctttcctggt catcatgttc tttatgctgt aattattatt gttttgtta    22380
ttatcatatg ataattttgc cactgcttat tcagtgctta atatatgtca gtcttttctt   22440
acattatatg tagttttttc ttatttgaag acagagtttc ttgctctgtt gcctgggcag   22500
gaatatagta gcgtgatcat ggctgactgt aaccttgacc tcttgggccc aggtgatcct   22560
cccaccttag cctcctgagt agctgggagt acaggtgtcc accaccatgc ctggcgaatt   22620
tttaactttt ttcatagaga cagggtctca ctatgttgcc taggctgatc ttgaactccc   22680
cggttcaagt gatcccctg cctctgcctc ctaaagtgct gggattatag gcgtgagtcc    22740
ccgtgcctgg cccatttaaa attttaattc tcaaaatacc ctgagaggta catagatata   22800
ttcttatttt acagatgaaa aactcaaggc cgagagagat tatataattt acctaactaa   22860
ggtcatgcca ctagtaagtg gcatagtgag gatttaaacc taaactactt caaaccagag   22920
```

```
ctcctactaa tattaatgct gtttctgcct ctttaatata tatctttact tggatatcta    22980
gttttcttag tacacagaac atttagaagt gccaaatact gtgtgagttg ttagttgtaa    23040
gtgtatgtgt gtttttatgt gtgtatcgag agggaggagt tttgaacaaa tccggaagtc    23100
agaggtctga cgtgggtctc actgggcatt tcttcttcag gctctagggg agaattggtt    23160
tccttgcctc ttttccagct tctagaggct gtatttcctc ctttgcctct ggtctctcct    23220
attttcaaag ccagcagcct ggtgtcttca aatctgtctc tgacactatc tctcctgcct    23280
ccctctttca cttataagta tccttgtgtt tatattaaat agggctcacc cagataatac    23340
aagctaatct cccctttca aggtcaacta attagcaact ctgattccat gtcagcttta     23400
aatttcccct tgatagataa cattttcaca tgttttggag attcggatgt ggtcattttg    23460
tggggagggg gagtgcattc tgcctaccag agtttcctta gtgtggcaaa atgatttagc    23520
ttcttaggcc tcgctataaa atgagattag tatttactat ttaccacaaa ggaattttat    23580
gaagatggaa attacgtact aatacagaca ggccatgcat agaatacact taattagcag    23640
atgctttctg cttgatctta tctgctaggt atatgcttgt ggtgatgggt agtctccaag    23700
gtaaccactg ggtttgataa actccaattt gagtgcctga ctcttctaaa ggcagatgtt    23760
tgttttagaa ttcagccttt ccagaccttt gcatgatgag gatggtgatg atttatagca   23820
caatggtgga aaaacagatg agtgcccctt aactcttaat ttgttttatg atttgaatct    23880
gtcttaatct ctaagataca gttcactttt taagtaggca gcttttctgt ttaacatgat    23940
tttctaaagg attgctatag aagataatga aaagggacct tgagtaattg cacttttaaa    24000
tcacacaaga ttgttttgta tgtgctcaga tggtattttt tgaagttaat gttgtcattt    24060
cttttctttt tttttatttt cgggacaggg tcttcctctg ttgcccaggc tggagtgctg    24120
tggtgtgatc ttggctcact gcagcctcca cctcctgggc tcaagtgatc cacccacctc    24180
agcctcccaa gtagctgaga ctacaggtgt atgccaccac gcctggcaag ttttttgtag    24240
aggcagggtt tcaccatgtt gccacgctgg tctcaaactc ctggactcaa gatatctgtc    24300
caccgcagcc ttccaaagtg ctgtgataat aggcgtgagc caccgtgcct ggcctaggca    24360
atttacttct ttgagtttta ttttcagtat atgagaaatg tggctaataa catttacttc    24420
attgcttgct ttgttattaa atatgatgat gcatgtaaaa tactcatgtt tggtttatat    24480
gtgccaaaaa aataatacct gtaatatatt gtagagttag ggatgaacca ctttactaaa    24540
tgtctccaaa taaccaattt ctaataattt agaatatgta gtatagctag tgtgcattgc    24600
attatgataa aagagtgctt attacctgtg cacctaattt ttggaagtca gattcatata    24660
gctttggtta atctttgttc tttttacatt ttattgtatt ttagacaggg tctcgctgtg    24720
ttctgcaggc tgcagtgcaa tggcatgatc atagctcact gcagccttga acccctgggc    24780
tcaagtgatc ctcccacttt agtgtcccaa gtattaaata gctggcatta cagacatgtg    24840
ccaccatgcc tggctgtttc tcgttttttt tagagatggg atctcactat gttgccaagg    24900
ctggtctcga acttctggcc tcaaatgatc ttcttgcctt ggcccctcaa agtgctggat    24960
tacaggagtg agctactgtg tccagcctaa tcttcgttct tggagtcaag ttgtgtaggc    25020
tttgtttttt gctttgcttt ttttttttc ccccacctct agtttttaat ttaaaaaagg     25080
actggctttt agaaccactg gaaaatattt gttttggggg cagtgtcttt agataacata    25140
aaattcagga atacaaattt tgggtggaag atagtacagc gtcattggtt aagaatataa    25200
actctctggc cgggtgtggt ggctcaggcc tgtaatccta gcactctggg aggccgaggc    25260
aggcggatca caaggtcagg agattgagac catcgtggct aacacggtga aaccctgtct    25320
```

```
ctactaaaaa tacaaaaaat tagccgggtg tggtggcggg cgcctgtagt cccagctagt   25380
cgagaggctg aggcaggaga atggcgtgaa cccgggaggc ggagcttgca ttgagccgat   25440
cgcgccactg cactccagcc taggcgacag agcgagactc cgtctcaaaa aaagaaaaa    25500
aagaagaata taaactctca aactgaattc taatcctggc actattactt actgccttgt   25560
gatgttaggc aagtaatgta accttctgtg atgcttaaat tttaatcttg tctgaaatga   25620
ggacaatgat aaaatgtacc tcctactttg aaggattga atgaggtaat ccatgtaaag    25680
catttagcat ggcctctact aagtgaccca cagcagttat tagtaatgac aaataagaga   25740
aaggagaagc agtgggcagg tgttcaagtg ctaacgtgta ttgtttagag cagtgttatc   25800
aataggagta taatgcaagc catgtgtaat tttaactttt ataatagctg tattaagtaa   25860
ataaaaagaa acaggtgttg aaattcatta tgataatgtt taatttaacc cagcatatcc   25920
aaaacattgt tatttcaaca tgtaatgata tcaaaattat tgagatattt tacatttttt   25980
aatactatat ctttgaaatc tggtgtatat ttatacctat ggcatgtctc aatttggata   26040
ctaaattctt tctgtctttc tgtccccact cctttccctc cctcccctc ccctcctttc    26100
ccctccttct cttccacttc cctttccctt tttccttcct tccttccttc ctcccctccc   26160
tccctttaca cttcccccctc cccatctctt tcccttccc ctttcccttc ccttccctt    26220
ccttttcctt gtttctttgt tttttttttgc tgtttttttt tttttttttt ttttccgttt   26280
tttgagacag agtcagccag gcacagtggc ttatgcttgt aataccagca ctttgggaag   26340
ccgaggtggg tggatcactt gagcctagga gtttgagacc aggttgggca acatggcgaa   26400
accccgtttc cactaaaaat ataaaagagt tagttggctg ggcgcggtgg cccatgcctg   26460
taatcctagc actttgggag gccgaggtgg gcggatcacc tgaggtcagg agttttgaaa   26520
cccctctct actaaaaaca caaaaattag ctgggtgtgg tagcaggcac ctgtaatccc    26580
agttacttgg gaggctgagg caggagaatc acttgaactt gggaggcaga ggttgcagtg   26640
agctgagatc aggccactgc actccagcct gggtgataag agcgagactg catctcacaa   26700
aaaaaaaaga attagttagg caaggtggtg ggcacctgtg gtcccagcta ctccggtagc   26760
tgaggtggga ggattgcttg agcctgggag gtggaggag gttgcagtga gctgagattg    26820
caccactgca ccctagcctg gccagggca aggccaccct gtctcaaaag gagaaaaaaa    26880
aaaaaaaaa aagaaatag gtctcactc tcaccggctg gagtacagtg gtgtgatcac     26940
agctcactgc aaccttgact ttctaggctc tagcgatcct cccacctcag tctcccaagt   27000
aattaggact acaagtgtgt gccagcacgc ttggctaatt ttttgtattt tttgtaaaga   27060
caaggtttca ccatgttgcc caggctggtc tcaaactcct gggctcaagc gattctcccg   27120
ccttggcctc ccaaagtgtt cagataacag gcgtgagcca ccacactggg cactaaattt   27180
tcagcagaga tgcttgttct gtatttagat ttaataaaat ttacagtaga aaagtagat    27240
tcgcctgggt gtggtggctc acgcctataa tcccaacact tgggaggct gaggcaggaa    27300
gattgtttga gccaggaat tcaaaccag cctgggaaac atagtgagac cctgtctgta    27360
tactaaaaaa aaaaaaaaa aaaaaaaaa agaatactta aaaaaatgta ttgttggctg   27420
ggcgtagtgg ctcacgccta taatcccagc actctgggag gccgaggcag gcagatcatg   27480
aggtcaagag attgagacca tcctggccaa tatagtgaaa ccccgcctct actaaaaata   27540
tacacacaca aaattagctg gacgtggtgg catgcacctg tagtcccagc tactcgggag   27600
gctgaggcag gagaatcgct tgaacctggg aggtggaggt tgcagtgagc tgagatcgtg   27660
```

```
ccactgcact tcagcctggc tacagagcga gactctgtct cacaaaaaat aaaaaaaaaa  27720
gtattcttgt agttccttit ttctccttgc aaggcatctt taatgtagaa taagctaaat  27780
atagtaataa taataataat taaaaatgat gaagtttatt gagtactgct ttgtatgtgt  27840
tatgttgtct tctaagcaca gatatctcat ttaatcttca tgatagcact atgagaatac  27900
tttaattttc cctgtttaca gatagggaaa atggggacca gagaaagtta tagagcatag  27960
agttgaactc aattttgacc tccagagtct gttttctt ttttttttt tatgagacgg     28020 agtctcattc tgtcgcccag gctggagtgc agtggcatga tctcggctca ctacaacctc  28080
cacctcctgg gttcaagtga ttcttgtgcc tcagcctccc aagtagctgg gattgcaggc  28140
acccgccacc ccacctggct aaattttgta tttttggta gagatggggt tttgccatgt   28200
tggccagggt gttctcggac tcctgacctc aagcggtttg cccgcctcag cctcccaaag  28260
tgctgggatt acaggtatga gccactgtgc ctggcccaga gcctgttttt ctgacagtca  28320
caccgcttat tggttgctgg atagaatgaa aaagcaaatg gaagtacctc tccccaccag  28380 tagttttct gggtttcttt tatggggag cgagggtaga gtaacatgtg ggtagaggga   28440
cagtgtttca ggaacccatt tggatattta agaacaggac taaatactta aattacttct  28500
gtgacaataa aaagatacc aggaagctac actcttttt agttctatat ttttgcatc    28560 atacgtttaa aaattggttg ctcctaaatg aagcttaga atcctttgca agatagtact  28620
actgcttcaa gcagctaacc accaatgaac aagaattatg agttcaaact ctggcataga  28680 ccaacccct aacttggatc tcctaactca taatccagag ttcttttcca gagaactgct   28740
ccgcttttaa aaaccagtgc caggattcag atctcaaatg ataccattaa acactgatag  28800
gcaagaagca tttgtttcta tgagtaaata actctctgat gtattagagg ctggtgttaa  28860 ttttgacta ggctgaactc tgagcgttta ttatttcttc aggtattaaa ccttcagata   28920
atttcaaaaa cacagtttag gccaggcaca gtggctcacg cctttaatct gagtactatg  28980
ggaggcagag gtgggtggat aacaaggtca ggagttcaag aaaccccgtc tctactaaaa  29040
atacaaaaaa tagctgggcg tggtggtggg ctcctgtaat cccagctact cgggcggctg  29100
aggcaggaga atcgtttgaa ccctggaggc ggaggttgca gtgagccaag atcacgccat  29160
tgcactccag cctgggtgac agggcaagac tctgtctcaa taaaaaacaa aaccaaacca  29220
cagtttatcc cttaggaaaa caccaaaaag cttcttatgt acatgaactt gtattagggt  29280
cacactttaa ggtggctcta gaaagtataa tgagagactt acagtaagac tgcttttttt  29340
ttgacgtggc atctcacttt gttgtctagg ctggcttgga actcctgggt tcaagccatc  29400
ctcttgcctc tgcctcccga gtagcttac aggaggatta caggtgtatg ccactgtgct   29460
gggctgagac tgcagttttt aatgaatgaa atgccactgt gctgggctga gactgcagtt  29520
tttaatgaat gaaatgcctc tgtgcatgga ttgaagccag cttttatggc aaacattaac  29580
agtatggttt ggttccccat ctctgtgccc cttgagttat aacttaaatt gttctgattg  29640
tagtattaac tgtgattagg tgttgatgaa agagatatgg agttctaatt aagtaaaatg  29700
aagatctcaa ataaaattga agtagaatga aacgctatat gtaaatacaa ttctgctaaa  29760
caaatattta actgtggata ggcacagtga ctttataatg cagatagtca ttttcatata  29820
tatggatata tataaatata cattatattc atatatatgg atatatataa atatacattg  29880
tattcatata tatggatata tataaatata cgttatattc atatatatgg atatatataa  29940
atatacgtta tattcatata tatggatata tataatgtaa tacggtaatt gattttaga   30000 ctaaatatat aagttgaaac ataacatttt ctaattttg gaaaattagt ggtgttaatt   30060
```

```
ctggagacta gtaaaaataa atgattagag acgaatacac ttcatggtaa caaacatgct   30120
ggtgatacag ctttaaaact ttatggaaat ttacaacata caaaaataaa gttcactgat   30180
gttttacata ttcatggcct agcatcacca gttgccaata ttttgccatc ttggtattat   30240
ctgtttcact ctgctgcccc tcttctctcc tttctccctc accatgtagc attttaaagc   30300
aaattccaga tatcatttca cccatatgta tttcggtatg tatctctgac acacttgaac   30360
tttcctttca tagtacaact gtcataccat tgtcacaatg aataacatta acattaattc   30420
cttaatggca tctggtagca agaacatgtt cagattagcc tgtctctaaa atgtctttgc   30480
aatttgttcg tttacattag gacccaaata aagtcttcat attgcagttg gaagatacgg   30540
ttctaaatgg tctcttaaat ctccacccct ttcatgccct ttatttgatg aagaaactgt   30600
tatttaacct gtagaatttc ccacattctg tttggctgat tacatctttg tggtttggtt   30660
taacccctgt aatttcctgt aaactgaaca ttcgttctag agggtatttt ttttggtga   30720 gcattgttta taagaggtgc tgtattcttt ctattagtta ccatcatgag gttggttcac   30780
tttcagtatt gctgggattg gtcagtggtt ttagattatg ttggcttgat ctatccttta   30840
taaagttctt atcaactttc acacaaaggt tttcgcagca tctgaggatt gttgactaga   30900
tccattatat aaggattgca aaacggtgat tttggaatta tatcactcct acatttatta   30960
gttgaaattc ttttgtaaag aaaacttta tttcatgtat ttactgtctt taaaatctag   31020
aagtggaggc tataaaaatt taattcctct cccacctcgt tttgccagtt tttataataa   31080
tgagttggtg tcctaggaac ccactaaaac gaccagtaaa tttttcttct ttcttttatt   31140 attttagtg ttagggattt ttatgtatgt gatgtgtttt aatccattgt agttgctgtt   31200
tttcatgttt caattgtctc atctttggcc agttggaacc ccttcagatg ggttcctgtg   31260
ttcttttgaa tattgtccca tcggttttca ataacttact ctctttctgg cacaagggat   31320
atcaggttca ctttgtacat ttcctgctcc gcatctggaa tcagctattt ctttaaggaa   31380
ccctggttgc tgagacatta atgacatcaa atatatatat aaaaagaaaa gaacaagtag   31440
ccctggtttt ctcaagtggg aaatggtttt tagagatcac aatcagggtg ttaagggtgc   31500
tcattgctgc tgggttggtc atgacttcta tggttttta gtatttagat acaggaagta   31560
ctctctccct tccttccctc cctcctctcc ctccctccct cctctttct ctcccttcct   31620 cccttcctcc cttccttcct tccttccttc cttccttcct tccttccttc cttccttcct   31680
cctttttttt ttttttaatt agagtaaatt atggctgggt gaggtggctc actcctgtaa   31740
cctaagcact ctgggaggct gaggtgggcg gatcacttga gcccaggagt tcgagactag   31800
cctgggcaac atggcaaaac cctgtctcta caaaaagctc aaaaaaatta gccaggcatg   31860
gtggtgtgtg cctatagtcc caactacttg ggaagatcac ccgagcctgg aggtcaaggc   31920
tgcagtgagt tgagattgtg ccactgcacc ctagcctggg tgatagagtg agaccctgtc   31980
tcaaaaaaaa agagaagaat aaattttcaa ttcatactga tatttccagt tttcatgaaa   32040
aattacagag gttttgttta acttatttta tgatttattt attttatttta tggtgaaaaa   32100 tatgtctatt tagtgttagc cagctgggct cactttagat gatcccaatt ttgttggcaa   32160
cgtcatcata gtcaggaacc ggtagaacat gggccttctt tccatcaggc ctgatcaggg   32220
tgttgatatt ggccatgtca gtgccacaga cttttttctt agcctgtttg atctggtatt   32280
tgttggcctt gacatccaca gtgagcacaa gaatgttgtt gacttctgt tcttttcatg   32340 gctgactcag tggtcagggg aaacttgata gcatagtggt caagctggtt tctcctggac   32400
```

```
tggaccagtc ttccaaggat atttgggctg cctccagaac agcagcagtg ttttgggctg   32460
tccttaggtg ggtgacgtga agatcttctc tttttttgtgt ggctgtggat acggatacct  32520
ttcagcactg ctgttttggc ctttagagcc tttggtttgg ctttgacgtt gggagagcag   32580
gggcttccct ctttgcctgt gatgccttct tgatgagtac agccatgtaa cttcttttat   32640
agttgtgtct tttttttttt ttgggacgta gtctcgctct gttgtccagg ctggagtgca   32700
gtggcgtgat cttggctcac cgcaacctcc acctcccagg ttcaagcgat tcccctgcct   32760
cagcctcccg agtagctggg attataggca ccctccacca tgcctggcta attttttgtat 32820
ttttagtaga gtcagggttt cactatattg gccaggctga tctcgaactc ctgacctccg   32880
gatccgcctg ccttggcctc ccaaagtgct gggattacag gcgtgagcct ccgtgcctgg   32940
cctttttttt ttttaaattg agatggagtc ttgctttgtc cccccgcagg ctagagtgca   33000
gtggcatgat ctcggctcac tacaacctct gcctcccagg ttcaagcaat tctcctgcct   33060
tagcatccca agtagctggg attacaggca cgtgccacca tgcctggcta attttttgtat 33120
tattattaga gaccaggttt tgccatgttg gccaggccgg tctcgaactc tggacctcaa   33180
gtgatctacc tgcctttagcc tcccaaagtg gtgggattac aggcgtgagc cactatgccc  33240
ggcctatatc attttttatc ttatgctaaa aatgttggtt cctaacaaca ttaacattat   33300
attatacata taacacatat tagctttgag ataacaatac cataatgtag tttgagattc   33360
ctttgtctgt ctatttacat ccttaggctg tattccagta gggatgtaag ctcagaatac   33420
tttttaaatg aaaataaaat tttataaatt ttaataaaaa ataatatttt aaatataaatat 33480
taatatttaa gatacttgaa ataataattc tctgtgtatt tatgtcagca gttgaaaata   33540
gaacatttac ttcagtttgg ttttggtttc taaggagtgc tgttttttcc ttttcaattt   33600
ttttgatgta aaatatttac atggtttcaa aatgttgagc atatttttaa aaagatatgg   33660
ctgggcacgg tggcttgcgc ctgtaacccc agcaatttgg gaggctgagg cgggcggata   33720
acttgaggtc aggagttcaa gaccagcctg gccaacatgg tgaaacccccg tctctactaa  33780
aaatacaaaa aatcagccgg gtgtggtagc aagcgcctgt aatcccagct gctcaggagg   33840
cttgaacccc tgggttcaag cgggagaatt gcttgaaccc ctgggttcaa gcgggagaat   33900
tgcttgaacc cctgggttca agcgggagaa ttgcttgaac ccgggaggcg gaggttgcag   33960
tgagccgaga tcacacctct gcactccagc ctgggtgaca gagtaagact ctgtctcaaa   34020
aaaaaaaaaa aaaaaatgct gctggtttgc atatcattat tctgcccata tcctatcagt   34080
aacgaaagag gtattatttt actgtatgtt tttacttaaa atttaattta tgcttacatt   34140
aatttttaaa ggttcagatt tgaaagtcca gtgtcaattt tccaggtggc caggtggtac   34200
tagatgtcag taaatagttc ttgtttatat attgcgtttt ataattttaa atattttact   34260
gggttttgga catattgtat gtcaatagaa ggcaactgga actctaattt tagaaactaa   34320
gattatgata tttgtagatg atcagttta ctccttgtag tccaccccct ccaattactt    34380
aataactatt ttaagatgtt ttacagtcta atatactgaa atttctgaca taaagtcaga   34440
cttccagatt acattgctta aatttgccaa actaggcatt tttctggtgg aggagaaagg   34500
aatcttttcc taaagtctg gtatatatat attttttgct taatgcctag ttaccatgga    34560
aatagatgtt agaatcagct cttaagtagg taggtagtga caaactggct gtattgctga   34620
attgagttgc tagactgtat ttggcccttt cctgctttca tctttccacc ttctctttca   34680
tcatttttt tttttggttt atgtgctttt tagaatattc tatatagtta aatccaaact    34740
tgacttaacc taggtttgag caacaatttg cttttgctta caatttatac tatctatagg   34800
```

```
tagacatttt acctcatatt tacatatgta tagtataagt agataattgt actgacttgg    34860
cacatcagct gttaatgctt ttaagaaaag gtctggaaag acctgtaaca agttaatagt    34920
gatggtctct agctggtgac agtatagaaa atgtttaatg tctactttgt gaagttacaa    34980
tgtttggttt ttaaaatgag catgtactac ttcattatat aaaatttttt tacttgtaga    35040
agtttgtgtt aatgatcagt atttaaaata tagtaaaaaa taagagagga aaagtggaaa    35100
tcctctagta gcatatattt ttttggcctt aactttgacg tttgtgtgat gttgatcttt    35160
agttactgcg cttcggtact gaggatagca gcacctatgt catagtgttg ctgagatgaa    35220
atgagattac taaagcataa tgcttggcac aaggggagca gttaataaaa taggagctct    35280 ggttttgtg gatcttagat ttgctgccct gtaggttttg ggaaggagta gtctggctct    35340
acaggaatga ggaatgtatt gtggagtctt agaagagcta tctacgtatt catttgaatc    35400
cacaaccttc cctcggagct ttcttcttga ctatgtagtt ctactttagc tttctcttc    35460 tgtcagtata tttctagtca tttccagttt tctgctcagc agagactttg gggtccatgt    35520
tgtacctgtt ctgttactgt tacataaaag tagatctata aatttatctt gttagtaatc    35580
aaaaaagtta aagttcaagt tttatgcata ttctggatga gttttacctt acccaacctt    35640
taatttggtc atgtgattga aaaaagatt ttttagggggt tcctttttcct atcactgtag    35700 atggaaaatt tggaatttt ttttttttt ttgagacaca gtctcaccct gtccctcagg    35760
ctggagtgca gtggcatgat ctcaactcac tgcagcctct gcctcccggg ttcaagcgtt    35820
cctcctgcct cagcctccca agtagctggg attacaggca tgagccacca caactggcta    35880
cttttgttgt attttagta gagatgggggt ttcaccatgt tggacaggct gttcttgaac    35940
acctgacctc aaatgatcca cctgccttgg cctcccaaag tgctgggatt acaggcgtga    36000
gccactgcac ccagccaaaa cttggaattt ctaagagcct ttattaattt gtaaatcagt    36060
aacattggaa ttgaatattt gaaactggaa ctgtccccag aatattgagg atgcaaagtt    36120
tctgtaggca caattcttca caaaggcaga ctcttgggga caatcaggat gattgcaaaa    36180
tcatatgaaa tataatatgt aacgaaatga agaagcaaac aacttacatt ataagttgta    36240
tctgtattat taaagtccaa atatcctagt ttaattttt gaatattcaa acatatggct    36300
gaaaagtttt aaaaaatact tataaaagaa tatagtaaaa accctttcat cctacctttt    36360
acctccaatt gttaaatttc ccttctttct gtacagtcat tgttttgtg tattgtttcc    36420 acacgtagaa aggcaaacac aagtttgccg tcttacttcc ctatctctcc taccctttac    36480
tttcagcttg taaattacac acactgttct gcactttaa attttgtcac ttaacacatc    36540
tgggagatgt ttgtgttatt attacataga gatcccctca tttgtgggtg ttttttttgtt    36600 tgttttgttt ttgttttttt aagacagtct tgctatgtca cccgggctat tttttagtat    36660 ttttttgtatt ttttagtaga gacggggttt ggccacgttg gccaggccag tctcaaattc    36720
ctggcctcaa gtgatctgcc cacctcggcc tcccaaagtg ctggaattaa caggtatgag    36780
ccaccacgcc tagccttgtg tgttcttatt aacaacttt attgaggtat aacttgcaca    36840
ccaaaaaaat taaaccattc taagtgtaaa aatcaaggaa ttttagattc attttttaatt    36900 aaaaatttat tttatttatt tatttattta ttatttttt gagacagagt cttgctctgt    36960
tgcccaggct ggagtgcagt ggtgcgatct cagctcaccg caacctctgc ctcccaagtt    37020
cacgccattc tcctgcctca tccttccgag gtagctggga ctacaggcac ccgccaccat    37080
gcccagctaa tttattttta atttttttta tttttagtag agacggggtt tcaacgtgtt    37140
```

```
agccagggtg gtcttgatct cctgacctgg tgatctgccc acctccgcat cccaaagtgc    37200
tggaattata ggcgtgagcc accacgcctg gcctattttc ttcttttaga aacaaattgt    37260
tactctgtca cacaggcagg agtgcagtag cactatcata gttcagtgtt aacctcaaac    37320
tcctgggctc aagcaatctt ccaacctcag cctcctgaac aggtgggact gcaggtgtgt    37380
gctaccatgc ccagctaatt aaaacaaatt tgtttgtaca gacacggtag cactatgttg    37440
cctaggctgt tcttgaacac ctcctctcaa gagatactgc cacttggcct cctgaagctc    37500
tgggattaca ggcgtaagcc tccacacctg gctgttatgg aattttttgta aatgtctagg    37560 gttgttcacc catcaccaca gtccagttta agaatatttt tgtaatcctt aaaaagttgt    37620
ctccccgtct ctggtctttc atgcccatgt ccagctgcaa acaaccagtt tcctcaattg    37680
tttttgcagt tctgtatagg acagatgtat aagatttacg atgtaacata atttatttag    37740
ccacacccct attttggac atttaggttg ttttgacct tttgctttta caaacaggtc    37800
tgagatgagg taactttgta catatattat ttcatacatc tgtaagagta tctgtaggat    37860
taattcctaa gagtagggtt actgattaaa gcacatgtgc tttttttttt ttttggtga    37920 tggaatctca ttctgtcgtc caggttggcg tcatcttggc tcactgcaac ctctgcctcc    37980
ctggttcaag cagttctcct gcctcagcct ctggagtagc tgggattaca ggcatgcacc    38040
accatgcccc gctaagtttt gtattttttag tggagacagg tgtcaccatg ttggccaagt    38100
tggtcttgaa ctcctgacct caagtgatct gcccggcctg catttttat ttctataatc    38160 gtttcccgtt caggttatac agatttacat tctcagcagc aatatgaagg ctaacatttt    38220
cccataactt acctgccgtg tacattacta gacttctgaa tttctgaatt tttgccaatc    38280
tgatagtgaa aaatggtgtg ggttttttt ttttagagat agagtctcac tatatcgtcc    38340
aggctggagg gagtgtagtg gcatgatagg ggcacactgc aacctctgtc tcccaggttc    38400
aagcagttct tctgcctcag cctcccaagt agttgaaact atggatgcgt gcgaaaaatt    38460
gtgttttgaa ttgttttttat ttagtaggtt ttacatcgaa tttatgaatg agtatgagca    38520
tcttttcaag tgttgagtcc attgtaattc ttttatatg aaatatccttt ttatgtcata    38580 tgcccatttt tctgttgaat ggttggcttt tttttttttt tttgaggcag aatctccttc    38640
ctgtccccca ggctggagtg cagtggtcca ataacggctt actgcagcct tgaacctccc    38700
aggctcaagt gatcctccca cctcaacctc ctgagtacct ggggctacag gcacatgcta    38760
ccatgctggc taattttttaa attttttaat agagataagg cctcactatg ttgtccaggc    38820
tggtctcgaa ctcctgggct caagcacctc acctacctcg gcctcccagt gttgggacta    38880
taggagtgaa ccactttgcc tggcctgaat ggttggtctc taaaaaaaat tactgatttt    38940
agatgttctt tatgtatgag agtcaagctc tttagtgatg tgaattataa ataacttttt    39000
gtagagtttg tcatttatat tttgatatat ttgctttgtg tattttttttg ccattgagca    39060 attttttaat ggttaaattt atcaatattt tatagctccc aaactttgag ttaatttact    39120
gtttgaagta agtcatacat tgaattccct tccaggatca taatttatta tgtcactttg    39180
aatttagctg gactttttggc cagacctact gacttgcatc tgtgatgaat aactttgaat    39240
atatgttatc tcacacatgt gcaagtatag ctattggatg aatttggcca tttattcctg    39300
gggccagggt tgtgtgtttt taattttggt aattattgtt gaataaatgg atctttcaag    39360
actgttaaga tattgcattg ctaataactg gtgcagaaat taatggtgat ttctgttcaa    39420
gatgccagat tgttaaactc ctctaggatt agaaaagttt tggttgaaaa tagaacactt    39480
aactgtaact aagagtcttc ttttttcatt atgtgttggc ctttaaggca ccagaattat    39540
```

```
acttcagaaa ttccttggga gaatttgggt tatgtcttaa aataaaaaat gttcatgttc    39600
tttgtgctcc cttttgatac ctacccagaa gcagcccatg tacaggtgca caaggaagct    39660
ggcatgaata tgtttgtggc tgccctcttt aatagggaaa aacagaaaac cacttaatat    39720
caccagtaga ggacaagcta ataaccatg gcaaattcct acaatggtta tagcacaaaa     39780
ttaattcgac agtttgtgtt tactgatgta gaaagatctc taaaacattt tttgaatgaa    39840
agaaaagttg aaagacagta tattaaatgt agtaccagtt atgtaaaaat agattcacag    39900
aaatgttatt aaatatggat acatgtacgt gtatgtaagt gaaggtctgg aaaaaacctg    39960
gaagaacata tgccaaaatg agaatagtga ttattaatgg gaattgagtg tagtaattta    40020
ggacttactt ttttttttttt gaaatggagt ctcactctgt ttttcaggct ggagtgcagt   40080
ggtgcaatct cagcttactg caatctccgt ctcctgagtt caagcagttc tgcctcagcc    40140
tcctgagtag ctgtgactac aggtgcccac caccacgcct ggctaatttt tatatttctt    40200
taatagagaa ggggtttcgc catgttggcc agcctggtct tgagaaattc ctgacttcag    40260
gtgatccacc cgccttggcc tcccaaagtg ctgggattac aggcatgagc cactgcgccc    40320
agccacatta atgttttatt attttttacaa ggataatatg ctcatagact gtacaactaa   40380
aggccaattt aaaatttatt tggaaaaaat acattgtttt gtacataggt ccctgtaaag    40440
gcagagtaag actggaaaaa taccctaaat aaggagacag tagttatgtc cccgagggat    40500
gtgggaacag agaagataaa aggagacatt tgcttttttgt atacttctgt attttttatag  40560 ttttataaag caaatgaatt catgcattaa tttgtatgct gaagaaagga ctaaattctt    40620
taggaccagg aattcatgta agagtatctc attttgtcaa gcttatttaa cagtacttag    40680
tgaaaatagt agctgccggt tgaattactg ggtagagaat aaaggtgtca acagaaatag    40740
tttactaatt tgctgataat taggcattaa tttgcttgat gtgatgcatg tttattactt     40800
tagggcaagt agaaaaataa aaataagtag attctttctc atataccatc atgaacactg    40860
gtagtttctg gtacattcaa gacagaacac acaatgagac tgttcttgcc ctgtagcctc    40920
acctggaatt tccttttgtc ttctgctttg ttactacaac ctcccctgca gtttgggtgt    40980
ctctctagtt ctctttttctt tgtttagtag tctgggatca gatctgctct tctgaaatag   41040
aagtcagcag tgaggagaaa aaaggtaaaa aaaaaaaatt tatttttttct gagacagagt    41100 cttactctgt cgtccaggct ggagtgcagt ggcacgatct tggctcactc cagcctccgc    41160
ctcttgggtt caagcaattc tcctcccctca gcctcctgag tgtctgggac tacaggcacc   41220
tgccaccacg cccggctaat tttgcatttt tagtagagac agggtttcac cgtgttagcc    41280
aggctggtct ctaactcctg acctcaaatg attcacccac ctcaccctcc caaagtgctg    41340
ggattacagg cgtgagccac agtgcctggc caaaaggtaa aattttttaat cccttttattc    41400 agttagtcac taaatgtgag aatgtctttta cccagttctt ctctctccat cccagcatta    41460
gtgcaagcca ttgtatctca ttctagatta tggtagcaga ttcctaactg atctgtctga    41520
ttcagccttg tatttgtaca ttggtatctg ttttttcacat tgcagccaca gtgatctaag    41580
acatcagata atgtaactct tgctcataaa actttgtagt agttcttctc ctgttgctat    41640
caggccttgc ttctccagaa ctctggctat ggtcattaat aattgcagct ttctatattg    41700
tctactttcc tcatgcacta tagctcttct ccagaatcta tattgttttct catttcaacc   41760 catcagaatt cttttactag attaccagtc atccttcagg tatccttctc tgagatccta   41820
agatagattt acgtccttct tcgtgctcct cttgtgcaga atctgaccat agtagttaac   41880
```

```
ttcatatggt aacttaactg tttaacagat tcctccacta cactccatga aaacaaagac  41940
tgagttttaa atcaagtctc tggttcctaa ccagcacctg atacattata ggctttagtt  42000
taaatgtatg aataagcctg ggtgcgatgg ctcatgcctg taatcccagc actttgggag  42060
gccaaggtgg gaggatcact tgagtccagg agtttgagac cagcctgggt aacatagtga  42120
gaccctgtct ctacaaatta tcaaaaatta gctgggcatt gtggtacatg cctgtagttc  42180
tagctacttg ggaggctgaa acaggctaat tgcttgagcc caggaagtca aggctgcagt  42240
gagccacaga gctcagcttg aataacagag ggagaccctt tctcaaaaca aaacaaaaca  42300
aaacccaaaa gccagaaaca aatgtgtgaa tgagcgttaa ctcagtcatt ttttctctca  42360
tatcatttt ttctcttgtt ctttccctac ctagtaatta ataggttgtg gctcagtttg  42420
aaaaacactt gtgtaaggaa tcctgattta ctagttagaa ctctcagaat gagaactctc  42480
tgccagatct ctaaatattt agtaatttt tattctgttg ttaatggtat tttaaaaatt  42540
caatttctga ttgttgctaa tgtataggaa tcctattgac ttctctatat tgtgtatcct  42600
gtgatcttgc taaaaccacc tattggttac agcaggattt ttgtagattc ctttggattt  42660
ccttggtagc ggatcatgtt gtcagtaaag gcagctacta ttcttcatgt ccaattcaaa  42720
tatcttttct ttcttgattg cattggctct ccaaaacaat gcagaataga agtggtgagg  42780
tggatatccc tgtcttgttc ttaattgtag ggaaaagcat tcagtctttc accgttaagt  42840
ataatgttag ttgcagattt ttcatggatg cctttgtcc gattgaggaa gtttcattct  42900
gttcctagtt tgctgagaga ttacatcagg agtggcttat ggattttgta ttaataaaat  42960
gcattttctg gatatattga ggtaatctgt tttaaagtt tgttgatacg ttaattacac  43020
tcattgactt ctgaattta gaacaatcct ccattctac aataaatgca cttggtcatg  43080
atatattacc ttttagaaca tattgttgga ttctacatgc tagaattta tttagaattt  43140
ttgggctggg cgtgatggct cacacctcta atcccagcac tttgggttgg cttaagtcca  43200
ggagtctaag actagcctag gcaacatgac aaaaccctgt ctctgcagaa aataaatttt  43260
aaaaaaagtc agctgggttt ggtggtctgc acctgtaggt cccagctact tgggaggctt  43320
gggaggctga ggtgggagga tcacttgact tcaggagttg gaggttgcag tgagccaaga  43380
tggcaccact gaactgcagc ctgggtgata gaacaagacc ctgtctccaa aaaaaaaata  43440
tatatatatt gtttgcattt ttgctcatga gggatattgg tctgtagaga tgtggttttg  43500
ctatgttgcc caggctggtc ttgagctcct ggcctcaagc agtcctctcc tctcagcctc  43560
ccaaagtgtt gggattatag gcatgagcca ccatgtccag cctctagttt tattttctca  43620
taatgtcatt atatatcaga ataatgctgg ctttgtagaa tgagttggga ataattccaa  43680
atttaatt tagagatggt atcttgttat gttgcatagg ctgttctgga actcatgggc  43740
ccaagggatc ctctcacgtt agcttttccaa gtagctggga ttatagccat gagccactgt  43800
gcccagcaat tttatttga aatactaggt cataatcaca ttatggtttt aaagatcact  43860
tgtaatagaa aaagctagtg aagtatatgt aattaaattt ctctgatcaa ttcatcacat  43920
tgcatcatca attttatagg atacttggag agcagataat ttaggccttg aagaattttc  43980
tttcccccag agacggagtc tcgctctgtc gctgaggctg gagtgcagtg cataatctt  44040
ggctcactgc agcatctgcc tcccaggttc aagcgattct tctgcctcag cctcccgaat  44100
agctgagatt acaggtgcct gccaccacgt ccagctaatt tttgtatgtt tagtagagat  44160
ggggtttcac atgttggcca ggctggtgtc gaactccgac cttcagtgat ctgcctgtct  44220
aggccttcca aagtggtggg attacaggcg tgagccactg tgccggcctg gccttgaaga  44280
```

```
attaatgttg atttgtttta aatgtagaat gaggctgggc gtggtggttc agacctgtaa    44340
tcctaacact tgggaggcc gaggcaggcg gatcacttga ggccgggagt tgagaccag     44400 tctggccaac atatcgaaac cccgtctcta ctaaaataaa aaaaaaatta gcagggtgtg    44460
gtggcgcatg tctgtaatcc cagctactcg ggaggctgag gcatgagaat cgcttgaact    44520
gggaggcgga ggttgcagtg agccgcgatt gcaccattgc actccagctg gagcaagact    44580
gtcttggaga gcgagactgt ctcaataaat aagtaaataa aggattggtt tcattttctt    44640
tagggtctaa gttaactttt tcttaaaagt atcagcaaga atcttaaaa ttgactgtct     44700 taagtaaatg ttaaataata gtacttaata ttaataattt tataatttaa taatgaacat    44760
aaagcatttt atttgatttt aacattttct ggttattaaa aaactcatgg tagaaagtat    44820
ggaaaatcca gaaaatcagg taggaaaaag atcactcgta attcagacgt tacagaggta    44880
actactatta acattttagt atatactttc aaatctttac ctgtgtattt cttaaaacat    44940
agtttgtaat catcttttt caacatttta aacattagct tctgaattag taggtaagtt      45000
tatgttggtt acagataggt ttttttaaga gggtgttaag ttgttactac ctgataaggc    45060
agttatggta tgacatctgg atttaagctc ttttcctgc ctctagtgaa ttatgtcctt      45120
aaaatcactt aaagctccac ctctctttgc tcttttatac cagtgggtaa taatactttt    45180
ttatttatct acataattgt ttttgtgatg aaaatgaatg tgtttaaaa gatacataaa     45240 acttcttatt ttgttataaa atgaagtagt atcggccagg tgcggtggct cacgcctgta    45300
atcccagcac tttgggaggc caaggcaggt ggatcacaat aggagtcgag accatcctgg    45360
ctaacacggt gaaaccccgt ctctactaaa aatacaaaaa attagccagg tgtggtggca    45420
ggcgcctgta gtcccaacta ctcgggaggc tgaggcagga gaatggcgtg aacccggtag    45480
gcggaggttg cagtgagccg agatcgtgcc actgcactcc agcctgggtg acagagactc    45540
cgtctcaaaa aaataaataa ataaataaat aaaattaaat agtatgtaat gtaaatatttt   45600 ccatgtctgg ttaaatttgg ttgtcttttaa gtattcctgt tttctctttc tctaatttt   45660 ctgaaaattc agggtacaat aggagttctt aaactttttt gggtctgtcg aaagtacagg    45720
ctttattgtg tagatatatc atctctgaaa attcttgtag ggtcttcaga aatccacaga    45780
aacagtgtta tggtttccag gttaaaattt tccatattta taatagtttt cacccattgt    45840
ccatggcacc ttggtttacc tacttgtgct tccaaaagtt tgacacactc atacaactaa    45900
ttttcgcatt cactaaattt gcattgactg ttatcccaaa gcctaccaaa aagaaggttg    45960
ctttgcgttg attatatcct gtgaagtagc cttgagcagc aaatattact ttttgtaagt    46020
tagagacagc gctgaggaat aaaatcaatg catttctcaa gtagatcttg ggtttctgag    46080
accatgtaaa aactttgaat cctgaggata taattaaaca aaactgtaaa cagttttcat    46140
aagtatcaca gggctaaggg atgagcaagt gatactaggt taaccaggac tccctgaaga    46200
cattgttaga ttatatgctt taggagtgat tgtgttttgt atgattttca attccttcaa    46260
atatgccact atattctagt atttcactgt tttatttca tagcagagtc cccttctgaa     46320
tcatggtgta tattcatgat gtatgttcct aggctagtat tttacccaaa ataggaaagt    46380
tttagagatc attttgtatc tgaaaagtat tcccttattt ataatgttga tatctaatat    46440
aagtaatgtg ataatttctt ttaattttg tatttctgat tttttcagca tttcttattg     46500
gtcttctgaa ttgtataaag aacaggtttt taaaaataca ttcaccagcc tccctaagaa    46560
ttgcatgaga gtacctctta ccactgttaa ataaataact cctgctccct ttgttttttg    46620
```

```
tttttgtttt tgtttttctg aggcaggctg ttggtctgtc actcaggctg gagtgcagag    46680
gcatgataac aactcactgc aggcttgatc tcctgggctc aaatgatcct tctacctcag    46740
cctccaccac gagtagctgg ggccacaggc atgggctacc acgctcagct gttttttga    46800 gacggaatgt cgctctgttg cccaggctgg agtgcagtgg catgatcttg gctcactgca    46860
acctctgcct cttgggttca atcgattctt gtgcctcagc ctcccgtgta gctgggacta    46920
caagcatgca ccaccacgcc cagctgattt ttgcatttttt agtagagaca gggtttcacc    46980
acgttggcca ggctagtctt gaactcctta cctcaggtga gcacccgcc tcagcctccc    47040 aaagtgctga gattacaggt atgagccact gtgcccggcc tttatttttg tttttaacag    47100
aggcagtttc cctatgttgc ccaggctggt tttgaactgg gctcaagtga tccacccgcc    47160
ttggcctccc aaagtgctga gattataggc tgagccatcg cacccaaccc tcctgctcac    47220
tttaaagcat gctgtataga gttgtcctgg tgagaagcca ccttgatggc aagcttgtaa    47280
gctgtagagt tggtgagtgt ttacttagga ctcacatttg aaaccgcttt ttttttttctg    47340 ttatctttta atatgtaaaa taataatcag aagttactca ggactctttt ttttcgttt    47400 ttatacatat gatttaattt ttgaactgag aattagcgct cacccaatat taagaatttc    47460
tttcaaaaaa cgtgctcggg tcaacacaag gcctctctgt acattatcct tccgaaacca    47520
tggtttcttt gcttgcacct ttatccccac tgccttgcca gtccttcccg ccagcaggac    47580
tggaagcctg gcgactccct aggtcacagg gttttccttg ccataaccaa gtgggctctg    47640
cgcgtggctg atggcagccc caccctgcgc ccctgctgtt aggcaccgag caaggagggg    47700
cccctggctg ttcttcgcct gggcactggt gtgctttcgg cgatcctggc cacctgccca    47760
cctgaagctg ccatcttggg ttctggcagg agccgtttgc gtggcgagga gcggagaggc    47820
aggaacccag tgagctgctc aggacctgag ttgtgggaga tcatgactat ttctttgcga    47880
tgcttcccca atattcttta agtcaatttt gtttgtcaaa tagcctgatt ttagtgatcg    47940
tctcttgtta gagcctgccc agtatgtatt ccaccttgtt tgttaacaac ataccaattt    48000
cccttggatt gtcagtgaag gtgtcctgtt ctttactgta caagaactaa gcatgtgatt    48060
caaataaggt tactggatat gttaaaaaga ataagacaat ggaaataaaa taatattaaa    48120
atgttttatt ttattaatgg gtggagtaag agtaatacaa atgttttaga cttgaagtta    48180
ctgtcagtgt ttttatcatt atatgactgt caaagagctc ataatagaat taagagaatg    48240
tgttggatat ttccagcacc agtgttagat ttggtaattc acaaggtgcg ctcacaggac    48300
tcagtgtatt gtattagtca tgtttacggc tgcgatttat tacaagagga taggaagcat    48360
tatcagcaaa aggaaaagat acattgggta aagtctggag gaaaccaggt gcaaatttct    48420
cccggtagag ttacacaaga cacacataat tcccctaacc aagaattgtg acaacatgaa    48480
atgttacaac ccgggaagct ccttaaaact cagcatccag gttttttagt gggagctgtt    48540
cacataggta ctgcatgtct ggcatatatc aaattctaga ctctgataat gaaagcttaa    48600
gccatattgt tttagacaca accacccact cttaccagtt ggtggtagga accctcccta    48660
aatccaggtt cctgtgagtt cttagccaag ggccagcttt gcaagcagcc ctttctaagg    48720
aaagccatct caggtctgct gttaactttt ttctgcatag aagattagct ttttatttac    48780 taattctttta gttgtttgcg ttgattattt tatctcaatt gctgatttct ttgctagagt    48840
cctctcaatt tttaaataat gtattatttt aaattggtct gcctttatgg ccgtattta    48900 ttttgtgtgt atgttacatt gttttcatta tcactatcct gatatctttc aggtcttaa    48960 tgacttctga aatttccaaa atggctttca gattttgatt cctaccagaa tacctcatac    49020
```

```
tacgtggttc aggaaactaa atggagattc tgttagtttc tgagcatatc tattacaaat   49080
atctacttaa gacctagagg aataacctct gggtcagtgt ttctcagtct tgccggggt    49140 gggggtgca tcagagtgtc ctggagggct tgttaagaca caaaatgctg tttccctccc    49200
ggagagtttc taattcggaa tgtctggagc ggtgcctggg aatttgcatt tctaacaaat   49260
ttccaggtgt tggcttggcg ctgtatgcac tttgctgtaa tcccagcact ttgggaggct   49320
gaggtgggtg gaccacttca gcctgggagg tggaggctgc agtgagttag gatttccagc   49380
ctgggtgaca gagtgagtga gaccctgtct caaaaaaaca aattttcaga tgttgctgat   49440
ggtgttggtc ctgggagcat actttgggaa ccacttttct agtttataat acaatccaca   49500
aacttatgta aacaagaaaa atgtaatctg taaaattccc atgtacagga ataccaaata   49560
cagtgtgcca aaagtggtag gacaattgaa gacttcattg tcaaccctgc tgtgttgtgc   49620
agctgccact tttccctcag aatgtgtgtg ttcacaaggt gtgttgcttt tgtagatcaa   49680
cataagaaat acttactagt aaagtttatt tcttatctgt ttttaagata agtaaattaa   49740
cagttcacta ttttttgtgt gtgctcagtt aatcttcctc atatcacctg gaatttatca   49800
tctcccttgg gtaatcacag tctagtagat tctctcttca ccattttctt agggaaaatg   49860
gattggcaag ggaaatgcta gactatttta agggatttat tggcttttct gtcccactgg   49920
gaatgcttat aggaggggat gccatgaaat gttttcatg atctcagtgg ggatcagaaa    49980
attccagcag aacggaggct aggtgggcat ggttaacaca tttaggtagg agggcatgtt   50040
tgataatgaa attctgaaaa tgtttgcatg tgcattgaga tccctaggta gataagtaac   50100
ctagtaactt atttgattgg tatagttttt taaaactcca ggtctgatga taatctaata   50160
taaactattc tattgaatgc tttgaaattg agtctgttta gttctgagag gccattgaaa   50220
gaaggcaaga ccgagtatcc tggaaggcct gttacatacc cctgtatgta gcatggccct   50280
ttctacttgc ctttgctaat gatactttgt gtgtgtacat ttacttaaat agctgtgcag   50340
tgggataggg gaataatact caggttttaa aatctgattt tggctctgac ttaaccatta   50400
attactggtg actcaaaaga ataccactgt gacctaccag taagagtagg tgcatatgga   50460
gagtcaggaa atagcatttt gatagagttt tgacttaaat atgtttcctt acactcatct   50520
tgaaattgtt tcttatggtc ctaagtgaat agttggaata gatatcctca gcaactaata   50580
gaatctccat ttagtgtgag gtagtatgga aggaatggcc aagaaaagcc atttagtgcc   50640
accattaaaa tcctgaaaga tgctgggcaa ggtcatcagg agaaaaatgt aaaacaaaac   50700
caatgaaaca cacacacaca cacacacaca cacacacaca cacacacaca caatataagg   50760
cattaaaaat ggtctcattt acattattat tattattttt tttttttttt gagacgagt    50820 ctcgctgtcg cccaggctgg agtgcagtgg cgggatctcg gctcactgca agctccgcct   50880
cccgggttca cgccattctc ctgcctcagc ctcccgagta gctgggatta caggcgtgcg   50940
ccaccatgcc aggctaattt tgtatttta gtagagaccg ggtttcacta tgttggtcag    51000
gctggtcttg aacttctgac ctcaggtgat ctacccttct cagcctccca tagtgctggg   51060
attacactgc acccagcctc taaaatcttt tttaaatttt agagagagag tctctctctg   51120
ccacccaaac tgaagtgcag tggcacgatc atgtcttgtt gcacctttgg cctcctgagc   51180
tcaagtgatc ttctcacctc agcccccctga atggttggga ccataggcgt gtgccactga   51240
gcccagataa ttttttttatt ttttatagag ccatgtcttc ctttgttgct cagggttttt   51300
cttggcaaaa gcatattgcc agaacatatc ttttttttttt ttttcggag atggtgtttt   51360
```

```
gctccatcac ctaggcttga ttgcagtgca caatctcgac tcactgcaat ctccacctcc    51420
cgggttcaag cgattctcct gcctcagcct cccgagtagc tgggattaca ggcacccgct    51480
accactccca gctaatttt tgtattttta gtagagatga ggtttcacca tgttggccag     51540
gctggtctca aactcctgac ttcaggtgat ccccctgct tcggcctccc aaagtgctgg     51600
gattataggc atgagccacc gcgcctggcc aacatctctt ttttaagaga ataacttgt     51660 aatttcttc tttcctttt taaagagaca gggtcttgct gtgtctccca gactggagtg     51720
cagtggtgtg atcatagctc aatacagcct tgaacttctg ggctcaagca atcctactgc   51780
ctcagcctca caagtagcta ggactacaga tgtgcaccac catgacaatt agtattcttg   51840 ctttatttt tcttttatt tgataagaag tttataactt tgaaaaatat gagtagaaat     51900
gtaagagtct gttgaagatg taaactattg tttttaaaa agtgtaaata tattttaat     51960 aagattgtag ggccagacgc atctggtaag ggcttaaaag ctgattttta aaattgata    52020 gccagaggtt atatcttact aatgtttgct aatgctacta attagcgtta gtttgctaat   52080
gctactaatg ttataataat gatctgatga cctcaaatag cttttcaaaa aaaaaatctt   52140 tttttttt ttttgcttc gtatgttcac atttcattat ttcttactgg tcaagatttt      52200 ttttctttt ttgaaagtct ctgtctgtca cctaggctgg agtgcaatgg tgtgatcaca    52260
gcttgctgca gcctctactc cccaggctca agtgatcctt ctgcctcagc ccctcacta    52320 gctaggagcc acaggtgtgt gctaccacgc ctggctaagt ttttgatatt tgtagagat    52380 gaggttttgc cgtgttgtcc cggctggtct tgaactcctg ggctcaagca gtcctcccac   52440
cttggccttc cagcgtgttg ggattacagg cgtgagccac tgtgcccagc ccaggatttt   52500 tgtatattt gacagtttag cttaaaaatg taaactggaa ttggtttaat atttgtctag    52560
atgtgatcta agttctgaat atcccagggc attgtgggtg ctcaattaat gtttgtggaa   52620
ttgtaactgt atttgatatt atttctattt tgataatagg catctgatgg gtttaattaa   52680
agctattttg gttatgggta atagaaccca tttcaggtga tgaaaagcag aaaagagaat   52740
ctattataag ggtacagagc atctcatggt acccaaagag gggaactcca gtttggcttg   52800
aggaggcagt tggaaagcta gcaggaacta aggctagcta ttctctcagt cactcagaga   52860
acccacagtt tcttatgtgc acttttttccc cctctgcatc tgtttatttt cttacttcct  52920
ctcagcagac tggttttctc tacttctccc tgtgcatgcc agaaaatggc taccataggc   52980
tgcatcacat cctttctcta ccggctaatt ggttaaccta gctttaactt catagcagag   53040
taaaaccgat cggcccagtt tggatcaggt ggctagcagt ctaatgaatt acttgttggc   53100
aaagcatatt gccagaacat atctctttgt taagagaaat aacttgtaat tgatacttgt   53160
catgttagtg acttagtctt tgtaaagctg tgtgggcttc tttgtcgtaa aaatttggtc   53220
atctgtaaga tagtttgtcc ttatttact tattaaaata tgatttgttg ggtccctcat    53280
atgtgcatag tcattgaata ggcagagcgg tctgcgcgcg tgcacacaca cacacacaca   53340
cacacacaca caaaattagg cctagtgttg gattttccta ctcttaccat tgtgcctgtt   53400
tttagtatgc atttgattta gcacatgata atcataattc aaagataagt ctgcagcaga   53460
cttaacattt atatataaag tgttttttaag gcagaaggta ttatttaccc tcttttttaga 53520 agtggagaaa ctgagaatca gggagtaaaa atcagtcaac taataggttg cagatcgtag   53580
ccatagctga gttgagatat tctttacaca aattatggcc ttattcttct atatcctttt   53640
acctctatgt gagtgtatat caaactggac ttctccgaaa ttctcttttgg cctagtttgc  53700 aagttctctg tgtagaataa aaaattacat ttttaattga ttattttat caagtaatac    53760
```

```
atgcaaatga cactaaattc aaaaggtata tactttatta ttgttttatc ttgagtttct  53820
tccatttcat ttcatacaga gagctaaaaa gatttaatat aaacattttc tgggtcattt  53880
gtacatctgg atagcagaga actattaggt tggtgcaaaa gtaattgtgg ttttgcaatt  53940
acttttattt ttatttattt atttattatt tttgagtcgg agtctcactg tcacccaggc  54000
tggagtgcag tggtgtaatc tcagctcact gcaacctcca cctcccgggc tcaagtgatt  54060
ctctctgcct caacctccca gtagcctcc caagccacca ccacgcccag ctaatttttt  54120 tttttttgtat tttagtagct tttttgtatt tcaccatgtt gcccagagtg gtcttgaact  54180
cttgagctca ggtgatccac ctgccttggc ctcccaaagt gctgggatta caggtgtgag  54240
ccactgtgcc tggcatgcaa ttacttttaa tggcaaagac cacaattagt tttgcaccaa  54300
actagtataa tttcagtttc tgcaattact tttttatgttt tacaaccagc gttcatagtg  54360
agtagtatta cttcgcttgt tgcaggtttg attataaaac aacggagatg gagttcacag  54420
taagtgatat gttcctacat catgaggcaa cattgatctc tccagcaaag gttttgtact  54480
agtttacata gggaaaagtg gtgggagaat tgattcgtta cactgtgctc aatattaaaa  54540
gcatgctagt ccaaagtagt ctgtgccata tttgtgtttt gagtgtgtag ttgtagcaga  54600
atatcatcca tcatattgaa ttaatgttct tacttgaatt tcattgatttt tgttggtttg  54660 tggaatttag tttgcagatt tggttttata cttgtacagt tccgtaagaa taaataattc  54720
ttagctacta tatgactaca ttttatcagg tacaagtata cattttctac attttaacat  54780
ctctgaaatc aggatgcatt tagcagtcaa ttgatggtat atcgtagttt aattggcagc  54840
ttttttcttt tttagtggta ggtgtggttt acaattagtg acttaaatta gatgaaatat  54900
ggtaacttta tgtttgtatg aatttcagta acataaaaat aaaccatcat ctctgtaaag  54960
gagagataat ttactttttt taagtttaag aacagctgtg taggctgagt gcggtggctc  55020
atgcttgtag tcctagcact tgggaggcc aaggctggcg gatcatctga ggtcaggagt  55080
tcgagaccag cctggccaac atggtgaaaa ctcgtctcta taaaaataca cacacatgaa  55140
attagctggg tggggtggtg cacgcctgta gtcccagcta cttggaaggc tgaggcagga  55200
gaatcacttg aacctgggag gcagaggttg cagtgagcca agattgcgcc actgcactct  55260
agcctgtaaa tataactgcc aggaacttga gatttcagaa aacatttctc cagagtatct  55320
ggaaaatcac ctggcttacc caaacaaaat tgccacttgt ggatatttgc taccaatgcc  55380
cctatcattc ttctctgtag tcctgtactc ataagcttag ctgcttagct gctcatacct  55440
attcttgaac tgcttctgtc actaatttct acgtgatctg attgttaagt acaaaatctt  55500
ctttaaaaag aatggtaata ataaattaat atagacattt atttatattg agtgcttatt  55560
acatgtgatt ttatgtgtaa taggccacat tggtattgta tgtatttaat atgtaattta  55620
tatttaatta taatatgtaa taaatgtata atataaaagt gaacatatgt tttattagta  55680
tgataaacta cactttacaa atgtgaagct atgctcagat aagttaaata attttttccca  55740 aggatgatgg atctagtaag ttatgaacct aaagtttgat ctcagatatt gattccatag  55800
ctcatgcttt ttcacctgtt tatataagac gcttctgatt ataaggtatt tttgaaatat  55860
aaataatatt caacttaaga ggaatctcat ttagcagggc ttaactaatg tctaatctttt  55920 tttgtgttaa caattatctc atgaatttct tctatatgta ggtgctattc taggaccagg  55980
gcattcatag gtgaataaga cactatttct atcttaagta gctcagtcta gaggacagat  56040
aggaatcatt aaaatatggt ataaaatggt cacttttgca aaatgttggt atatttggga  56100
```

```
aaaggaaagt cagtatatag tgttacatca atgagtattt agcataagtt accaaagggc    56160
ttactacagt aatattctga atctagaatg aattttgtga cttagtgttt aatacatgtt    56220
gtgtgggtcc gtttcttttg gtcactagac aagtaattga taggttttca agtgattaaa    56280
gattgatgtt tcttgttgat gacgtctttc aaaatcatat tcttgaggat atgaaacacg    56340
attaaaaact tggttggtgg ggattattat tattatttat tattattatt acttttttgag   56400 atggagtctc gctctgttgc ccaggttgga gtgcagtggc gtgatctcgg ctcactgcaa    56460
cctccacctc ctgggtttaa gtgattctcg tgactcaacc cgtgagtagc tggcattaca    56520
ggtgcctgcc accatggcca gctaatttt tttatttta ttagagacag ggtttcacta     56580
tgttggtcag gctggtctca aactccttac ctcaggtgat ctgcccacct tggcctccca    56640
aagtgttggg attacaggtg tgagccaccg tgcctggctg gattattatt attatttatt    56700 ttatttatt tttttgaaac agagtttcac ttttgttgcc caggctggag tgcagtggtg    56760
caaactcggc tcactgcaat ctccgcctcc cgagtccaag tgatactcct gcctcagcct    56820
cccaagtagc tgggattaca ggtgcctacc accatgcctg gctaattttt gtattttag    56880 tagagactgg gtttcaccat gttggccagg ctggactcga actcctgact gcagatgatc    56940
cgcctgtctc agcctcccaa agtgttgtga ttacaggtgt gagccatggc atccgaccta    57000
tcattttttt agcttggtca tccaggctgg agtgcagtga tatagtcact gcggccacaa    57060
cctcctgggc tcaagcagtt ctcccacctc agcctcctta gtagctggga ccataagtgt    57120
tcaccacctc ttctggctta ttttttcaaaa ttatttgtag agatgaagtc tcgctatgtt    57180
gcccaggctc gtctcaaact cctgggctca agtgatcctc ctgccttggt ctcccgaagt    57240
gctgggatta caggactggc ccagtaggga ttttaaggat tttttttttt aaatcaaact    57300
cttttaaatg ttctccagat gctgtctta gtgacttgtt atactaaaaa atgttctact    57360
tattgccttc taatccatgc cagtagttat tactaacatg cccagataca ttaaaccata    57420
acaatgccag tttctgtttc tgtttgtatt ctgaattttg aactgcctga atcctccact    57480
aggctcctct aatttccaga tcatgaaagt ttatgttctg agagtgctgt tactccaaag    57540
aagattcatt tgcatttgaa tatgattgtg acctcactag caagatgaca aataacctct    57600
tctcaaggca gagtagattg gctgtgttac atgagaaagc tcctttgctt ttttgatact    57660
tagaacagtg ccttaagtat agttggcttt taataatgtc tctcccaatt tctctcttgc    57720
ctgtttgccg aggcagaaaa ttctagttag aatatttctt tggagttact taaatttcca    57780
ggaatatgca gatactcttc tgttaatatt tgtgactatg cagatatccc tctggtttat    57840
gagatgtgga tctaaaattt acttataacc taaagtagct taggttttgt ctcctaaagt    57900
agcttaaatt ttaagaagat acacagtggg gccatgtaaa aaaccaaaaa taaacttaa     57960 aaaattgtaa gaagaatatt aagaaatata gataacatcc aaagattttc gtgttttggg    58020 aagggggttga gttttttttgt tttgttttgt ttttgttttt tttgagacgg agtctctctc    58080
tgtcgcccgg gctggagtcc agtggcatga tctcggctca ctgcaagcac cacctcctgg    58140
gttcacacca ttctcctgcc tcagcctcct gagtggctgg gactacaggc gcctgtcatg    58200
acgcccggct aattttttgt atgtttagta gagacggggt ttcaccgtgt tagccaagat    58260
ggtctcgatc tcctgacctt gtgatctgtc cgcctcggcc tcccaaaatg cttggattac    58320
aggcgtgagg caccgcgccc ggctggcgtt gagtttttaaa atatgcagta actcttacaa    58380
tccagcaaaa aaaacagaca aacaaaaaac aaaaacaaaa atgagcaatt cagaaagatg    58440
ggtaaataat ataaatagat aattaataga aaaatatgca aatgcccaat aaatatatat    58500
```

```
tactttacaa aataatttat tttcaaataa ttccaaattt gctgtataaa tagttcatgt    58560
aatctccttc accagactgg ccagttgtta acattcgatg tcatttgctc tatatctaat    58620
ttatcttttt ctctgtgtgt gtgtatacac agagagagat atatacacag atttgtatgt    58680
gtgtgtatat atatgtgtgt atatatacac atatatattg tatacatata tgtgtacata    58740
tgtatgtact cattatcatt acgttcaaac tttttaagag caagcttaaa acacaatgtt    58800
ctgtcaccca ttgtactcca gtgtgtaatt cctgataaat agaacagaat aacttcaact    58860
tcggtctgtc tactttttct catttccagt tactcttggc agatatacca cagaaagttg    58920
ctcttttgat actacagtgc aaaacgttgc acaattacac cactaaaaat aattcagtag    58980
tattcaaaga tgatgtgaat attctgttca tcaaaccacc tgtcagctta gcatcttttg    59040
atagctctct gaatcagcca cctttatgat ggttgccaaa cgctgattct ctgtcagttc    59100
tgttacagtt attaacattt tagtataagg aaaagcttta tcttttctac attttaaaac    59160
attcattcat tcattcttgt caatatggac tcacggattt cattttttact gaatgcattg    59220 taatttgtta ccaactttttt aaagtgagat ataattaatt tactgtggaa tacacagatc    59280
ttaagttgat cagtttgaca tacatatata tccctaagga gataatagca caaataatat    59340
ttattttaat gctcaaactt tcccccattt gaccagtaag aggaaaaccc cttcaagatg    59400
cttcctgtgt ctgtttgaaa tgtccctatc attaatcgca ccatttcttt actttctgac    59460
acaagatgtt tcagattctt cttgtgcttt tctctgtcca accttgaaat caaccatttt    59520
tctaaggatc ctaattcctt ataatggaga gagttattta gaaatcaaga cgtgggccga    59580
ggcgggtgga tcacgaagtc gggagtttga gaccagcctg accaacatgg tgaaatcccg    59640
tctctactaa ttagctggac atggtggcga gcgcctgtaa tcccagctac ttgggaggct    59700
ggggcaggag aattgcttga acctgggagg cagaggttac agtgagccga tatcacacca    59760
ttgcactcca gcctgggcaa cagagcaaga ctccatctca attaaaaata aataaataaa    59820
tcaagatgta ggctattgct gtttgttgtt gttgttactg ggctgtctttt tggttgctct    59880 tagtactttc tttttggaca gagctaggaa aatataggga cacacacgca cacctagaag    59940
tacttgttta ttttttctgtg tgtgtgtgtg tgtgtatgta tatatacaca tatatatata    60000
ttatacaatc atgaattcaa accaaatttc caattccagt ccaatattta gacttctctg    60060
tagtctgctc ccttccttcc atttttaactt cttttggagtg aaaaacatgg cccccactat    60120
attcagtgta tttacttatt tgattagtcc atttacttat ttggtccggg taatggatct    60180
tccagccttg cagcttatct cctctgtccc tattcagctc tcatccatgt cctccgccac    60240
aggactgcac ctccatgtgg ttcccccagg cctcctcttc actgccttgt atattcagct    60300
tctgtccttg tgcctattca acccttaccc cttcacaaat ccatgtcctt agtgccacat    60360
gaaaaaggag agaagaaatg gccccagaga atattttgaa gttatattgc atggttttct    60420
tttcttttct tttctttttt ttttgagac gtagtctcac gtcactcagg ttggagtgca    60480
gtgactcgat ctcggctcac tgcaactccg cctcccaggt tcatgccatt ctcctgcctc    60540
agcctcccga gtagctgggc ctacaggtgc ccaccaccat gcccggctac ttttttgtat    60600
ttttagtaga cgggggttt caccttgtta gccacaggc acccgccacc acacccggct    60660
aattttttat attttagta gagacggggt ttcaccgggt tagccaggat ggtctccatc    60720
tcctgacctc gtgatccacc cgcctcggcc tcccagagtg ctgggattac aggcgtgagc    60780
caccacacct ggccatggtt ttcttcattt cctcgatgta ttcatttttt ttatattccc    60840
```

```
tcccaccaaa ttgtgcattt taagcttggt ttttaaatgg tacactgttt ggtatataaa   60900
tgcaagtata ttttgttcat tcatcttttg gaattatctc cattatttta atagttcatt   60960
gggattgcta tatataaaat aggctgtttt catagattta ttgtcacgtg gtttgtgttt   61020
aagtacattt attaatgatg gttttttgtt ttgttttgtt ttgtttttg  acagagcctt   61080
gctctgtcaa cccggctgga gtgccgtgtt gcagtcatgg ctcactgcag cctccatttc   61140
ctgagctcta gcgatcctcc cgcctcagcc tccttagtag ttgggaccat acgtgcatgc   61200
cactatgcct ggctaatttt tgtatttctg gtagagacgg ggtttcaccc tgttacccaa   61260
gctggtcttg aactcctgag ctcaaacaat ctacacacct cgggctccca aagtgctggg   61320
attgtaggtg tgagccattg cacccagcct actgatggtt tttatgatca aatttaatac   61380
tcttgttttc tgattcttct ggctacattg gcactgtaac caatttgaat ccctcacttt   61440
ttaaaataaa ctacctcaat aaaatgtcat ctagcatgtt ttgctttta  aaaccatct   61500
cgaataattg agtatttcct agtcagtgtc tgtgttagcc agccatttga agatttgatt   61560
taactattgt ctttctaaaa cttaatttat gtatttgatg tgctgcagcc cagagacaca   61620
ttagagatta ctgttgattc atttgtgcac ttctgtgctt ccttggcatt ttggcatctt   61680
gaaggattat tatccactaa tagctaattt taaaattgct tatgctttt  agtgttccca   61740
tggaattcag tgtttttag  gtgccactta ggacatttcg tagactggct aggaaaataa   61800
ttatttaagc aatgctggaa aactgtgagg tagctgttgc cttgacaacc agaaaactgt   61860
tctgtttgct caacaaaggg atggtaattt agtagtttaa tttcctttt  ggcatggagg   61920
tgctacataa aaacatctta ttttagcctc tgagatgatc catactactg atcagaatta   61980
gagaagcaga gcaaaagaa  aaggcaagag tttttttttc tggctacgta tagatagaca   62040
tgcatattta tcagggttgg tgttggtcaa aagaatctta gttaacctgc tgacataatc   62100
ttttttatgt ctctaaattg gaccaaagta aattaacctc aaaatactgg tgcaatcttg   62160
gtacactaag gggtcgtgat acacttttat tatggagcat ccccacaaag atttaagatt   62220
ctcttgccgc tggaattcaa catgattact tcatgtctgg attgaataag ggagaaaata   62280
ttttaaagga accctcttc  cccacgtata tacacaatta cattggcatc tgctctattt   62340
atgtgggaat ttttttatg acttaaccca tttgtatata gacttaaaca ttttttttta   62400
aaaacaatt  gcctcccagg ttgtaaagta aaaataatag cctttatttg gcaatgtgtg   62460
ctgggccctc ttctaagcat tttgtgtgca ccgtcttact cctcatcctt gtgacagaac   62520
tgttattgta tgctgaggca cttagctaag tggcttagcc caaggtcacc tcactactaa   62580
gggatagatt tgaagctagg catctagttt aggaacatat accctttttt ttcttttctt   62640
ttttttttga gacaaggtct cagtgtcgcc caggttagag tgcggtggcg cgatctctgc   62700
tcactgcaac ctcagtctct caggctgaag tggtcctccc accttagcct ccctcatagc   62760
caggactaca agcaggtgcc accatgcttg gctaatttt  tgtattttag tagaaacagg   62820
gttttgccat gttgcccagt ctggttttga actcctgggc tcaagcagtc cgcccactta   62880
ggcttcctaa agtgctggga ttacaggtgt gagccactgt gcttggcttg gaacctata   62940
ctcttaatta ctgtattata ctgacttttt ttttttttg  aaatggagtc tcacagtgtc   63000
gcctgggctg gagtgcaatg gcacaatctt gactcactgc aacctctacc tcccaggttc   63060
aagtgattct cctgctttag cctcccgagt agctgggatt acaggcgccc gccaccacac   63120
ctggctaatg ttttgtattt ttagtagaga ggggttttc  accatgttgg ccaggctggt   63180
ctcgaatgcc tgacctcgtg atccacctgc ctcagcctcc caaagtgctg ggattattat   63240
```

```
aggcatgagc caccgtgccc agccgaaaac tttttttttt ttttgagacg aagtttcact   63300
cttgttgccc aggctggagt gcaacggcat gatctcggct cactgcaacc tccgcctcct   63360
gagatcaagc gattcttctg cctcagcctc ccgtgtagct gggattacag gcgcccgcca   63420
ccatgcctgg ctaattttt atatttaag tagagatggg gtttcaccat gttgaccagg    63480
cttgtctcga actcctgacc ttcaggtaat ccacccgcct tggcctccca aagtgctggg   63540
attacaggca tgagccacct tgcccagcca aaatgtggtt ttgcccctcg aatattaaga   63600
agaaataagg aagggaacca aatctgaatt actattgata aaatgacttg tttgtccaca   63660
tcaagtgttt cataatatta attataactt cctagctgac tacctcagac atcacaatgg   63720
agtgctttct aatattgact ctgtttttt gatgtggcag ctgaagctta gagaggtgag    63780
aggttcagta gcctacaaaa actcatctag ttggtgtaag gagtagagct tggattagga   63840
ccttgcctct ctgctttcaa agcctgtgct attaatcagt ctgctctatt acctcatgtt   63900
aaagtaatga tagagtgata ccttatgccc agctaaaatt acatactcaa atctgaccac   63960
ctcagttatg gatttgattt gggtttctgt gtaaagtctc attcatattt tggttggcat   64020
tgaaaaatag tttgacagtt tcattctaga tgattatata tgtctcaaaa cttgccgttc   64080
tgaccacctt tgtaatgcca gtgctttgat ataggcttgc taaacaatta tgtgtaagat   64140
tcaaattatt gtgctgaatg agaatttagg aacagaaaag taacttacct gagataatgt   64200
ataataaata gaggtggcag cagtaagatc agaacacaga tcactgcttt ttctgtgctc   64260
tttctaacga attaacactg ctctgatgat gtgtttcagt tttagcagct tttattagac   64320
tttggtttcc ttctgcaagt ctttttttt tgagatggag tctcgctctg tcacccaggc    64380
tggagtgcag tggcacgatc ttggctcact gcaagcccg cctcccaggt tcacgccatt    64440
ctcctgcctc agcctcctga gtagctagga ctacaggtgt gcgccaccac gcccagctat   64500 tttttgtat tttttttt tagtagagac ggggtttcac cgtgttagcc aggatggttt      64560
tgatctcctg acctcgtgat ccgcccgcct cagcctccca aagtggtggg attacaggtg   64620
tgagtcccgc gcccagccct ccttctgcaa gtctttctaa aggcatttc tttatatgcc    64680 ttgtaattcc ttttcctgtg ttctagcatg aaggaaagaa aatattgccc ttcaaaagaa   64740
tagtttgccc cacaataatt tgaagtaata aataccttc tcccgtcaac acggattttt    64800
atattgttga agatgtggga tgggcttaat ttggggcgg agggagtccc ctttctcaaa    64860
ttcagcttta ataaatatgc ccaataagca aatctgcagt ttgctgtagt tgaaatgttg   64920
ctagtgtctg tgaatgttaa tgaaaagaat acgcaaatgg gtttctgaat actaatagtc   64980
taaagatgtt agtattctat accctatttt tgttaagaat tatctattaa aaatttaaaa   65040
gtgtatcaat tcctaaattt ttatatgttc ctcagtaggt acaaatatgc aacttttagt   65100
tgatttattg ttctcttcta tgtttcataa tttagttgc ctcatcagtt ttaatttatt    65160
tttaactata ctgtttgtct ctgaaaataa aatttactg gctagtatgg cagaatgtgt    65220
taatagagga ggttgcaaat tgtggaaagt tatgagcctg tggtcatgaa gactgccctg   65280
ccatttgggt tttatagca gtaatacca gtaccaattg aaccacaaag tgaactgaaa    65340
tttccttaaa ttgtttctct ctctataaaa catttaaaaa aaatttaatt gatgagtaaa   65400
gcttgaatat attcagtatg tgcaacatga tgaattgatg tacattttat gattaccaca   65460
gttaaattaa caaacacatt cattatcact tgtgctgtac attatattcc catccttatg   65520
ataaaaattt tttttttaatt aattgagata ggatcttgct gtgttgcttg ggctgatctt   65580
```

```
gaactcctga gctcaagcag tcctgcttcg gcctcccaaa ttgctgggat tacaggtgtg    65640
agccacaatg cgtggccatt tttatgattt tggagcgaag tggtgtgagt ccctttttcat   65700 attattgctt aaataaagcc actagtatgc ctggaatgta accataattt tggccaggga    65760
aaatgatatt ttaagagacc taaggcaggt aggtaaagta gaaatgcatt tattcactag    65820
gtacaacagc aatgtaaagt tatcaagttg tagttaataa tataaaaaaa ttagaaagta    65880
ttagtgcaga aatgattatc tttctgtaag ggtatattcc cattatggta taaatgaact    65940
gatgaatagg cattttccta agttgatttt aaaaattgta taactgatat gttttgagtt    66000 tacttttat  gaaatacatg gaatgtgaag caggtggcca ttatggaggt ctgatataat    66060
tgtgggcact cctgttatag cactagaata ttgttttttt ccctttttct ttgggaaata    66120
gattactctg tatgatagct acaactttta ggggagaatt tattttaaaa tctaaatgaa    66180
attattcttt cattatttat tactcgtaac agcatttctc actttatatt ctatgggatt    66240
tctgtaggat gttaatagat gtcaatgaaa agaaagggt tctttggaca aatagattgg     66300
gaaatgttga gttaaaatgt aatcattttc tctattatag ggtttctcag atcttttagc    66360 ttacattttat gaatctccaa agttgaggca gagaagtaat tcattcaata tagtgaattt   66420
cccccaactc ctgcctcctt tccttttggt ggaacgtcct gggatgttag tacttttat    66480 aaagcacttt ggaaaaagct tacttccatg attttccttt ggctatggaa ttactataag    66540
cagaagaact ccttagaaat aaaaatgtag aaatgtacct gaatgtaaaa cgtaagagca    66600
gctattaaaa actaaatcac aactgaggaa acataaatat tagttaaggt agaagagtaa    66660
atatccagcg aatccctcct attaaagcat ttaagatatt ttggcttcaa agttttgaga    66720 cttttccagat gactttcttc atatagtttt cactagtagt ttaaatatac taacttttct    66780
cccttgtatg ctatactaca ttcttttttg tttgcttttt tgagacaggg tcttactctg    66840
tggcccaggc tagagttcag tggcacgatc acttttcact cgagtctcga cctcttgggc    66900
tcaagcactc ctcccacttc agtctcccaa gtagctagga gtacaggcgc atggcaccat    66960
agccagccag ttttttatttt tttattttgt agagttgagt tttccctatg ttgcttgggg   67020
tggtctcaaa ctcctgggct caagtgatcc tccagccttg gccttccaaa gttctgggat    67080
tataggcagg aaccaccaca ccaggcacta cactaaacta ccttagactt ttctagatag    67140
agatataaca gagctattct gaatctgggt gactgccaag atacagccta aatattagaa    67200
gatttccccc ccaccccaga atttgagctt taaagatctg ccttctggcc aacggaccct    67260
tttcttgtaa gtggtcatag aataaataaa tatttgaatg aatgagtgac tagagggta    67320 tacttgtgag tgagctaatt catatcatgg accatatgta tttaatggaa ataagatacc    67380
tttatatttt atgtgatgta catttaaata gtctttatga taaacatttt acttgttttt    67440
taatttatag tattttatag attggtcttg ttaacataca tttcatattt ataactgttg    67500
tagcttaaca agattaggct cactattctg aggtctgatt atgggaaaga attagagagt    67560
ttaaatctaa ttatatttct ttgcattttt aggcccttga tgagcctccc tatttgacag    67620
tgggcactga tgtgagtgct aaatacagag gagccttttg tgaagccaag atcaagacag    67680
caaaaagact tgtcaaagtc aaggtacagt atttatagat ttcataaatt gtatgttcag    67740
catttgatat gtaaacttttt atttggtgag tgtatttaag attttttctgc aaaataagtt   67800 tctaggagtg aaggttgtaa aaataccctca aaacaaagca ttttttgtta ttttaaaagt    67860
attataattg gaaagaaatt agattatcac agttggtatt ttgaatgcca tttcactata    67920
gacgtcttat tgtttgtata gtgttttaga gctggaaagg aagttagaag tcatctagtt    67980
```

```
taattgcttc attttattac aagaaaaatg aggctcggag agggttagtg atttctccaa    68040
ggccattatg ccaaattcat ggcagaattg gaactaccat agttcatcaa ttttaaggca    68100 tcacccccctc tatttcagcc ataaaattag aatgtgactt gtaattgatg gtgccttaga   68160
taacagtgaa ataaggtaca tctagttgtt gactccttat gctctgcctt tcttgaaaca    68220
tctttctaaa gtactgagt tttgtcttaa tatagaaaaa ggagtgtaat tgcttccatt     68280
ttaataaatt atcagcactg aaaaatacca gacaagtgaa cttgaatata gacatttatt    68340
catttgtcaa taatttattg agtgacaaac cttttgcagg gaacttttag gtgggaagga    68400
ggatggggat attaggatga gattgacctg atctgtcctc aaggaattta taatctagat    68460
tagcagatac cttttaagcc attggttttt atttcaccaa ttacatagac tgtagaggtg    68520
ttgtgcttct gtggagggta tcagtctctt ctggagcttt tactgttcct atattcctta    68580
tgcatggatg tgttgaaaaa gctacctggg tgattctaat ttacactcct ggttaggaac    68640
cattgtgata agtcctttaa attaactaca aactggtagg gggctagtct tggccccacc    68700
ctaccttcag tttccacatg cttggtggtt ggtgctttta tagtgtgcat ttcctgttct    68760
ggcttcacac actggtattc cccaagcact gttttttgcc agtactatcc tgtagaggaa    68820
gagaaagcct tttatcaatg tttgtacttt ttcaggacta ctggtagcac atgtatcacc    68880
tttgtgtgaa gtagacaaaa gccctctctc ctggtggaaa gccttcttag cagcgcttgg    68940
catgcagata gcaagtttgt gccagttgga aaagacattc tctttggact ggagctgtgt    69000
cactccagga cccatgcttt ggcccacaaa gcaaaggctg gatttaagcc ccatcttgca   69060
tccttagctg cacatttcct gtgtaatgaa tgaactagga aaatgacatg tagcagtcct    69120
gccatttctt gctgtaaatg aaaggaacaa aactcttact ggactctact gcctctattg    69180
atagcacaga gtaccttgtg ctttataagt aatgaatatc taaagcttat ttttaatttt    69240
ttcggctgcc ctaaaaattt gtttctgtgg aggtgatgtc cattaaaaca catacacaag    69300
gaaaaagaaa gtgtatttca ttcagtgatt ttgtcagtag atatagggat atattttta    69360 acatgtgtaa tttctttatg attcaaagtt aatatatttt taacaaattt gttgatatgt    69420
tttcactacc tgttttcatt tgttgaacat ttactatgtg ctaagctcta tctaaaggtg    69480
aaactctagt gttaagacct agtctccatc tgtaagtagc ttatagttta agtgaagggc    69540
acagatatct aaacatgtga tttaaataaa aagtgtgata atgcttttgt atgacacaga    69600
aatgcctggg atgctgtggg tataaggcat ctcctttcat agctggtttt tgagtgggcc    69660
tgcctgttac ctaaaataat tatcacatat acctgataaa gaccatgtta atgattcaat    69720
ccctataaga actcttttcc cttgttagag aaaacaattg ttttctatac tgagtagtgg    69780
aagctatctt gttttttcacc agctaattaa gtatttaaat ttgaactcat tattttaact   69840
tactcttttc acctctggtt tcccattctc tgatttctgt aatgatatag agcacagtaa    69900
agttctggaa ctagactgcc tacatttaaa tatcagctcc accatgtcta gctctgtaaa    69960
cttggaccag gtacttacac tttctgttttt ttgttttgtt ttgttttgct tttgagacgg   70020
agcttgccct gtcccccagg ctggagtgca gtgacgcaat ctcggctcac tgcaacctcc    70080
acctccctgg ttcaagtgat tctcctgcct aagcctccgg agtagctggg attaacaggc    70140
atgcgccacc atgcctgggt aatttttgta ttttttaatag agatggggct tcaccatgtt    70200
aaccaggctg gtcccatctc ctgatctcag gtgatccacc tgcttcggcc ttccaaagtg    70260
ctgggattac agggatgagc caccgcacct ggcctgtttc tcagttttct tatcaacaaa    70320
```

```
atgggaacag tcatacctac ctaatagggt tgttgtgaag attaaatgtt tggtactaga    70380
gactgatgct cagatctcag ttaagtgttt gctgctactg tttattatta aggtaggcct    70440
tcacaaaatg atataatacc taatagccta aaatccccat atctttcttt ctcattttt     70500 aggaaaagca attttacaac taaattcata actgatagta ttgaaataaa ggatgatatg    70560
tgggaccagg cgtggtgact cacacctgta atcccagcac tctggtaggt caaggcgggc    70620
ggatcacttg aggttgggag tttgagacca gcctggccaa tgtgttgaaa ccccatctct    70680
attagaaata caaaaattag ttggcctggt ggtaggtgcc tgtaatccta actacttgaa    70740
agactgaggc aggagaatca cttgaaccct gaggtggagg ttgcagtgag ccaagattgc    70800
gctactgcac tccaacctgg gcgacagagt gagactgtgt atcaaaaaag aaaaaagtta    70860
aaaaaaaaaa aaatgacatg tggaacatct agtaatttag atgtgctatc attgattact    70920 tttattttg  aaaacagata cggtctgagc agttgtctgt aaataatttt ttagttaatc    70980
tacttaggga ttgggatgtt gtataaacta ggcagctatt atttatatt  tcttttacta    71040 caaatgaata attggtgcat tgatgagctt gtgttgcttg gtttatttt  ggtggctaat    71100 taaacttata atctctaggt gacatttaga catgattctt caacagtgga agttcaggat    71160
gaccacataa agggcccact aaaggtaatt catgtattca ttgttaattc taatggttgt    71220
ttgggaaaaa ataatcatac ttggtattaa ttcattggct cttttgttat tgagttgata    71280
aattcaatat gtaattttct ctaaaaagac taatagaaaa aatagactta atctcagtga    71340
ctaaggaggc tgaggcagga ggatagcttg aggccaggag ttcaaggttg caataagtta    71400
tgattgtgta cactgcactt ggggacagca tgagatgctg tcttttaaaa aaaagattta    71460
atattaaata atacttgata tggtagtaaa accagtttat tcagaaataa aatgagtatc    71520
aaagaagcat tgactacatt tatttactta atccaccata tttccattac taaaatgatg    71580
gattttccaa aattaataga tgatgaacta gggattagtg atgtcagttc cacgatgatc    71640
tgaaaagtga gaaagttaga aaaccaaaaa aatcggagct cttacttctt tggagccact    71700
actggcaaat gaaatctttt aagggtcatc agcctttaca ctaacagttg gagagttta    71760 tttctttgca ttcattttc  ctcattggca agtgaaataa atgctgcttt gcttttgcc    71820 agtgagcaag ctaaaagaga atgtgtgggt aaaccactat gtgctctttg gctggtttag    71880
ggccaaaagg aaaccccaga gcaatttta  aattgtccct atccttcctg aggttccttg    71940
aaagaagagt ggaaatacgg ggcaaggaca gtcagtttca cagatggtgg tactcacggt    72000
gtagtctact gaccctgggg attcccagga ttcttttggc ggggggttgta agggtaaaac    72060 tttataatag tacttaggta ttatttgcct tttttactac attaacattt tcactgatgg    72120
tacaaaaata ttgatcggta aaactgctgg cactttttt  tttttttttt ttttgaggc    72180 agagtcttgc tctgtcaccc aggctggagt gcagtggcgc gatctcggct cactgcaacc    72240
tccacctccc aggctcaagc aattctcctg gctcagcctc ccgagtagct gggattacag    72300
gcgcctgcca ccacgcctgc ccaattttg  tacttttggt agagacgggg tttcaccatg    72360
ttggccaggc tggtctcgaa ctcctgacct caagtgatcc acctgcctca gcccctcaaa    72420
gtgctgggat tgcaggcgtg agccactgtg ctcacgccaa ctgctggtac ttttaaatga    72480
agtcaatagt cattttattc ttccatcatca tgcactcagt aaaagaaaa  caacccagg    72540 ttttggtttg ttaattacc  ttttaaaagt ttttctaaca tgtttaaaaa tactttaggt    72600
aggagctatt gtgaagtga  agaatcttga tggtgcatat caggaagctg ttatcaataa    72660
actaacagat gcgagttggt acactgtagg taagaaaata aattttcttt taaaaatgtg    72720
```

```
tttttagtta cacaaagaaa acttaataca aataaaatga aatttcctgg attcacttct   72780
taatacccta gatrttatta ctgttactgg attttatctt tccacatctt ttaaaaattt   72840
atttccaaag tatatgtatg tatatgtaac aaaaattgaa attatttaat gtgtatatta   72900
tgcaattgga attctagctt tttttacttc aaagtatatc ttaggtaaat ttctttttt    72960
ccccaatctt acctattttt aagtttatag ttcagtaatg ttaaggatat tcatgttgtt   73020
ttataataga aatgtctttt aactgtgtat atatatatat atatagagag agagagagag   73080
atatatctat ctatctatct atctatctat ctatctatct atctatctat atagctccca   73140
gcaggaaaca aagtagtagt gtattttata atagttgatg tgctagttta ttttttctta   73200
ctgatgaggt ttccagtttt cttactatta caataaatgc tggattgaat gtcttttta    73260
cctaattagg tacttaatta ggatacctac tgtatcctag tatttcttta gtgtacatac   73320
tgagaaatag aggttgaaga aaatatgct ccaaaaactt tagtagttaa tgaaaactgc    73380
cttcctaaaa gacactgtct gttttctcaa tccttgtcag attttatgtc atttaaaaaa   73440
attttttgct aatttggaca taaagtagta tctcagtttt gttcagtat gcccttccca    73500
tgattactag tgagattgaa catcttttca tatgtttatt gaaaggaaca taatttcatt   73560
tgtgttttct ccgttttgag ttgctggctc ttttattctt tcccttttc tcttgagatg    73620
atttatcttt ttcttattag ttttggtata tgtgttcttt atatatttg gatattaact    73680
gtttactact tcagttataa atatatttct cctgttgctt tattcttgtc tctgcttta    73740
attttcatgt agtcagtttt tgtatggtca ccttttattt tgtaatttta gtttgaatc    73800
ttaaagcctt ccatcagtgt tataaatcta ttttctaatg tattcttcaa atttttata    73860
cttttaaat ttatttttat tttgttta caaacagatt tttatttcac ctacagtagt      73920
atgtattttt tccaacattc taaaataatg attaaaagt atttgtccta gattggtagc    73980
catttattcc agtattattt attaaaggta acaattctta ccatttaatg acctcagaga   74040
tgaaagtaaa cacctagtaa aatgtctttc gtgatttcag agtttgatag aactttcaga   74100
tagaataggt gagtttgtt tatacttctt tggtgtgaga ataaaacctg gtgaaaatag    74160
agggaaaatt atttgatttt gagacataag gaaatatttg actttatgta agtgagaaga   74220
ctgtgagcaa ttctatgtag gaagtctaga tggtgattgg ttgtaatagt ctactaaatg   74280
tgacacttat gttgtatatt ttagttacat catttaaaga tgtactgaaa attatttatc   74340
cagtttcaca taatgtaact tgttatgtaa cgtataagaa tctaattta gttcagccag    74400
taaggaaagg gtattggctt tcttttaacc attaatcatt tctcaataaa cgtgagatcc   74460
tgttgagcat cagaaaaaga aaggaaaga agagtatcta attttagtag gtaggcagaa    74520
aatgtaattt ctaaaataga gatctggtaa cattatttaa aacagagtta ctgtcttccc   74580
atgatttcta aggaatgtag catatcccta aattatttat gtatatcaca gatttatgca   74640
tataatacaa atagtcatac attccatatc tgttaactta tggtggtttt gctggggtgc   74700
tttaagtact ttattttat taaaattttt cccctacttt attgagatat aattgacaaa    74760
atcatataaa tgtatatgta acatgatgat ttgataggca aatatattgt gaagtaatta   74820
ctgcagccaa gttgcttaac acttccatca ccttttaata gacatttag tattttaagt    74880
cgctagtttt caactgggat gaatttaccc ccagggaaca tttggcaatg cctggagctg   74940
gagacatttt aggttgtcac agctgggaag ggggtgctac tgacatctag tgggtagagg   75000
ccaggagtgc tgctaaatat cctgcagtgc acaggacaag cctgccacaa cagagaattt   75060
```

```
tctggtgcag tatgtcacta gtgacagtgc taagggtgag aaaccctact ttaaataatg   75120
aaaatacagt tatttttta aaggggcagt ctgattgcat atacttgtaa tctttcttag   75180
gtaaatctgt caatatctgt cagtaggaaa acttggcatt tctttaccat tttgagaaga   75240
gttaattagc atttaaatgt tttcctcttg aaataccaac ttcttatttt tatttggtat   75300
atcctgtttt atacaagatg ttttcatttc atatatgttg tttctttttc actagaaatt   75360
ggaaaagtta ctttaataac tctatatttg aagttactca ctagaaaaca taaaatgtga   75420
attgaattcc aaatgtagtc ttaaatagta gatctgtttg cactcagaaa attgtaatac   75480
atgtcatctc tttgatcttt gaaaaaatcc ttcagtagct tccattttta cccctctca   75540 tagtttttga tgacggagat gagaagacac tgagacgatc ttcactgtgc ctgaaaggag   75600
agaggcattt tgctgaaagt gaagtaagtc atcatttaac aaatgaacat gtcttaatat   75660 ttttattgg gaggaataaa ttttgcttt ctcaactcag taaacctact tcctaatcag   75720
gaaagttcat taatacacaa tacccttatg atgtaatctg tgaagcctgt ttaaggccct   75780
gtgtttgagc accaggttct gtcttctttt ttgtctatgt aaagtgtttc agtatttgtc   75840
cacagagaaa atacaatggg ctttaattat tatctttagg cagtttttaa acagacttaa   75900
aatttgtaaa taactagaaa acagatttct gatttgtaat ctacttgatc cttgtcgtag   75960
ttaaaggatg tgtagataca acagtcttta actactgcta ctgctattag ctgatattat   76020
tatgcccttt cctcttgcct gactgcccctt cctaaaattg tcccttccat tccttatcat   76080
cctttcagat tgatttaggt cttattccct aacatcaaaa tatgagtaca taattattta   76140
ttgtctgcct tcctcactag aatgtgtcac acggtcagag actttgtata tcttcttcat   76200
ggctttgttc ctagttgctg taacagtgcc tgatgcagag tatgaacttc ataagtgtta   76260
gttggatgaa tagatgaggt gcttataatt gccagggatt ttgctaagtg ctttacatac   76320
attattgtat ttgcaacatt atgaggtagt tactattatt atccccaact ttcagattag   76380
gaaatggata gctagagctg ttttctaac cagcactttc tagcaccaaa gccatatcct   76440
taaattgaaa gatgttacta agagcagagg gttcacaaag ttttgtaact aactcgcttg   76500
caattcagaa tttaaaaggt agatgttgct ctaaatggtg ttacgttctc taatccagtc   76560
tacagatatt cattgataca cagtgtggcc gagctatttc ttttctctac tcactatttg   76620
gaatagtgtt tctttgggga tatttttaata ttactaatta atattactta tttgttatta   76680
tttattactt taatattact ttatattac ttatttagta gtgttattac ttaaacacta   76740
tttggaatag tgtttctttg gggatatttt aatattactt attaacctat tagactttat   76800 gttttttgttt tgaaaaattt ttgcttctct taatgattga attcccactt aaatttagaa   76860
tttggacagg ttctctgtat tataattcca gcctatccct ttagtctcat attcaaccac   76920
ttccctgtac ttctgcctta ttagactgct tggtatttc agactatggt ccatactttc   76980
ctttattgac tcctttcctc ttgttggaat ctcacttatg ttgaaggcca ttataaatgc   77040
ttcctcctct atgtctttcg tgagctctct acccaaattg gtcgttttgc acttctcttg   77100
cttattcttg ttttaggacc ttttttttt ttaactttt ctcattttg ctgtaagatt   77160 ttaagctgtt ttaggggaat atcctttctt tcctcacttg ataggccccc ttttcctag   77220 caatttctac acaaaagcct tcaataaata tgtgtggaat aaactgaagg tttacataca   77280
ataaatacag acagctttgg ggcaagtata gtgataaagt acagaattct ccctgagttc   77340
gtggaattat tttaatttca tttccgtaca gtcagtgagt atgaggactt gaagacatgg   77400 ttttctcct gttaagtgaa ggtctgcatt ttatttttt agtctagaga aatagccaaa   77460
```

```
atattatttt ttttaaccag gagaattttc agttggaatg gttcataaga cagttgtaag    77520
ttaaatgctg aagtaatat gaacaagtgg ctatgtatcc ttcatatctt caaggaggtt    77580
cagttttagt gtgtctgtgc aggtgtgtac ttctaattta tgttttgcta gaaggaaatt    77640
agaatactgg tgtgtgattc ttcaattccc ttcccatgtg cccggagctg tgtagtgcta    77700
ggtaccggga caaaggttaa gccaacccat gtaaacatgg aacttatctt tgggtactta    77760
ctccctgttg gaggagaaaa agcattaatc aaaccaagcc atgtaaacat ggaacttatc    77820
cttggatact tactctccgt tggaggagaa aaagcattaa tcaaacaatc aaacatattt    77880
taaaatttga gtatattaag ccctgtgaag atgtggtcca gagtgcaccc aatagggaa     77940 tttaatctac catctgtatg ttcttttctc tttatttggt atttttcata ttgttttaaa    78000
agttttaacg ttttgaaag accattcaga gtattagtag tagtagtagt ccataacatt     78060
gtcctttaag aggaaagctg cttcatactg ccagtatttt gggtcactaa tcccatttaa    78120
taaactactg aaattaatcc catctcataa acactgaaat tcaggatttt catggaaaga    78180
gatcacattt gcacttcagt cagtttatct ttttattta ttttattatt attattatta    78240
ttttttgaga cggagtctcg ctctgttgcc caggctggag tgcagtggtg cgatctcggc    78300
tcactgcaag ctccgcctcc caggttcacg ccattctgct gcctcagcct cccgagtagc    78360
tggaactaca ggcacctgcc cccacgcctg gctaatttt ttttttttt ttttgagatg      78420 gagtctctct ctgtcgccag gctggactgc agtggcacga tctcggctca ctgcaacctc    78480
tgcctcccgt gttcaagtga ttctcctgcc tcagcctcct gagtagctgg gactacagtc    78540
gtgtgccacc acgcccagct aattttttgta ttttagtag agacggggtt tcaccatgtt    78600
ggccaggctg acctcgatct cttgacctcg tgatacgccc gcctcagcct cccaaagtgc    78660
tgggattaca ggtgtgagcc accgtgcccg gccacgccca gctaattttt aaatatttgt    78720
tagtagagac agggttttac tctgttagcc agggtggtct cgatctcctg acctcatgat    78780
ctgcctgcct tggcctccca aagtgctgag attacaggct tgagccacca cgcccagcct    78840
cagtcagttt aaattccaac actgaagcca ctggttttag ccataaccag cttaatgagt    78900
atgttacctg ctgcctaaca tctgtaggac agtttaggta tttctaaaga ccattcatac    78960
tttgagtatt atacaaaagt agattcatca tctgatattt atttatttat ttatttttt    79020 gagacagagt cttgctctgt cgcccagact ggagtacagc ggcatgatct tggcttactg    79080
taacctctgc ctcccgggtt caagcgattc tcgtgcctca gcctcttgag tatctgggac    79140
tacaggcgtg cagcaccacg cctgactaat ttttgtattt ttagtagaga tggggtttcg    79200
ccatgttggc caggctggtc ttgaactcct agcctcaagt gatccgccca ccttggcctc    79260
ccaaagtgct gggattacag gcgtgagcca ccgcgcccag ccaattatct ggtattcttt    79320
ctttgtattt actatgtgca attgaaaact ctagagaagt ttaggtaaaa tcccagttcc    79380 atatttctg cagcccattt taggtaacag gccatagac attttccctc taggcctacg      79440
gagttttcta tgtgccttta atacagcttt caggagcctc tggttttgc tctttaggtc     79500 taagatggga caaattctac cctacccca ggtctttta gtcccttgaa acaaacatgc      79560
ccctactttc ctggacattg agatagggac agagatattg cttatgtttc ttcttgttat    79620
gtactaggga gagactgtgg tctcttattt gaaaattact atgtgtgatt cttaaacaac    79680
tctttagaaa ttttctttcc tgtagcaagt gaaatgacta acagatactt aaaatagaaa    79740
tcacactgtg tgatataaat ctctctctct cttttatttt tctgctttaa agagagcaac    79800
```

```
cttaattttc ggtggggaga gcatacattt aatccatctg tttgcttgac agaaagtgaa    79860
tccggattaa tttattttcc ctgtttacca aataaagtca tttagtaata ctctatagtg    79920
atacagtatt accaaaataa tatttcagat tacatagaaa ttttcaccat aggagttaat    79980
gacaggcaac gtctagattt tccgggtggg tgtggtggct catgcctgta atcccagcag    80040
tttgggaggc cgagttgggc agatggcttg agcccaggag ttcgagacca gcctggacaa    80100
catggcaaaa ccccatctct acaaaaaaca aaaattagct gggtgtgata gtgcacacct    80160
gtggtcctag ctacttggga ggctgaggtt ggaggatcac ttgagcccag gaggttgagg    80220
ctgcagtgag caatgatcat gccgccactg cactccagcc tgaatgatag ggtgacattc    80280
tgtctcaata aaaatagttt ctgtttggta tatactgagt ttaggacagt ttttgcctcc    80340
aaataatttt tatttttatt ttttgagatg gaatttcgct cttgttgcac aggctggagt    80400
gcaatggtgt aatcttggct caccgcaacc tctgcctgcc gggttcaagc gattctcctg    80460
cctcagcctc ccgagtagct gggattacag gcacccacca ccatgccagg ctaatttgt    80520 atttttagta gagacggggt ttctccatgt tggtcaggct ggtctccaac tcccgatctc    80580
aggtattcca cctgcctcgg cctcccaaag tgctgggatt ataggcgtga gtcactgcac    80640
ccggcccaaa taatatttt taaatgcctg atttaaggtt cattaggaca gggttaggtt    80700
ctgtacaaac taaatttgaa agattagatt ttttgcccta tgagagttgt gaaagctatg    80760 attttgtca gtcttttgaa ggaatcaatc tttagttaat cctttatggc tagtacctt    80820 tttcttgatc atactgttcg ttgttagata catacatcta tgtaccttaa acacatttac    80880
atatattcta atgaattatg taaaaagtg ttaatatggt tcatcttttc acagttttgt    80940
tcattgtagt tataacaaaa ttgtctcaat tttaaaaaag ttatataaca tttctttta    81000 catattacat tagtttagat gcctgctctt taattctaag ttcatggata ctctttctta    81060
taccaccctg gtttgtatct ttaagaagtc tctgtcttaa atagttcctc acttttattt    81120
tcatctgggc agttttcttg gaaatctcta gttgctctga tgtttgtgaa attatttata    81180
acaggaaaga ttcttcttag gatgaggaaa ggaacagaaa ctgtggaaaa tcttaagaaa    81240
acgtaggaaa ggaaaaaaat caaatgtaga aattaaatgt aatttaaaaa attaaattaa    81300
tgttacattt tattaaaaaa ggtttattgc agaaaatgtt tgcagagtag taatataact    81360
tactccgagg cttttttgttc gtgcgattga tgctttatct tcataattaa ttttgtttct    81420
tattaataat tttattttat ggattatgat tccccatgta caaattaata ttggagctgc    81480
agttggccct aaccttacaa atagatttct taattctcac atttgtcttt ccactgagct    81540
gtgtttgttt tgtatttaa tcattcttag atgcctatca accttcacat aggtaatgaa    81600
tcatctagag agagcagcca aatttctttt cactttttt ttccagtaat gagctcattc    81660
atctttattc taatatcttt gaaactagaa ttttctatct ttaggaaagc tgtgttttag    81720
cttccctggg gggagagttt aatctcaaaa tctgagcata ttcttaaatt gatttggttt    81780
aaaacaaaga aggcacttgc aaagtgttaa ttttttgatg ggtttatgtt cttacccaca    81840
gacattagac cagctcccac tcaccaaccc tgagcatttt ggcactccag tcataggaaa    81900
gaaaacaaat agaggaagaa gatctaatca tatgtaagtc cattttcatg actgttagtt    81960
gaacctgaat tcatttctcc ttctagtatt gtttatagtt attttaaaat tgtaatttgc    82020
aaaatgctaa ccagatctaa tagtaatttc ggatctaata gtaatttcag actcctcagc    82080
atgggtgatt gaggttctcc atgctcagcc aaccttactt aacagctgta tctgccttca    82140
atttctccct gcatgttatc ttgatgctgt agtcaaaatg aaaccagtca ataattcctg    82200
```

```
aatacatcgc ttgttttcta atatcatgct tttattcatg ctattatttt tggtctccat   82260
gcctcccttc ctggtaactg tcttgtccat gccttaattc tcaacaaaaa tgcttaaacc   82320
tttatgtgaa ccattttgtg tctccccaca ctttccttga aaccagagat gtttctctcc   82380
cctgtaaacc caattctctg gcatagtatg aactgtggag ccagttggtc tgggtttgaa   82440
tcctggctct gccacttcct tgctgtgtga tcttgggatg gttacttaat cttttcatac   82500
ctcacttcct atctataaaa tttggataat aatattacct atctcttagt gttgttgtga   82560
aaattaagtg aattcatatc ctttaagtgt ttatagagta aatgttacat aagtactaga   82620
taatcaacat catatactga catgaaaaat ttcatgatga aataccagta tgtaacagtt   82680
tcatttatat atgaaaatgt gtttacatgt atatataaaa attctgcttc ctggtgttta   82740
tgtctgacaa ttaggactgg ttcttgctga attattcgaa ctttaaaaaa tttctacgtt   82800
tttatatata ttataggaaa aatagtctct tatttgtcaa taagttttt taattttag    82860 aagattgcat ctagtattta gacatatttt tacgatttta tacacatcat cctaaagtgt   82920
aaaaataaat ttaaaaatga atttattgtg caatatcacg taatattgac ctgcaaatgt   82980
gactaaaaat tatgatctgt taaaaagtca gttattttt atttcctctt ctgtcgttcc    83040
ccaactgtta gatgtttctt agttgaggcg tccgttttgt gaatatgaga ataaagcacg   83100
catttgttgc tgaataagtt gatctttgct ttctaaagac tccagcaaac attctaagtt   83160
agtggttttc ctgttgagaa tctctatgtg taatgagaga tttgctgttg agattgtgtt   83220
atacatgtgt aaagtatgaa tgcagacaaa aggttgaaga ttactagtgt aggaatgaag   83280
acctgctcca tctgtaatct tgttttgctt gctcttcctt gcccttctct accacggttg   83340
gtcattctca ctgccaagga acctgacaat gttactcttg cttggcgttt taagccttgg   83400
tgtgtaagca ttacaggcaa gtactacagt ttgaaatgcc catctccttg attacatttc   83460
ctcaaagttc tttctcccct ttcttcaaag tgattttctg caacaaagtc ttaaacctag   83520
atcttaaggg cattcatctg accttcattt cctcttccat tactccattg aaaaaagtct   83580
ttgctgtgat ctcagattgc catttaaaat gtatttttgt acaaagatat gtaaagttat   83640
ctcttcttag gattcccagg acttcgttgt tggagtgatg tatcaccaaa tttgttttct   83700
tttagcagct gttattccac gtatcagtta atctaccccct agttattcca aaattgatta   83760
cttttaacat cttccattaa attgagtttc agtatattct acctttaatc ctagtaagtt   83820
caagtatttt ctttttttaa tgattatcat cctctagcta aattttttt aaagcaagtt    83880 attgattctt ttaatcaatg tattactgga ttgaattttc tccttataac ttacccattg   83940
tttgcagcga ttgtgtttaa gtcatccaga agaatagaat acctgaaatt atggaaatac   84000
ttgtttgtcc ctctcctctt gaagttgttt tcccataatc tggcaaaagt ttatgtgcaa   84060
ctgctacaat aggaaagcag tctatttgct gttatatttt tccccttcag aaaaaagata   84120
aagcataagg tttacaatga atcttgttaa caagggatta tttatgagta tggatttttac  84180 ccagtaacag tgctaagatt tacccaatac ctggtttata cttgctattt aaatacaggc   84240
ctgcagatct gaacacattt ttaaattagt gtataattca tgtatcataa aatttactca   84300
tatattttaa tctgtagatt tgtatccaat acttcaccct tttaaagtgt acagtttagt   84360 ggttttagt atattcataa aattgtgtaa ctatcatcac taattccaga agatcttttt    84420
attttgccgc tttatttaa tatgagaatt tgattcattt cctccttgat aaaaattgag    84480
aaaaaaatta aaacccttttt atagttaagc gtacataggt tctgtgtgtt tctaagaagg  84540
```

```
tatgtatacg ttgtcagtct tccagatact aatagaacat ttcaatttac aaagtttgaa   84600
actgagtaaa ctgatttgcc taaaataaaa aataatcaga attgcatgtc aaaggttgag   84660
cctcttgttt ctagctcaat tgtatcatt atttggtatt ccttggccca tatcttgtct   84720
aaagttcgtc tttcttgatt tacaactaat tagagttaat agtgaagtgt gatcagcttt   84780
aagtgattgg ctgttagagt attatggtaa aaatttccat gtaattagct ttctttctag   84840
tgacatcatc agatttttatt tcatagagac agcgcattat tttgttgtgg ctctacaaat   84900
accttgccac caaagaaata acaatgtcag aaatgaataa aaatcaagca ggctctctgc   84960
ttgctctgtc tttgctcctg taaaatattt tggatgctca ttaattttag ttcattagtt   85020
tattgagtac ctgtgtaaac agttttctgg ctaagctcct ctaaaaggaa aagttaagga   85080
gcttcatgtg taatagtatg gtttacactg atgtatacat tttgtgattt tagaataaaa   85140
atcagaaata ccataataaa aaaataaatg catcttttttt attttatgaa caagtattta   85200
tttagcatct atactgtgcc aagcattgtt caggtacttg agatatatca ataaacaaaa   85260
aaaaattact taaaaaatct tcaacttgag agcttacatt ctctcagggg aggagatagc   85320
gaattaaaca ttggattcac atacttggtg tgaaaaaaaa gaataaacat aagaaataag   85380
taaattatat agtatgataa aagtgaatgc tgtggaaatg aagagcaaaa tgaaaagagg   85440
tagatgggca gggactgtaa atttgaataa ggtggaacaa agtcttgagt aggtgagggg   85500 gaagggcat ctagtctaaa aatggagatg attttagaca ggaaccttgc aattttatat   85560
gtaaggtgga tagatgtttc agctagctga acaaaggtgt tttgttttc ttttttgatat   85620 actgtgaaat ctgaagtctt aacacttgtt aagtcttaag aaaagttaca attttttacaa   85680 tgatgcagat aattttgtta gtcaaataaa gcccaattttt ctctatgttg tacagatttt   85740
gatatgtgtt atctctgaca ttgtagcttt ctagctgcta ctgataatag agtgttcata   85800 aaccccctagc tgaatgagtc ttctgtggct actttgagaa agcagtaatt atgattttaa   85860
gcttggttgt atcctgtagt cattagacag taaaaaaagt cactactctt aagctcttgt   85920
aaatcaagta gaaatcagac ttgtgaggac tgtcgttact gtcccaagct gtgtgtctat   85980
gtgtagggtc ttattctcca ctaatgtaaa ggtggttgag ttttcttatt gttacctact   86040
ttctaagtag agattgaact tctttaagtg ccattgaagt acaatacatc ttttttttt   86100 tttttgagac ggagtctcac tctgtcgccc aggctggagt gcagtggtgc gatatcggct   86160
cactgcaacc tccgcctccc gggttcaggc aattctcctg cctcagcctc cagagtagct   86220
gggattacag gcacccgcca ccatgcctgg ctaattttttg tatttttagt agagacgagg   86280
tttcaccatt ttggccaggc tggtctcgaa ctcctgacct caggtgatcc acctgccttc   86340
gcctcccaaa gtgctgggag tacaatactt ccagccaaag tacagtactt ctattcaata   86400
gcaagctttg aagatttgct ttgtttctgc cagggaacaa ttttttaagtt atttgactga   86460 tcattgaaat caagggggtg gtattcccca tgtcactttta aaaagcttaa tattattata   86520
atagttttta cttttttggc caggtggggt ggctcacgcc tataatccca gcactttggg   86580
aggcgaggtg ggcggatcac gaggtcagga gatcgagact atcctggcta acatggtgaa   86640
accccttctc taccaaaaat acaaaaatta gctgggcgtg gtggcaggca cctgtaatcc   86700
cagctactca ggaggctgag gcaggagaat tgcttgaacc caggaggcgg agcttgcagt   86760
gagccaaggt ggtgccactg cactccagcc cggcaacaga gctagactcc gcctcaaaaa   86820
agaaaaaaat agttttcact tgtttacat ttatattgga atatataaat ataaaggcat   86880
gacggttact ttgtcatact tttggaaagg catcaaagac aacttcagag tatactagat   86940
```

```
agtatactaa ataggtaaat catgtttaaa gtttttagt agtttaatct gtcagttttc   87000
cttttttggg cagtgaaact gatcattgca aactatctga aaaacactt tatctttgta    87060 ggtattcaat aatagccatt ctaaaaagga catatgttgt tgtccatcaa acatttccta   87120
gtctttactc attctgggca ttttctttgg tgctgattct ttattagaat cagattcaaa   87180
ttggaatagc ttttgtttt gttttccttt ttactacact ttcctcaaac atcaagttga    87240
tggtttcaga tacttccttt ttcttctgac agttatcttt ctaatttact agtccaatat   87300
ttaatgttac tgaaaggatt ttctgttttt cttttaattt tgaaagtttt tagcatcata   87360
caaaagaggc ttattggaca ttttatgaat acctaattgg tgtgtatttg ttgttatgga   87420
tagcagtggt gatctctttt cagattgcct cctcttccca acctaacctc agttaataaa   87480
ggtctgctct cctacctttt aaaattaact ttgtactgga gatatagaat tactgtctcc   87540
agaattcctt taatttgaga ttgggattgt gtatatttta gtgtaatact gggatgttta   87600
atatggggcc ttcaccttt tgaggatttg ggaaccagtt atttgtcctg atcttcctcc    87660 tcaattttt acagtagcac taaataaacc agaaatattt ttgggaaaat gatgtgcttt    87720
cctctcatga taaactcttg ctgttatttt ttagaaattt agaaaatgat ttaagattta   87780
aattagccat tttacaggtc ttaggaaatg taataagagt ttgggaatac ctatattcat   87840
cattggcatg cttattcttt gtgaggataa atggaaatat tttattttt tctctcccta    87900 gaccagagga agagtcttca tcatcctcca gtgatgaaga tgaggatgat aggaaacaga   87960
ttgatgagct actaggcaaa gttgtatgtg tagattacat tagtttggat aaaaagaaag   88020
cactgtggtt tcctgcattg gtgagtagct tcagtataca agagtttaat ttmaaacttt   88080
ataagtttat gaagaaaaca attttcttac taatgttttt cataggtaca aaatgaggaa   88140
atgtttttag cattatttag ttcacactaa gcttactttc aacgttgtct ttgaatacaa   88200
agaactcttg atgtcattca ggaaaggcaa aatcttgata atcttagagg tttagctatg   88260
tggaagttga attctctctc tctcggtaga aaattcatga tgcaaacttt taaagctcct   88320
aagtccatgt aggtctagat tgcaaaagaa caacagaatc tttcttggtt gacagggata   88380
actagacctt ttcctcatac ttagtgaatc agggtgtttc catccttgat cttaatcttg   88440 cctttaggt actccctata taatcatgac tgcaattata cattacccca ctcttcaatt    88500
ttctctacag tagattgtta attctaccta cttttaatg ttttctctc caaaagattg     88560 caattcctta gattccaggt tgaatatttt gcatttttc cttgttttct cacgttgcct    88620
ttttgtgatt ctgaggaggt actcaagatt tattatcagg agtatcctca tgattgtccc   88680
aagttcttgt atttcaaact gttaagacat gacagaaagc cttttgagct ttttatctct   88740 ctgttttcg taaccactag cttctttagc aagttgaaag ggccatgtat agaccatttt    88800
ctttgacttt tagaaaggga acatatacta atatctttca cggacataac taggctgctt   88860
ttcaaataat cttttggtag acaaaataat ttgtagctct taaagcaaat agaggttcaa   88920
ctaataatta gctatatatg atactttaat gaagatttaa ctctgtggca ataagaatgc   88980
atttttttct ggacagcata taattggata aatcacttaa ggttttaaat ttcaagtagg   89040
agactgaagt taataatcag tatctcttaa gaattatctt ggctggggtg tggtggctca   89100
cacctgtaat cctagcactt tgggaggccg aggtgggcaa atcccctgag gtcaggagtt   89160
cgagaccagc ctggccaaca gggcaaaacc ccgtctctac taaaaataca aaaaattag    89220 ctggctgtgg tggcacatgc ctgtaatccc agctaggcag gagaatagct tgaacccagg   89280
```

```
aggcggaggt tgcagtgagc caagatcgcg ccactgcact ccagtgtggg cgacagagca    89340
agattccctc tcaaaaaaaa aaaaagaag aaaaaaaag aattatcttg aactctttaa     89400
aattttgata tgtctgaatt gtcctatgat gattttatct gaagaccatt gagtcatttg    89460
catcaaacag tgagatccac ttttttttt ttccccgga cacagaggct tactccgtta     89520
cccaggttag agtgcagtgg tgtgatcctg actcgctgca gccttgacct cctgggctca    89580
acaattctcc cacctcagcc tcctgagtag ctcacactac aggtggagac caccacatct    89640
ggctaatttt taaatacttt gtaaatacga ggtctcccta tgctgcccag gctagtctta    89700
aactcctgga ttcaagtgac cttcccacct tggcttccca gagtgctggg attacaggtg    89760
ggggctactg agcccagccc acatctttta caaatatgtc ctcccctcac ttcatattta    89820
ataagctata aactgaagat ccgctgataa acaaaagaca ctttgaaagt actattctca    89880
cgtttgacaa ctaatttgtt ctcaaatatc gagagacaga atgggtcaaa attattctct    89940
gtctctgttt tgtatgttct cactcccctta ctaaaaataa ttagccaaat tctcctctaa   90000
tgcttttttc ccttatgtta atgacattca ataaaatttt tgtgttctca agattaacac    90060
atatttgtta ggtatgcatt tatcatatac caagttctgt tcaaaatatt taacaaagat    90120
agactcattt agtggtgtag aggttttttg ttctcatgat taataaactt tccttttttc    90180
ttttctttc ttttctttt ttttttttg agatggagtt tcgcccttgt tgcccaggct       90240
ggagtgcaat ggtgcgatct cggctcactg caactccgcc tcccaggttc aagtgatcct    90300
cctgcctcag cctcccgagt agctggtatg acaagccacc atgcccggct aattttgtat    90360
ttttagtaga cacagcgttt ctccatgtcg gtcaggctgg tctccaactc ctgacctcag    90420
gtgatctgcc cgcctcagcc tcccaaaatg ttgggattac aggcatgagc cagcacaccc    90480
ggtgatgatt aataaacttt tctctacaat ttgtgcttga gaatctgcta actctttatt    90540
ctcattctct cattttcctg ctcattgact aacaattgca gagacttaga aatgggatta    90600
aaacactgtc ctttgtttat atgtatttgt atgaaaactt atgtccataa tatatataaa    90660
ctcttttgta tatttgtggt ttttgtgcta aactaggtaa ccatggtctc aaatgaaaaa    90720
gaaacaatag aactacctttt gttttactg ttttctactt gtgatgtcca tttacccttt    90780
ttagtcaaca tgtcttattt ctttatctcc actgcttagt tcagtgttcg gcacaaatta    90840
artatgcagt aaatgtcagc tcttgtaatg atagtgaaaa atgaggacaa ttatttgttt    90900
taataaatat aaatatttta taatacctttt gtaccttcct gtgtatccaa catttagtgg   90960
atacctatat gtacaaggag tgtgctaaca cctattatga gataggtatt attatttatc    91020
ccgatgtaga gataaggaaa ctgagtatta gcagggttaa gttagttgcc acactttggg    91080
ttaattatta agctgaaaaa aagcatcagt gtttgcgatt ctttctttct ttctaaagca    91140
ctaggagtct ttgtgagttt cttttgaaag tatgttttaa ggccagctgc agtggctcac    91200
acctgcagtc ccagcacttt gggaggccga ggcaggcgga tcacctgagg tcaggagttc    91260
aagaccagcc tggccaacat agtgaaaccc cttctgtact aaaaatggaa aaatttgcag    91320
gacatggtgg tgcgtgctta tagtcccagc tactcgggag gctgaggcag gagaatcgct    91380
tgaacctggg aggcggaggc tgcagtgatc tgagatcaca ccactgcatt ccagcctggg    91440
tgacagagca agactttat ctcaaaaaaa aaaaaaaaa aaaaaaaaa aaatatata       91500
tatatatata tatatatatt tttataaaa ccgttttgtg ggccaggcgc ggcggctcac     91560
acctgtaatc ccagcacttt gggaggccga ggtgggcaga tcacttgagg tcaggagttc    91620
aagaccagcc tggccaacat ggtgaaaccc tatctttact aaaatacaaa aattagccga    91680
```

```
gcatggtggc gggagcctat aatcccagct acttgggagg ctgaggcagg agaattgctt   91740
gaacacggga ggtggaggtt gcagtgagct gagaccgtgc cacagcactc cagcctgagt   91800
gacagagcaa gacccatct caaacacaca cacacacaca cacacacaca cacacaactg   91860
ttttgtaagt cttttctca ataggaacat taaatttttt aatattagtg ttttgagtta   91920
ttaatttaag cttctcacac cataatcact aaaaagtttc tttgacgaaa atgaaaaatc   91980
taaggatttt taatattgaa aggttagtaa tctgtttagt cagccatttc actgttgttt   92040
ttaaattctt agaattattg atgtatgtta tctcctccca aaattgagat ccattggacg   92100
gtgatggata gttttggta actagagtga aaaattatgt tctaaatcga ccaatcttga   92160
tataatcgca caaatagtat ttgtgtttct aatttatgtt attttataa atcgagtaaa   92220 ttcaaagtgt tttagtaaca tcataagaaa acagttaact gggtctgggt ggcctgtgcc   92280
tgtagtccca gctacttggg agactgaggt gggaggatcg attgaaccct gggaggttga   92340
ggctgcattg agtcgtgatc acgccactgc acagagtgag accttgtctc aaaaaaaaaa   92400
aaagaaaaag aaaaaggaaa caactacata gtcccaggaa ctataaataa ctaccatgca   92460
ctgagtattt accctgacta ggactgtgct gagcttatta atataagtag tattgtttaa   92520
tcctaattga gacttactct cagtctcaat ttttatttt ccaatttcat tttaagaggg   92580
ggaaatctta gattccatgg ctcatgcagt tctccttttc agtttttttc accaggttct   92640
cctcttctaa tcaccctttc aagctgtaat tcaggattca gaatgtatcg ctgtattttc   92700
tttacggtga tctcatctcc tttaaagct tcaccttgca gagatagcaa agagataaag   92760
tgaccaagaa aataacatac atgggtgaat gggataaaat gcatattgtc gttctgtggc   92820
agaactggac agtgagccca cttactcata caccagtgtc atcactggcc aaagctatca   92880
catgtgcagt tttcgaaatc cttcgctcat cagggaaaag taatgagtgg atttggctca   92940
caagccccaa gttttagacc cctaatattt aggctgtggg ctctcaaatt tatatccttg   93000
agtccagacc tctacgcttt gctccagacc tgattttct gttcactgtc ttcatttgga   93060
tgtcttttag ccacctaaaa cttagtagtc ccaaaactcc tcttattatc ccttccctca   93120
tgcacaaact tggccctttt ttgttgtttt tctttcacag tgaataactc tgtcatctgc   93180
ctatttgtac aaggcagaaa actaagcatc ctcttattgt tcatcttct acttccctaa   93240 ttatcttgga tatttctcat tcctttaatt tgccattgcc accactttac atccaagcca   93300
ccacctctca ctcaggtgat cacagtagct tagtttcttt gaacagttgc ctctgcgtgg   93360 tccatttct tcatagcagc caaagtagat ttttaaaagg aaaatctatt atgacattct   93420
ttggtttcag attctttcaa caaagatgtt agatttatc ctaagaatta atatggccta   93480
caaggctctg gaaattctgg acccttgttt ttttcttagc catgatgtat cccttcagtt   93540
aaggatctaa ctctaccttt tttctgtttc tgactagaac ttcgtccaca gcttcatcct   93600
agtcatagct gtgcttctgc tttcaatgcc ttgcctatgc caaaaattct agattatcca   93660
gcagctggaa ggatgtagga tgccaattta aaattgcttg tgtgtgctcc cacgtgtgtg   93720
tgtgtgcctg tttaccctca aactaaaatt agtttttaaa cttcaagctt acacttttta   93780
aaaggattta aatggtgggt acttacctat ctatgagttc ttttagttat aatagcttca   93840 cccttttct taaaaggtgg tttgtcctga ttgtagtgat gagattgctg taaaaaagga   93900
caatattctt gttcgatctt tcaaagatgg aaaattgtaa gtataattta cttggtttga   93960 aaaccagtt tataaaatata tgctgttatt ttgaattagg atgttaaatg attaattagt   94020
```

```
tatttccaat taccttaggc ttttattttt catcatacag aatgtttcaa agagtcactg    94080
tttttcatat tatcttaatg tgttgtagtc ttatagtatg tttttcctta ctaattttgg    94140
taatcttttc caaactagac actcagtact gtctaatttg tcaacacttg tccacataat    94200
agctggttat ttgaggcaaa tttgccatat ctaatgtatt taatacttta ttgattttt     94260 tgttttttt gagacggagc tcactctgtc acccaggctg gagtgcagtg gtgcagtttc     94320
ggctcactgc aacctctgcc tcctgggttc aagctattct cctgcctcag cctcctgagt    94380
agctgggact ataggtgcat gccaccgcac ccagctaatt tttatatttt taatagagac    94440
ggggattcac tgtgttgtcc aggctggtct cgaactcctg atctcgtgat ctgcccgcct    94500
cgaaccccaa agtgctggga ttataggcgt gagccatcgc gcccggccta ttgatgtatt    94560
tattgacatt atttccttag ggtttgttct tgatggtcta attaggaatt tccaatactt    94620
ctactagtta tgtctaatgg ttatagtgat acctgttgga taatactcaa cttttgcagt    94680
agtctgagga ttaaaatggg ttacttgtat atggatggta agtgttaaga aaatgatttg    94740
ttaatttttc tttaagaatt atatgactag agaagccaga tattttatac agaattgtat    94800
tgggtataaa taccttaaaa aggtcatcat gttttaagat ttgatgtttg aattttcaag    94860
ttcgggaaag gtattttat tttaattat tttattttac tttatttcat tttttggtg      94920 agggtctcac tctttcaccc aggctggagt gcagtgacat gatcatggct cactgcagcc    94980
atgacccttt gggctcaggt tatcctttca cctcaatttc tcttgagtag ctgggactac    95040
acctggctat ttttgtattt tttgtagtga taaggtttca ccatgttggc caggctggtc    95100
tcgaactcct cagctcaagc gatccaaatg ccctggcctc ccaaaatgct gagattacag    95160
gcgtgagcct ctgcacccag tctgaaaagt tagcttcaaa aacagtatgt aggctgggcg    95220
cggtggctca cgcctgtaat cccagcactt tgggaggcct aggcaggtgg gatcatgagg    95280
tcaggagtgc aagaccagcc tggctaacat ggcaaaactc cgtctctact aaaaatacaa    95340
aaattagcca ggcatggtgg tgggcgcctg taattccagc tactagggag gctgaggcag    95400
gagaatcgct tgaacctggg agatggaggg tgccgtgagc agaaataatg ccattgcact    95460
ccagcctggg tgacaacaac aagattccat ctcaaaacaa aacaaaacaa aacaaaaaaa    95520
aatgtagaac caacttttaac aaaattggga taatcagagg aatttgagca cagaaattga    95580
atattgactt aatattaaat tgttgggggg taaggaaaat gggaaaacgt tagtaaaacg    95640
gcacaaactt ttattggtaa gatgaataaa atgtacagga tctgatgtac agtgtggtaa    95700
ctagtattct ggcagcctcc caagtagcta gcactacagg tgtgtgccac cacgctcggc    95760 aaattttgt agggtttttt tttttgcca tgttgcccag gctggtcttg aactcctgag      95820
ttcaagtgat ctgcccactt tggccccaa agtgttggga ttacagttgt cagccactgt     95880
gtccaacctt tatttattta tttatttat tttatttact ttttttgag atggagtttc      95940 actcttgttg cccaggctgg agtgcaatgg cgcaatctca gctcactgca acctccgcct    96000
cccaggttca gcgattctc ctgcctcagc ctctcgagta gctgggacta caggcatgca    96060
ccaccacacc cagctaattt ttatattttt aatagagatg gggtttcacc atgttggtca    96120
ggctggtctt gaactcctga ccccaggtga tccactcgcc tcagcttccc aaagtgctgg    96180
gattacagtt gtgaaccact gcactcagct caacctttat tttttaagag atgggatctt    96240
gctctgttgc ctacgctaga gtgcagtggc acgatcatag ctcactgtaa ccctgccctg    96300
ggttttttcc agtcagctcc ctgcctcaga ctcccaagta gctgggacta caggcacatg    96360
ccaccactcc tggctaattc tttgcttact tttttagttt gtctgtggag actgggtctc    96420
```

```
gctatattac ctatcctggt cttgaacttt ggcatgaagc agtcctccca ccttgacctc    96480
ccaaagtgtt gggattacag gcatgaatca ccatggctgg ccccaaacat tttatcatta    96540
tattgccata aatcgttttt ggccgggtgt ggtggctcat gcctataatc ccagtacttt    96600
gggagactga ggtgggtgga tcagttgagg ttaggagttc aagaccaacc tgtccaacat    96660
ggtgaaaccc tgtctctact aaaaatacaa aaattagccg gtggtagtg gcatgtgcct    96720 gtaatcccag ctactcggga ggttgaggca gaagaatcgc ttgagcctgg gaggtagagg    96780
ttgtggtgag ccaagattgt gccactgcac tccagtctgg atgacagagt gagaccctgt    96840
ctcaaaaaca aacaaaaca aacaaaaaa agttttcagt gttgcatttg ggcaggggac      96900
tctggtattt gggaacacgt tggtgtttat aaaatagctc ttatggtagg atccttctgt    96960
agatgattac gtattttaac atcctgtctt gtatgttatt tctgacttgc tactctgtgt    97020
gcaatcactt ttattgtaaa cgtcaacatt cccatatttt cagtatcttt ctgtgatatg    97080
taatcatctg gattcttaat taatctcagt catattttgg gktttttttc ttctcttata    97140
attaaaaaaa atatatagta cttcagttcc aagaaaagat gtccatgaaa ttactagtga    97200
cactgcacca aagcctgatg ctgttttaaa gcaaggtaag gataatcttg gaataaatta    97260
caagtactgt aaaaactgct aaagtgtttt tgaagattaa attttctctt gctctttaaa    97320
atttttcttt aaattatgtt tttatggtta tatttggttc cttgtgacct ttattttat    97380 aaacccatgt gtcttctgtg ttataagttt ccttttcttt ttttttttg gagacagagt    97440 cttgctctgt cgcccaggt ggagtggcgc aatctcggct cactgcaacc tctgcctcct    97500
gggttcaagc aattctcttg cctcagcctc ccgagtaact gggactacag gcacacgccg    97560
ccatgcccgg ctaattttt gttatttaa tagagctggg gtttcaccgt gttgcccagg    97620
ccggtctcga actcctgagc tcaggcagtc cacctgcctc agcctcccga agtgctagga    97680
ttacaggtgt gagccactgc gcccaaccat aggtttcctt ttttttctg ttttttttt      97740 tttttttttt tttagcttat agtcagtcat aataatctag aataatggga gagaactgtg    97800
tagtcagctg ttactataat ctagcttttg cctggtaaat aaaatattag tttctgggaa    97860
tggtagaaga aaggaatcaa agtaactttg tgttgttgtt ttttttgttt tgttttgttt    97920
tgttttgttt tgttttttg agatggagtc ttgctctgtc gcccaggttg cagtgcagtg    97980
gtacaatctc ggtgcaccct ccacctcccg ggttcaagcg attgtcctgc ctcagtctcc    98040
caagtagctg ggactatagg ggcccaccac tatgcccggc taattttgt gttttagta    98100 gagacagagt ttcaccattg accaggctgg tatcaaactc ctgagctcag gcagtccacc    98160
cgccttggcc tcccaagtgc tgggattaca ggcataagcc atcacgcctg actgaggaat    98220
caaagtaatt ttggtttggt atttctcact aatgaatgta catccttaac cacaaggctc    98280
cagtagtttt atttgaggaa tatgtggtaa ttgcatctgt cacttgattt ttggcactgt    98340
aaatagttgt cttctcttg cccttattcc ttgaattcag taatatgcta tgtagattgg    98400
ttaaaatcat caagatttt tggtatataa tttattccca tatattataa aatgagaata    98460
attgtgtcta gctaattta gttgaaggta attgttacca tagttttaat tgaagttcaa    98520
ctgaaaatgt aaaaatcatg tgtggtcagt tttcaggtat tgtatattta ttttaatggc    98580
tctgtgcctg gtattaatac tgtttgataa ttgtttgttg cataagatat tacatgattt    98640
cctgtattaa aggttttac tagtgaagct taatctttgt ttaaaagaat aaaactgctg      98700 ttctttatt tatttaaact taagtaatct tccaatggtg gcagttttgc catctataaa    98760
```

```
atgactacct aatgcatagg atggatagga ttaaatatat tgctacattt aaaagcactt    98820
aacacagttt ctggtacata gcaaacaata aatgtcagtg gtattagcac agtagttttt    98880
atttctttat cgtgtttaat acttttgag aaaacaattg tcttaatttc ttcagttcat     98940
gtaccttgtg gtctgtttcc agcctttgaa caggcacttg aatttcacaa aagtagaact    99000
attcctgcta actggaagac tgaattgaaa gaagatagct ctagcagtga agcagaggaa    99060
gaagaggagg aggaagatga tgaaaaagaa aaggaggrta atagcagtga agaagargta    99120
agtgaaaaca gttgataccct tttaaaatta taaataacag ttgggtttcc cttgtgggtt   99180
aggatttggc attaagtcat tactcatata agtatttta gtatgagaaa tatttcataa     99240
tcttgtattt gagatcctca taatcagata gtttacttgg ttactttaga tatatgatct    99300
tgtgaaatag aaaatattaa gcctgatttt cctaataacc tcaaaaacat gtcttagtct    99360
tcctatgctt ttttaatga gatgattaag aaagtatcca ccaggctggg cgcagtggct     99420
caggcctgta atcccagcac tttgggaggc caaggcaggc ggatcacgag gtcaggagat    99480
cgagaccatc ctggctaaca cagcgaaacc ccgtctttac taaaaataca aaaaattagc    99540
cgggggtggt ggtgggcacc tgtagtccca gctactcggt aggctgaggc aggagaatgg    99600
catgaaaccg agagacggag cttgcagtga gccaagatcg cgccactgca ctccagcctg    99660
ggcgacagag cgagactctg tctcaaaaaa aaaaaaaaac gagaacaaaa acaaaaaaac    99720
ttaccatcta ggccaggcac ggtgactcac gaccataatc gtagcacttt gggagggcaa    99780
ggcaggtggc taacttgaac tcaggagttt gagaccagac tgggcaacat ggtgaaaccc    99840
catctcaaca aaaataaaaa taaaaataat tagcagggca tgtcagtgca ctccagcccc    99900
agtgcactca gtagcccag ctactgagga ggctgtgttg ggaggacggc ctgagccctg     99960
gaggtggagg ttgcaatgag ccgtgaattt accactgccc tacatcctgg gtgacagagt   100020
gagaccctgt cttattaaaa aaaaaaaaaa aaaaaaaaaa agaacctacc tacctaattc   100080
tttaaaatgc ttttcattac catgttgaca gctgtcacct catgaaatgc ttacatctcc   100140
atattttatt gattaaccca gaaaagtata aaatacatct ttcatttaat atttaaaaga   100200
aaaatcaggc cgggtactgt ggctcatgct gggatgacta atcctagcac tctgtgaggc   100260
cgaggcgggc agatcatgag atcaggagtt cgaggccagc ttggctaaca tggtgaaacc   100320
ccgtctctta ctaaaaatac aaaataatta gccaggtgtg gtggtggaca cctgtaatcc   100380
cagctactcg ggaggctgag gcagtagaat tgcttgaacc cgggaggcgg acttgcagtg   100440
agctgagatt gcgccattgt tctccagccc gggtgacagt aggagacccc gtctcaaaaa   100500
aaaaaaaaaa aaaaatagca gaaagtaaaa gatcaatatc tctttgattc agagaatctt   100560
gaatcatttt atctaagaca aatgggtaga tagttctgat tagatcataa ataagccata   100620
aaatatggct caaagagctc aaattttgga tttattttta cctggagctt tagatctggc   100680
agtgacaagg tactctttaa tggtttgctg aacagcctcg taaaagttaa tgagtggtgc   100740
agatagtgaa ggctgctata tttgaccatg aaatgaaatg tatttaatgt gtttagtaaa   100800
ttaattggtc agtatgtaat acttaggta agttatgaaa ttctgccttt taactgtagt    100860
aaagtattaa tgaaatgaga ttgttttgga ggttatattt tagggtgtag tgatctgtaa   100920
tgacaatgta taatgtagaa atttccctgc ttcagtcttc tccctgactg ctttctattt   100980
aaattgctaa aatcagcaat cattcccttg ctgctaaaaa cctcctgagt agcttttgt    101040 cactgtaaaa gttaagcttt catatagaat ctcctttata gtccaattcc tgcctcaatt   101100
ttttctcatc atttcccttt ctgtgtcctc ccccttgaac tttatgctat agcaatgtca   101160
```

```
aattacatat gttgctgcta ctcacctttg catatgctag tacctctgta ggcaccacct   101220
tttcctcccc tccttccttc gtcagcatgg tacattcctg ttcaattttc agaaccctac   101280
ttaggtgcca tctctctaaa gagaaacctg tgaaccatca cctccctcac ctcaggaaag   101340
caccagttca tttgctagtc taaactacta ctgctcctgg caggcacggt gggtcatgcc   101400
tgtaatccca gcactttggg aagctgacgc tagcggatca cctgaggtca ggagtttgag   101460
accagtctgg ccaacatggt gaaacccgtc tgtactaaaa atacaaaaat tagctgggtg   101520
tggctgggcg cggtggctca cgcctgtaat cccagcactt tgggaggcca aggcaggcag   101580
atcacctgag gtcaggagat cgagaccatc ctggctaaca tggtgaaacc ctgtctctac   101640
taaaaacacc aaaaaattag ccgggcatgg tggtggacgc ctgtagtccc agctactcag   101700
gaggctgagg caggagaatg gtgtcaaccc gggaggcgga gcttgcagtg agccgagatc   101760
acgccactgc actccagcct gggtgacaga gccagactcc atctaaaaaa aaaaaaatta   101820
gctgggcgtg gtggcaggtg cctgttatcc cagctactag ggaggctgag gcagcaggat   101880
tgcttgaacc caggaagcgg aggttgcagt gagccgagat gacaccactg cactccagcc   101940
tgggcgacag agcaagactc tgtctcaaaa acaagacaaa acaaaaaaag aattactact   102000
gctccttata catatttttg tcatttatat ttattgtcta ttttttcttc cccacgaatt   102060
tgtaagttcc ttaaagttag gaatgctgtc ttactcgtat tcatacttaa agtgtctgtc   102120
atagtgtgta aaatataaca gatgataaat agctaccaaa ccttttggtg cttagtgttt   102180
tcacaagtgt ttttgtaaaa gcaaatctgt agtgtagtgt aaacattttc ttgagttaaa   102240
agcttacctt aaatgttttt ggaataggaa aaattgtgct gtttattaaa gttaaatatt   102300
gtaccatggg aacatttaag ataacatcta gaaaatagat gtccttagat ttgtatttga   102360
tcaccttacc aaaacctgaa tgtatggagt gtgtttaaat tgagaaatac agattcatca   102420
ttagcaaatt aatggttgtc atttatttt ctctgcccaa ttagaaaacc taatagttga   102480
tcaacatagg ctttaaaaaa aaaattacct ttctttgttg tactagcttt taaattaaaa   102540
agacaatctc gctaaagcag tggcattagg cacatgattt tccaaattga aaatgctat   102600 gtttttattt atttagatta ccagttgaat atcctaactt ttactgttac aaatctgtat   102660
atttaagcca gagtaactgt aaagcctagc tgtatatttg gaatcatttt ctctgcagtt   102720
actcctaatc atgttctgta acagtaggct ccatagccta ttttttcttt tatttgattc   102780
agcacctggc atagtaccta cacttacagg tgctcaagtg tttgttgaat ggatgaaagt   102840
cattgaattg gtgagttcct caatcttaac ctactaccct gctccttgca ggttgcttca   102900
ggaccagctc cctgctgcca cagcccttgg ccacagcagc aagaagctag tccttcccctt   102960 gtaattgata aattggggaa ctattttatt acttgaagat ttccctaagt ctgaatcttc   103020
aggtattgta gatcaaattt gttccccact ttactgatta tgtaagcttg aagtatatac   103080
agtggggctg cataaaatga aggatacttg cagtcagcta atgggaccca acttttata   103140 gtaccttgag gagcaataat agaattagtt ttgatgttta actctgatcc agtttcgcat   103200
aagttgagag taggtattct tgaacctgtg atcctgattt gaaaaatagc tctctcatat   103260
ggtaaaaaaa acaaaacaaa acaaaacaaa accacgaaca gtcttgctag tcccttttct   103320
catatgggaa ttttactgt ggggattcta actattggga tactttttaa ggcatattcc   103380
tctataaaac ataaaatgtc tagacttacc tggttttgaa cagcttagtg ttaaagagt   103440 aactttgatt acgtaaaaag cctttgaagt attttaatga acactagtct ttgctattgg   103500
```

```
taagaaatct gcttgtttta ttaaaatgct taattgaaga aaataatatt cttctgtgat 103560
taaaattagg aagaaataga accatttcca gaagaaaggg agaactttct tcagcaattg 103620
tacaaattta tggaagatag aggtgagtat tttttattta tcattaacgt ggtaagtttt 103680
ggacagataa ttagtatctt aaaaataaga atagaatttt gtttactgaa ctttatgtca 103740
tcagtaatta tggctgtctt tttgactctg atatcaccag cacctagcat agcgcctgtc 103800
acgtawcaag tagaatgagg aatttgatag cattttgaca gatattgtgg ctatggacac 103860
ataaatgcac ttattaccct gtcctgccaa tccctttacc tatccatggg tccctaaaga 103920
acagtagcaa aatgggaatt aagccagaaa tagataaaga agtgtgacaa agtctcaaaa 103980
gtgagccttg gctcagctta tttaatctgc cagaagctgc taaggccacg gaaggattga 104040
aggaagaaga ataacttagg gtaatgaact aatccttccg taacctcaac actgttattc 104100
tctagcttat cttcttggtc agagtctact ttcttctttt ctgggaagat gcttgtaagg 104160
gagtaaggag aggctttcta gctggaaggg aagggcaaaa tgaatgatta gtgtttggaa 104220
acaccacaat actctgggaa ttgaacgttt tctaaatccc tgattgtaat gctgatgagt 104280
agaaactgac tctgtttgtc atgtttagtt ttcataaatg ataacaacgc ctaacacaat 104340
ataagtatat tttctttttc aatataaaat gtctttgatt cttgtattat ttctttacat 104400
gaatggaggg ttggcctaag aagtatgctg tttcataggc tcttgtataa gataaatgaa 104460
aaagcaaaga aaatgaataa aatctaatac tagaaaagaa tgaaaaaata tgattaagcc 104520
agtcatatat tttgtagaaa tggccatatg aggcattgta cccctacect gttacctcct 104580 ctaccacttt ctcatggttt gtttgattta gcatccttgc cttgcgtttt cttgtgttag 104640
aatgaaaaaa aaaaaaaaat gtagctttac tatagaatca ttatttagag tagtagtaaa 104700
ttggtaaaat acaagaaaa tgccataaaa gtaactctta ttgggaagca gttatctagt 104760
atttcttccc tcagcagagg gaagaaagta gaatgaaaat aaaaggtttc aagaatctgg 104820
ttatggtttt taaaatttaa aaaatttaa agtggccatg ggcttattta tgtgtagata 104880
ccatgtcttt gattaacaag ataatttctc atatatatat atacatatat atgtatatat 104940
acacacacat atatatacgt gtatatatat atatacgtgt atatatatat aaaatactat 105000
aaatacttgt attatttgaa tcttttgaaa ttttaaatta aaaatgtagt gtggatctaa 105060
tatagtttgt gttttctgta acaggtacac ctattaacaa acgacctgta cttggatatc 105120
gaaatttgaa tctctttaag ttattcagac ttgtacacaa acttggagga tttgataatg 105180
tgagtgttgt agtcaaactg aaacatcttt ttcatgtaac atgttttctc aggtatctgc 105240
catctctgaa attgttttc taaacaacaa aacaaagttt ttcagtaaaa acctaagaag 105300
aagataaagt ggaaagtaca gctagcctcc tcagacaaaa tttaaatttt aaagattttt 105360
taggccaggc atggtggctc atgcctgcaa ccccaacact tgggaggct gaggcgggta 105420 gatcacttta ggccaggagt tcaagaacag cctggccaac atagcaaaac cccatctcta 105480
caaagaatac aaaaatcagc cagacgtggt gacgcacgct tgtaatccca gctacatggc 105540
aggctgaggc acgagaatcg cttgaaccca ggagacagag attacagtga accaagattg 105600
caccgctgga ctgcattcca gcctgcgtga cagaatgaga ctctgtctca aaaaaaaaa 105660 aaaaagatt ttttttcata tcagcttct gattactgtt aaattggtca atctttcata 105720
aaccttcttt ttttatctga gtcacagcac agccatattg gtggaaatcc ttcctgtgtc 105780 tcttttttcat tagacagtat gctccttaag agcaggatc tgtcttaata ttctgtatat 105840
tcttaatccc tttcagaata taaagggatt aaagcaggaa atgtttgttg aactgatctg 105900
```

-continued

```
aagaaattat tttaaggttg acgtgatgta cgatacttat ccaattgaga atattctatg   105960
gaataaaata ctttacaaat ttctgcagaa ctgcatttat tagcctgtat attttatgcg   106020
aaataataaa tcctttaaaa atgtttgtct ccatttcttt gttaaaaatt ttgatttaag   106080
agcctgaata ttttcccatt ttccataact gggtttattt aaaagtcaaa tggggccagt   106140
tatggtgact catgcctgta atctcagcac tttgggaggc taaggccagg ggattgctgg   106200
agcccaggac tttgagaccc gcctgggcaa catggtgaga ctccatctcc acaaaaaaaa   106260
tttttaatt agccaggtgt ggtggtgtgc atctatagtc ccagctactt gggttgttga   106320
gtcaggaaga tcccttgagc ccggaagttc agggctgcag tgagctgtgt tgtgccact   106380
gttgctgcac tttagcctag gcaatagaat aagatcctgt ctccaaaaaa aaaaaaaaa   106440
aaaaaaaaa aaaaaaaata gtcaaatgac ttaatatttc aacatttata attttctgat   106500
atttgttaga gtactaaaac ctttatttt aaaccaaatt tagaatttat caagttttta   106560
aaaattcttt tgagtctagg accaataaat ataaaaatat actcatatat actgtgtcta   106620
tcaaaatgtt attatattaa cacctttaa tttgagagtt tttgttttcac tttgtccatt   106680
agattgaaag tggagctgtt tggaaacaag tctaccaaga tcttggaatc cctgtcttaa   106740
attcagctgc aggatacaat gttaaatgtg cttataaaaa gtaagttagt ataattgata   106800
tgattatctt cagtatttt acctagaaag caggatgaaa tttaccttat aactgaggtt   106860
aattatttct ttaaagaaat cagaacattt tactagagta gtcattctat gatagtattt   106920
tctaaagtgt attctatgat actagatcta tgagaaattc tgtgaagaaa gttttgtgg   106980
ctaagtacat ttgtcaagta cttcatagag gttaaaagc taatattctg aagtcaagta   107040
aatccacatt tgaatcctag ttctgccaat tattaactgt ttatgcccta gggccagtta   107100
tttattctcc taagcctcag tttcttcatt tgtaaaatgg aatgcttggc caggcacggt   107160
ggctcatgcc tgtaacttca gcactttggg aggccgaggc gggcagatca cttgaggtca   107220
ggagttcaag accagcctgg ccagcatggc gaaaccttgt ctccactaaa aatacaaaaa   107280
ttacctgagc atagggctaa cgcctgtagt cccagctact caggaggctg aggcaggaga   107340
attgcttgaa cccaggaggc ggaggttata gtgagctgag attgcgccac tgcacttcag   107400
cctgggcaac agagtaaggc tgtctcaaaa aaacaaaaaa aaacaaaaaa aaacaaaaaa   107460
aggatgctgc tgtgtgcccc agggttactg tagtgactaa atgagattta ctaaggagtc   107520
cagcctcaca cataagaaat gtgcaaaaaa tagatgctat tactaatact tttaatagct   107580
gttattgtta tgactctgag cacagtgttt taaatgaatt tttttgacaaa attttttttt   107640
tgcattgaaa agattagaaa gaactagaat aaattagaat gttaatatgg ctcaatatct   107700
gagagtttag acaaaagaaa tgaatacaca ttaaaaataa ctctatagtt atattttgaa   107760
atgttttcac caaatgtaat ttctcttcat gtttccagat acttatatgg ttttgaggag   107820
tactgtagat cagccaacat tgaatttcag atggcattgc cagagaaagt tgttaacaag   107880
caatgtaagg agtgtgaaaa tgtaaaagaa ataaagtta aggaggaaaa tgaaacagag   107940
atcaaagaaa taaagatgga ggaggagagg aatataatac caagagaaga aaagcctatt   108000
gaggatgaaa ttgaaagaaa agaaaatatt aagccctctc tggtaaatca gatattgtta   108060
attgtctttt gctttctttg gtatattttc catatcctct ataaagttcc aaaatcaata   108120
tattgtataa tattattctt tattattgt ttattttctt cattaagtgc acttttgta   108180
taattttat cataacttca aaatagctgt tagctatttt tgtctagagc tttaaagtag   108240
```

```
caggagtttc ttaaaagtaa tttataactt ttaatattag aattggttga tacctcctgt 108300
tgctaagrga taaaccatgg ataggttg aaaatttta cttttgttgg tttctttcct 108360
ctgatctttt tctagggaag taaaaagaat ttattagaat ctatacctac acattctgat 108420
caggaaaaag aagttaacat taaaaaacca gaagacaatg aaaatctgga ygacaaagat 108480
gatgacacaa ctagggtaga tgaatccctc aacataaagg tagaagctga ggaagaaaaa 108540
gcaaaatctg ggtaagaaaa ttgttttggg ttacgatgca tttcagcttg atggattctt 108600
atcatttgct ctttgtatgt gtttatgtat gaatctaaat taattgacaa aatattaaat 108660
aatagagtga ttggcattta ttaattaaat agcattcact tctttcagag accctactga 108720
tagaaatttg tagagaaaga tcatactttg atccaccctt cttgctctca tcatggaaat 108780
tgataaaatt tttagctaga gcaaagtact ttttaggtct gctgaattac ttgataatat 108840
aaacttgggg ctatgtccat gttttatata ttgtatgttg gctatagatt ctgagagttg 108900
tatttatttc ttaagcaaaa gcaagagtgg aaaaatacta aagttttaaa aggccaaaaa 108960
ttgtatgttc tattttatgt gatagtagca tttgtttgtt ttagtcactt ggaatgatga 109020
attatttgac aatgtaattt atgcactgct agtggacccc tggattttat agataatctt 109080
tggcattgaa tctttttct gaggcttaaa aaacataaac atatctgtta gtgtctcatt 109140
taaataagta caatgaatta aaaaaaaaat catttagcag gccaggtgcg gtggttcacg 109200
cctgtaatcc cagcactttt gggagaccgg ggcgggcaga tcacttgatg tcgggatttc 109260
aagaccagcc tggccaacat accgaaaccc tgtctcttct aaaaatacaa agaagtcagg 109320
cgtggtgaca tgtgcccata atcccagcta ctcaggaggg tgaggcagga gaatctcttg 109380
aaccctggag gcagaggttg cagtgagctg agatcgtacc actgtaggcc agcttggggg 109440
atcgagtgag actctgtctc aaaaaaaaaa aaaaaaaaa aaaaaaaaa aaaaaatca 109500 tttagcgtac tgacatttgg ccacagtatg cagacgaaca gggaagggga aaataaaaaa 109560
tggggcttat atgaatatag taaaaaatgt ttattatact ttgttgtatt tttgtgtata 109620
aaaatatata tttgaagtat gccttactgc tgttgggagac tatttcaagt attaagaaac 109680
agtaaagatt tcagctttt gcctaaaatc ttttgattga tcagagttct gaaattttgg 109740
tggcaccata caaacatgga agaaaaacat cctgggttta gaagaatgta gtaaagtgt 109800 ttgttgatta tactttgtta tatttctatg tgtagaagtg tatgtttaaa gtactgctaa 109860
aggagatcat tttgataaga atcttaataa agattcagct ttttaccaaa aaatctgatt 109920
tttaaatctg cagatgtttc tggaacatct gctgtttgca aggcactgtg ataaatctgt 109980 attttttct ttgctaattt tttaagttgg tgcttctgct tattttatag aataaactgt 110040
attttgtagg tttttaacaa cccctttaac tgtataatta tatggatttt tatgtactac 110100
agatatttat tagtatatgc gtacctcaaa ctaaaatttt cctgatgtga ctgccctagt 110160
ttggtagata ttttttagaa gcattgcagt tgggactgtt tatatagtac tccctgcttt 110220
tccacagttt cagttacctg tggtcaactg tggtctgaaa acaggtgagt acagtgcaat 110280
aaaatatttt gagagagtga gacaagacca tattcacata actgttatta tagcatatta 110340 taattgctt gttattagtc attgcttatc tcatgctgtg ccttattaat aaattaaact 110400
ttatcagagg tatgtatgta taggaaaaaa cacagtatat ataaggtttg gtactatcca 110460
cggtttcagg catccactgg ggatcttgga ctgtatccct tgcagataag aggggcttac 110520
tgtaattgat ttttgagttt tattagataa ttgcagtgga aaattttaca gtgataatta 110580
atatataggt atttttctgg catataaact ttctctaagt aataggctac taccaagaat 110640
```

```
gttcagtgtc cttcttccat tgtccagatg tgggagattg aagaagttga tatatgtaaa    110700
atgtctagtt cagtgccttg gccatagcac gtacttaata cactatcttt tttaaaattt    110760
ttgtttcatt gtaaagagtg taatatcaag tagggaagta ttgatatttc tttgtgaatt    110820
cagatgaaaa tccttgctga tacatttcgt ttcccaagat attcttctct aaaatatgac    110880
tagcttaaat gcatatgtgt gtgtatgtat gtatgtatgt atgtgagtgt atgtatgtat    110940
atgagtgcat gtatgtagtg tatgcatcaa cttaattttt tttaacctgt atgtatgttg    111000
gttgcatttt atactttcag aggctctctt tcttggcatt ctgtgttcca tctggtttag    111060
cacattagtc ttgaatttgc cactgaagtc ttagagagta gaatagtttt ctttggttga    111120
ttgccagtaa ttatgttgtt tttttcttta tacttcagtg tattattaaa gtgaatttca    111180
tttggtttgt gtctgagggt gatattaaat gtatatttt  aattttgat  tgcttgattt    111240 cattaataaa agagtgttgg gttttgttg  tagattgaat gaaaatttgc ctgggctact    111300
acttaaagta tgattgtgct tgctgttggc atttagaatt gtttgtattc atcaactcag    111360
tgtattctat gatgtaagat acagcttgga gtttgtcgtc atttcaaaaa atttagaatt    111420
ttgattctat atctcatttt tatatgatga ttctgaggtg catgataaat ctctttatt     111480 gtggccacaa taaaatatgc ttcttttccc cactatgcaa agatagagtc ttatgactta    111540
ggcaagtatt ctttcaaaaa aaaattgttt taatttacta tataaaataa aattcctcat    111600
aataatttat cattgataat cccatttctg ttaattttt  tgatatttta gccttaataa    111660 aattacttt  ttataataga aatatattt  tcaataacat tgttaatatt ttaatctcag    111720
gctgggtgcg gtggctcatg cctgtaatcc ctgcacttcg ggaggccag  gcaggcggat    111780 cacctgaggt caggagttcg agaccagcct ggccaacatg gtgaaacccc atctctacta    111840
aaaatacaaa aaatcagcag agcgtagtgg catgtagtcc cagcttattg ggaagctgaa    111900
gcaggagaat tggttgaacc tgggagacgg aggttgcagt gagctgagat cacgccactg    111960
tactccagcc tgggcaacag agcgagactc tgtctcaaaa aaaaagtata tatatataca    112020
cgtatatatg tgtgtgtgtg tgtgtgtgtg tatacatata tatgtatatc tcagattata    112080
gctggtttca tgaaggtttt agattttta  aatacttata tatttgactg taactgagtc    112140
tttaaaatag gaataaatct tgagaatttt tgaggaattt gtgttatagt tcagacaaaa    112200
ttgatatatt tgatactttc gtgaacacgg acttacttcc accggtccat taaacatcct    112260
gccaacactc ctgccccact atacaaaagg acaaggagaa taaaaaagca ttatagtgct    112320
gcttatatca ctatttatat attattttg  ttgcctgtat aattaattag gaatgataaa    112380
gtatattatc cctaaaaagg ttgcatatag agatataaag ctgaaatttt cagtggagga    112440 agttttttt  ttaatataaa tattatattc atcaggtggg cacagtggct cacacctata    112500
atcccagcac tttggaaggc caaagtatga agattgcttg agcccgggag ttcaagacca    112560
gcctaaacaa catagtgaga cccctgtctc tacaaaaata aaaataaaa  aactatctgg    112620 gtgtggtggt gtgtgcctgt agtcccagct acttgggatg ctgaggtggg aggatcattt    112680
gagcacagga agtcaagacc acagtgagca gtgatcaggc cacttcactc caacctggat    112740
gacacagtga gaccatgtct ccaagggggg gaaaaatata tacacacaca cacacacaca    112800
cacacacaca cacatatata tgtgtgcatg gtgtaatata tgtatatata taatcattac    112860
tcttaatata taatatagca tatattttaa tatatcatgt attttacata ttattaattt    112920
ttaaagctta aatactaaac tatctggttg ttctgcctta tgatgtttag tcatttgtga    112980
```

```
gccctaaagt gatggagtct ttaagtacag acatacagga cagcaaataa aaccagacta   113040
aatgtagcct tggatttcat attgaaattt tttaaaaaat aaatctagtg tttggaaaga   113100
tttatgattg aagattttct ccaacttgtt gaatacagat tggtggtcaa tataaaaagg   113160
atatgaatgc tcagttttag aaagtacatg gtactaagaa gataaaaatg ggtgtaaggc   113220
caggtgtggt ggctcacggc tgtaatccca gcactttggg aggccacggt gggtggatca   113280
cctgaggtca ggagtttgag accagcctga ccaacatggg gaaaccctgt cactactaaa   113340
aatacaaaaa aaattagctg ggtgtggtgg tgggtgcctg taatcccagc tacttgggag   113400
gctgaggcag gagaatcgct tgaacctggg aggcggaggt tgcagtgagc cgagattgcg   113460
ccattgcacc actccagcct gggcgacagg agtgaaaatc tatcaaaaaa aaaaaaaaaa   113520
aaaaggatgt aatactcttt ctagaatagt ttgacttttg gtttcatata cttgtaattg   113580
gcctctcatc tgtctatttc tttggaacat caaagttgag aagatttgta gaagatgtta   113640
ataaatctgt ggtaatgaga gtagaaattg tgttgaagtt taaaggaaag aacaaacatg   113700
ataagatatt ggtagtacat tattagaata tttctgttta aattaaaata gtatttcagt   113760
tattataaca tttgaaaatt cggttggaga atgttttaaa gttattaaga ctgccatctg   113820
ctagtaaaaa ttattgtttc aaacttcctg aggcctccag cttgggtgac agagcaagac   113880
tctgtctcta aaaaaatgaa acaaacatct tgaggctgga aatatttgaa tgaaaaataa   113940
tttttagttg taaaatggca atgaagtata atgaattttt ttgtcaattg agatgttaaa   114000
acacttttat taataaaaca tgaaaaaatt gttagagttg accatacttg cttcttgctg   114060
ttcggcacaa attctgttct tctgactttt ggaaattttc ttttactgca cttatttttg   114120
aatcttcatt ttctctaaat gtgtctttct gtaaccttgg ttgtcttaca gttttagttt   114180
ttaatagtaa aatgaaactc tgagaatttc atacacgtgg aacctgcttt tcctggaaca   114240
atcacagcca caacttttat caatatatgt ggtttggaac tgaaaaactt atgaagtgtc   114300
ttttattaac tctgcaattt tttaaacctt tcaagagatg aaacgaataa agaagaagat   114360
gaagatgatg aagaagcaga agaggaggag gaggaggaag aagaagaaga ggatgaagat   114420
gatgatgaca acaatgagga agaggagttt gagtgctatc caccaggcat gaaagtccaa   114480
gtgcggtatg gacgagggaa aaatcaaaaa atgtatgaag ctagtattaa agattctgat   114540
gtcgaaggtg gagaggtcct ttacttggtg cattactgcg gatggaatgt gaggtaactt   114600
gagttttagc tagtgattat tacctaaaaa caattataaa atacttttct atttaaaaac   114660
ttaagtaatg gattacagat ttattagtat tctaattgag gtcatagtac cttataaaaa   114720
atagttttta gcatgtaaat acctcactta gtgacttaca attaatgttt tcactactta   114780
gaagatatcc ctaatgtcta gaaaaccgag gtctacacac ttgatttta tgtactacat   114840
gtagatcagc agacaaaaca ttgttgaaat gatcagaact tctggacatc tacaaaccaa   114900
ttatcaggct gcttgctgtc ttgcatttta aactacattg ccacagtaac ctctttttg   114960
tattctgaag tcatttcttt ccttctgtag tcagggattt aaaatcctag gaaacattag   115020
ctattttaag aaagccttat ctccttatta acagctattg cattcagcc ttattcagaa   115080
gtctcagaaa tttattagta tctttgaaaa aatctggttg aacatgtaag cagacctgct   115140
tcactaaaat agaatgcact ttttgactgc tcctaaccta gggaactgaa aggcaagagt   115200
gaaatttggt tttaagtcat gttcaatgac ttaagcattt ttcttagata aattttcttt   115260
ggctttccaa agaaatttg tattttgatt ttatccaaaa ttggcaagcc agttttggga   115320
tctattcatt cagttatctt ttaagaatca tttattttag aatatttgat agtatatttg   115380
```

```
aaatgtagcc tataagacag atacctggaa agattaacca tagaagttta agttgtggtt   115440
tcatggtgta cctagtgtct tcaaggagga atacagttct catgctttat acttaaatta   115500
tattctgtgg tttgggaagt taataggaag gcatcatctc aaattctgtg tttgagtgtt   115560
gcaaatgaaa ttttgattct ctttaatcac ttcccacaat gcccttctc taaagaaaat    115620
cacttctgag agttttgagg ctgtccttac taacttttca ttctactttc acatacatat   115680
aaatgtactc atagaaaata tatagtattc ttacatgcat gtgttttaaa taaattatac   115740
tatacaaaat tctgtttctt aaattttttg ttgtcctgtt gtgtaatagg aagctcatga   115800
tctaatctga ttacctttct tattttgaga aaagtaccag tccgatccat tctgatgctt   115860
ggaagaaaat agcaaatagc aaatagcaac ttaagtcatg aggagatgtt cagaagtttt   115920
gttttggtct cattctttat tatgtctaat caggatacag ttttagattt taagaatacc   115980
tatcgtcaga gctagatgt gatagtcatc cagaaacata agttttttcca gataccactt   116040
taacacactg cacaatttat cctttcacct gttggttctt tttttctgtt ttttgttttt   116100
gttttttgtct ttttttggag atagagtcta gctctgttgc ccaggctgga gtgtagtggc   116160
acgatctcta ctcactgcaa cttccacctc ccaggctcaa gcgattcttg tgctgcagcc   116220
tcctgagtag ctaggattat aggcgcccac cattgtgcct ggctaatttt cgtattttta   116280
gtagagatgg ggttttgcca tgtttgtctt gaactcctga cctcaggtga tctgccttgg   116340
cctcccaaag tgctgggatt acgggtgtca gctgttggtt cttatgctgc ctttctggta   116400
tgtgattttc ctcacctgaa ggtctggcta ttaatgaata tattccaaag aaggtacttg   116460
agatctcaga tatagctacc aaaagaatat tttgcccaat ttttacttc tagtcatttt    116520
gatcttacta aattatctta ccgaatataa atgtagaggg agttctactt ctgcctagga   116580
tataaatgta aatgtagaat atgttagttt aaaattagga agaaaaaagc tgggtgtggt   116640
gttgcatgcc tgtagtccca gctactgagg tgggaggatc acttgaaccc aggaattcga   116700
ggctgcagtg aactatgatc atgccactgt actccagcct gagtgccaga atgagacctc   116760
atctcttaaa ttaagaaata cttggattag caaaaacgaa taattactgc ataatgccca   116820
tgagatagag tcacaacacc ttttgcctct cttttttagtt tttctgatta ttttgctagt   116880
ttacatgtag aggcagtttt tcctcttggc ctttatgaag tatttgaaat tctatgaaaa   116940
agggatagaa tttaggtgtt ctccaacttt cactgtatat aatcagggct catttccttc   117000
ccttcttcct tccctccttc cctccttcct tccacggagt ttcactctta atgcccagcc   117060
tggagtgcag tggctggatc ttggctcacc gcagcctccg cctcccgggt tcaagcgctt   117120
ctcctgcctc agtctcctga gtagctgaga taggcacgca ccaccacgcc cagctaattt   117180
ttgtatttt agtagagatg gggtttctcc atgtttgtta ggctggtctc aaactcctga   117240
cctcaggtga tccacctgcc tcagcctccc aaagtgctgg gactacaggc atgagccacc   117300
gtgcccggcc aaggcttatt ttctattaat tggctcttta aacaaaaaag gcttagtaga   117360
tataagaact gagtcattca tgaaactgtt ttacaattaa gatatagctt tgttttgtta   117420
agaaaagatt gactaaaaga aagagaattc caggagtatt ttgattttag atggtagaaa   117480
gaatctctag taatttagtt tttaaatagc aggaagggaa aggaaagaat ttaaattgag   117540
gcattcaagt ttttaataat atagggagga aaatgcgacc tagttcaaca agacatgctt   117600
gtgttactgt gaacgttgcc atctatttct gagaactcaa gtgcttgtat gctatgaact   117660
ttcaaaagaa gaaaacttaa catcttgatg aagacctgta ggatggatct ctatacactc   117720
```

```
caacatcatg gagaaaacaa atgtacttca gtagattaag cagttaatct tcttagagtt  117780
aacataacta ttttatttct ttctgcaata atcagtctgt cttattgata aataagcaat  117840
aattttatt  tttgcggctc ctccagttct gaagctaatt taataaggac tgcaacaaat  117900
cctcatcagc tgtatgacaa ttttctttt  attttaggg  tcttcagctt gatctctaaa  117960
tttatactta acagatgtga aattggaaat gaagatttat gcgtggaggt tcatgaaaat  118020
agttttatct tcagtggtag tcattcatga caagcagttt gggagatttg tgtgaccta   118080
tttccatggt ttttttaatc tgaaacaagt atttcagatt aaaaaaaaag agagagacag  118140
acaggacctt gttctgtcac ccaggctgga gtgcagtggt gcaatcatgg ctctccagcc  118200
tcgacttctt gggctcgagt gatcctccca cctcagcctc tggaataggt gggactctag  118260
gtgtgcatca ccacacctgg ctaatttttt atcttttgta gagatggggt ctcactgtgt  118320
tgcccaagct ggtttcaaac tcctgggctc aagcagtcct cctgccttgg cttccaaaag  118380
tgctgggatt atagacatga accaatgctc ctggccatga acatgtttt  tccggtaaag  118440
agattttctc aaataatgta agagtgtctg tcttttgtt  taaaaatact gtttttaggc  118500
caggcacggg tagctcatgc ccataatccc agcactttgg gaggccgagg cgggcagatc  118560
acctgaggtc aggagttcga accagcctg  gccaacatgg cgaaacctca tctctactaa  118620
aaatacaaaa attagccaga catggtggca ggtgcctgta atccgatcta cttgggaggc  118680
tgaggcatga gaatgacttg atccaggggc acagaggttg cagtgaacca agatcacacc  118740
attgcactcc agcctgggtg acagagcaag actccatctc aaaaaaaaaa aaacaaaaca  118800
aaaacaaaaa aaatcaattt tcttgttaat ttttacattt ttcttttttt tctaactaaa  118860
atgctgtttg tttgtttgtt gtttgttttt gagatgaggt tttgctcttg ttgtctaggc  118920
tggagtgcag cgccgtgata tcatctcact gtcacctccg cctcccaggt tcaaaagatt  118980
cccctgtctc agcctcccaa gtagctggga ttgtaggcac atgccaccat gcccagcaaa  119040
tttttgtatt tttagtagag atggggtttc accatgttga ccagactggt ctcaaacgcc  119100
tgacctcagg tgatccacct ctgccccgt  aagtggtggg attataggcg tgagccactg  119160
cgcccgacct gtataaatct ttaatataat tttcatgtat gtccctattt cacagctgaa  119220
aatgttgatt tttgttatac aaaggttaac atttgggcaa gtttgttttc tactgttgtg  119280
atgaaaaaaa gtcatatttt aacatgttca caccacattt actggaaagg gcttgaactc  119340
tttaaccaca aatattataa tactcttaca gaattttttct gatgcagtga cagtatctaa  119400
aactattgtc tagcactata ttacttacta tgtcaccaag cactaggcat gtttggagta  119460
tgctcataaa ttatttttta aactcttcta aaaataacaa tttagaaaaa tacataaaag  119520
tagaaagata aaattattgc tggccggccg ggcacggtgg ctcacgcctg taatcccagc  119580
actttgggag gccgaggtgg gcggatcacc tgaggttggg agttcgagac cagttcgaga  119640
ccagcctgac caacatgaag aaacccatc  tctactaaaa aaaacacaaa attagccag   119700
gcatggaggc acatgcctat aatcccagct actaggtagg gtgaggcagg agaatcgctc  119760
gaacctggga gacggaggtt gcggtgagcc gagattgcgc cattgcactc cagcctgggc  119820
aacaagagcg aaactccatc tcaaaaaaat agaaaaaaaa taataataaa attactaata  119880
ttatagtgtg ttctcttta  gtcttttaaa atgtctccct acatttaaaa aaatttagt   119940
tctgcttaag tagttttaa  tagtaggctc tctatttaac ttttcttagt gatgttaata  120000
ttttatagag aatcttagca taattatcta attgatccct ttcactctca agtttctaag  120060
tcgtgtcgta aatatgggat tgattttga  aagtaagggt acacattgaa attaacatgc  120120
```

```
cgtaaactag ttgagtgtgt tggatttctt tgtttagtaa caactgagtg aaactatcta 120180
gactaattgg catggaattt aaaatacatc aatattttgt aatagtgtat caatactgat 120240
tgaattttct cgctcatttc caacttggct ttctgtaatc aaagagttgc aaatttagtt 120300
agagaataat ttttttgtatg ttgaagatca ccagctgcat taatgggaac ccaaaagtaa 120360
aagagacact gtaaaacttc agttgtaaaa ctcttaaata agccacaaca gttcagtgc 120420
atgttaacag ttacagagaa ctgaaaataa gctaaattat gctaaatata ttatttgaaa 120480
ttaaaaatgt gttacattta aaaatatttt tcgccaaaca aattaaatcc tcttaggagg 120540
gaatgagtta ggggatgaaa aaacctggta aaaggctttc acaaatgagt aggctcaatc 120600
ctattttttg ccatcattca gttgcttttt atcacacttt attcctttat tttccaaaca 120660
taagttgaat acccactatg tgccaaatac tgtgcttgtc accaaagata ccaagaagtg 120720
gtccttatta aggaattcat aataataata aattctttat taaggtattg atcctaccac 120780
cccttacctc ttcaccccag ttaatgcact cagtcttccc ttgatattgc ttacattccc 120840
tggcattatt attataatca cttcttttga ctcaagctgt tcttttttctc tccttttgct 120900
ttatagtact catctgacaa accacaaga accttgatta aatctaaccc tccagctcct 120960
tgcctgcacc tgtgcagccg atcgtggttg gagtaaagca agcaaccaca atgactgttc 121020
ttattttaaa ttcattactg tgaacctcaa gtgggtcctt aattctctat gtccttcttc 121080
cattcacttt cctactttct tagaagacta tttcatactg ctgcttatgt cttcacatcc 121140
ccaacatctc ttccctatcc tcattttcag ctggtgacct tgctttgtac ctactgagag 121200
atagaaacaa gaaaaacatt tctacacact tcataagatc tgcctaccta actgcgtttg 121260
ctgccacatt ctctgtgttt tcatctttag ccatagatat acagtcatgc tactgtctga 121320
agccagtctt cataagcatc ccttcttgac tgatcaaaga catggcccat tttcttgctc 121380
tgttctgagt cattcccact acttacagat ctgtggttat tgtcacatc tcaaggaaaa 121440
tcttttctgg agcctgactt ctactgtgac atttcttcgc tccatttca ttcagcagaa 121500
ctgtttgaaa gttacctaca cttgttactc agtttctctc cttttctgt gtaaatccac 121560
tctcatcagc cttttgttca ctgtgtctcc acaactgtgc ttaccaggaa cactagtgac 121620
cctttgtaga taaattcctc ctgcttttct tgccctctta cgtacctat cagtggcttt 121680
acagtcagtt gatcactcct tccgtgatat gctttgcttg ggctccagct gctccagcta 121740
caaccatttt tcttgtttat tttccttttc ttccttctc aaaattaaga aaccactcct 121800
caattatctt ttctgtcttc ctcatcttta tgtgttttct cccttctaat ttttcccta 121860
tttctttctg atatccattt aacatttttt tggtttctgt tcctattttt ccaatcctaa 121920
cttgagtcac aattctgata ttgaattttt ctaaattatt tttccgagcc aaaggaattt 121980
gatctggaat ataactttca cctaggactc tgggtaaatt cttttccctc aactctcctc 122040
ccctccttt tctttttttc ttcatcgttc aagctttcta cattaggact acgttatgta 122100
ttattacaaa agtgaactta attttaaaat atgaaaaaaa tttctgtttc atatctattc 122160
tcctaatatc ccttaccaca tctagaaaag tattcatttg gcatatgata agtactaaat 122220
gaatgttgaa ctaaattgga cctcctgaca acaaaatgga agtagagcag aaggtaaaat 122280
ccaaataaaa gccactggtt ttttaaagtg atacctataa tagggggattg ggacagatat 122340
ggcttgaccc tctcactgga gctgcttctc acctcattta tatataactc tgtgtttcac 122400
attctaagga actgtcaaac ttttccacag agacgacacc gttttacatt ctcaccagca 122460
```

```
atgtgttagg gttccaggtt ctctgcagcc ttgtcaacac ttgttattct ctgtttatct  122520
cattgtgctt ttttgatttg catttttccta atgcaacatt ttttcatgta cttgaaatgt  122580
agagttgaac atttttttcat gtacttatta gccatttgta tatcttcttt agaggaacgt  122640
cccttcaagt ttttgccatt tttgaattgg tcagttgttt tgttgttgtt gaattatagt  122700
tcttcatata ttctagatgt tattcccttta tcagatacat gattgcaaat gtttcttttg  122760
ttgcctctgc ttttgatgtt atttccaaag aaacattgcc aaatccagtg ttctgaaaat  122820
tttcctttat gttttcttct aagaacttta tagtttttagc tgtaatgttt acattgttgt  122880
tctaatctga gttcatattt gtatatgata tatgtgacct ctttgggtta cataaagagc  122940
tcatctctta gcaaacaaaa tggagtcgag actgagagac tggaatgaat ttgattggaa  123000
atattaattt tctgttactt tttagctatt cttagtctcc ttttgtcctt aaaaaatttt  123060
taagtcactt ttcagcttaa tttctttgtt ctttcctgct ctaaaatgtt ttgtgtcctt  123120
catttttttt ctttcttatt tccatgtaat ctgatccctg ctgtacttga gttgtgtatg  123180
ccattggatt taggaatatt gaaatagagt acaaagttgt tctactcatt ttctttgaaa  123240
taattgtcct ggtaatgata gaaagcaagg taccctggga agttgtctgc gttgtttcta  123300
tagtacagaa gtcagaggcc tataaaatga ccatttgaca gtggtttcca ttatctgtaa  123360
gtttgtatta aaagagagtg gcttttgagt taaccataga ttttgagtac aaatgaacat  123420
aaacatttcc ttcatgaaaa aaagatgata attcagttat gtgttgtact caaatgggct  123480
ttaattttc tttgtgtatt catccttagaa tgtttactaa acttggacct gtttcattca  123540
gtagtttcgt agattggcag gtacattgat attttttgtct aagtacgcac aaataactaa  123600
ttccatacat ttatcaaata ttaacaaagt acacttttgg ggaatttaaa aaacttagca  123660
tctgcattac aatatgcaat taatggcaca gttaaccatt tgcagttgtc tttgtacgct  123720
ttggtaaaat gctgtattag tgttcttatt attacatatt acctctgcct aaagacctat  123780
acttccgttt catttatag cgttacattg cttaggaaaa cctattgata taattactat  123840
accattccgt tgagctgttt atgtcaactc ttaaatatga ctatgctata atatttatgg  123900
ttctgtcatt ctgctgttat attcttaagt gtgaggaata ccatcgctgt ctctctgatg  123960
tagatttaag tgttatatga agtagaaata tgaaatgttt atatcatact taggaatttc  124020
attttatttt attttatttt gaagcggagt ttcgctccgt cacccaggct agagtgcagt  124080
ggcatgatct tggctcactg caacctccgc cttctgggtt caagcaattc tcctgcctca  124140
gcctcccgag tagctgggac tacaggcgtg tgccaccatg cccggctaat ttttgtattt  124200
ttaggagaga tgaggtttca ccatgctggc caggctggtc ttgaaatcct gacgtcatga  124260
tccgcctgcc ttggcctccc aaaatgttag tcttacagat gtgagccact gcacccggca  124320
ggaattttat ttttgaataa tatactactt ttttgtttca ttttattgta gatacatgat  124380
taaaagtatt aattgtgatc agttgttatt ttcatatatc ttgttttaga tagtcagatt  124440
aaaatacata taaattgaga ttatataaaa ttcataaagt aggtaaatat tgataaaatt  124500
gcttatgaag tttataatta ataatgatta acactgcttt ttatcttgac ttggtgtttt  124560
tttctattat tttgtcatac ttttatttat ttaattcagg tggggaaatc cctttccata  124620
ctaagacagt acaaatttcc actttagatg tgaggttctt aaaaactaag taagttaatt  124680
atatgacata cattaacttt tttgattata gagaggcaag atataaaata catattgtgc  124740
aacaattatt aaatgaatct attcattata gaaagcaaaa tatagatgat tttaacatttt  124800
acttaatggt tggttattag atttttatct tatctataca tatttcaaag agtgaggttt  124860
```

-continued

```
caagtttata ttaatttgat tttacttacg aagttatttt taaaataccct ttattctgca 124920 tgctgtttat ttttaaatct cttaagactg tgctttttag gtatatatta actatatgct 124980
gataatattt cttttaaaat tgggtttaag aagaaccaaa agctgaattg atgtgggcat 125040
attaaccatt ttggtagtat atctggtcga ctaatgttct tttccatttt tattattaca 125100
aaatgatttc ttacataatt tgccaatgca tctgtacaaa agccataaag ttttcttttt 125160
agaaatccaa tttttctgtg gtgagagcaa gtatgctgtg gtctctgaat ggtatctttt 125220
agccttgtat gaatatttt aaacatttga aaaatcaaat atttgtgtgg tggcttcttt 125280
cagaaagttt cacgtttgta ttcacaattt gtcattactg tttagtattg tcttcttttg 125340
ttgaattgta agctcctcgc aggcaagggc tgtgtttgtt gattcattgc tgagtaccca 125400
gtgcctagca gactctgtta ttacataata gataccttag aggtgtttgt caaatgaata 125460
cgtccacatg tgtacttatg gtcttggagt ctcatataat ttttcattct acggccaggt 125520
gtggtggctc acgcctgtaa tcccagcact tcaggaggct gaggcaggca aatcacctaa 125580
ggtcaggagt tcaagacaag tctggccaac atggcaaaac ccagtctcta ctaaaaatac 125640
aaaaattagc tggacgtggt ggcacacacc tgtaatccca gctactcagg gggctgaggc 125700
aggagaatca cttgaacctg agaggcggag gttgcagtga gctgagatcg caccattgca 125760
ctccagccag ggcaacagag caagactccg tctcaaaaaa aaaaaatt tttttcatt 125820 gtacttcatt ttatgtaggt cagggaacat actagatctt cagaagttaa atgagtttat 125880
catgcatatg ttattttatg ttttgttagt tgaatgttaa gtgatctcaa tagaaatatt 125940
atcagacaag tcatatatat accttggaaa tattttcctt agtactttag ataaatattc 126000
aataagatac ttgtttagat tccatctgta gaattaatta cattgactgt attgataact 126060
gaattgaaaa agtataggct aatcactgtc ttaattttct aactcaatat ttgtttttaa 126120
tatttgtttc aatacttttt gtttatttca gtatttctt ttaaatggaa gcatttagta 126180
atgctgtttc ccttgtgccc tgcaaaatta atttatttcc tgttattatg aaaaggccaa 126240
ttatgatttg taatcataat tcctaaaggt taagaccagt taaagccagg atagataaac 126300
tatcctggat tgtatatata tgtatatatt gtgtatatat atgtatatat tatatacaca 126360
tatatataaa ataacaaccc agtctacctg aattttcaca ttttcagaaa actgtattgc 126420
ttgaatctaa aattgcaaga caatttattt tatttttttt tattttacat atttttttga 126480
gacagagtct tgctctgttt cccaggttgg agtgcagtag tgcagtcttg gctcactgca 126540
acctctgcct tctgggatca agtgattctc ctgcctcagc ctcctgagta gctgggatta 126600
tagacatgcg ccaccgtgcc cagctgattt ttgtattttt agtagagatg gggtttcgcc 126660
atgttagcca ggctggtctg gaagcatttt aaaaccaaaa ggtttgtatt taacttactt 126720
actaagatta ttgtattccg ccagatgcgg tggctcacac ctataatccc agcacttcgg 126780
gaggccaagg tgggcgaatc actagagccc aggagtttga gaccagcctg agaaacatag 126840
tgacaccctc tctctacaaa atataaaaaa attatccagg tgtggtggtg aatgcctgga 126900
gtcccaactg ttcaggagtc tgaggtggga caattgatac tgggaggtca aggctgcagt 126960
gagccaggat ggcgctaccg cactccagtc tgagcaacag agactctgta tgaagaagaa 127020
aaaaaaaaaa agaagattct cgtattcctt aagaatgtac tttcggggat gaatagatat 127080
cttacttgac gtggtacccc aaggagaaat tgagaaatat tttatggcct tctatttctt 127140
agctgcagtt tcactctttg ccacttcctt tccagttatt ttgttttact ttattttat 127200
```

```
ttatttatt tttttggag acagagtctc gctgtgtcac ccaggctgga gcacagtggt   127260
gcgatcttgg ctcactgcca cctctgcctc ctgggttcaa gtgattctcc taccccagcc   127320
tcccaagtat ctgggactac aggtgcccgc cgccacagcc agctaatttt ttttgtattt   127380
ttattagaga cggggtttca ctatgttggc caggctggtg ttgaacacct gatcttgtga   127440
tccgccctcc tcggcctccc aaagtgctag gattacaggc ataagccacc gggcctggcc   127500
tattttaatt tttatgaaa ttcaagatat gtgaacttga gctaaaattt cccattttct   127560
atctgcattg actatttcct tatctattat gtctaaggta aatttggtgt tgtctctttt   127620
taatatatac taaatgtact gtattttaa aagtctaaat ttataaagaa gaagtaggat   127680
taactgtagc ttttttgttgt agttctgaag taaattcttc tttgaagcct gtgcttcttt   127740
ggtaaggaat gagaaatctt gacccactaa tattgctttc ttaaattaat tggcaccagt   127800
aattatgcca gtctaagacg ttcttctta tataatttta atgtctgtag gaaatatggg   127860
gttttcatgt agagttttttc cccgcatgaa ttttatttt ttgagatgag tcttgctctg   127920
tcacccaggc tagggtaccg tggcatgcga tctcggctca ctgcaacctc cgcctctcgg   127980
gttcaagctc ttctcctgcc tcagcatccc aagtagctag gactacaggc gcccgctacc   128040
acgcctggct gattttttgta ttttcagtag agacacggtt tcaccatgtt ggccaggctg   128100
gtctcgaact cctgacctca tgatctgccc acctctgcct cggcctccca aagtgctggg   128160
attacaggca tgagccactg cgcccggcct aattttatc ttttgttag agacggagtt   128220
tcaccacgtt ggccaggctg gtctcgaact cctggcctcg ggtgatctgc ctgtctgggc   128280
ctcccatagt tctgggatta caggtgtgag ccaccgtgcc cggcctcccc acatgaattt   128340
gcttttttt tttttttcc ctattctttg aaaatatcct gtagagaaaa tagaaggaac   128400
acttgggtag tattgtaatg ggtaattaca tatacggaag gaacatttct tatttttaaa   128460
agcaatgatc agttatagtt atttaatctt ctgaccatct ttatttttct tgtaagatct   128520
atcagacaac taaagtgcta tttaacgtct cattaggttt tgaaatactt gtctgccaat   128580
atgtttgtgt cagtgatctc agcttgtatt tggtaaggac atttgtaatt cgaaaaagct   128640
tccccaacca aaattctcac atgttatttt ctccttttct tcctcttcac gccactggtc   128700
tctcactctt cactaaactt actctgaata gggcctggaa tgcccctac cgttatttc   128760
gtgttagaat cttttcccgg gcagtccatt tccttctctt ctctaattct ccacaggagt   128820
gcttttggc aagcactgtc tttcactttc attgttggaa tttcttaact tgtgaaataa   128880
aggccctgat aaattttaa gatatgctct agttctaaaa gttattagtt ttgataacag   128940
taacaatatt gtgtaactgt gttttataca aagagcataa ttggcaaggt aaaaaaaaat   129000
gcaaaaactt agtgtcaaaa caagggcctg aattaaacaa ataaaagcac tgagaaagta   129060
gaatagaaag aagccaaata acagaagagt cataatatta gctaatattt atagatctgt   129120
taagttagat ctataaatat aatgtaatat tattatacat tatgtttgct gttagattac   129180
attattactc tatagtaagt tttcagggaa tttcttaaaa ccatacagag tattccatga   129240
gaattttttt tgttttgttt tttgagacgg agtcttgttc tgtcacccag gctggagtgc   129300
aatggcgcga tctcggctca ctgcaacctc cgcctccgg gttgaagcga ttctccagcc   129360
tcagcctccc gagtagctag gattacaggc atgcgccatc atgcctggct aattttttgtg   129420
tttttgtaga acagggttt caccatattg gccaggctgg tctcgaactc ctgacctcag   129480
gtgatctgtc cacctcagcc ttccaaagtg ctgggattac aggcgttagc cactgcgccc   129540
ggccccatga gaattttaaa acaaaaattt tccagaatag taaggccata ctgttaatta   129600
```

-continued

```
caactatgta tgtagtttgt ttcatctaat ttaagaattt attttttgtgt gtgtgtcctg 129660
cctgctccaa cacactttg acatctaaac tcaactactt aacattttttc tgacatccag 129720
tcctcttgta ccatccttct tttataattg agtagaagag aacatgatta ccatatagga 129780
tttacagagc ttaggcagtg ggccccagcc tgtaccatac caagcatcca tcattttatt 129840
atttatgtgt atgttcttgc caccttgttc ttaagagaat ttaaacaaca tacattatat 129900
ctgagtaata aaggaatctt cctttatcac agtggcctta cccatgaggc agtaactgtt 129960
tttccttgtt tgatgtgttt ggtgttgcat gtaaaatata caaatgtgca atatcatgca 130020
tgtattctta aattgaaaac tactatttta ccctacttca aaatataatt gataataaaa 130080
cccaggttga attgagtcag ttttttattg atagtaaaac atgtctggta taaaactagc 130140
tacagaacag atagcctttg gttaagaaag gtagaacatg attataactt tgtttagctc 130200
acattaatgt tatgtgcagc catcatgaac tgacttcagt ttctctcata aaaaattaga 130260
aagcttgttt tgttttctttt taaaaacaaa gttgatatct tgacttcttc tttccataac 130320
tcttctaata gagcaacttc taggagttca tactgaaatc tacagaggat ggaggtgttt 130380
tcttttcgtt tcccaccatg cccccgattt tggaaggaag taaattgctt tcctaagcat 130440
tatacaattt tcgatattaa taggaaaggt aaaagtactg ctgcaaatat atggatagat 130500
gctacagtgc caggtagaag taccaaaagg agtgtattta gtagaagaat acttacttta 130560
aagcttttca aagtacttac catatatttg tacttacacc agtacttacc atatatttct 130620
acaaaaaaac ccatatatgg tatgtaccat tatttttttat tttgttttta aattgtagtc 130680
ttatttttata cagaaataaa ctaagcctta gattgagaat gagttgatca ggaccacata 130740
actaggaagc agggattatg ttaagtctgt cctaaagctc attccattcc ctcttattct 130800
tattacggcc ctcagcatct tccagcatat aaacagaacc ccttgcatgg ggatgaatcc 130860
tcagcttttc tggcttttac tggctacaag ccagtagttt gtaccagcag agtaactgcc 130920
caggagtttg ctacagatac tttccaggcc tatgctagag taagaatata atttattagt 130980
caagtaatga ctcaagtcat ttacttcttg atttggggac tttgttactt ccttttaata 131040
cctctaacaa tgaggacatt ttaatttaaa agctcgtttt caggtgtcca tgttctagag 131100
ttttgtgttt tctatgagta atgtatataa ctttgaacac aaaaagagaa tgtcaattag 131160
tttttaatgt ttacttcttc tagctgttat aattcttgaa tgaatgaaga acgaataaac 131220
tgtcattctt ttttttttgc tttaaacaaa tagttttatt gcagttaata gtaatttgca 131280
ccctatgaaa ttgtgaagac catcagcatt gaatcaagag gccatcacag ctgttgactc 131340
agctgtctgt acatgtaggg agcatttcag aatactgaaa aactttgcag agtaatgttt 131400
ttctggtatt ttatgagcaa gcatttttttt ttttctagtt gattttgcat tatccatacg 131460
ttacaatatg gtgctttttct tttcttattt ctttttttttt tttttttttg tgaaacagag 131520
tctcgctctg tcgcccaggc tggagtgcag tggcgcgatc tcagctcact gcaactccgc 131580
tcctgggttc acacgattct tctgcctcag cctcctgagt agctgggct acaggccccc 131640
accaccacgt ctggctaatt ttttgtattt ttagtagaga tggggtttca ccgtgttagc 131700
gttgatggtc ttgatctcct gacttcgtga tctgcccgcc ttggtctccc aaagtgcta 131760
ggattactgg tgtgagccac tgtgcctggc tgtaatacgg tgcttttcta ttacacaatg 131820
ccatttaaaa ctgaagctat taccttagct ctctgatgtg tctagagaaa aattgcctac 131880
ctgctgctta agaatgaaac aaagtaaaac aaaatgtaga aaatactgtg atttatctta 131940
```

```
atacttactg tacagattca gtttctcttt gttgtagccg agtaagcagt gctagttgag 132000
gaatcatgag atcatgctct ctagtcttgg ctcggccagt agctaacttt aagtccatgg 132060
gcaagttatt acctccctct cttttgtgcct tggtagcttg ctcttcaaac caggaagctg 132120
agatgatttc caaggtcctt tcccttctaa aatgtcaaga ttctatatga gtttctcttt 132180
aatatggcat aggttatttc cgtggtatat attgtacata tttatattaa tttcctttaa 132240
ttttagatac gatgaatgga ttaaagcaga taaaatagta agacctgctg ataaaaatgt 132300
gccaaagata aaacatcgga agaaaataaa ggtaagtgct tgttttact acacactatt 132360
agctcttaaa aagaagtttt cctccaaatg atgcaattaa atatgtgtta gtgttacact 132420
ttattgaaat agcacatttt tcaaatgcta gatttgtata taattaattt tgtcaggtta 132480
gggaaagcat tttagaaaca gtactggatg atctttgaga cttttcagt cccaacatta 132540
tataaagcca ttcaaccaga ttttatttat ctatttctgc catttccttc ccctctagtt 132600
cccaaccagg agccataagg cagtgtgact tggagagaca taggttatta ttgtagctgt 132660
aaaccattcc aaggaagaaa aggctatctg gcaactcctt tttctcttct tctttatctg 132720
attatagtca gtggcttaga atatattcac aagatttttt tttttttttg agacagagt 132780
ctcgctctgt tgcccaggct ggagtacagt ggtgcaacct cggctcactg caacctccac 132840
ctcccagttc aagcgattct catgcctcag cctcccgagt agctgggatt acaggcacac 132900
accaccacac ctggctaatt tttgtatttt tagtagagat ggggtttcac catgttggcc 132960
aggctggtct cgaacttctg acctcaggtg atccgcccgc cttggcctcc caaaatgccg 133020
ggattatagg tgtgagccac cacgcccagc cccacaggat cctattaacc acgaaaatgc 133080
catgaggatt tacttaggag ctcatatgga aaattaatgt tactttatg tatgatagaa 133140
ttattcattc taagactaaa ttttcctaaa tgtttgatta gcatcttcta tgcatctgga 133200
atgatactag atatgtacca tccttaggag aattactctc actcaaaatt tatagtgctt 133260
actgctaact catgcttcag agagcttatt tttcctataa atcaacaaaa tttttaagag 133320
tagtttccag gaaatatatc ggcctttgct tatctatttg taaacaaata atttgagaaa 133380
atttctcatc ttttctcaaa acattaatat atcactgagg taggaaggtt gccctgact 133440
tgactttaca aaagtacctg gaattttgtc attcccaacc cacatatagt gagattttaa 133500
aatgaccacg ttgcaatcgt ttctttttt tcttgttttt ttgagacgga gtttcactct 133560
tgttgcccag gctggagtgc aatggcgcga tcttggctca ccgcaacctc catctcccag 133620
gttcaagcga ttctcctgcc tcagcctccc gagtagctgg gattacaggc atgcgccacc 133680
accccggcta cttttgtatt tttagtagag acggggtttc tccatgttgg tcaggctggt 133740
cttgacctcc tgacctcagg tgatccacct gccgcggcct cccaaagtgc tgggattaca 133800
ggtgtgagcc acctcacctg gcctcttttt ttagttagta tttaatttaa acgtattgtg 133860
attttaattc tgaagagcaa gttgtaggtt tgctagtcct aatcacctat ctgattgcta 133920
atttgattcc cgttattaaa gtataaatac aaaaccttt gatcatcctg tgtagtattt 133980
tgttaagtag ctttaaaaat ctggctgttt tgagggggctt cttatgttct ttctttttat 134040
gttaaatatt taacaacata ttctgtaata gtgagttaaa agtggacatt aacattgttt 134100
ctgataaatg cctatgata aattacgaca tacyttttt cttaacctag aataaattag 134160
acaaagaaaa agacaaagat gaaaaatact ctccaaaaaa ctgtaaactt cggcgcttgt 134220
ccaaaccacc atttcagaca aatccatctc ctgaaatggt atccaaactg gatctcactg 134280
atgccaaaaa ctctgatact gctcatatta agtccataga aattacttcg atccttaatg 134340
```

```
gacttcaagg taaacataac aatcgttctg ttgtgcaagt atttgatttt aatttatgag  134400
tcaagttcta taaaggtaat tcagtgacat taccaactac tgttttttct accagagttt  134460
tgtttgctct cttattacag gttgaatatc tcttaactga aattcttgga accagaaatg  134520
ttttggattt cagatttttt tttgattttg gaatatttgc attccacaag ccaaatccga  134580
aaattctaaa tctgaaatgc tccagtgagc gttaccttc agaatcacgt cagcactcaa   134640
aaagtgtatg attttggagt cttcagattt tggatttggg atgttcaacc tgtacttgaa  134700
ataaaatcag ccattgattg aggcctcaaa ttttttatta ctagtagatc caagggcacc  134760
ataaaatttt ggttaacatt taatattcaa cttttagcat tgttacttta gttttttaat  134820
cttttctgtg ccatcctttc tgttgcaatg taatgcatag tttgtgttat acaacatcag  134880
accataaaag tatactgaca agttgttgta aagaacacca aactttgttt gtcctgatta  134940
tgactattat gatctctgtt tctttgagac agggtctcac tctgtagcct aggttggagt  135000
acagtggtgc aatctcagct cacttcagcc tcaacctccc agactctaaa gatcctcaca  135060
cctcagcctc caaggagct ggagctgcag gcgcatgcca ccatgcccgg ctaatattta   135120
tattgtttct agagacgggg ttttgccctg ttgaccaggc tcgtctcgag ctcctaggct  135180
caagcaattg gcctgtctta gcctcccgag tgctaggatt acaggcagga gccactgcac  135240
ctggactgac tgcttttttt ttttttttga dacggagtct cgctctgtca cccaggctgg  135300
agtgcagtgg cgcaatctca gctcacttgc aagctccacc tcccgggttc acactgttct  135360
cctgtctcag cttcctgagt agctgggact acaggcgccc gccactgcgc ctggctaatt  135420
ttctgtattt ttagtacaga tggggtttca ccatggtctg gatctcctga ccttatgatc  135480
cgcccacctt ggcctcccaa agtgctggga ttacaggcgt gagccaccgc gcctggcctg  135540
acatgacctc ttttatgatg ggattattgc ttagtattta aggcaaaatg aagtataggt  135600
aataaaagca atgaggattg gagcagagat ttattaaatc tgactggcag ggaaggggac  135660
atatctatga gataaaagaa tggatctcca taaaaatatc ttatcatttc tcataactta  135720
aaagaggttt cattttttact tattttgaat gttaatagaa gctagttttt gtttcttatt  135780
gtagatgtgt gtttatatta actcattatt ttataaacca aatgctgtac tatattttta  135840
tttactcacc actgtactaa ttagggcaat atttttaaat tgattttaa aaaatttcc    135900 catgtatcct acatgcaaat agtgcatgga aaatacatgt atagtttaaa gaacagtaat  135960
aatatggata ctagtatgtc tccacagtag caatcaaata ctatttactt aaaacatgta  136020
gtatgtctcc tcccagaagt aattatagtc tggacttttg tgtaatcctt gctttacttt  136080
tcttcagaat tgaattatct atatttatat tcctaagtaa ttttattttt acttcgtagt  136140
atgtctcctc ccagaagtaa ttatagtctg gacttttgtg taatccttgc tttacttttc  136200
ttcagaattg aattatctat atttatattc ctaagtaatt tttattttac ttcattttt   136260 tagggtgttt ttttgttttg ttttgttttt tgaggcagag tctcgctctg tcacccaggc  136320
tggagtgcag tggtgctatc acgactcaag tgacctcctg ggctcaagcg acctttccat  136380
ctcagcctcc taagtagctg gaactacagg tgtgtgccac catgccaggc tatttttgt   136440 agttttgta gagatggggt ttcaccctgt tgcccaggct tgtctcaaac tcctggactc   136500
aagcaatcca atccatctgc ctcagccttc caaagtgtta ggattatagg catgagccac  136560
tgcacccagc ctgtttttta gttttttaaa aattgagtaa caagcataag cctagtttta  136620
taagaaggct cagatgaagg ctttctgaga atgttacctg aatagagatt ctaagtcata  136680
```

-continued

```
ctctgatttc agatttagct tctctgagag tttacaaaag cccctctaga gaattcagtt    136740
ggacaggtca taagccagtt ctgataaacc taggggtcca ctacagttag aatatctgac    136800
acatttggct gggcatagta gctcactcct gtaatcccag cacttttgga ggccaaggcg    136860
ggcagattac ctgaggtcag gagtttgaga ccagcctggc caacatggtg aaaccctgtc    136920
tctactaaaa aaaaaaatac aaaaactttg ccgggtgtgg tggtgggtgc ctgtaatccc    136980
agctacttgg gaggctgagg caggagaatc gcttgaaccc aggaggcaga ggttgcagtg    137040
agtcaagatc acaccattgc actctagcct gggtagcaac agcgaaactc catcttaaaa    137100
aaaataaaat aaaaagaata tgtgacacat tcgcagtgga tgttatgtgg gagtgtgctc    137160
agtcgtagta gcagactact ctatatatat tctcattcta ggcttatggt gatttacccc    137220
tatttttcac aagtaggtca gaatgttcct gctggataaa atgatgtcat tagctgatct    137280
aggtagtggc ataagacatg gaagggagt agctggaatt tcattgacac atagttgaaa    137340
caagataaat acagattta aaatccagtc tgggtcactc aggcattcaa agactacaga    137400
gaggcggtaa ggtagcttaa tgataatagc ctgcagtatg actttctttg gaaataacac    137460
tgctgtagtc tggactggtt tccctctata tctgttgcac agctatttc ctagggagat     137520
cccattctag ggatctcctt taatgtagtt cttggatttc tttgtttttg gcatctcagg    137580
ttcctcccca cccccatact ttcattttgg tggagcacat tctctagtag cttctaaaga    137640
acaagtgcat gagatggaat tttagagat tggctgcatt taaatatctg tatttatttt     137700
tgcaaatatc tttattctat tcatagtttg gctggattgg aagttttttcc ttcagtattt   137760
tattggcagt gttgaattgt ttttttgctt ccagtattgc ttttgtgaag tccagagctc    137820
ttccaattcc tgattctttg tatgtgactt gttttattct ttattttttg cttttctgtc    137880
tctggaatct tttttttttc ttttcttttt ttgagatgga atctcactct gttggccaag    137940
ctggagtgca gtggcacaat tttggcttac tgcagcctct gcctcctggg ttcaagtgtt    138000
tctcctgcct cagcctcccg agtaggtggg attgcagggg cctgccacca cgcctggcta    138060
gttttttctat ttttagtaga gatggggttt tgccatttg gccaggctgg tctcgaactg    138120
ctgacctcaa gtgatccact cacctcagcc tcccaaagtg ctgggattac tggcatgagc    138180
caccatgccc tgctaggaat cttgaatctt tgttttttcgt atccagaaat ttaactctga   138240
aatatatcta cacaaggcca aaggaagaga acagatatat ccacagtaca cttggctgtt    138300
ctctttcttt agccttgtgt agatatattt tcatcccctg tgatgcctac ttgctagact    138360
ctttcattct agcaacttct gtctttctgt tctaggcagt tttttttgaat gattttcttg    138420
atgatttcct ctcctgcatt ttactgttct ctccttttta attttttgttc attgttacta   138480
tttttgagat gaggtgttac tatattgccc aggctggtct caaacttctg agctcaagcg    138540
atttttcctgt ctcagcctcc caaagtgcta ggattacagg catgagctac tgtcccagcc    138600
ctgccaaatt tttttttttc tttaattgag actgtgtttc actatgttca gcccaggctg    138660
ttctcacact tctgggctca agcagtcctc ctgcctcagc tcccaagta gttgggtagc     138720
tggggtatag gtgcatgaca ctgcacttgg ctgttatctt tctttggcca gccattattt    138780
gatattatac cttctgtaat atactctaat atgctcacct tttaatttct tgctttttat    138840
taatttttt gtcttttat ttcttgaaa tttatctgc tttgtctttt aatccttttg       138900
ttgactttt gctgtaatgt ttaagttttc aatgattttt ttttttttt ttttttttg      138960
agactgagtc tcactctgtt gcctaggctg gagtgcagtg gcatgatctc ggctcactgc    139020
aatctctgcc ctccaagttc aagcgattct cctgcctcag cctcccgagt agctggtatt    139080
```

```
acaggcgcct gccaccgcac ccagctaatt tttgtatttt ttagtagaga tgggtttca    139140
ccatcttggc caggctggtc ttgaactcct gaccttgtga tccacctgcc tcagcctccc    139200
acagtgctgg gattataggc gtgagccact gcgcccagcc tttcaatgaa tatttttaaa    139260
ttaaactagt ttaattttc aagagctctg ttttctgtgt gttttgtacc actctgttct    139320
tatagatgga tgcaatacct tacctttcgg attttgatct ttcaaaggat tttataattt    139380
ttggtttttt cagttaccte taatttgctt ttttctgtgt tgttgttttg agctcttccc    139440
tattaagaat ttttttcct ggctgtctta tgattatgaa ggaaagacta aactgatttg    139500
gaaattgcaa gcatatggtt ggcacttgtt gaccttgagt ttcactatcg ggtgatctgg    139560
ttggccatgt cctagggaat tcataatatg aagtctttag gtcttttct cttagactag    139620
ttggcttcca gagaaaagag ttccaatctc ttgactggag ggtggtaaga gaatggtttc    139680
cagtgttcta ggatctagtt gaagaacaga gagtggggtg gaggattctt agtggttaga    139740
tatgttcatg aatcccccta atttcagcat cgcatctgta cctgtgcctt caacagttgt    139800
tagcatctcc caggctagga gccctctcct actgtcttca gagaataaag ctctagaagg    139860
gcagtcacct tccaacctga agtgaggtgg ggatctaggc atctaagtaa ttttagtct    139920
tcacccagtg ctccttgtat gaggctcccc actgcccttt ttaattttca taggcactag    139980
ggcagtcagt aattattgag gtttctatgg taaactgggg tggttttgg ctttcctcac    140040
tgctggtatg aggtttagcc ttctttggtg cccgtcattc atttatctgc tttctgactt    140100
gcaaattgtg ttgctttct ttcgtatttt cccccatttt tataggttta tattatttca    140160
gaaattgcat ttatataccca tatatatgac atatgagtat atacacac acacatacat    140220
ataacacata tacaatgacc ccaaacccccc ccacacacat atttatccta tatgtgtaat    140280
agacactcac atgtgtgcag tcttttaca gatgggatca ttaacatatt acaaactctt    140340
tttttcccct acttagtggt ataacttata aatctttcca aatcggcaca tccacatcta    140400
ctgaatagat atatcataat ttatttaatt agttgctaaa aaaagacatt ttgatccttt    140460
cccatatttt tcctgttagt tcaacaatga gtatcatatt tgcatacttt taacatttta    140520
agtattctct tcatattttc tttttcagt gaatttatt ttttatcttt ggccacagat    140580
caaattgaag acattcaaa tatttccagt taattaatga tcatcatatg aatgcatatg    140640
tgtatgtata tgtatacata aaaatttgat gccccttgtg agtagagaac acagacagct    140700
aagattctat cctcttgtcc tgagatgggt tgggaataaa actagaggta cagtggtagt    140760
tggagttctg tggagaaatt gaatgtctct ggagaataat cttctacatt ctggcagtgg    140820
aaatcccta gagtaaacta gatccgggat gaatcacgta aagcctatca gttaataaat    140880
cctactaaca gtagtgtcaa tcaagtttta ataggggcatt cttaatcatc tcttgttaat    140940
ctcagagaac ctacagtatc tataaaacaa gaataagctg ggcacggtgg ctcacacctg    141000
taattccagc attttgggag gccaaggtag gcggatcacc tgaggtcggg agttcaagac    141060
cagcctgacc aacagggaga aacctcgtct ctactgaaaa tagaaaacag ttagccgggt    141120
gtggtggcac atgcctgtag ttccagctgc ttgggaggct gaggcaggag aatcacttga    141180
acccacgagg cggaggttgc ggtgagctga gatcacgcca ttgcgctcca gcctgggtaa    141240
caggagtgaa actccgtcta caaaaaaaaa aaaaaaaaaa agaataagat gcagtgaaaa    141300
agaaaagaat aagatgcagt gaaaagaaa agaacaagaa agacttggag ataaaaatct    141360
aaaggccagg cacagtggct catgcctgta atcccagcac tttgggaggc caaggtgggc    141420
```

```
agatcacttg aggtcaggag ttcgagacca gcctaaccaa catggtaaaa ccgtgtctct   141480
aataaaaata ttaaaattag ccgaatgtgg tggttggtgc ctataatccc agctgctcag   141540
gaggcagaag catgagaatt gcttgaacct gcaccactgc actccagtct gggcaacaga   141600
gagagaccct gtctcaaaaa aaacaaaaac aaaaatcta aattaaaatt cagtagagct   141660
gggcacagtg gctcacacct gtaatcccag cactttggga ggccgaggca ggtggatcat   141720
ctgaggtcag gagtttgaga ccagcctgac caatagggtg aaacccatc tctgctaaaa    141780 atacaaaaat tagcttggcg tgtgcctgta gtcccagcta ttggggaggc cgagacagga   141840
gaattgcctg aacccgggag gtggaggttg tagtgaactg agatcttgcc agcgcactcc   141900
agcctgggca acagagcgag actctgtctc ttaaaaaaaa aaaaaaataa gcaaattcag   141960
tagagcatta agaattttaa atggaggaaa tcttcagaaa gtttaaaaga gcagtgatgg   142020
aaattttaga gaaaagatag gttacataat gtattaatct aggaaggggg aactatgaaa   142080
acagaggaga gaggccaggc gcggtggctc acgcctataa tccctgcact ttgggaggct   142140
gaggtgggcg gatcacgagg tcaggaaatc aagaccatcc tggctaacac ggtgaaaccc   142200
tgtctctact aaaagtacaaa aattagctgg gtgtggtggc atgcacctgt agtcccagct   142260
actcaggagg ctgaggcagg gaatcactt gaacctggga ggtggaggtt gcagtgaact    142320
gagattgcac cactgcactc caacctgatg acagagcaag actcagtctc aaaaaaaaaa   142380
aaagcaaata actaaagaaa aattccagaa ctgacagaca caaatcttta cattgaaatt   142440
gctcactagg taccgaataa attaatagag tcataccgta gtacatcatt atgaaattat   142500
aaaatatcaa gaatgaaaaa atcaccacaa aggaatgaga aaccaaagga aggttatggc   142560
ttataacccc ttaagcaaag aagcaataca ttcggaagga ttcagaactc tgaaggaaac   142620
aatttttaac ctagaattct gtacctcgtg aaactctcaa tcaatgaagt ttgagggtaa   142680
ggatgtattc agataagtaa ggacgatgaa tatttatatc ccatgtacct ttttaaggaa   142740
actactcgat gagctctagt acagatgaga taaccaagga agaagaagat gtgagattca   142800
gttaacagtg gacctagctc aaaagaaagc agtgaggagg attccccgga tgacagctgt   142860
tagagcagac ccagagagat accacccaga tgctactgca gaaaatagct ctctagggtg   142920
cagagatagg atgaataagg ggaaattgga tacaacgctt aatttaatga ataaaaataa   142980
tgtaaaagag atacaaagga agatgtaaca tgcagaaaag tagttggaaa ctcttggaaa   143040
aataaaatgc tgtataagaa aggaagttta tcaaatgtac tacttatttc tgcagggaac   143100
cacatttaca tatgttataa atactatatt gtaaaaatga aagataacta tatatagaaa   143160
ggatggtaga ggggagatat gggtgttgat aagtaagaat ccccattgct catagaggat   143220
aaactttata aataagtcag caggccaggg acgttggctc atgcctataa tcccagtgct   143280
ttgggaggct gagatgagca gatcacttgg ggtcaagagt tcgagatcag cctgtctaaa   143340
atgatgaaac ttcatctcta ctaaaaatac aaaaattagc tgggcatggt ggcatgtgcc   143400
tgtagtccca gctgcttggg aggccgaggc aggagaattg cttgaatcca ggaagaggag   143460
gttgcagtga actgagatca caccactgta ctccagcctg ggtgacagag tgagattccg   143520
tcacacacac aaaaaaataa ataaaacaaa tagtatatta tgaatagtaa gagatgacta   143580
taactatcag atgttaacac tttggaggtg aaaaacaga ttttatcct cttttggtt     143640 tttcattatg agtctagatt tgttttttaat gatgtatatg tattgttttg ataatttaaa   143700
aaatgtggcc atgcagacac acattgtaaa ggtgaaatgg tttcacaatc ttagttatgt   143760
cagttatgtt ttacattta tgaatttagc taaagaacat gcatggattt ctcagtagag    143820
```

```
agctatagtt aaggttgtaa gttctggagt taaatgactt agatttaact accttggggg  143880
gtagattaac ctctaaaccc cagtcccttt tttttgctt tgttttgttg tgttgctttt   143940
tgtttgtttg ttttctttat ttatttaaga ccctagtctc ttgaactata aagtggggct  144000
gataacatgt atctcgtagc attgttctga ggattgaatg agatggtctg ttcaaagtgt  144060
atcaaaagta accagcatgt agtaagttct caggaaatgt tatcttaaaa taacaataaa  144120
atgatttacc agaatgaaca cactgaagca gtaagttcca taattaattt tacataagtt  144180
atcagtaact aaaattaatt atatctattc tttaaaacat catggaaatc attgattaca  144240
aaattattgg atattcatta ttacattgaa aaatgaagct ggccaggtgt ggtggctcat  144300
gcctttaatc tcagcacttt ggaaggctga ggtaggcagg ttgctagagc tcaggagttc  144360
aagaccagcc ttggcaacat gacgagaccc tgtctctaca aaaatacaa aaattcactg    144420
gatgtggcac acctgtagtc ccagctactt gggtggctga ggtgggagga tcatttgagc  144480
ccaggaggtt gaggctgcag tgagccatga tagtgcctgg gaacagagt aagaccctgt    144540
ctcagaaaaa aatagagaga gagagagaaa taaagaaaga gaaaggaaag agaaaggaag  144600
ggaggcaggg agggaaagaa aataaaacaa aacaaaacaa aggaaagaaa aatgagaggc  144660
caggtgcagt agcttgctcc tgtgatccca gctactcagg aatctgaggt gggaggatct  144720
cttgagccta ggagtttgag gctgaagtgc actgtgattg tgccactgca ctccagcttg  144780
gatgagagag tgagaccgtc tctgatgaaa agaaaaatga aggctatagt ttcataagag  144840
tataaacttg gggccaggcg tggtggctca cgcctgtaat cccagcactt tgggaggccg  144900
aggagggcgg gtcacgaggt caggagatca agaccatcct ggctaacaca gtgaaacccc  144960
gtgtctacta aaaatacaaa aaattagccg ggcgtggtgg tgggcgcctg tagtcccagc  145020
tgctcaggag gctgaggcag gagaatggcg tgaacccagg aggcagagct tgctgtgagc  145080
cgacatcacg ccacttacac ttttagcttg gatgacaaag tgagactcaa aaaaaaaaa   145140
agaagaatat taacttggag gtagcacaat ctgggattat atcctgactc cactattttc  145200
tcagatatat tatgataaaa atattatact tatataaact tggagaagct ttttctttt    145260
ttatttcagc tttattaagg tacagtttac ataaaagtga tgactttat gtttaaaatg    145320
tgatgggttt tgcaaaaagt atacagtgtt acaaccatca ccgtgatcgt aatagaaacat  145380
ttccatcatt ggaagagcct cttagcctct ttgaaaccca gtttctttgc atgttacata  145440
gagataaaag ccagcaacct cgggtggctg tatacacagg acctaatata tacagtccct  145500
ggcacataga agacattgct agtgttctta tcatactcat cattttttt tctgttatt    145560
tctagcttct gaaagttctg ctgaagacag tgagcaggaa gatgagagag gtgctcaaga  145620
catggataat aatggcaaag aggaatctaa gattgatcat ttgaccaaca acagaaatga  145680
tcttatttca aaggaggaac agaacagttc atctttgcta gaagaaaaca aagttcatgc  145740
agatttggta atatccaaac cagtgtcaaa atctccagaa agattaagga aagatataga  145800
agtattatcc gaagatactg attatgaaga agatgaagtc acaaaaaaga gaaaggatgt  145860
caagaaggac acaacagata aatcttcaaa accacaaata aaacgtggta aaagaaggta  145920
ttgcaataca gaagagtgtc taaaaactgg atcacctggc aaaaaggaag agaaggccaa  145980
gaacaaagaa tcactttgca tggaaaacag tagcaacagc tcttcagatg aagatgaaga  146040
agaaacaaaa gcaagatga caccaactaa gaaatacaat ggtttggagg aaaaaagaaa    146100
atctctacgg acaactggtt tctattcagg attttcagaa gtggcagaaa aaaggattaa  146160
```

```
acttttaaat aactctgatg aaagacttca aaacagcagg gccaaagatc gaaaagatgt  146220
ctggtcaagt attcagggac agtggcctaa aaaaacgctg aaagagcttt tttcagactc  146280
tgatactgag gctgcagctt ccccaccgca tcctgcccca gaggaggrgg tggcagagga  146340
gtcamtgcag actgtggctg aagaggagag ttgttcaccc agtgtagaac tagaaaaacc  146400
acctccagtc aatgtcgata gtaaacccat tgaagaaaaa acagtagagg tcaatgacag  146460
aaaagcagaa tttccaagta gtggcagtaa ttcagtgcta atacccctc ctactacacc  146520 tgaatcgcct tcatcagtca ctgtaacaga aggcagccgg cagcagtctt ctgtaacagt  146580
atcagaacca ctggctccaa accaagaaga ggttcgaagt atcaagagtg aaactgatag  146640
cacaattgag gtggatagtg ttgctgggga gctccaagac ctccagtctg aagggaatag  146700
ctcgccagca ggttttgatg ccagtgtgag ctcaagcagt agtaatcagc cagaaccaga  146760
acatcctgaa aaaggtgaga aggaaaatgt gtatgttgac ttattttagg gtttcccctc  146820
ttaaagtttc aatgatttca cagtatctct tgttataacc tgaggcgatt aagtgtcata  146880
tttgtgtgaa catggtaaaa atggaaattt taaaggtaat ttgaaaatga atagtggaat  146940
gcatttaaaa gcttgagaag ctttaatgt gctttgcttg agccatccat ggcattttat  147000
tgtggaccag aacacatgct agaaattgca cccaggccca aatccaaacc tgtttgagaa  147060
ttcattatat gcagtggttg actatatggc atgagcagct taaatctatt tctgtaacat  147120
tgtttttgca attgtaatgt gcagtttctc acgaacattt tgatttattg acagacccct  147180
ccacccttaa ccaaatactg tatgtagggg tttggagcaa ccaactgtcc aggcactgct  147240
ttcctcagac aaccgtgtca aactgatttt caagcctgac taacttgtgt gagtttgtaa  147300
aggaatttga tgctttctta gatgcatagc ttccaaattg aaggaccaat gtgtacgtta  147360
ataacctaca gtaatacttt tttgattttc cgtgaaattg ttaaaagtgg aaattcaaat  147420
cggtaccttc ccaaagtatt agtgcctttc gatggtgcca tagccatact tctgtcatca  147480
tttttcttat aaaccacttc attcaggtat ctttaaatca gtatactcta ggctgacacc  147540
tggctttgga acacacttttt ccatcgtaaa gacagagcac tggagtatgt ttttttatata  147600 ccgtaaaaga ttttagaatg ctagctttag gttttcagca aagcttaaag agatatggtc  147660
tagatcaaat tagttaattc tatgtttttct caggaatctt gacttaaaac atttctgttt  147720
taaaataaat taaaaaaata cttgcaatta aattgaaatg ttctttgctt ttttttcacat  147780 ttacaagtat aactactatg attttatctg tgccatacta tctcatgcaa ctgaactatc  147840
caggcatgac taatcttcaa aatgaaagaa tcctttattt cagaatatta ggctttcaac  147900
agtaagattt tactggccag gtgtggtcac tcacacctgt aatcccagca atttgggagg  147960
tctgggaggt caaggcggtg gatcgcttga gtccaggagt tcaagaccag cctggacaac  148020
atggcaaaac cccatctcta ccaaaaatac aaacgtcagc cagctgtggt ggcgcatgcc  148080
tgtagtccca gctaccttgg gggctgatga gggagaatca cttgatcccg gaaaggctgc  148140
agtgagccaa gatcacgcca ctgcactcca gcctgggtga taaaacaaga ccctgtctca  148200
aaaaaaaaaa aaaaaaaaaa agaaaaaaca agaaagaaaa gaaaaaaaca ggttttattg  148260
ttataggttt tcttgggggt ttttttttttg agatggagtc tcgctctgtt gcccaggctg  148320
gagtgcagtg gtgtgatctg ggctcactgc aacctccgtc tcctgggttc aagtgattcc  148380
cctgcctcag cctgctgagt agctgggact acaggcgtgt gccaccatgc ccagctaatt  148440
ttttgtattt ttagtagaga tggcatttcg ccatgttagc caggatggtc tctatctctt  148500
gacctcatga tctgcctgcc ttggcctccc aaagtgctag gattacaggc atgagccacc  148560
```

```
gtgcctagcc tattgttgta gttttttaaga ggttgtatcc ttattatgtt cgtaatatct 148620
tacaaaagat taaaattaac aacaaaaaaa aagaggatat cttctctgct aatagactaa 148680
gtcaacactg cccttttgaa tcttaatctt gactaggtta ataattgtgg aatttgaaag 148740
ctactcctaa atttagggta atttatatct ctttagaaat aattggtgtt tttcttttg 148800 ttgggttttt tttttttttt tttttttttt ttttgagaca tagagttttg ctcttgttgc 148860
ccaggctgga gtgcagtggt gcaatcttgg ttcactgcaa cctccacctc tcaggttcaa 148920
gagattctcc tgcctcagcc tgctgagtat ctgggattaa cgcccggcta attttttgtat 148980 tttgtttagt agagatgggg tttcgccatg ttggccaggc tggtctacga actcctgacc 149040
tcaggtaatc cacctacctt ggcctcccaa agtgctggaa ttacaggcat gagccaccgc 149100
gcccagccag aaataggttc ttaagcacct gtttcacatg ccacattttt aataaattta 149160
cttactatga atattggaga ctccccacta tatcacaagt taaaattttaa gttttactat 149220 ttagatgtag tttttttcctc ttaatttact ctacattgaa ggttttttatt tcttagtatc 149280 tgaacacttt agaattaaac tctcttggag agaaacctga caattatggt tctgtgcttc 149340
agtatggtca atatctacgt ctcctttatg tttcacttaa attgtgatat taaaatgaca 149400
ttaggtgggt cacatacttg gtgtaaaaaa taaaaaagaa atattaaaaa tttaaaaagg 149460
tattaggaaa agttgtaagt aagattatat gacccattaa aaaaaagcta ggaagttgca 149520
gacagttaat tacttgtcct gttttttgatc aaggaagtta ggttttatac acagaaggtt 149580
gatttggtgt ctgacattgg aactgaatgg agatagtact ttattagtct ctggagaaaa 149640
aatcttactt tatatagtct gagagataac atatatgaat tagacagaaa tatagcagat 149700
gttaaggacc aaatgagtag tatagaaaaa tgctacagtt cagagtagtg attgatcagt 149760
gaagcctgga acatcttagt gaagatgtag gacttgggct agtccttgaa gaaagggag 149820 acatttattt gtaatgtttt gcaataattt cccaccaaga agatgagacg ttttttagaa 149880
ctactatgtt ggatttgtaa atggtatgca tgttaaccaa acagtgccct gggagcttag 149940
ttattcttga cataaattgg taaaaaagaa ccaagtatga attactgcta aaatttacct 150000
catttatatc atttaaaaat tatattaata tgattataag acataatgtc attaacattt 150060
taacctgtga ttaagtctta atattttggt tttattgaat cttaacaaat ttcagttttt 150120
attttcagca tatactttta attactaggc ttataaactc ccagtactat attaaggact 150180
attttcagtt tatatctgat ttttttaaag aaggatgtgc atactttgtt tgccttttta 150240
aaaaccctga cttttattat gtataagaat tgagcttcca ttaatgacag tttatttaaa 150300
aattgtagta agttctgtga caacttatra atgtcataaa gaacatgtag ttttggattg 150360
ttctatgttt ctaaaatgtg gaattaattt atacttaggg aatgttggat tttattttgt 150420
gttacttaat tccttttccct tcatagcctg tacaggtcag aaaagagtga agatgctca 150480 gggaggagga agttcatcaa aaaagcagaa aagaagccat aaagcaacag tggtaaacaa 150540
caaaaagaag ggaaaaggca gtaagtgtga aatctctaat ttttaaaata taaaaataat 150600
agctgataat tttaccccca gtaagaaaat ggtattcagg gtatgggata gtacactatt 150660
ttgattttgt ctgtacactc aaaaaaagtc acacaaattc tgtaaggcta cttgctttaa 150720 aaacaaaat agacaaaaaa aaaacatgca ctaggacaaa tacctaatgt aaatgatgag 150780
ttgatgggtg cagcaaacca acatggcaca tgtataccta tgtaacaaac ctgcacattg 150840
tgcacacgta ccctagaact taagtataa taataaaaag aaaaagaat ttctgcaaaa 150900
```

```
acaaacaaaa caaaacaaaa aaaacacagg ttttctaatc ttaggtaaat tctagttta    150960 agcaagttgg tgttattcag cggtggtatt gattgctgat gaaaaatcaa gtaatctgtt  151020
tttgaaataa tagccaatat attataaaca tcaacatatt tgttaccttt gtattccaca  151080
gttcttttca cttgctataa aatgtatcac acattgtgaa atatttcaac tacatgttat  151140
ttttattaca gtgaaattga ttgcttagta attcttcaag gcaaaatcag catagaagta 151200
taacaatcaa gataacttta gaactataat tccaacaact ccagtctaca acatttgtct  151260
ttggtactct atattatgtg acctgagagt aactacaaac aatactttt  gctaagtatg  151320 ctccaacttt agcaacgact ccgtgcatca atccacagaa aatatatata ctgtatttct  151380
tctgagggct gcacatttta tctctctttt gtagacaaag taagaagcag aaaatatgta  151440 aagaatttt ttttcaggtgc cccacactga cctcctgctg ctcttccagg agactcctgc   151500
cacctccact gcctgacctt tgctagcagc cggcttggct gcacttcagt gcagaaaagg  151560
gttattcggc cagctcccg  aggttctgct gagcccatat gacttccagg cggtgaatat  151620
ggcgtccctg gggccccggg cggctgtgct cagcaaggcc atgaaagcca ggctgagaca  151680
gtccactgca tagagtgggg ccaagccttg ggtggcttag ctaggagttg ccaggggttc  151740
cagagcagca gtgggggagc tgggagggaa tttgtgtata tgtgtcaacc agtggtggag  151800
tttctttatt cccaaaattt cacagtggga ggagttgctg ctatctacct ttactatttg   151860
gaataatttc tggctttgag agtttaactc ctttttttttt ttttttttttt ttttttttt  151920 tggtgatgtt gttaagtgaa aaatcagtaa atatatgcca aatcagtcag tcatcaattg  151980
tttggtgtaa ctggtaggat atttaaagtg ttttttcttt cactgtgatg ttttttgtctt 152040 caagagttta ctatttaaat gacatttcct aagagagcgc atcttcaatg agttatttag  152100
tatattcata taatacagag atatagtgtt ctcccatttt acttattggg attctgccat  152160
ggtaaatcag aatgagttaa ccattcaaga gaataattta gtaacatgaa ttaattctga  152220
tggaatctaa actaatactt tgtatccaga aagaggttat ctatggaaat actaatccca  152280
tcacctacct gttcacatgg taagctgtca aggtcaagta tttccatttt agtgctgaag  152340
tttaattagc aatagcagtt gtaacataat tgttacacag acttctgaat tgttcataaa  152400
atactgaata ttttattagg gtgaaactga ttattttagt caacccacag cataggagtt  152460
atttaagagt aatttcatta tacatatcaa acttcagagt ttattcccga ggagttcttt  152520
attgaatatg atgattgtgc atcattattt gtttgtggcc aaaggagcag gaaaatgttg  152580
catataccca atgttacata ttcattgtag aggtttctac aattaatcat tttaaaagat  152640
gatatatttt atgtattaac ataatagagt aaaaagccat tcagatgatt actgtatatt  152700
tgacagtcta ccaagcataa tgatagatta gtgtgagtga ttttaaaagt atacatatta  152760
ttggcagttc aggtaagaag aattttttgt ttttgctttt cctaagatgc tgctgcattt  152820
gtatatgatt ttccaggttt ctaggcaggt tgttttctgt aggactaaat tcaaatggct  152880 aatttaaat tacctactaa aatctgtgac aaatttattg ttacatttt gtttattaaa   152940 tcttttcttt ctctttcagc aaatagtagt gatagtgaag aacttcagc tggtgaaagt   153000 ataactaaga gtcagccagt caaatcagtt tccactggaa tgaagtctca tagtaccaaa  153060
tctcccgcaa ggacgcagtc tccaggaaaa tgtggaaaga atggtgataa ggatcctgat  153120
ctcaaggaac ccagtaatcg attacccaaa gtttacaaat ggagttttca gatgtgtaag  153180
tgacatgtta aattgacaag catacaaact tcatcctagt aactcttttt gttttatttt  153240 gttttttgttt ttagagacag agtctcgctc tgtcaccagg ctggagtgcg gtggtgcgat  153300
```

```
cttggctcac tgtaatcttc agcctcctgg gttcaagcca tcctcctgcc tcagcctccc   153360
aagtagctgg gattacaggc acgcgccacc acacccagct aattttttg tgtgtttagt    153420
agagacaggg tttcaccatg ttggccagga tggtctccat ctcctgacct catgatccgc   153480
ccgcctcggc ctcccaaagt gctgggatta caggcatgag ccactgcgcc tggccttttt   153540
ttttgagaca gagtctctct gtcgcccagg ctagagtgca gtgcagtggc atagtctctg   153600
ctcactgcaa cctccatctc cctggttcaa atgattctcc tgcctcaacc tcccgagtag   153660
ttgggattac agacgcccac caccacacct ggctaatttt tttgttgttg ttgtatttt    153720
agtagacatg gggtttcacc atgttggcca ggctggtctt gaactcctga cctcaggtga   153780
tccatccgcc tctgcctcgc aaagtgctgg gattttgggc atgagccacc atgcccagcc   153840
ccaatcctag taactcttca tgccaatact ctgaaaaaga ggctttacca aacttaatag   153900
atgtactaat gtacaatgta tagacctttat ttggatcccg gtttgaataa ataaattggt  153960
taaagaaaaa tttaaggca gttgaggcaa atgccaacac tgactagata tttctgatat    154020
ggctgggcgc agtggctcat gcctgtaatc ccagcacttt gggaggctga ggtgggtgga   154080
tcacgaggtc aggagttcga ccagcctg accagcatgg tgaaaccctg tctctactaa     154140
taaaacaaaa aattagctgc gcgtggtggc acgcgcttgt agtcccagct actcaggagg   154200
ctgaggcagg agaattgctt gcacctggca ggtggaggtt gcagtgagcc gaggttgcgc   154260
cactgcactc cagcctgggc gacagagtga gaccccatcc cagaaaaaaa aaaaagata    154320
cttctgatat gatgtcggta atttgattta aaagtatctg gtgttagggg tgaggaatgg   154380
ataggggtgc agatgataca ggttttgcca taaattgatg attactgaag ctggataatg   154440
agtacatggg gttcactatc cttctctcta tacttttgta tatgtgagaa atcttcataa   154500
atcttcattt aaaaaaaggt atatatatat atgttttagg tatacatata tatatatata   154560
tatatatata tatatatata tatttttttt ttttttttt tttttttttt ttaaatagag    154620
acgaggtctc attatgttgc ccaggctaat cttgaactcc tgagctcaag actgagctga   154680
tccttccacc tctacttccc aaagtgctag gattacaggt gtgagccacc acacccagcc   154740
aatatgtata ttttttttaat actactctag agttttcac acaaggaaat accttaagta   154800
ttcttaggag attgaagatt gctttagagc ttttttaaaat tgccttctaa ttaaattt    154860
tacacactct ttaaaaaaac ctaaaaaata acagagaaca gaagagaaaa atttatccac   154920
agtcttgtta ctcacaaaat gtgtacaatt tagcattttg gtgtctttcc aggttttttg   154980
ttttgttttg tttttgtgtt tttgttattt ttagacagag tctcactctg ttgcccaggc   155040
tagcgtgcag tggcacaatc tcggctcact ccaacctcca ccttccagat tcaagcgatt   155100
atcctgcccc agcctcccga gtagctggga ttgcaggcac ccgccaccat gcccagctaa   155160
ttttttgtagt tttagtagag acagggtttc accatcttgg ccaggctggt atcgaactcc   155220
tgacctcgtg atccgcccac ctcggcctcc caaagtgcta ggattacagg tgtgagccac   155280
cgtgcccagc cccagttta tttttaagtg tgatttttta ctgtggtaat actgtatatg    155340
gatgtggata tatgtagatc ttaaggtgtt taatgctgta catattcatt caacaaatac   155400
tgtgcattta ttatgtgcca ggcattgttc taggctagat aaaaaatttg gaaacaaat    155460
atttcagaag ccttagtttt ttagttcatc tgcctcaacc ttattcagca gccatgctcg   155520
atgttctctc ctttttgtat gttaaaattt tcttttaaaaa tgtctgttaa tgaaagcttt   155580
aaatttatag cggacctgga aaatatgaca agtgccgaac gcatcacaat tcttcaagaa   155640
```

```
aaacttcaag aaatcagaaa acattatctg tcattaaaat ctgaagtagc ttccattgat    155700
cggaggagaa agcgtttaaa gaagaaagag agagaaagta agtattttta ctttattttt    155760
atttatttat ttattttgag acagagtttc actcttgtcg ccaggctgga gtgcaatggc    155820
gcaatctcgg ctcactgcaa cctccacctc ctgggttcaa acagttctcc tacctcagct    155880
tcctaagtag ctggaattac aggcatgcac caccaagccc ggctaatttt gtattttta     155940 ggtagagaca gggtttcgcc atgtcaatca ggctggtctc taactcctga cctcaggtga    156000
tctacctgtc ttggcctccc aaagtgctaa gattacaggc gtgagccaag agtgccctgc    156060 cagtatttt actttattta aacataaacc agaatttctc actctgcagt tagactgcca     156120
tgactttgtc tattttcagg caaattcttt aatttcttta tcttattttc ctcatctcta    156180
aagtgaaatt atctcaaata aaaaattat ttcagatcat aatattcact ttcatagagt     156240
ttatactcta ccaaaaacat cctaataaga taatttcaga tattgaaagc actatgaaga    156300
aaatgatgtt aaggtagtga ttggatgggt tactttagat tacaaatggt cagtatattt    156360
ttgttgatac ctgaatgaca tgaggaagtg agataaatta aaatctggga ggaggccggg    156420
cacagtggct catgcctgta atcccagcac tttgggaggc tgcggtgggt ggattgcctg    156480
aggtcaggag gtcgagacca gcttggccaa catagtgaaa ccccgtctct actaaaaaat    156540
acaaaaaatt agctgtgcgc ggtggcgggt gcctgtaatc ccagctactt gggaggccga    156600
cgcaggagaa ttgcttaaac ccaggaggca gatgttgcag tgaacggaga tcatgccatt    156660
gcactccagc ctgggcaaca agagctaaac tctgtctcaa aaaaaaaag acatctatcc     156720 agaaactcct tctaaacaat gttttgtaaa tatagtcacc acaaattctt tataatgaat    156780
gattttgcta aatagagcct ctctactggg ttagcattaa aagtcggttc ctaaatacta    156840
ttttaagaaa aatccatagg aaaatgctta tcctggttac caaagaaatg caaatcaaat    156900
aaggtatcat tcttttttt tggagatgga gttttgctct gtcgcccagg ctggagtgca     156960
gtggcgcgat ctcagctcac tacaacctcc gcctcctgag ttcaagcgat tatcctgcct    157020
cagtctcccg agtggctggg attacaagcg tgctgccacg cccagctaat tttttatttt    157080
tagtagagat ggggtttcac catgttggcc aggatgcagg atggctcgat ctcttgactt    157140
cgtgatccgc ctgcttcagt ctcccaaagt gctgggatta caggcatgag ccactgcgac    157200
tggcccaaat aaggtatcat tcttaccaaa aaaattaaaa ctaaaaccaa tgcaggaaca    157260
gtgtagtgaa atatataagt tatgagttgt aatatagtag aatattactc aactttgaaa    157320
agaaaaggat ctgtatgtac tgatatgaaa caatctctta aaatatattg tttaaaaaaa    157380
agtcagacac tgaactatgc ttccacttgt gtgtgtgtgg tttttttttt tttttttttt    157440
ttttgagacg gagtctcggt cagtcaccag gctgagtgc agtggcgcga tcttggctca     157500
ctgcaacctc tgccttccgg ttcaagcgat tctcctgcct cagcctcccg ggtagctagg    157560
actacaggtg cgtgccgcca tgcccagcta attttttgtaa tattattatt aattttgag    157620 acagagtatc tctctgtcat ccaggctgga gtgtagtggt gcaatcttgg ctcactgcaa    157680
ctccgcctcc cggttcacg ccattctcct gcctcagcct ctctagtagc tgggactaca    157740
ggcgcccacc accacatctg gctaatttt tgtattttta gtagagactg agtttcattg     157800
tgttagccag gatggtctcg atctcctgac cttgtgatcc gcccacctag tcctcccaaa    157860
gtgctgggat tacaggtgtg agccaccgtg cccggcctcc acttatgttt ttaaaggtgt    157920
tgctatatct atatatttta aatttgcata tcatatctct agattctaga gataaaattc    157980
ctgtagaaca ggggttgcaa acattttctg taaagagaca ataaatatgt taggctttgt    158040
```

```
gggccatgtg gtctctgtag aaactactta tctctgccat ggtaagtgtg aaaactccca 158100
taggcaatat gtaaacaaat aggcatggct gtgttccagt acaattttc tttccaaaga 158160 caagtaagcc agatttgccc ctggggtagt tttttgcca gccttttttc tagagttgta 158220
atgaatatga atcaactggt agcaatgggg aagggaattt gggtgattag gaggttcctg 158280
gatgagagtg agatttgctt ttctatccta ttaccctgt actgaatgaa ttttttaaat 158340
ctgtgcatgt atttaaaaat attaatttat gaacactaat ttataacaga gaggccgggc 158400
gcaattgctc acgcctgtaa ttccagcact tagggaagcc aaggcaggca gatcacctga 158460
ggtcaggagt tcgagaccag actggccaac atgacgaaac cccatctcta ctaaaaatag 158520
aaacattagc cggacatggt ggcgcatgcc tgtaatccca gatactcagg aggctgagac 158580
aggaaaattg cttgaaccca ggaggcaaag gttgcagtga gctgagattg cactgctgca 158640
gtccagcctg gcaacagag caagacccc atctcaaagg aaaaaaaaa aaaggaggc 158700 tgaggcagga gaatggcgtg aacctggaag gcggagcttg cagtgagccg agatcgcacc 158760
actgcactcc agcctgggcg acagagtgag actccgtctc aaaaaaacaa acaggctggg 158820
cgcggtggct cacacctgta atcccggcat tttgggaggc tgagatgggc ggatcatgag 158880
gtcaggagat cgagaccatc ctggctaaca tggtgaaacc ccatctctac taaaaataca 158940
aaaaaattag ccgggcgtgg tggcgggcgc ttatagtccc agctactggg ggggctgagg 159000
caggagaatg gcgtgaactc aggaggcaga acttttagtg agccaagatc gagccactgc 159060
actccagcct gggcgacaga cagagcgaga ctttgtctca aaaacaaac aaacaaaaaa 159120 aaacgaaaaa aggaaacagt gagagacttc ctctgatgaa ataactaat gtgttatttg 159180 ctttgtaaac ctagtggcgg agaatgcaac agttgagcta tgcactgttt tgatccaact 159240
tgaagaagca attaagcctc ccactcttgt caccatttac atgtacaaga aaactcctaa 159300
gtacagaaag atggagggat taggagggga caaatgattt ttggatggat tgcagatttt 159360
tcctgttttg atacttgttt cactgttaca aaaagtgtat tctgtatttt atttctgtgt 159420
cttgtagact aggcacagtt cttccctct ttgacccacg caggagcctt ccctggtctg 159480 tcctttcat tacttctgta gttgggcact gtctagcttc ttgagctaca ctagcttttc 159540 cttcttcac atcgtagaac tgtgagaatt gaccactgtt gttgtaagct aaatgatttt 159600
ggacaatata gcggaatttt agttcagagg actagtattt tctgtctatt gttagacata 159660 aattttatt aagctcttgg tttggtctcc cttttcctta ggtgctgcta catcctcatc 159720
ctcctcttca ccttcatcca gttccataac agctgctgtt atgttaactt tagctgaacc 159780
gtcaatgtcc agcgcatcac aaaatggaat gtcagttgag tgcaggtgac agcaggactt 159840
gctaaagcac tttgcactta atggctgttg agggccactt ttttttata ctgcacagtg 159900 gcacaaaaa atatcagaca agcactattt tatatttaaa aattgttct tgacaagctg 159960 acttggcact taagtgcact tttttatgaa gaaaagtac aatgaactgc ttttcctcaa 160020
gcaataattg kttccaactt gtctgggaat tgtgtgtctg gtaactgaa ggccttccac 160080 tgtggcaaat ggaggctttt cactgcctgt agagacaata cagtaagcat agttaagggg 160140
tgggtcagaa catgttaaga taacttactg tatatgtatt cccttgtatt tgttaaagc 160200 tggaacattt gatattttc catttattta tgaaaaata tgaacctatt ttcatttgta 160260
caaggtaatt gttttttaaa gcaagtcacc ttagggtggc tttaattgta taagtcaagc 160320
acatgtaata aattcaaaac ctgcagttaa caggatatta gacatcaatc ctggtaacca 160380
```

```
aatattaaag attctctttta aaaaagactg aacatgttta caggtttgaa ttaggctaaa    160440
aggtcttgca gtggcttttc atggcccttc aaattggaat ggaactactg tactttgcca    160500
tttttctata aatcagtatt ttttttaat tttgatatac attgtgtgaa aaagaaaat      160560 ggctaataaa ctgtattaaa tcttaaacaa tgtataaaga ttgtacttag ccagttcaaa    160620
gtgtatattt attcataatg aattataaca gttatatttt tgtgttttct tgtaaatgtt    160680 tcttttcct taaatacaga taattcattt gtattgctta ttttattatg agctacaaca     160740
aaaggacttc aggaacaagt aatgtattag tatggttcaa gattgttgat aggaactgtc    160800
tcaaaaggat ggtggttatt ttaaatataa atagctaatg ggggtggtag gcctataaaa    160860
ttaaatgcct tgtataaaat ccaaaatgaa tgcaaaattg ttttcacttg tattgacttt    160920
atgttgtatg attccaatct ctgttctgtt tggcacttgt atttaattct tcacctttgt    160980
aagacatttg tatattgtgg atgtgttcat tcaagctatt taatatctgg cactgttaat    161040
acacagtact ttattgtaca gactgttta ctgttttaat tgtagttctg tgtactttt     161100 ttggatgggg ctggcatgtt ttctttgttt cctggcaata cgacgtggga atttcaatgc    161160
gttttgttgt agatgctaac gtgtcagaat cctttacatt caacttttct aagaaaagca    161220
ttttcagtct tgtagtgtgt gcttacagta actaattttg ttgaaaatgg tttcaagtta    161280
ttcaaatttg tacaggactg taaagatttg ttgacagcaa aatgtgaag aaaaaagctt     161340 atagaataaa agctataaag tatatattag gatctgcaaa caatgaagaa ttatgtaata    161400
tattgtacaa atgtaagcaa aggctctgaa ataaaatgcc atagtttgtg aatccttgat    161460
ttttgtttct aaaagattta gtaattttag ttcatttctg tatgtgatga ctgactggaa    161520
catacatatc cagcacgtat tatcacaggg gattaattga tacacaaaaa aaggaagatt    161580
ctacctatga aaattaaaag tccattaatc agataaggaa tgtattaggc attcttttt     161640 ttttttttt ttttggacac ggagtcttgc tctgtcaccc aggctagagt gcagtggcgc     161700
aatctccagc tcactgcaac ctctatctcc cgggttcaag caattctcca gcttcagcct    161760
tccgagtagc tgggattata gacatctgcc agcactcctg gctaattttt gtattttag    161820 cagagacggg gtttcaccgt actggtcagg ctggtctcaa actcctgacc tcatgtgatc    161880
cacccacctt ggcctcccaa tgtgctggga ttacaggcgg gagccaacac acccagccta    161940
ggcattcttt tatctttgca cacactattt tgcttgagtc tgaatttaaa tattttcctt    162000
atcacttgaa gaattgtcca aatttgaaaa ttaagtgttt tttttaaaat ttatttaaca    162060
cttgaaacca ttaccagcgg ctttttaaaa tttttaattt agttagacct ttccgggtct    162120 tttatcttc agtgtgttct attgcacatt gcaatcatct ggacattgtt aaaagtatat     162180
tcagtactca caccccactc ccaaggagtt atatttaatt ggttggggt agtacctgga    162240 tgttgatctt taattttaa aggtctctag tgatattaat atgcatctgg gttgagaaac     162300
actgctttgc cgcaaacttc taaaaatcta taatctagtt ttttggcccc acttattgga    162360
ctttctacca acagaaaacc tttcttggct gggcgcagtg gctcaacgcc tgtaatccta    162420
gcactttggg aggccgaggc aggcggatca                                      162450
```

<210> SEQ ID NO 2
<211> LENGTH: 273
<212> TYPE: DNA
<213> ORGANISM: Homo sapiens
<220> FEATURE:
<221> NAME/KEY: CAAT_signal
<222> LOCATION: 139..147
<223> OTHER INFORMATION: AACCAATCC

```
<220> FEATURE:
<221> NAME/KEY: TATA_signal
<222> LOCATION: 199..205
<223> OTHER INFORMATION: AAATCTA

<400> SEQUENCE: 2
ccccagagta tggactttat ttcccagaaa gccttgaggc gtaactttct gtttccatag      60
aactggtggg aaaatggcgt cgttgtttgt atccagggac caataggaac agtgtatagg     120
cgggttctaa agaacttaa ccaatccaag gtcgtctaag aggccatccg ggaaagaggt     180 agggagggg gggaaaaaaa atctagggga ggggagaaag ggggggaacc tagagtcggt     240
gggggggaag cgatgtttgc ccgtcagtcg agt                                  273

<210> SEQ ID NO 3
<211> LENGTH: 999
<212> TYPE: DNA
<213> ORGANISM: Homo sapiens

<400> SEQUENCE: 3
atccttgatt tttgtttcta aaagatttag taattttagt tcatttctgt atgtgatgac      60
tgactggaac atacatatcc agcacgtatt atcacagggg attaattgat acacaaaaaa     120
aggaagattc tacctatgaa aattaaaagt ccattaatca gataaggaat gtattaggca     180 ttctttttt tttttttttt tttggacacg gagtcttgct ctgtcaccca ggctagagtg     240
cagtggcgca atctccagct cactgcaacc tctatctccc gggttcaagc aattctccag     300
cttcagcctt ccgagtagct gggattatag acatctgcca gcactcctgg ctaatttttg     360 tattttagc agagacgggg tttcaccgta ctggtcaggc tggtctcaaa ctcctgacct     420
catgtgatcc acccaccttg gcctcccaat gtgctgggat tacaggcggg agccaacaca     480
cccagcctag gcattctttt atctttgcac acactatttt gcttgagtct gaatttaaat     540 attttctta tcacttgaag aattgtccaa atttgaaaat taagtgtttt ttttaaaatt     600
tatttaacac ttgaaaccat taccagcggc ttttttaaat ttttaattta gttagacctt     660
tccgggtctt ttatacttca gtgtgttcta ttgcacattg caatcatctg acattgtta      720 aaagtatatt cagtactcac accccactcc caaggagtta tatttaattg gttgggggta     780
gtacctggat gttgatcttt aattttaaa ggtctctagt gatattaata tgcatctggg     840
ttgagaaaca ctgctttgcc gcaaacttct aaaaatctat aatctagttt tttggcccca     900
cttattggac tttctaccaa cagaaaacct ttcttggctg ggcgcagtgg ctcaacgcct     960
gtaatcctag cactttggga ggccgaggca ggcggatca                            999

<210> SEQ ID NO 4
<211> LENGTH: 6002
<212> TYPE: DNA
<213> ORGANISM: Homo sapiens
<220> FEATURE:
<221> NAME/KEY: allele
<222> LOCATION: 1319
<223> OTHER INFORMATION: 5-130-257 : polymorphic base A or G
<220> FEATURE:
<221> NAME/KEY: allele
<222> LOCATION: 1338
<223> OTHER INFORMATION: 5-130-276 : polymorphic base A or G
<220> FEATURE:
<221> NAME/KEY: allele
<222> LOCATION: 1944
<223> OTHER INFORMATION: 5-136-174 : polymorphic base C or T
<220> FEATURE:
<221> NAME/KEY: allele
<222> LOCATION: 3329
```

```
<223> OTHER INFORMATION: 5-143-84 : polymorphic base A or G
<220> FEATURE:
<221> NAME/KEY: allele
<222> LOCATION: 3346
<223> OTHER INFORMATION: 5-143-101 : polymorphic base A or C
<220> FEATURE:
<221> NAME/KEY: allele
<222> LOCATION: 4582
<223> OTHER INFORMATION: 5-148-352 : polymorphic base G or T
<220> FEATURE:
<221> NAME/KEY: allele
<222> LOCATION: 1107..1125
<223> OTHER INFORMATION: polymorphic fragment 5-129-144 SEQ ID33
<220> FEATURE:
<221> NAME/KEY: allele
<222> LOCATION: 1107..1125
<223> OTHER INFORMATION: polymorphic fragment 5-129-144 SEQ ID54
<220> FEATURE:
<221> NAME/KEY: allele
<222> LOCATION: 1315..1338
<223> OTHER INFORMATION: polymorphic fragment 5-130-276 SEQ ID35
<220> FEATURE:
<221> NAME/KEY: allele
<222> LOCATION: 1315..1338
<223> OTHER INFORMATION: polymorphic fragment 5-130-276 SEQ ID56
<220> FEATURE:
<221> NAME/KEY: allele
<222> LOCATION: 1921..1967
<223> OTHER INFORMATION: polymorphic fragment 5-136-174 SEQ ID41
<220> FEATURE:
<221> NAME/KEY: allele
<222> LOCATION: 1921..1967
<223> OTHER INFORMATION: polymorphic fragment 5-136-174 SEQ ID62
<220> FEATURE:
<221> NAME/KEY: allele
<222> LOCATION: 3306..3352
<223> OTHER INFORMATION: polymorphic fragment 5-143-84 SEQ ID46
<220> FEATURE:
<221> NAME/KEY: allele
<222> LOCATION: 3306..3352
<223> OTHER INFORMATION: polymorphic fragment 5-143-84 SEQ ID67
<220> FEATURE:
<221> NAME/KEY: allele
<222> LOCATION: 1296..1338
<223> OTHER INFORMATION: polymorphic fragment 5-130-257 SEQ ID34
<220> FEATURE:
<221> NAME/KEY: allele
<222> LOCATION: 1296..1338
<223> OTHER INFORMATION: polymorphic fragment 5-130-257 SEQ ID55
<220> FEATURE:
<221> NAME/KEY: allele
<222> LOCATION: 3323..3369
<223> OTHER INFORMATION: polymorphic fragment 5-143-101 SEQ ID45
<220> FEATURE:
<221> NAME/KEY: allele
<222> LOCATION: 3323..3369
<223> OTHER INFORMATION: polymorphic fragment 5-143-101 SEQ ID66
<220> FEATURE:
<221> NAME/KEY: allele
<222> LOCATION: 4559..4605
<223> OTHER INFORMATION: polymorphic fragment 5-148-352 SEQ ID48
<220> FEATURE:
<221> NAME/KEY: allele
<222> LOCATION: 4559..4605
<223> OTHER INFORMATION: polymorphic fragment 5-148-352 SEQ ID69
<220> FEATURE:
<221> NAME/KEY: misc_feature
<222> LOCATION: 442..444
<223> OTHER INFORMATION: ATG
<220> FEATURE:
<221> NAME/KEY: misc_feature
<222> LOCATION: 4378..4380
<223> OTHER INFORMATION: stop : TGA
<220> FEATURE:
<221> NAME/KEY: polyA_signal
<222> LOCATION: 4878..4883
<223> OTHER INFORMATION: potential
<220> FEATURE:
<221> NAME/KEY: polyA_signal
```

```
<222> LOCATION: 5116..5121
<223> OTHER INFORMATION: potential
<220> FEATURE:
<221> NAME/KEY: polyA_signal
<222> LOCATION: 5896..5901
<223> OTHER INFORMATION: potential
<220> FEATURE:
<221> NAME/KEY: polyA_signal
<222> LOCATION: 5981..5986
<220> FEATURE:
<221> NAME/KEY: misc_feature
<222> LOCATION: 209..756
<223> OTHER INFORMATION: homology with EST in ref embl:W84531
<220> FEATURE:
<221> NAME/KEY: misc_feature
<222> LOCATION: 391..815
<223> OTHER INFORMATION: complement homology with EST in ref
    embl:W37603
<220> FEATURE:
<221> NAME/KEY: misc_feature
<222> LOCATION: 453..898
<223> OTHER INFORMATION: complement homology with EST in ref
    embl:H39516
<220> FEATURE:
<221> NAME/KEY: misc_feature
<222> LOCATION: 818..1306
<223> OTHER INFORMATION: complement homology with EST in ref
    embl:W67770
<220> FEATURE:
<221> NAME/KEY: misc_feature
<222> LOCATION: 844..1303
<223> OTHER INFORMATION: complement homology with EST in ref
    embl:AA262427
<220> FEATURE:
<221> NAME/KEY: misc_feature
<222> LOCATION: 1351..1702
<223> OTHER INFORMATION: complement homology with EST in ref
    embl:AA485189
<220> FEATURE:
<221> NAME/KEY: misc_feature
<222> LOCATION: 1866..2109
<223> OTHER INFORMATION: homology with EST in ref
    embl:AA296993
<220> FEATURE:
<221> NAME/KEY: misc_feature
<222> LOCATION: 2181..2281
<223> OTHER INFORMATION: homology with EST in ref embl:T61718
<220> FEATURE:
<221> NAME/KEY: misc_feature
<222> LOCATION: 2253..2482
<223> OTHER INFORMATION: homology with EST in ref embl:AA082927
<220> FEATURE:
<221> NAME/KEY: misc_feature
<222> LOCATION: 2480..2842
<223> OTHER INFORMATION: complement homology with EST in ref
    embl:H38607
<220> FEATURE:
<221> NAME/KEY: misc_feature
<222> LOCATION: 3334..3733
<223> OTHER INFORMATION: homology with EST in ref embl:AA279595
<220> FEATURE:
<221> NAME/KEY: misc_feature
<222> LOCATION: 3631..3870
<223> OTHER INFORMATION: complement homology with EST in ref
    embl:AA169631
<220> FEATURE:
<221> NAME/KEY: misc_feature
<222> LOCATION: 3883..4221
<223> OTHER INFORMATION: homology with EST in ref embl:H08612
<220> FEATURE:
<221> NAME/KEY: misc_feature
<222> LOCATION: 4277..4796
<223> OTHER INFORMATION: homology with EST in ref embl:AA399016
<220> FEATURE:
<221> NAME/KEY: misc_feature
<222> LOCATION: 4516..5016
<223> OTHER INFORMATION: homology with EST in ref embl:AA479433
<220> FEATURE:
<221> NAME/KEY: misc_feature
```

```
<222> LOCATION: 5580..6002
<223> OTHER INFORMATION: complement homology with EST in ref
      embl:AA167428

<400> SEQUENCE: 4
ccggagtgag gagctcggtc gccgaagcgg agggagactc ttgagcttca tcttgccgcc      60
gccacggcca ccgcctggac ctttgcccgg agggagctgc agagggtcca tcgccgccgt     120
cctctggagg gcagcgcgat tgggggcccg gacctccagt ccggggggga ttttcgtcg      180 tcccctccc cccaaccagg gagcccgagc ggccgccaaa caaaggtacc agtcgccgcc     240
gcgggaggag gaggagccgg agcctctgcc tcagcagccg ctggacccgc cgccttctt     300 ccccatctct ccccgggcc tgctggtttt gggggggaga aggagagagg ggactctgga     360
cgtgccaggt tcagatctcg cctccgagga aggtgcagct gaacctggtg ttttagagga     420
taccttggtc ccagagtcat c atg aag gcc ctt gat gag cct ccc tat ttg      471
                         Met Lys Ala Leu Asp Glu Pro Pro Tyr Leu
                          1               5                    10 aca gtg ggc act gat gtg agt gct aaa tac aga gga gcc ttt tgt gaa      519
Thr Val Gly Thr Asp Val Ser Ala Lys Tyr Arg Gly Ala Phe Cys Glu
            15                  20                  25 gcc aag atc aag aca gca aaa aga ctt gtc aaa gtc aag gtg aca ttt      567
Ala Lys Ile Lys Thr Ala Lys Arg Leu Val Lys Val Lys Val Thr Phe
        30                  35                  40 aga cat gat tct tca aca gtg gaa gtt cag gat gac cac ata aag ggc      615
Arg His Asp Ser Ser Thr Val Glu Val Gln Asp Asp His Ile Lys Gly
    45                  50                  55 cca cta aag gta gga gct att gtg gaa gtg aag aat ctt gat ggt gca      663
Pro Leu Lys Val Gly Ala Ile Val Glu Val Lys Asn Leu Asp Gly Ala
60                  65                  70 tat cag gaa gct gtt atc aat aaa cta aca gat gcg agt tgg tac act      711
Tyr Gln Glu Ala Val Ile Asn Lys Leu Thr Asp Ala Ser Trp Tyr Thr
75                  80                  85                  90 gta gtt ttt gat gac gga gat gag aag aca ctg aga cga tct tca ctg      759
Val Val Phe Asp Asp Gly Asp Glu Lys Thr Leu Arg Arg Ser Ser Leu
                95                 100                 105 tgc ctg aaa gga gag agg cat ttt gct gaa agt gaa aca tta gac cag      807
Cys Leu Lys Gly Glu Arg His Phe Ala Glu Ser Glu Thr Leu Asp Gln
        110                 115                 120 ctc cca ctc acc aac cct gag cat ttt ggc act cca gtc ata gga aag      855
Leu Pro Leu Thr Asn Pro Glu His Phe Gly Thr Pro Val Ile Gly Lys
    125                 130                 135 aaa aca aat aga gga aga aga tct aat cat ata cca gag gaa gag tct      903
Lys Thr Asn Arg Gly Arg Arg Ser Asn His Ile Pro Glu Glu Glu Ser
140                 145                 150 tca tca tcc tcc agt gat gaa gat gag gat gat agg aaa cag att gat      951
Ser Ser Ser Ser Ser Asp Glu Asp Glu Asp Asp Arg Lys Gln Ile Asp
155                 160                 165                 170 gag cta cta ggc aaa gtt gta tgt gta gat tac att agt ttg gat aaa      999
Glu Leu Leu Gly Lys Val Val Cys Val Asp Tyr Ile Ser Leu Asp Lys
                175                 180                 185 aag aaa gca ctg tgg ttt cct gca ttg gtg gtt tgt cct gat tgt agt     1047
Lys Lys Ala Leu Trp Phe Pro Ala Leu Val Val Cys Pro Asp Cys Ser
        190                 195                 200 gat gag att gct gta aaa aag gac aat att ctt gtt cga tct ttc aaa     1095
Asp Glu Ile Ala Val Lys Lys Asp Asn Ile Leu Val Arg Ser Phe Lys
    205                 210                 215 gat gga aaa ttt act tca gtt cca aga aaa gat gtc cat gaa att act     1143
Asp Gly Lys Phe Thr Ser Val Pro Arg Lys Asp Val His Glu Ile Thr
220                 225                 230
```

| | | | | | | | | | | | | | | | |
|---|---|---|---|---|---|---|---|---|---|---|---|---|---|---|---|
| agt | act | gca | cca | aag | cct | gat | gct | gtt | tta | aag | caa | gcc | ttt | gaa | 1191 |
| Ser | Thr | Ala | Pro | Lys | Pro | Asp | Ala | Val | Leu | Lys | Gln | Ala | Phe | Glu | |
| 235 | | | | 240 | | | | | 245 | | | | | 250 | |
| cag | gca | ctt | gaa | ttt | cac | aaa | agt | aga | act | att | cct | gct | aac | tgg | aag | 1239 |
| Gln | Ala | Leu | Glu | Phe | His | Lys | Ser | Arg | Thr | Ile | Pro | Ala | Asn | Trp | Lys |
| | | | | 255 | | | | | 260 | | | | | 265 | |
| act | gaa | ttg | aaa | gaa | gat | agc | tct | agc | agt | gaa | gca | gag | gaa | gaa | gag | 1287 |
| Thr | Glu | Leu | Lys | Glu | Asp | Ser | Ser | Ser | Ser | Glu | Ala | Glu | Glu | Glu | Glu |
| | | 270 | | | | | 275 | | | | | 280 | | | |
| gag | gag | gaa | gat | gat | gaa | aaa | gaa | aag | gag | grt | aat | agc | agt | gaa | gaa | 1335 |
| Glu | Glu | Glu | Asp | Asp | Glu | Lys | Glu | Lys | Glu | Xaa | Asn | Ser | Ser | Glu | Glu |
| | | 285 | | | | | 290 | | | | | 295 | | | |
| gar | gaa | gaa | ata | gaa | cca | ttt | cca | gaa | gaa | agg | gag | aac | ttt | ctt | cag | 1383 |
| Glu | Glu | Glu | Ile | Glu | Pro | Phe | Pro | Glu | Glu | Arg | Glu | Asn | Phe | Leu | Gln |
| | 300 | | | | | 305 | | | | | 310 | | | | |
| caa | ttg | tac | aaa | ttt | atg | gaa | gat | aga | ggt | aca | cct | att | aac | aaa | cga | 1431 |
| Gln | Leu | Tyr | Lys | Phe | Met | Glu | Asp | Arg | Gly | Thr | Pro | Ile | Asn | Lys | Arg |
| 315 | | | | | 320 | | | | | 325 | | | | | 330 |
| cct | gta | ctt | gga | tat | cga | aat | ttg | aat | ctc | ttt | aag | tta | ttc | aga | ctt | 1479 |
| Pro | Val | Leu | Gly | Tyr | Arg | Asn | Leu | Asn | Leu | Phe | Lys | Leu | Phe | Arg | Leu |
| | | | | 335 | | | | | 340 | | | | | 345 | |
| gta | cac | aaa | ctt | gga | gga | ttt | gat | aat | att | gaa | agt | gga | gct | gtt | tgg | 1527 |
| Val | His | Lys | Leu | Gly | Gly | Phe | Asp | Asn | Ile | Glu | Ser | Gly | Ala | Val | Trp |
| | | 350 | | | | | 355 | | | | | 360 | | | |
| aaa | caa | gtc | tac | caa | gat | ctt | gga | atc | cct | gtc | tta | aat | tca | gct | gca | 1575 |
| Lys | Gln | Val | Tyr | Gln | Asp | Leu | Gly | Ile | Pro | Val | Leu | Asn | Ser | Ala | Ala |
| | | 365 | | | | | 370 | | | | | 375 | | | |
| gga | tac | aat | gtt | aaa | tgt | gct | tat | aaa | aaa | tac | tta | tat | ggt | ttt | gag | 1623 |
| Gly | Tyr | Asn | Val | Lys | Cys | Ala | Tyr | Lys | Lys | Tyr | Leu | Tyr | Gly | Phe | Glu |
| | 380 | | | | | 385 | | | | | 390 | | | | |
| gag | tac | tgt | aga | tca | gcc | aac | att | gaa | ttt | cag | atg | gca | ttg | cca | gag | 1671 |
| Glu | Tyr | Cys | Arg | Ser | Ala | Asn | Ile | Glu | Phe | Gln | Met | Ala | Leu | Pro | Glu |
| 395 | | | | 400 | | | | | 405 | | | | | 410 | |
| aaa | gtt | gtt | aac | aag | caa | tgt | aag | gag | tgt | gaa | aat | gta | aaa | gaa | ata | 1719 |
| Lys | Val | Val | Asn | Lys | Gln | Cys | Lys | Glu | Cys | Glu | Asn | Val | Lys | Glu | Ile |
| | | | 415 | | | | | 420 | | | | | 425 | | |
| aaa | gtt | aag | gag | gaa | aat | gaa | aca | gag | atc | aaa | gaa | ata | aag | atg | gag | 1767 |
| Lys | Val | Lys | Glu | Glu | Asn | Glu | Thr | Glu | Ile | Lys | Glu | Ile | Lys | Met | Glu |
| | | 430 | | | | | 435 | | | | | 440 | | | |
| gag | gag | agg | aat | ata | ata | cca | aga | gaa | gaa | aag | cct | att | gag | gat | gaa | 1815 |
| Glu | Glu | Arg | Asn | Ile | Ile | Pro | Arg | Glu | Glu | Lys | Pro | Ile | Glu | Asp | Glu |
| | | 445 | | | | | 450 | | | | | 455 | | | |
| att | gaa | aga | aaa | gaa | aat | att | aag | ccc | tct | ctg | gga | agt | aaa | aag | aat | 1863 |
| Ile | Glu | Arg | Lys | Glu | Asn | Ile | Lys | Pro | Ser | Leu | Gly | Ser | Lys | Lys | Asn |
| 460 | | | | | 465 | | | | | 470 | | | | | |
| tta | tta | gaa | tct | ata | cct | aca | cat | tct | gat | cag | gaa | aaa | gaa | gtt | aac | 1911 |
| Leu | Leu | Glu | Ser | Ile | Pro | Thr | His | Ser | Asp | Gln | Glu | Lys | Glu | Val | Asn |
| 475 | | | | 480 | | | | | 485 | | | | | 490 | |
| att | aaa | aaa | cca | gaa | gac | aat | gaa | aat | ctg | gay | gac | aaa | gat | gat | gac | 1959 |
| Ile | Lys | Lys | Pro | Glu | Asp | Asn | Glu | Asn | Leu | Asp | Asp | Lys | Asp | Asp | Asp |
| | | | 495 | | | | | 500 | | | | | 505 | | |
| aca | act | agg | gta | gat | gaa | tcc | ctc | aac | ata | aag | gta | gaa | gct | gag | gaa | 2007 |
| Thr | Thr | Arg | Val | Asp | Glu | Ser | Leu | Asn | Ile | Lys | Val | Glu | Ala | Glu | Glu |
| | | 510 | | | | | 515 | | | | | 520 | | | |
| gaa | aaa | gca | aaa | tct | gga | gat | gaa | acg | aat | aaa | gaa | gaa | gat | gaa | gat | 2055 |
| Glu | Lys | Ala | Lys | Ser | Gly | Asp | Glu | Thr | Asn | Lys | Glu | Glu | Asp | Glu | Asp |
| | | 525 | | | | | 530 | | | | | 535 | | | |
| gat | gaa | gaa | gca | gaa | gag | gag | gag | gag | gaa | gaa | gaa | gaa | gag | gat | | 2103 |
| Asp | Glu | Glu | Ala | Glu | Glu | Glu | Glu | Glu | Glu | Glu | Glu | Glu | Glu | Asp | |

-continued

```
        540                 545                 550
gaa gat gat gat gac aac aat gag gaa gag gag ttt gag tgc tat cca    2151
Glu Asp Asp Asp Asp Asn Asn Glu Glu Glu Glu Phe Glu Cys Tyr Pro
555                 560                 565                 570 cca ggc atg aaa gtc caa gtg cgg tat gga cga ggg aaa aat caa aaa    2199
Pro Gly Met Lys Val Gln Val Arg Tyr Gly Arg Gly Lys Asn Gln Lys
                575                 580                 585 atg tat gaa gct agt att aaa gat tct gat gtt gaa ggt gga gag gtc    2247
Met Tyr Glu Ala Ser Ile Lys Asp Ser Asp Val Glu Gly Gly Glu Val
            590                 595                 600 ctt tac ttg gtg cat tac tgc gga tgg aat gtg aga tac gat gaa tgg    2295
Leu Tyr Leu Val His Tyr Cys Gly Trp Asn Val Arg Tyr Asp Glu Trp
        605                 610                 615 att aaa gca gat aaa ata gta aga cct gct gat aaa aat gtg cca aag    2343
Ile Lys Ala Asp Lys Ile Val Arg Pro Ala Asp Lys Asn Val Pro Lys
    620                 625                 630 ata aaa cat cgg aag aaa ata aag aat aaa tta gac aaa gaa aaa gac    2391
Ile Lys His Arg Lys Lys Ile Lys Asn Lys Leu Asp Lys Glu Lys Asp
635                 640                 645                 650 aaa gat gaa aaa tac tct cca aaa aac tgt aaa ctt cgg cgc ttg tcc    2439
Lys Asp Glu Lys Tyr Ser Pro Lys Asn Cys Lys Leu Arg Arg Leu Ser
                655                 660                 665 aaa cca cca ttt cag aca aat cca tct cct gaa atg gta tcc aaa ctg    2487
Lys Pro Pro Phe Gln Thr Asn Pro Ser Pro Glu Met Val Ser Lys Leu
            670                 675                 680 gat ctc act gat gcc aaa aac tct gat act gct cat att aag tcc ata    2535
Asp Leu Thr Asp Ala Lys Asn Ser Asp Thr Ala His Ile Lys Ser Ile
        685                 690                 695 gaa att act tcg atc ctt aat gga ctt caa gct tct gaa agt tct gct    2583
Glu Ile Thr Ser Ile Leu Asn Gly Leu Gln Ala Ser Glu Ser Ser Ala
    700                 705                 710 gaa gac agt gag cag gaa gat gag aga ggt gct caa gac atg gat aat    2631
Glu Asp Ser Glu Gln Glu Asp Glu Arg Gly Ala Gln Asp Met Asp Asn
715                 720                 725                 730 aat ggc aaa gag gaa tct aag att gat cat ttg acc aac aac aga aat    2679
Asn Gly Lys Glu Glu Ser Lys Ile Asp His Leu Thr Asn Asn Arg Asn
                735                 740                 745 gat ctt att tca aag gag gaa cag aac agt tca tct ttg cta gaa gaa    2727
Asp Leu Ile Ser Lys Glu Glu Gln Asn Ser Ser Ser Leu Leu Glu Glu
            750                 755                 760 aac aaa gtt cat gca gat ttg gta ata tcc aaa cca gtg tca aaa tct    2775
Asn Lys Val His Ala Asp Leu Val Ile Ser Lys Pro Val Ser Lys Ser
        765                 770                 775 cca gaa aga tta agg aaa gat ata gaa gta tta tcc gaa gat act gat    2823
Pro Glu Arg Leu Arg Lys Asp Ile Glu Val Leu Ser Glu Asp Thr Asp
    780                 785                 790 tat gaa gaa gat gaa gtc aca aaa aag aga aag gat gtc aag aag gac    2871
Tyr Glu Glu Asp Glu Val Thr Lys Lys Arg Lys Asp Val Lys Lys Asp
795                 800                 805                 810 aca aca gat aaa tct tca aaa cca caa ata aaa cgt ggt aaa aga agg    2919
Thr Thr Asp Lys Ser Ser Lys Pro Gln Ile Lys Arg Gly Lys Arg Arg
                815                 820                 825 tat tgc aat aca gaa gag tgt cta aaa act gga tca cct ggc aaa aag    2967
Tyr Cys Asn Thr Glu Glu Cys Leu Lys Thr Gly Ser Pro Gly Lys Lys
            830                 835                 840 gaa gag aag gcc aag aac aaa gaa tca ctt tgc atg gaa aac agt agc    3015
Glu Glu Lys Ala Lys Asn Lys Glu Ser Leu Cys Met Glu Asn Ser Ser
        845                 850                 855 aac agc tct tca gat gaa gat gaa gaa gaa aca aaa gca aag atg aca    3063
```

```
                Asn Ser Ser Ser Asp Glu Asp Glu Glu Glu Thr Lys Ala Lys Met Thr
                    860                 865                 870 cca act aag aaa tac aat ggt ttg gag gaa aaa aga aaa tct cta cgg              3111
Pro Thr Lys Lys Tyr Asn Gly Leu Glu Glu Lys Arg Lys Ser Leu Arg
875                 880                 885                 890 aca act ggt ttc tat tca gga ttt tca gaa gtg gca gaa aaa agg att              3159
Thr Thr Gly Phe Tyr Ser Gly Phe Ser Glu Val Ala Glu Lys Arg Ile
                895                 900                 905 aaa ctt tta aat aac tct gat gaa aga ctt caa aac agc agg gcc aaa              3207
Lys Leu Leu Asn Asn Ser Asp Glu Arg Leu Gln Asn Ser Arg Ala Lys
                    910                 915                 920 gat cga aaa gat gtc tgg tca agt att cag gga cag tgg cct aaa aaa              3255
Asp Arg Lys Asp Val Trp Ser Ser Ile Gln Gly Gln Trp Pro Lys Lys
                925                 930                 935 acg ctg aaa gag ctt ttt tca gac tct gat act gag gct gca gct tcc              3303
Thr Leu Lys Glu Leu Phe Ser Asp Ser Asp Thr Glu Ala Ala Ala Ser
940                 945                 950 cca ccg cat cct gcc cca gag gag grg gtg gca gag gag tca mtg cag              3351
Pro Pro His Pro Ala Pro Glu Glu Xaa Val Ala Glu Glu Ser Xaa Gln
955                 960                 965                 970 act gtg gct gaa gag gag agt tgt tca ccc agt gta gaa cta gaa aaa              3399
Thr Val Ala Glu Glu Glu Ser Cys Ser Pro Ser Val Glu Leu Glu Lys
                975                 980                 985 cca cct cca gtc aat gtc gat agt aaa ccc att gaa gaa aaa aca gta              3447
Pro Pro Pro Val Asn Val Asp Ser Lys Pro Ile Glu Glu Lys Thr Val
                990                 995                 1000 gag gtc aat gac aga aaa gca gaa ttt cca agt agt ggc agt aat tca              3495
Glu Val Asn Asp Arg Lys Ala Glu Phe Pro Ser Ser Gly Ser Asn Ser
                1005                1010                1015 gtg cta aat acc cct cct act aca cct gaa tcg cct tca tca gtc act              3543
Val Leu Asn Thr Pro Pro Thr Thr Pro Glu Ser Pro Ser Ser Val Thr
        1020                1025                1030 gta aca gaa ggc agc cgg cag cag tct tct gta aca gta tca gaa cca              3591
Val Thr Glu Gly Ser Arg Gln Gln Ser Ser Val Thr Val Ser Glu Pro
1035                1040                1045                1050 ctg gct cca aac caa gaa gag gtt cga agt atc aag agt gaa act gat              3639
Leu Ala Pro Asn Gln Glu Glu Val Arg Ser Ile Lys Ser Glu Thr Asp
                1055                1060                1065 agc aca att gag gtg gat agt gtt gct ggg gag ctc caa gac ctc cag              3687
Ser Thr Ile Glu Val Asp Ser Val Ala Gly Glu Leu Gln Asp Leu Gln
                1070                1075                1080 tct gaa ggg aat agc tcg cca gca ggt ttt gat gcc agt gtg agc tca              3735
Ser Glu Gly Asn Ser Ser Pro Ala Gly Phe Asp Ala Ser Val Ser Ser
        1085                1090                1095 agc agt agt aat cag cca gaa cca gaa cat cct gaa aaa gcc tgt aca              3783
Ser Ser Ser Asn Gln Pro Glu Pro Glu His Pro Glu Lys Ala Cys Thr
1100                1105                1110 ggt cag aaa aga gtg aaa gat gct cag gga gga gga agt tca tca aaa              3831
Gly Gln Lys Arg Val Lys Asp Ala Gln Gly Gly Gly Ser Ser Ser Lys
1115                1120                1125                1130 aag cag aaa aga agc cat aaa gca aca gtg gta aac aac aaa aag aag              3879
Lys Gln Lys Arg Ser His Lys Ala Thr Val Val Asn Asn Lys Lys Lys
                1135                1140                1145 gga aaa ggc aca aat agt agt gat agt gaa gaa ctt tca gct ggt gaa              3927
Gly Lys Gly Thr Asn Ser Ser Asp Ser Glu Glu Leu Ser Ala Gly Glu
                1150                1155                1160 agt ata act aag agt cag cca gtc aaa tca gtt tcc act gga atg aag              3975
Ser Ile Thr Lys Ser Gln Pro Val Lys Ser Val Ser Thr Gly Met Lys
        1165                1170                1175
```

| | | |
|---|---|---|
| tct cat agt acc aaa tct ccc gca agg acg cag tct cca gga aaa tgt<br>Ser His Ser Thr Lys Ser Pro Ala Arg Thr Gln Ser Pro Gly Lys Cys<br>　　　1180　　　　　　　　　1185　　　　　　　　　1190 | | 4023 |
| gga aag aat ggt gat aag gat cct gat ctc aag gaa ccc agt aat cga<br>Gly Lys Asn Gly Asp Lys Asp Pro Asp Leu Lys Glu Pro Ser Asn Arg<br>1195　　　　　　　　　1200　　　　　　　　　1205　　　　　　　　　1210 | | 4071 |
| tta ccc aaa gtt tac aaa tgg agt ttt cag atg tcg gac ctg gaa aat<br>Leu Pro Lys Val Tyr Lys Trp Ser Phe Gln Met Ser Asp Leu Glu Asn<br>　　　　　　　　　1215　　　　　　　　　1220　　　　　　　　　1225 | | 4119 |
| atg aca agt gcc gaa cgc atc aca att ctt caa gaa aaa ctt caa gaa<br>Met Thr Ser Ala Glu Arg Ile Thr Ile Leu Gln Glu Lys Leu Gln Glu<br>　　　　　1230　　　　　　　　　1235　　　　　　　　　1240 | | 4167 |
| atc aga aaa cat tat ctg tca tta aaa tct gaa gta gct tcc att gat<br>Ile Arg Lys His Tyr Leu Ser Leu Lys Ser Glu Val Ala Ser Ile Asp<br>　　　1245　　　　　　　　　1250　　　　　　　　　1255 | | 4215 |
| cgg agg aga aag cgt tta aag aag aaa gag aga gaa agt gct gct aca<br>Arg Arg Arg Lys Arg Leu Lys Lys Lys Glu Arg Glu Ser Ala Ala Thr<br>1260　　　　　　　　　1265　　　　　　　　　1270 | | 4263 |
| tcc tca tcc tcc tct tca cct tca tcc agt tcc ata aca gct gct gtt<br>Ser Ser Ser Ser Ser Ser Pro Ser Ser Ser Ser Ile Thr Ala Ala Val<br>1275　　　　　　　　　1280　　　　　　　　　1285　　　　　　　　　1290 | | 4311 |
| atg tta act tta gct gaa ccg tca atg tcc agc gca tca caa aat gga<br>Met Leu Thr Leu Ala Glu Pro Ser Met Ser Ser Ala Ser Gln Asn Gly<br>　　　　　　　　　1295　　　　　　　　　1300　　　　　　　　　1305 | | 4359 |
| atg tca gtt gag tgc agg tga cagcaggact tgctaaagca ctttgcactt<br>Met Ser Val Glu Cys Arg *<br>　　　　　1310 | | 4410 |
| aatggctgtt gagggccact tttttttat actgcacagt ggcacaaaaa aatatcagac | | 4470 |
| aagcactatt ttatatttaa aaattgtttc ttgacaagct gacttggcac ttaagtgcac | | 4530 |
| ttttttatga agaaaaagta caatgaactg cttttcctca agcaataatt gkttccaact | | 4590 |
| tgtctgggaa ttgtgtgtct ggtaactgga aggccttcca ctgtggcaaa tggaggcttt | | 4650 |
| tcactgcctg tagagacaat acagtaagca tagttaaggg gtgggtcaga acatgttaag | | 4710 |
| ataacttact gtatatgtat tcccttgtat tttgttaaag ctggaacatt tgatattttt | | 4770 |
| ccatttattt atgaaaaaat atgaacctat tttcattgt acaaggtaat tgttttttaa | | 4830 |
| agcaagtcac cttagggtgg ctttaattgt ataagtcaag cacatgtaat aaattcaaaa | | 4890 |
| cctgcagtta acaggatatt agacatcaat cctggtaacc aaatattaaa gattctcttt | | 4950 |
| aaaaaagact gaacatgttt acaggtttga attaggctaa aaggtcttgc agtggctttt | | 5010 |
| catggccctt caaattggaa tggaactact gtactttgcc attttctat aaatcagtat | | 5070 |
| tttttttaa ttttgatata cattgtgtga aaaagaaaa tggctaataa actgtattaa | | 5130 |
| atcttaaaca atgtataaag attgtactta gccagttcaa agtgtatatt tattcataat | | 5190 |
| gaattataac agttatattt ttgtgttttc ttgtaaatgt ttcttttccc ttaaatacag | | 5250 |
| ataattcatt tgtattgctt attttattat gagctacaac aaaaggactt caggaacaag | | 5310 |
| taatgtatta gtatggttca agattgttga taggaactgt ctcaaaagga tggtggttat | | 5370 |
| tttaaatata aatagctaat gggggtggta ggcctataaa attaaatgcc ttgtataaaa | | 5430 |
| tccaaaatga atgcaaaatt gttttcactt gtattgactt tatgttgtat gattccaatc | | 5490 |
| tctgttctgt ttggcacttg tatttaattc ttcacctttg taagcatttt gtatattgtg | | 5550 |
| gatgtgttca ttcaagctat ttaatatctg gcactgttaa tacacagtac tttattgtac | | 5610 |
| agactgtttt actgttttaa ttgtagttct gtgtactttt tttggatggg gctggcatgt | | 5670 |
| tttctttgtt tcctggcaat acgacgtggg aatttcaatg cgttttgttg tagatgctaa | | 5730 |

| | |
|---|---|
| cgtgtcagaa tcctttacat tcaacttttc taagaaaagc attttcagtc ttgtagtgtg | 5790 |
| tgcttacagt aactaatttt gttgaaaatg gtttcaagtt attcaaattt gtacaggact | 5850 |
| gtaaagattt gttgacagca aaatgttgaa gaaaaaagct tatagaataa aagctataaa | 5910 |
| gtatatatta ggatctgcaa acaatgaaga attatgtaat atattgtaca aatgtaagca | 5970 |
| aaggctctga aataaaatgc catagtttgt ga | 6002 |

<210> SEQ ID NO 5
<211> LENGTH: 392
<212> TYPE: DNA
<213> ORGANISM: Homo sapiens

<400> SEQUENCE: 5

| | |
|---|---|
| ccggagtgag gagctcggtc gccgaagcgg agggagactc ttgagcttca tcttgccgcc | 60 |
| gccacggcca ccgcctggac ctttgcccgg agggagctgc agagggtcca tcgccgccgt | 120 |
| cctctggagg gcagcgcgat tgggggcccg gacctccagt ccgggggga tttttcgtcg | 180 |
| tcccccctccc cccaaccagg gagcccgagc ggccgccaaa caaaggtacc agtcgccgcc | 240 |
| gcgggaggag gaggagccgg agcctctgcc tcagcagccg ctggaccccgc cgcccttctt | 300 |
| ccccatctct cccccgggcc tgctggtttt ggggggggaga aggagagagg ggactctgga | 360 |
| cgtgccaggg tcagatctcg cctccgagga ag | 392 |

<210> SEQ ID NO 6
<211> LENGTH: 55
<212> TYPE: DNA
<213> ORGANISM: Homo sapiens

<400> SEQUENCE: 6

| | |
|---|---|
| gtgcagctga acctggtgtt ttagaggata ccttggtccc agagtcatca tgaag | 55 |

<210> SEQ ID NO 7
<211> LENGTH: 111
<212> TYPE: DNA
<213> ORGANISM: Homo sapiens

<400> SEQUENCE: 7

| | |
|---|---|
| gcccttgatg agcctcccta tttgacagtg ggcactgatg tgagtgctaa atacagagga | 60 |
| gccttttgtg aagccaagat caagacagca aaaagacttg tcaaagtcaa g | 111 |

<210> SEQ ID NO 8
<211> LENGTH: 66
<212> TYPE: DNA
<213> ORGANISM: Homo sapiens

<400> SEQUENCE: 8

| | |
|---|---|
| gtgacattta gacatgattc ttcaacagtg gaagttcagg atgaccacat aaagggccca | 60 |
| ctaaag | 66 |

<210> SEQ ID NO 9
<211> LENGTH: 91
<212> TYPE: DNA
<213> ORGANISM: Homo sapiens

<400> SEQUENCE: 9

| | |
|---|---|
| gtaggagcta ttgtggaagt gaagaatctt gatggtgcat atcaggaagc tgttatcaat | 60 |
| aaactaacag atgcgagttg gtacactgta g | 91 |

```
<210> SEQ ID NO 10
<211> LENGTH: 80
<212> TYPE: DNA
<213> ORGANISM: Homo sapiens

<400> SEQUENCE: 10
tttttgatga cggagatgag aagacactga gacgatcttc actgtgcctg aaaggagaga    60
ggcattttgc tgaaagtgaa                                                80

<210> SEQ ID NO 11
<211> LENGTH: 92
<212> TYPE: DNA
<213> ORGANISM: Homo sapiens

<400> SEQUENCE: 11
acattagacc agctcccact caccaaccct gagcattttg gcactccagt cataggaaag    60
aaaacaaata gaggaagaag atctaatcat at                                  92

<210> SEQ ID NO 12
<211> LENGTH: 139
<212> TYPE: DNA
<213> ORGANISM: Homo sapiens

<400> SEQUENCE: 12
accagaggaa gagtcttcat catcctccag tgatgaagat gaggatgata ggaaacagat    60
tgatgagcta ctaggcaaag ttgtatgtgt agattacatt agtttggata aaaagaaagc   120
actgtggttt cctgcattg                                                139

<210> SEQ ID NO 13
<211> LENGTH: 80
<212> TYPE: DNA
<213> ORGANISM: Homo sapiens

<400> SEQUENCE: 13
gtggtttgtc ctgattgtag tgatgagatt gctgtaaaaa aggacaatat tcttgttcga    60
tctttcaaag atggaaaatt                                                80

<210> SEQ ID NO 14
<211> LENGTH: 77
<212> TYPE: DNA
<213> ORGANISM: Homo sapiens

<400> SEQUENCE: 14
tacttcagtt ccaagaaaag atgtccatga aattactagt gacactgcac caaagcctga    60
tgctgtttta aagcaag                                                   77

<210> SEQ ID NO 15
<211> LENGTH: 155
<212> TYPE: DNA
<213> ORGANISM: Homo sapiens

<400> SEQUENCE: 15
cctttgaaca ggcacttgaa tttcacaaaa gtagaactat tcctgctaac tggaagactg    60
aattgaaaga agatagctct agcagtgaag cagaggaaga agaggaggag gaagatgatg   120
aaaaagaaaa ggaggataat agcagtgaag aagag                              155

<210> SEQ ID NO 16
<211> LENGTH: 73
```

```
<212> TYPE: DNA
<213> ORGANISM: Homo sapiens

<400> SEQUENCE: 16
gaagaaatag aaccatttcc agaagaaagg gagaactttc ttcagcaatt gtacaaattt      60
atggaagata gag                                                        73

<210> SEQ ID NO 17
<211> LENGTH: 95
<212> TYPE: DNA
<213> ORGANISM: Homo sapiens

<400> SEQUENCE: 17
gtacacctat taacaaacga cctgtacttg gatatcgaaa tttgaatctc tttaagttat      60
tcagacttgt acacaaactt ggaggatttg ataat                                95

<210> SEQ ID NO 18
<211> LENGTH: 98
<212> TYPE: DNA
<213> ORGANISM: Homo sapiens

<400> SEQUENCE: 18
attgaaagtg gagctgtttg gaaacaagtc taccaagatc ttggaatccc tgtcttaaat      60
tcagctgcag gatacaatgt taaatgtgct tataaaaa                             98

<210> SEQ ID NO 19
<211> LENGTH: 244
<212> TYPE: DNA
<213> ORGANISM: Homo sapiens

<400> SEQUENCE: 19
atacttatat ggttttgagg agtactgtag atcagccaac attgaatttc agatggcatt      60
gccagagaaa gttgttaaca agcaatgtaa ggagtgtgaa aatgtaaaag aaataaaagt     120
taaggaggaa aatgaaacag agatcaaaga aataaagatg gaggaggaga ggaatataat     180
accaagagaa gaaaagccta ttgaggatga aattgaaaga aaagaaaata ttaagccctc     240
tctg                                                                 244

<210> SEQ ID NO 20
<211> LENGTH: 176
<212> TYPE: DNA
<213> ORGANISM: Homo sapiens

<400> SEQUENCE: 20
ggaagtaaaa agaatttatt agaatctata cctacacatt ctgatcagga aaagaagtt       60 aacattaaaa aaccagaaga caatgaaaat ctggacgaca agatgatga cacaactagg      120 gtagatgaat ccctcaacat aaaggtagaa gctgaggaag aaaaagcaaa atctgg         176

<210> SEQ ID NO 21
<211> LENGTH: 258
<212> TYPE: DNA
<213> ORGANISM: Homo sapiens

<400> SEQUENCE: 21
agatgaaacg aataaagaag aagatgaaga tgatgaagaa gcagaagagg aggaggagga      60
ggaagaagaa gaagaggatg aagatgatga tgacaacaat gaggaagagg agtttgagtg     120
ctatccacca ggcatgaaag tccaagtgcg gtatggacga gggaaaaatc aaaaaatgta     180
```

```
tgaagctagt attaaagatt ctgatgttga aggtggagag gtcctttact tggtgcatta        240
ctgcggatgg aatgtgag                                                      258

<210> SEQ ID NO 22
<211> LENGTH: 85
<212> TYPE: DNA
<213> ORGANISM: Homo sapiens

<400> SEQUENCE: 22
atacgatgaa tggattaaag cagataaaat agtaagacct gctgataaaa atgtgccaaa        60
gataaaacat cggaagaaaa taaag                                              85

<210> SEQ ID NO 23
<211> LENGTH: 199
<212> TYPE: DNA
<213> ORGANISM: Homo sapiens

<400> SEQUENCE: 23
aataaattag acaaagaaaa agacaaagat gaaaaatact ctccaaaaaa ctgtaaactt        60
cggcgcttgt ccaaaccacc atttcagaca aatccatctc ctgaaatggt atccaaactg       120
gatctcactg atgccaaaaa ctctgatact gctcatatta agtccataga aattacttcg       180
atccttaatg gacttcaag                                                    199

<210> SEQ ID NO 24
<211> LENGTH: 1209
<212> TYPE: DNA
<213> ORGANISM: Homo sapiens

<400> SEQUENCE: 24
cttctgaaag ttctgctgaa gacagtgagc aggaagatga gagaggtgct caagacatgg        60
ataataatgg caaagaggaa tctaagattg atcatttgac caacaacaga atgatctta       120 tttcaaagga ggaacagaac agttcatctt tgctagaaga aaacaaagtt catgcagatt       180
tggtaatatc caaccagtg tcaaaatctc cagaaagatt aaggaaagat atagaagtat       240
tatccgaaga tactgattat gaagaagatg aagtcacaaa aaagagaaag gatgtcaaga       300
aggacacaac agataaatct tcaaaaccac aaataaaacg tggtaaaaga aggtattgca       360
atacagaaga gtgtctaaaa actggatcac ctggcaaaaa ggaagagaag gccaagaaca       420
aagaatcact ttgcatggaa acagtagca acagctcttc agatgaagat gaagaagaaa       480
caaaagcaaa gatgacacca actaagaaat acaatggttt ggaggaaaaa agaaaatctc       540
tacggacaac tggtttctat tcaggatttt cagaagtggc agaaaaaagg attaaacttt       600
taaataactc tgatgaaaga cttcaaaaca gcagggccaa agatcgaaaa gatgtctggt       660
caagtattca gggacagtgg cctaaaaaaa cgctgaaaga ctgctttttca gactctgata       720 ctgaggctgc agcttcccca ccgcatcctg ccccagagga ggggggtggca gaggagtcac       780 tgcagactgt ggctgaagag gagagttgtt cacccagtgt agaactagaa aaaccacctc       840
cagtcaatgt cgatagtaaa cccattgaag aaaaaacagt agaggtcaat gacagaaaag       900
cagaatttcc aagtagtggc agtaattcag tgctaaatac ccctcctact acacctgaat       960
cgccttcatc agtcactgta acagaaggca gccggcagca gtcttctgta acagtatcag      1020
aaccactggc tccaaaccaa gaagaggttc gaagtatcaa gagtgaaact gatagcacaa      1080
ttgaggtgga tagtgttgct ggggagctcc aagacctcca gtctgaaggg aatagctcgc      1140
cagcaggttt tgatgccagt gtgagctcaa gcagtagtaa tcagccagaa ccagaacatc      1200
```

```
ctgaaaaag                                                              1209

<210> SEQ ID NO 25
<211> LENGTH: 114
<212> TYPE: DNA
<213> ORGANISM: Homo sapiens

<400> SEQUENCE: 25
cctgtacagg tcagaaaaga gtgaaagatg ctcagggagg aggaagttca tcaaaaaagc       60
agaaaagaag ccataaagca acagtggtaa acaacaaaaa gaagggaaaa ggca           114

<210> SEQ ID NO 26
<211> LENGTH: 216
<212> TYPE: DNA
<213> ORGANISM: Homo sapiens

<400> SEQUENCE: 26
caaatagtag tgatagtgaa gaactttcag ctggtgaaag tataactaag agtcagccag       60
tcaaatcagt ttccactgga atgaagtctc atagtaccaa atctcccgca aggacgcagt      120
ctccaggaaa atgtggaaag aatggtgata aggatcctga tctcaaggaa cccagtaatc      180
gattacccaa agtttacaaa tggagttttc agatgt                               216

<210> SEQ ID NO 27
<211> LENGTH: 147
<212> TYPE: DNA
<213> ORGANISM: Homo sapiens

<400> SEQUENCE: 27
cggacctgga aaatatgaca agtgccgaac gcatcacaat tcttcaagaa aaacttcaag       60
aaatcagaaa acattatctg tcattaaaat ctgaagtagc ttccattgat cggaggagaa      120
agcgtttaaa gaagaaagag agagaaa                                         147

<210> SEQ ID NO 28
<211> LENGTH: 1750
<212> TYPE: DNA
<213> ORGANISM: Homo sapiens

<400> SEQUENCE: 28
gtgctgctac atcctcatcc tcctcttcac cttcatccag ttccataaca gctgctgtta       60
tgttaacttt agctgaaccg tcaatgtcca gcgcatcaca aaatggaatg tcagttgagt      120
gcaggtgaca gcaggacttg ctaaagcact ttgcacttaa tggctgttga gggccacttt      180 tttttttatac tgcacagtgg cacaaaaaaa tatcagacaa gcactatttt atatttaaaa      240
attgtttctt gacaagctga cttggcactt aagtgcactt tttatgaag aaaaagtaca       300 atgaactgct tttcctcaag caataattgt ttccaacttg tctgggaatt gtgtgtctgg      360
taactggaag gccttccact gtggcaaatg gaggcttttc actgcctgta gagacaatac      420
agtaagcata gttaaggggt gggtcagaac atgttaagat aacttactgt atatgtattc      480
ccttgtattt tgttaaagct ggaacatttg atatttttcc atttatttat gaaaaaatat      540
gaacctattt tcatttgtac aaggtaattg tttttttaaag caagtcacct tagggtggct      600
ttaattgtat aagtcaagca catgtaataa attcaaaacc tgcagttaac aggatattag      660
acatcaatcc tggtaaccaa atattaaaga ttctctttaa aaaagactga acatgtttac      720
aggtttgaat taggctaaaa ggtcttgcag tggcttttca tggcccttca aattggaatg      780
```

-continued

```
gaactactgt actttgccat ttttctataa atcagtattt ttttttaatt ttgatataca      840
ttgtgtgaaa aagaaaatg gctaataaac tgtattaaat cttaaacaat gtataaagat      900
tgtacttagc cagttcaaag tgtatattta ttcataatga attataacag ttatatttt      960 gtgttttctt gtaaatgttt cttttccctt aaatacagat aattcatttg tattgcttat    1020
tttattatga gctacaacaa aaggacttca ggaacaagta atgtattagt atggttcaag    1080
attgttgata ggaactgtct caaaaggatg gtggttattt taaatataaa tagctaatgg    1140
gggtggtagg cctataaaat taaatgcctt gtataaaatc caaaatgaat gcaaaattgt    1200
tttcacttgt attgacttta tgttgtatga ttccaatctc tgttctgttt ggcacttgta    1260
tttaattctt cacctttgta agacatttgt atattgtgga tgtgttcatt caagctattt    1320
aatatctggc actgttaata cacagtactt tattgtacag actgttttac tgttttaatt    1380
gtagttctgt gtacttttt tggatggggc tggcatgttt tctttgtttc ctggcaatac    1440
gacgtgggaa tttcaatgcg tttttgttgta gatgctaacg tgtcagaatc ctttacattc    1500 aactttcta agaaaagcat tttcagtctt gtagtgtgtg cttacagtaa ctaattttgt    1560
tgaaaatggt ttcaagttat tcaaatttgt acaggactgt aaagatttgt tgacagcaaa    1620
atgttgaaga aaaagctta tagaataaaa gctataaagt atatattagg atctgcaaac    1680
aatgaagaat tatgtaatat attgtacaaa tgtaagcaaa ggctctgaaa taaaatgcca    1740
tagtttgtga                                                            1750
```

<210> SEQ ID NO 29
<211> LENGTH: 1312
<212> TYPE: PRT
<213> ORGANISM: Homo sapiens
<220> FEATURE:
<221> NAME/KEY: CARBOHYD
<222> LOCATION: 294..296
<223> OTHER INFORMATION: potential
<220> FEATURE:
<221> NAME/KEY: CARBOHYD
<222> LOCATION: 432..434
<223> OTHER INFORMATION: potential
<220> FEATURE:
<221> NAME/KEY: CARBOHYD
<222> LOCATION: 755..757
<223> OTHER INFORMATION: potential
<220> FEATURE:
<221> NAME/KEY: CARBOHYD
<222> LOCATION: 856..858
<223> OTHER INFORMATION: potential
<220> FEATURE:
<221> NAME/KEY: CARBOHYD
<222> LOCATION: 859..861
<223> OTHER INFORMATION: potential
<220> FEATURE:
<221> NAME/KEY: CARBOHYD
<222> LOCATION: 910..912
<223> OTHER INFORMATION: potential
<220> FEATURE:
<221> NAME/KEY: CARBOHYD
<222> LOCATION: 1151..1153
<223> OTHER INFORMATION: potential
<220> FEATURE:
<221> NAME/KEY: CARBOHYD
<222> LOCATION: 1226..1228
<223> OTHER INFORMATION: potential
<220> FEATURE:
<221> NAME/KEY: PHOSPHORYLATION
<222> LOCATION: 102..105
<223> OTHER INFORMATION: potential
<220> FEATURE:
<221> NAME/KEY: PHOSPHORYLATION
<222> LOCATION: 663..666
<223> OTHER INFORMATION: potential -continued

```
<220> FEATURE:
<221> NAME/KEY: PHOSPHORYLATION
<222> LOCATION: 808..811
<223> OTHER INFORMATION: potential
<220> FEATURE:
<221> NAME/KEY: PHOSPHORYLATION
<222> LOCATION: 885..888
<223> OTHER INFORMATION: potential
<220> FEATURE:
<221> NAME/KEY: PHOSPHORYLATION
<222> LOCATION: 17..19
<223> OTHER INFORMATION: potential
<220> FEATURE:
<221> NAME/KEY: PHOSPHORYLATION
<222> LOCATION: 31..33
<223> OTHER INFORMATION: potential
<220> FEATURE:
<221> NAME/KEY: PHOSPHORYLATION
<222> LOCATION: 41..43
<223> OTHER INFORMATION: potential
<220> FEATURE:
<221> NAME/KEY: PHOSPHORYLATION
<222> LOCATION: 100..102
<223> OTHER INFORMATION: potential
<220> FEATURE:
<221> NAME/KEY: PHOSPHORYLATION
<222> LOCATION: 140..142
<223> OTHER INFORMATION: potential
<220> FEATURE:
<221> NAME/KEY: PHOSPHORYLATION
<222> LOCATION: 216..218
<223> OTHER INFORMATION: potential
<220> FEATURE:
<221> NAME/KEY: PHOSPHORYLATION
<222> LOCATION: 471..473
<223> OTHER INFORMATION: potential
<220> FEATURE:
<221> NAME/KEY: PHOSPHORYLATION
<222> LOCATION: 507..509
<223> OTHER INFORMATION: potential
<220> FEATURE:
<221> NAME/KEY: PHOSPHORYLATION
<222> LOCATION: 531..533
<223> OTHER INFORMATION: potential
<220> FEATURE:
<221> NAME/KEY: PHOSPHORYLATION
<222> LOCATION: 591..593
<223> OTHER INFORMATION: potential
<220> FEATURE:
<221> NAME/KEY: PHOSPHORYLATION
<222> LOCATION: 656..658
<223> OTHER INFORMATION: potential
<220> FEATURE:
<221> NAME/KEY: PHOSPHORYLATION
<222> LOCATION: 801..803
<223> OTHER INFORMATION: potential
<220> FEATURE:
<221> NAME/KEY: PHOSPHORYLATION
<222> LOCATION: 812..814
<223> OTHER INFORMATION: potential
<220> FEATURE:
<221> NAME/KEY: PHOSPHORYLATION
<222> LOCATION: 815..817
<223> OTHER INFORMATION: potential
<220> FEATURE:
<221> NAME/KEY: PHOSPHORYLATION
<222> LOCATION: 876..878
<223> OTHER INFORMATION: potential
<220> FEATURE:
<221> NAME/KEY: PHOSPHORYLATION
<222> LOCATION: 888..890
<223> OTHER INFORMATION: potential
<220> FEATURE:
<221> NAME/KEY: PHOSPHORYLATION
<222> LOCATION: 939..941
<223> OTHER INFORMATION: potential
<220> FEATURE:
<221> NAME/KEY: PHOSPHORYLATION
<222> LOCATION: 1060..1062
```

```
<223> OTHER INFORMATION: potential
<220> FEATURE:
<221> NAME/KEY: PHOSPHORYLATION
<222> LOCATION: 1128..1130
<223> OTHER INFORMATION: potential
<220> FEATURE:
<221> NAME/KEY: PHOSPHORYLATION
<222> LOCATION: 1129..1131
<223> OTHER INFORMATION: potential
<220> FEATURE:
<221> NAME/KEY: PHOSPHORYLATION
<222> LOCATION: 1135..1137
<223> OTHER INFORMATION: potential
<220> FEATURE:
<221> NAME/KEY: PHOSPHORYLATION
<222> LOCATION: 1181..1183
<223> OTHER INFORMATION: potential
<220> FEATURE:
<221> NAME/KEY: PHOSPHORYLATION
<222> LOCATION: 1208..1210
<223> OTHER INFORMATION: potential
<220> FEATURE:
<221> NAME/KEY: PHOSPHORYLATION
<222> LOCATION: 1249..1251
<223> OTHER INFORMATION: potential
<220> FEATURE:
<221> NAME/KEY: PHOSPHORYLATION
<222> LOCATION: 47..50
<223> OTHER INFORMATION: potential
<220> FEATURE:
<221> NAME/KEY: PHOSPHORYLATION
<222> LOCATION: 126..129
<223> OTHER INFORMATION: potential
<220> FEATURE:
<221> NAME/KEY: PHOSPHORYLATION
<222> LOCATION: 157..160
<223> OTHER INFORMATION: potential
<220> FEATURE:
<221> NAME/KEY: PHOSPHORYLATION
<222> LOCATION: 158..161
<223> OTHER INFORMATION: potential
<220> FEATURE:
<221> NAME/KEY: PHOSPHORYLATION
<222> LOCATION: 159..162
<223> OTHER INFORMATION: potential
<220> FEATURE:
<221> NAME/KEY: PHOSPHORYLATION
<222> LOCATION: 216..219
<223> OTHER INFORMATION: potential
<220> FEATURE:
<221> NAME/KEY: PHOSPHORYLATION
<222> LOCATION: 274..277
<223> OTHER INFORMATION: potential
<220> FEATURE:
<221> NAME/KEY: PHOSPHORYLATION
<222> LOCATION: 276..279
<223> OTHER INFORMATION: potential
<220> FEATURE:
<221> NAME/KEY: PHOSPHORYLATION
<222> LOCATION: 295..298
<223> OTHER INFORMATION: potential
<220> FEATURE:
<221> NAME/KEY: PHOSPHORYLATION
<222> LOCATION: 296..299
<223> OTHER INFORMATION: potential
<220> FEATURE:
<221> NAME/KEY: PHOSPHORYLATION
<222> LOCATION: 481..484
<223> OTHER INFORMATION: potential
<220> FEATURE:
<221> NAME/KEY: PHOSPHORYLATION
<222> LOCATION: 483..486
<223> OTHER INFORMATION: potential
<220> FEATURE:
<221> NAME/KEY: PHOSPHORYLATION
<222> LOCATION: 508..511
<223> OTHER INFORMATION: potential
<220> FEATURE:
<221> NAME/KEY: PHOSPHORYLATION
```

```
<222> LOCATION: 527..530
<223> OTHER INFORMATION: potential
<220> FEATURE:
<221> NAME/KEY: PHOSPHORYLATION
<222> LOCATION: 531..534
<223> OTHER INFORMATION: potential
<220> FEATURE:
<221> NAME/KEY: PHOSPHORYLATION
<222> LOCATION: 591..594
<223> OTHER INFORMATION: potential
<220> FEATURE:
<221> NAME/KEY: PHOSPHORYLATION
<222> LOCATION: 595..598
<223> OTHER INFORMATION: potential
<220> FEATURE:
<221> NAME/KEY: PHOSPHORYLATION
<222> LOCATION: 680..683
<223> OTHER INFORMATION: potential
<220> FEATURE:
<221> NAME/KEY: PHOSPHORYLATION
<222> LOCATION: 712..715
<223> OTHER INFORMATION: potential
<220> FEATURE:
<221> NAME/KEY: PHOSPHORYLATION
<222> LOCATION: 713..716
<223> OTHER INFORMATION: potential
<220> FEATURE:
<221> NAME/KEY: PHOSPHORYLATION
<222> LOCATION: 717..720
<223> OTHER INFORMATION: potential
<220> FEATURE:
<221> NAME/KEY: PHOSPHORYLATION
<222> LOCATION: 736..739
<223> OTHER INFORMATION: potential
<220> FEATURE:
<221> NAME/KEY: PHOSPHORYLATION
<222> LOCATION: 750..753
<223> OTHER INFORMATION: potential
<220> FEATURE:
<221> NAME/KEY: PHOSPHORYLATION
<222> LOCATION: 758..761
<223> OTHER INFORMATION: potential
<220> FEATURE:
<221> NAME/KEY: PHOSPHORYLATION
<222> LOCATION: 793..796
<223> OTHER INFORMATION: potential
<220> FEATURE:
<221> NAME/KEY: PHOSPHORYLATION
<222> LOCATION: 860..863
<223> OTHER INFORMATION: potential
<220> FEATURE:
<221> NAME/KEY: PHOSPHORYLATION
<222> LOCATION: 861..864
<223> OTHER INFORMATION: potential
<220> FEATURE:
<221> NAME/KEY: PHOSPHORYLATION
<222> LOCATION: 862..862
<223> OTHER INFORMATION: potential
<220> FEATURE:
<221> NAME/KEY: PHOSPHORYLATION
<222> LOCATION: 939..942
<223> OTHER INFORMATION: potential
<220> FEATURE:
<221> NAME/KEY: PHOSPHORYLATION
<222> LOCATION: 945..948
<223> OTHER INFORMATION: potential
<220> FEATURE:
<221> NAME/KEY: PHOSPHORYLATION
<222> LOCATION: 947..950
<223> OTHER INFORMATION: potential
<220> FEATURE:
<221> NAME/KEY: PHOSPHORYLATION
<222> LOCATION: 971..974
<223> OTHER INFORMATION: potential
<220> FEATURE:
<221> NAME/KEY: PHOSPHORYLATION
<222> LOCATION: 1025..1028
<223> OTHER INFORMATION: potential
<220> FEATURE:
```

```
<221> NAME/KEY: PHOSPHORYLATION
<222> LOCATION: 1034..1037
<223> OTHER INFORMATION: potential
<220> FEATURE:
<221> NAME/KEY: PHOSPHORYLATION
<222> LOCATION: 1046..1049
<223> OTHER INFORMATION: potential
<220> FEATURE:
<221> NAME/KEY: PHOSPHORYLATION
<222> LOCATION: 1063..1066
<223> OTHER INFORMATION: potential
<220> FEATURE:
<221> NAME/KEY: PHOSPHORYLATION
<222> LOCATION: 1067..1070
<223> OTHER INFORMATION: potential
<220> FEATURE:
<221> NAME/KEY: PHOSPHORYLATION
<222> LOCATION: 1153..1156
<223> OTHER INFORMATION: potential
<220> FEATURE:
<221> NAME/KEY: PHOSPHORYLATION
<222> LOCATION: 1159..1162
<223> OTHER INFORMATION: potential
<220> FEATURE:
<221> NAME/KEY: PHOSPHORYLATION
<222> LOCATION: 1222..1225
<223> OTHER INFORMATION: potential
<220> FEATURE:
<221> NAME/KEY: PHOSPHORYLATION
<222> LOCATION: 1228..1231
<223> OTHER INFORMATION: potential
<220> FEATURE:
<221> NAME/KEY: PHOSPHORYLATION
<222> LOCATION: 1293..1296
<223> OTHER INFORMATION: potential
<220> FEATURE:
<221> NAME/KEY: PHOSPHORYLATION
<222> LOCATION: 2..9
<223> OTHER INFORMATION: potential
<220> FEATURE:
<221> NAME/KEY: PHOSPHORYLATION
<222> LOCATION: 82..89
<223> OTHER INFORMATION: potential
<220> FEATURE:
<221> NAME/KEY: MYRISTATE
<222> LOCATION: 13..17
<223> OTHER INFORMATION: potential
<220> FEATURE:
<221> NAME/KEY: MYRISTATE
<222> LOCATION: 324..328
<223> OTHER INFORMATION: potential
<220> FEATURE:
<221> NAME/KEY: MYRISTATE
<222> LOCATION: 351..355
<223> OTHER INFORMATION: potential
<220> FEATURE:
<221> NAME/KEY: MYRISTATE
<222> LOCATION: 470..474
<223> OTHER INFORMATION: potential
<220> FEATURE:
<221> NAME/KEY: MYRISTATE
<222> LOCATION: 706..710
<223> OTHER INFORMATION: potential
<220> FEATURE:
<221> NAME/KEY: MYRISTATE
<222> LOCATION: 1124..1128
<223> OTHER INFORMATION: potential
<220> FEATURE:
<221> NAME/KEY: MYRISTATE
<222> LOCATION: 1125..1129
<223> OTHER INFORMATION: potential
<220> FEATURE:
<221> NAME/KEY: MYRISTATE
<222> LOCATION: 1149..1153
<223> OTHER INFORMATION: potential
<220> FEATURE:
<221> NAME/KEY: AMIDATION
<222> LOCATION: 136..139
<223> OTHER INFORMATION: potential
```

```
<220> FEATURE:
<221> NAME/KEY: AMIDATION
<222> LOCATION: 142..145
<223> OTHER INFORMATION: potential
<220> FEATURE:
<221> NAME/KEY: AMIDATION
<222> LOCATION: 822..825
<223> OTHER INFORMATION: potential
<220> FEATURE:
<221> NAME/KEY: AMIDATION
<222> LOCATION: 839..842
<223> OTHER INFORMATION: potential
<220> FEATURE:
<221> NAME/KEY: VARIANT
<222> LOCATION: 293
<223> OTHER INFORMATION: 5-130-257 polymorphic amino acid Xaa=Asp or Gly
<220> FEATURE:
<221> NAME/KEY: VARIANT
<222> LOCATION: 963
<223> OTHER INFORMATION: 5-143-84 polymorphic amino acid Xaa=Glu or Gly
<220> FEATURE:
<221> NAME/KEY: VARIANT
<222> LOCATION: 969
<223> OTHER INFORMATION: 5-143-101 polymorphic amino acid Xaa=Leu or Met

<400> SEQUENCE: 29
```

Met Lys Ala Leu Asp Glu Pro Pro Tyr Leu Thr Val Gly Thr Asp Val
1               5                   10                  15

Ser Ala Lys Tyr Arg Gly Ala Phe Cys Glu Ala Lys Ile Lys Thr Ala
            20                  25                  30

Lys Arg Leu Val Lys Val Lys Val Thr Phe Arg His Asp Ser Ser Thr
        35                  40                  45

Val Glu Val Gln Asp Asp His Ile Lys Gly Pro Leu Lys Val Gly Ala
    50                  55                  60

Ile Val Glu Val Lys Asn Leu Asp Gly Ala Tyr Gln Glu Ala Val Ile
65                  70                  75                  80

Asn Lys Leu Thr Asp Ala Ser Trp Tyr Thr Val Val Phe Asp Asp Gly
                85                  90                  95

Asp Glu Lys Thr Leu Arg Arg Ser Ser Leu Cys Leu Lys Gly Glu Arg
            100                 105                 110

His Phe Ala Glu Ser Glu Thr Leu Asp Gln Leu Pro Leu Thr Asn Pro
        115                 120                 125

Glu His Phe Gly Thr Pro Val Ile Gly Lys Lys Thr Asn Arg Gly Arg
    130                 135                 140

Arg Ser Asn His Ile Pro Glu Glu Ser Ser Ser Ser Ser Ser Ser Asp
145                 150                 155                 160

Glu Asp Glu Asp Arg Lys Gln Ile Asp Glu Leu Leu Gly Lys Val
            165                 170                 175

Val Cys Val Asp Tyr Ile Ser Leu Asp Lys Lys Ala Leu Trp Phe
        180                 185                 190

Pro Ala Leu Val Val Cys Pro Asp Cys Ser Asp Glu Ile Ala Val Lys
    195                 200                 205

Lys Asp Asn Ile Leu Val Arg Ser Phe Lys Asp Gly Lys Phe Thr Ser
210                 215                 220

Val Pro Arg Lys Asp Val His Glu Ile Thr Ser Asp Thr Ala Pro Lys
225                 230                 235                 240

Pro Asp Ala Val Leu Lys Gln Ala Phe Glu Gln Ala Leu Glu Phe His
            245                 250                 255

Lys Ser Arg Thr Ile Pro Ala Asn Trp Lys Thr Glu Leu Lys Glu Asp
        260                 265                 270

Ser Ser Ser Ser Glu Ala Glu Glu Glu Glu Glu Glu Glu Asp Asp Glu

-continued

```
                275                 280                 285
Lys Glu Lys Glu Xaa Asn Ser Ser Glu Glu Glu Ile Glu Pro
            290                 295                 300

Phe Pro Glu Glu Arg Glu Asn Phe Leu Gln Gln Leu Tyr Lys Phe Met
305                 310                 315                 320

Glu Asp Arg Gly Thr Pro Ile Asn Lys Arg Pro Val Leu Gly Tyr Arg
                325                 330                 335

Asn Leu Asn Leu Phe Lys Leu Phe Arg Leu Val His Lys Leu Gly Gly
            340                 345                 350

Phe Asp Asn Ile Glu Ser Gly Ala Val Trp Lys Gln Val Tyr Gln Asp
        355                 360                 365

Leu Gly Ile Pro Val Leu Asn Ser Ala Ala Gly Tyr Asn Val Lys Cys
    370                 375                 380

Ala Tyr Lys Lys Tyr Leu Tyr Gly Phe Glu Glu Tyr Cys Arg Ser Ala
385                 390                 395                 400

Asn Ile Glu Phe Gln Met Ala Leu Pro Glu Lys Val Val Asn Lys Gln
                405                 410                 415

Cys Lys Glu Cys Glu Asn Val Lys Glu Ile Lys Val Lys Glu Glu Asn
            420                 425                 430

Glu Thr Glu Ile Lys Glu Ile Lys Met Glu Glu Arg Asn Ile Ile
        435                 440                 445

Pro Arg Glu Glu Lys Pro Ile Glu Asp Glu Ile Glu Arg Lys Glu Asn
    450                 455                 460

Ile Lys Pro Ser Leu Gly Ser Lys Lys Asn Leu Leu Glu Ser Ile Pro
465                 470                 475                 480

Thr His Ser Asp Gln Glu Lys Glu Val Asn Ile Lys Lys Pro Glu Asp
                485                 490                 495

Asn Glu Asn Leu Asp Asp Lys Asp Asp Thr Thr Arg Val Asp Glu
            500                 505                 510

Ser Leu Asn Ile Lys Val Glu Ala Glu Glu Lys Ala Lys Ser Gly
        515                 520                 525

Asp Glu Thr Asn Lys Glu Glu Asp Glu Asp Glu Glu Ala Glu Glu
    530                 535                 540

Glu Glu Glu Glu Glu Glu Glu Glu Asp Glu Asp Asp Asp Asn
545                 550                 555                 560

Asn Glu Glu Glu Glu Phe Glu Cys Tyr Pro Pro Gly Met Lys Val Gln
                565                 570                 575

Val Arg Tyr Gly Arg Gly Lys Asn Gln Lys Met Tyr Glu Ala Ser Ile
            580                 585                 590

Lys Asp Ser Asp Val Glu Gly Gly Glu Val Leu Tyr Leu Val His Tyr
        595                 600                 605

Cys Gly Trp Asn Val Arg Tyr Asp Glu Trp Ile Lys Ala Asp Lys Ile
    610                 615                 620

Val Arg Pro Ala Asp Lys Asn Val Pro Lys Ile Lys His Arg Lys Lys
625                 630                 635                 640

Ile Lys Asn Lys Leu Asp Lys Glu Lys Asp Lys Asp Glu Lys Tyr Ser
                645                 650                 655

Pro Lys Asn Cys Lys Leu Arg Arg Leu Ser Lys Pro Pro Phe Gln Thr
            660                 665                 670

Asn Pro Ser Pro Glu Met Val Ser Lys Leu Asp Leu Thr Asp Ala Lys
        675                 680                 685

Asn Ser Asp Thr Ala His Ile Lys Ser Ile Glu Ile Thr Ser Ile Leu
    690                 695                 700
```

-continued

```
Asn Gly Leu Gln Ala Ser Glu Ser Ala Glu Asp Ser Gln Glu
705                 710                 715                 720

Asp Glu Arg Gly Ala Gln Asp Met Asp Asn Gly Lys Glu Ser
            725                 730                 735

Lys Ile Asp His Leu Thr Asn Asn Arg Asn Asp Leu Ile Ser Lys Glu
                740                 745                 750

Glu Gln Asn Ser Ser Leu Leu Glu Glu Asn Lys Val His Ala Asp
        755                 760                 765

Leu Val Ile Ser Lys Pro Val Ser Lys Ser Pro Glu Arg Leu Arg Lys
770                 775                 780

Asp Ile Glu Val Leu Ser Glu Asp Thr Asp Tyr Glu Asp Glu Val
785                 790                 795                 800

Thr Lys Lys Arg Lys Asp Val Lys Lys Asp Thr Asp Lys Ser Ser
            805                 810                 815

Lys Pro Gln Ile Lys Arg Gly Lys Arg Tyr Cys Asn Thr Glu Glu
            820                 825                 830

Cys Leu Lys Thr Gly Ser Pro Gly Lys Lys Glu Glu Lys Ala Lys Asn
        835                 840                 845

Lys Glu Ser Leu Cys Met Glu Asn Ser Ser Asn Ser Ser Asp Glu
850                 855                 860

Asp Glu Glu Glu Thr Lys Ala Lys Met Thr Pro Thr Lys Lys Tyr Asn
865                 870                 875                 880

Gly Leu Glu Glu Lys Arg Lys Ser Leu Arg Thr Thr Gly Phe Tyr Ser
                885                 890                 895

Gly Phe Ser Glu Val Ala Glu Lys Arg Ile Lys Leu Leu Asn Asn Ser
            900                 905                 910

Asp Glu Arg Leu Gln Asn Ser Arg Ala Lys Asp Arg Lys Asp Val Trp
            915                 920                 925

Ser Ser Ile Gln Gly Gln Trp Pro Lys Lys Thr Leu Lys Glu Leu Phe
        930                 935                 940

Ser Asp Ser Asp Thr Glu Ala Ala Ala Ser Pro His Pro Ala Pro
945                 950                 955                 960

Glu Glu Xaa Val Ala Glu Glu Ser Xaa Gln Thr Val Ala Glu Glu Glu
            965                 970                 975

Ser Cys Ser Pro Ser Val Glu Leu Glu Lys Pro Pro Val Asn Val
        980                 985                 990

Asp Ser Lys Pro Ile Glu Glu Lys Thr Val Glu Val Asn Asp Arg Lys
        995                 1000                1005

Ala Glu Phe Pro Ser Ser Gly Ser Asn Ser Val Leu Asn Thr Pro Pro
    1010                1015                1020

Thr Thr Pro Glu Ser Pro Ser Ser Val Thr Val Thr Glu Gly Ser Arg
1025                1030                1035                1040

Gln Gln Ser Ser Val Thr Val Ser Glu Pro Leu Ala Pro Asn Gln Glu
                1045                1050                1055

Glu Val Arg Ser Ile Lys Ser Glu Thr Asp Ser Thr Ile Glu Val Asp
        1060                1065                1070

Ser Val Ala Gly Glu Leu Gln Asp Leu Gln Ser Glu Gly Asn Ser Ser
            1075                1080                1085

Pro Ala Gly Phe Asp Ala Ser Val Ser Ser Ser Ser Asn Gln Pro
    1090                1095                1100

Glu Pro Glu His Pro Glu Lys Ala Cys Thr Gly Gln Lys Arg Val Lys
1105                1110                1115                1120
```

-continued

```
Asp Ala Gln Gly Gly Gly Ser Ser Lys Lys Gln Lys Arg Ser His
            1125                1130                1135

Lys Ala Thr Val Val Asn Asn Lys Lys Gly Lys Gly Thr Asn Ser
        1140                1145                1150

Ser Asp Ser Glu Glu Leu Ser Ala Gly Glu Ser Ile Thr Lys Ser Gln
    1155                1160                1165

Pro Val Lys Ser Val Ser Thr Gly Met Lys Ser His Ser Thr Lys Ser
    1170                1175                1180

Pro Ala Arg Thr Gln Ser Pro Gly Lys Cys Gly Lys Asn Gly Asp Lys
1185                1190                1195                1200

Asp Pro Asp Leu Lys Glu Pro Ser Asn Arg Leu Pro Lys Val Tyr Lys
            1205                1210                1215

Trp Ser Phe Gln Met Ser Asp Leu Glu Asn Met Thr Ser Ala Glu Arg
            1220                1225                1230

Ile Thr Ile Leu Gln Glu Lys Leu Gln Glu Ile Arg Lys His Tyr Leu
        1235                1240                1245

Ser Leu Lys Ser Glu Val Ala Ser Ile Asp Arg Arg Arg Lys Arg Leu
    1250                1255                1260

Lys Lys Lys Glu Arg Glu Ser Ala Ala Thr Ser Ser Ser Ser Ser Ser
1265                1270                1275                1280

Pro Ser Ser Ser Ser Ile Thr Ala Ala Val Met Leu Thr Leu Ala Glu
            1285                1290                1295

Pro Ser Met Ser Ser Ala Ser Gln Asn Gly Met Ser Val Glu Cys Arg
            1300                1305                1310
```

<210> SEQ ID NO 30
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-124-273
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 5-124-273.mis1
<220> FEATURE:
<221> NAME/KEY: primer_bind
<222> LOCATION: 25..47
<223> OTHER INFORMATION: complement potential microsequencing oligo
      5-124-273.mis2

<400> SEQUENCE: 30
attcacttct taatacccta gatattatta ctgttactgg wtttat          47

<210> SEQ ID NO 31
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-127-261
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23

```
<223> OTHER INFORMATION: potential microsequencing oligo 5-127-261.mis1
<220> FEATURE:
<221> NAME/KEY: primer_bind
<222> LOCATION: 25..47
<223> OTHER INFORMATION: complement potential microsequencing oligo
      5-127-261.mis2

<400> SEQUENCE: 31
ttcagtatac aagagtttaa tttaaaactt tataagttta tgaagaa                    47

<210> SEQ ID NO 32
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-128-60
<220> FEATURE:
<221> NAME/KEY: allele
<222> LOCATION: 25
<223> OTHER INFORMATION: deletion GT
<220> FEATURE:
<221> NAME/KEY: primer_bind
<222> LOCATION: 1..24
<223> OTHER INFORMATION: potential microsequencing oligo 5-128-60.mis1

<400> SEQUENCE: 32
aaaattgctt gtgtgtgctc ccacgtgtgt gtgtgtgcct gtttacc                    47

<210> SEQ ID NO 33
<211> LENGTH: 48
<212> TYPE: DNA
<213> ORGANISM: Homo Sapiens
<220> FEATURE:
<221> NAME/KEY: allele
<222> LOCATION: 1..48
<223> OTHER INFORMATION: polymorphic fragment 5-129-144
<220> FEATURE:
<221> NAME/KEY: allele
<222> LOCATION: 23
<223> OTHER INFORMATION: deletion T
<220> FEATURE:
<221> NAME/KEY: primer_bind
<222> LOCATION: 1..22
<223> OTHER INFORMATION: potential microsequencing oligo 5-129-144.mis1

<400> SEQUENCE: 33
cttctcttat aattaaaaaa aatatatagt acttcagttc caagaaaa                   48

<210> SEQ ID NO 34
<211> LENGTH: 39
<212> TYPE: DNA
<213> ORGANISM: Homo Sapiens
<220> FEATURE:
<221> NAME/KEY: allele
<222> LOCATION: 1..39
<223> OTHER INFORMATION: polymorphic fragment 5-130-257
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 5-130-257.mis1
<220> FEATURE:
<221> NAME/KEY: primer_bind
<222> LOCATION: 25..39
<223> OTHER INFORMATION: complement potential microsequencing oligo
      5-130-257.mis2

<400> SEQUENCE: 34
```
agatgatgaa aaagaaaagg aggataatag cagtgaaga                                  39

<210> SEQ ID NO 35
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-130-276
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 5-130-276.mis1
<220> FEATURE:
<221> NAME/KEY: primer_bind
<222> LOCATION: 25..47
<223> OTHER INFORMATION: complement potential microsequencing oligo
      5-130-276.mis2

<400> SEQUENCE: 35
gaggataata gcagtgaaga agaagtaagt gaaaacagtt gatacct                         47

<210> SEQ ID NO 36
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-131-395
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 5-131-395.mis1
<220> FEATURE:
<221> NAME/KEY: primer_bind
<222> LOCATION: 25..47
<223> OTHER INFORMATION: complement potential microsequencing oligo
      5-131-395.mis2

<400> SEQUENCE: 36
cctagcatag cgcctgtcac gtaacaagta gaaykgagga atttgat                         47

<210> SEQ ID NO 37
<211> LENGTH: 50
<212> TYPE: DNA
<213> ORGANISM: Homo Sapiens
<220> FEATURE:
<221> NAME/KEY: allele
<222> LOCATION: 1..50
<223> OTHER INFORMATION: polymorphic fragment 5-133-375
<220> FEATURE:
<221> NAME/KEY: allele
<222> LOCATION: 23
<223> OTHER INFORMATION: deletion A
<220> FEATURE:
<221> NAME/KEY: primer_bind
<222> LOCATION: 1..22
<223> OTHER INFORMATION: potential microsequencing oligo 5-133-375.mis1

<400> SEQUENCE: 37
ttttctaaag tgtattctat gaatactaga tctatgagaa attctgtgaa                      50

```
<210> SEQ ID NO 38
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-135-155
<220> FEATURE:
<221> NAME/KEY: allele
<222> LOCATION: 23
<223> OTHER INFORMATION: insertion
<220> FEATURE:
<221> NAME/KEY: primer_bind
<222> LOCATION: 1..22
<223> OTHER INFORMATION: potential microsequencing oligo 5-135-155.mis1

<400> SEQUENCE: 38
tattttccat atcctctata aagttccaaa atcaatatat tgtataa                47

<210> SEQ ID NO 39
<211> LENGTH: 50
<212> TYPE: DNA
<213> ORGANISM: Homo Sapiens
<220> FEATURE:
<221> NAME/KEY: allele
<222> LOCATION: 1..50
<223> OTHER INFORMATION: polymorphic fragment 5-135-198
<220> FEATURE:
<221> NAME/KEY: allele
<222> LOCATION: 23
<223> OTHER INFORMATION: deletion GTTT
<220> FEATURE:
<221> NAME/KEY: primer_bind
<222> LOCATION: 1..22
<223> OTHER INFORMATION: potential microsequencing oligo 5-135-198.mis1

<400> SEQUENCE: 39
ataatattat tctttattat ttgttttttt cttcattaag tgctactttt             50

<210> SEQ ID NO 40
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-135-357
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 5-135-357.mis1
<220> FEATURE:
<221> NAME/KEY: primer_bind
<222> LOCATION: 25..47
<223> OTHER INFORMATION: complement potential microsequencing oligo
      5-135-357.mis2

<400> SEQUENCE: 40
ggttgatacc tcctgttgct aagagataaa ccatggatat aggttga                47

<210> SEQ ID NO 41
<211> LENGTH: 47
<212> TYPE: DNA
<213> ORGANISM: Homo Sapiens
<220> FEATURE:
<221> NAME/KEY: allele
<222> LOCATION: 1..47
```

```
<223> OTHER INFORMATION: polymorphic fragment 5-136-174
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 5-136-174.mis1
<220> FEATURE:
<221> NAME/KEY: primer_bind
<222> LOCATION: 25..47
<223> OTHER INFORMATION: complement potential microsequencing oligo
      5-136-174.mis2

<400> SEQUENCE: 41
ccagaagaca atgaaaatct ggacgacaaa gatgatgaca caactag            47

<210> SEQ ID NO 42
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-140-120
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 5-140-120.mis1
<220> FEATURE:
<221> NAME/KEY: primer_bind
<222> LOCATION: 25..47
<223> OTHER INFORMATION: complement potential microsequencing oligo
      5-140-120.mis2

<400> SEQUENCE: 42
ccttatgata aattacgaca tacctttttt cttaacctag aataaat            47

<210> SEQ ID NO 43
<211> LENGTH: 49
<212> TYPE: DNA
<213> ORGANISM: Homo Sapiens
<220> FEATURE:
<221> NAME/KEY: allele
<222> LOCATION: 1..49
<223> OTHER INFORMATION: polymorphic fragment 5-140-348
<220> FEATURE:
<221> NAME/KEY: allele
<222> LOCATION: 23
<223> OTHER INFORMATION: deletion A
<220> FEATURE:
<221> NAME/KEY: primer_bind
<222> LOCATION: 1..22
<223> OTHER INFORMATION: potential microsequencing oligo 5-140-348.mis1

<400> SEQUENCE: 43
ggacttcaag gtaaacataa caatcgttct gttgcatgca agtatttga           49

<210> SEQ ID NO 44
<211> LENGTH: 48
<212> TYPE: DNA
<213> ORGANISM: Homo Sapiens
<220> FEATURE:
<221> NAME/KEY: allele
<222> LOCATION: 1..48
<223> OTHER INFORMATION: polymorphic fragment 5-140-361
<220> FEATURE:
<221> NAME/KEY: allele
```

```
<222> LOCATION: 23
<223> OTHER INFORMATION: deletion CA
<220> FEATURE:
<221> NAME/KEY: primer_bind
<222> LOCATION: 1..22
<223> OTHER INFORMATION: potential microsequencing oligo 5-140-361.mis1

<400> SEQUENCE: 44
aaacataaca atcgttctgt tgcatgcaag tatttgattt taattat            48

<210> SEQ ID NO 45
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-143-101
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 5-143-101.mis1
<220> FEATURE:
<221> NAME/KEY: primer_bind
<222> LOCATION: 25..47
<223> OTHER INFORMATION: complement potential microsequencing oligo
      5-143-101.mis2

<400> SEQUENCE: 45 aggaggggt ggcagaggag tcaatgcaga ctgtggctga agaggag               47

<210> SEQ ID NO 46
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-143-84
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 5-143-84.mis1
<220> FEATURE:
<221> NAME/KEY: primer_bind
<222> LOCATION: 25..47
<223> OTHER INFORMATION: complement potential microsequencing oligo
      5-143-84.mis2

<400> SEQUENCE: 46
accgcatcct gccccagagg aggaggtggc agaggagtca ctgcaga              47

<210> SEQ ID NO 47
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-145-24
<220> FEATURE:
<221> NAME/KEY: allele
<222> LOCATION: 24
<223> OTHER INFORMATION: polymorphic base A
<220> FEATURE:
```

```
<221> NAME/KEY: primer_bind
<222> LOCATION: 1..23
<223> OTHER INFORMATION: potential microsequencing oligo 5-145-24.mis1
<220> FEATURE:
<221> NAME/KEY: primer_bind
<222> LOCATION: 25..47
<223> OTHER INFORMATION: complement potential microsequencing oligo
      5-145-24.mis2

<400> SEQUENCE: 47
tagtaagttc tgtgacaact tataaatgtc ataaagaaca tgtagtt                47

<210> SEQ ID NO 48
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-148-352
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 5-148-352.mis1
<220> FEATURE:
<221> NAME/KEY: primer_bind
<222> LOCATION: 25..47
<223> OTHER INFORMATION: complement potential microsequencing oligo
      5-148-352.mis2

<400> SEQUENCE: 48
tgcttttcct caagcaataa ttggttccaa cttgtctggg aattgtg                47

<210> SEQ ID NO 49
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1437-325
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo
      99-1437-325.mis1
<220> FEATURE:
<221> NAME/KEY: primer_bind
<222> LOCATION: 25..47
<223> OTHER INFORMATION: complement potential microsequencing oligo
      99-1437-325.mis2

<400> SEQUENCE: 49
caagagctga catttactgc atacttaatt tgtgccgaac actgaac                47

<210> SEQ ID NO 50
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1442-224
<220> FEATURE:
<221> NAME/KEY: allele
```

```
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo
      99-1442-224.mis1
<220> FEATURE:
<221> NAME/KEY: primer_bind
<222> LOCATION: 25..47
<223> OTHER INFORMATION: complement potential microsequencing oligo
      99-1442-224.mis2

<400> SEQUENCE: 50
attaatctca gtcatatttt ggggtttttt tcttctctta taattaa                  47

<210> SEQ ID NO 51
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-124-273, variant version
      of SEQ ID30
<220> FEATURE:
<221> NAME/KEY: allele
<222> LOCATION: 24
<223> OTHER INFORMATION: base G ; A in SEQ ID30
<220> FEATURE:
<221> NAME/KEY: primer_bind
<222> LOCATION: 1..23
<223> OTHER INFORMATION: potential microsequencing oligo 5-124-273.mis1
<220> FEATURE:
<221> NAME/KEY: primer_bind
<222> LOCATION: 25..47
<223> OTHER INFORMATION: complement potential microsequencing oligo
      5-124-273.mis2

<400> SEQUENCE: 51
attcacttct taatacccta gatgttatta ctgttactgg wttttat                  47

<210> SEQ ID NO 52
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-127-261, variant version
      of SEQ ID31
<220> FEATURE:
<221> NAME/KEY: allele
<222> LOCATION: 24
<223> OTHER INFORMATION: base C ; A in SEQ ID31
<220> FEATURE:
<221> NAME/KEY: primer_bind
<222> LOCATION: 1..23
<223> OTHER INFORMATION: potential microsequencing oligo 5-127-261.mis1
<220> FEATURE:
<221> NAME/KEY: primer_bind
<222> LOCATION: 25..47
<223> OTHER INFORMATION: complement potential microsequencing oligo
      5-127-261.mis2

<400> SEQUENCE: 52
ttcagtatac aagagtttaa tttcaaactt tataagttta tgaagaa                  47

<210> SEQ ID NO 53
<211> LENGTH: 45
<212> TYPE: DNA
<213> ORGANISM: Homo Sapiens
<220> FEATURE:
```

```
<221> NAME/KEY: allele
<222> LOCATION: 1..45
<223> OTHER INFORMATION: polymorphic fragment 5-128-60, variant version
      of SEQ ID32
<220> FEATURE:
<221> NAME/KEY: allele
<222> LOCATION: 25
<223> OTHER INFORMATION: deletion
<220> FEATURE:
<221> NAME/KEY: primer_bind
<222> LOCATION: 1..24
<223> OTHER INFORMATION: potential microsequencing oligo 5-128-60.mis1

<400> SEQUENCE: 53
aaaattgctt gtgtgtgctc ccacgtgtgt gtgtgcctgt ttacc              45

<210> SEQ ID NO 54
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-129-144, variant version
      of SEQ ID33
<220> FEATURE:
<221> NAME/KEY: allele
<222> LOCATION: 23
<223> OTHER INFORMATION: deletion
<220> FEATURE:
<221> NAME/KEY: primer_bind
<222> LOCATION: 1..22
<223> OTHER INFORMATION: potential microsequencing oligo 5-129-144.mis1

<400> SEQUENCE: 54
cttctcttat aattaaaaaa aaatatagta cttcagttcc aagaaaa            47

<210> SEQ ID NO 55
<211> LENGTH: 39
<212> TYPE: DNA
<213> ORGANISM: Homo Sapiens
<220> FEATURE:
<221> NAME/KEY: allele
<222> LOCATION: 1..39
<223> OTHER INFORMATION: polymorphic fragment 5-130-257, variant version
      of SEQ ID34
<220> FEATURE:
<221> NAME/KEY: allele
<222> LOCATION: 24
<223> OTHER INFORMATION: base G ; A in SEQ ID34
<220> FEATURE:
<221> NAME/KEY: primer_bind
<222> LOCATION: 1..23
<223> OTHER INFORMATION: potential microsequencing oligo 5-130-257.mis1
<220> FEATURE:
<221> NAME/KEY: primer_bind
<222> LOCATION: 25..39
<223> OTHER INFORMATION: complement potential microsequencing oligo
      5-130-257.mis2

<400> SEQUENCE: 55
agatgatgaa aaagaaaagg agggtaatag cagtgaaga                     39

<210> SEQ ID NO 56
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-130-276, variant version
      of SEQ ID35
<220> FEATURE:
```

```
<221> NAME/KEY: allele
<222> LOCATION: 24
<223> OTHER INFORMATION: base G ; A in SEQ ID35
<220> FEATURE:
<221> NAME/KEY: primer_bind
<222> LOCATION: 1..23
<223> OTHER INFORMATION: potential microsequencing oligo 5-130-276.mis1
<220> FEATURE:
<221> NAME/KEY: primer_bind
<222> LOCATION: 25..47
<223> OTHER INFORMATION: complement potential microsequencing oligo
      5-130-276.mis2

<400> SEQUENCE: 56
gaggataata gcagtgaaga agaggtaagt gaaaacagtt gatacct                    47

<210> SEQ ID NO 57
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-131-395, variant version
      of SEQ ID36
<220> FEATURE:
<221> NAME/KEY: allele
<222> LOCATION: 24
<223> OTHER INFORMATION: base T ; A in SEQ ID36
<220> FEATURE:
<221> NAME/KEY: primer_bind
<222> LOCATION: 1..23
<223> OTHER INFORMATION: potential microsequencing oligo 5-131-395.mis1
<220> FEATURE:
<221> NAME/KEY: primer_bind
<222> LOCATION: 25..47
<223> OTHER INFORMATION: complement potential microsequencing oligo
      5-131-395.mis2

<400> SEQUENCE: 57
cctagcatag cgcctgtcac gtatcaagta gaaykgagga atttgat                    47

<210> SEQ ID NO 58
<211> LENGTH: 49
<212> TYPE: DNA
<213> ORGANISM: Homo Sapiens
<220> FEATURE:
<221> NAME/KEY: allele
<222> LOCATION: 1..49
<223> OTHER INFORMATION: polymorphic fragment 5-133-375, variant version
      of SEQ ID37
<220> FEATURE:
<221> NAME/KEY: allele
<222> LOCATION: 23
<223> OTHER INFORMATION: deletion
<220> FEATURE:
<221> NAME/KEY: primer_bind
<222> LOCATION: 1..22
<223> OTHER INFORMATION: potential microsequencing oligo 5-133-375.mis1

<400> SEQUENCE: 58
ttttctaaag tgtattctat gatactagat ctatgagaaa ttctgtgaa                  49

<210> SEQ ID NO 59
<211> LENGTH: 48
<212> TYPE: DNA
<213> ORGANISM: Homo Sapiens
<220> FEATURE:
<221> NAME/KEY: allele
<222> LOCATION: 1..48
<223> OTHER INFORMATION: polymorphic fragment 5-135-155, variant version
      of SEQ ID38
<220> FEATURE:
```

```
<221> NAME/KEY: allele
<222> LOCATION: 23
<223> OTHER INFORMATION: insertion A
<220> FEATURE:
<221> NAME/KEY: primer_bind
<222> LOCATION: 1..22
<223> OTHER INFORMATION: potential microsequencing oligo 5-135-155.mis1

<400> SEQUENCE: 59
tattttccat atcctctata aaagttccaa aatcaatata ttgtataa                    48

<210> SEQ ID NO 60
<211> LENGTH: 46
<212> TYPE: DNA
<213> ORGANISM: Homo Sapiens
<220> FEATURE:
<221> NAME/KEY: allele
<222> LOCATION: 1..46
<223> OTHER INFORMATION: polymorphic fragment 5-135-198, variant version
      of SEQ ID39
<220> FEATURE:
<221> NAME/KEY: allele
<222> LOCATION: 23
<223> OTHER INFORMATION: deletion
<220> FEATURE:
<221> NAME/KEY: primer_bind
<222> LOCATION: 1..22
<223> OTHER INFORMATION: potential microsequencing oligo 5-135-198.mis1

<400> SEQUENCE: 60
ataatattat tctttattat tttttcttc attaagtgct acttt                        46

<210> SEQ ID NO 61
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-135-357, variant version
      of SEQ ID40
<220> FEATURE:
<221> NAME/KEY: allele
<222> LOCATION: 24
<223> OTHER INFORMATION: base G ; A in SEQ ID40
<220> FEATURE:
<221> NAME/KEY: primer_bind
<222> LOCATION: 1..23
<223> OTHER INFORMATION: potential microsequencing oligo 5-135-357.mis1
<220> FEATURE:
<221> NAME/KEY: primer_bind
<222> LOCATION: 25..47
<223> OTHER INFORMATION: complement potential microsequencing oligo
      5-135-357.mis2

<400> SEQUENCE: 61
ggttgatacc tcctgttgct aagggataaa ccatggatat aggttga                     47

<210> SEQ ID NO 62
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-136-174, variant version
      of SEQ ID41
<220> FEATURE:
<221> NAME/KEY: allele
<222> LOCATION: 24
<223> OTHER INFORMATION: base T ; C in SEQ ID41
<220> FEATURE:
<221> NAME/KEY: primer_bind
```

```
<222> LOCATION: 1..23
<223> OTHER INFORMATION: potential microsequencing oligo 5-136-174.mis1
<220> FEATURE:
<221> NAME/KEY: primer_bind
<222> LOCATION: 25..47
<223> OTHER INFORMATION: complement potential microsequencing oligo
      5-136-174.mis2

<400> SEQUENCE: 62
ccagaagaca atgaaaatct ggatgacaaa gatgatgaca caactag                    47

<210> SEQ ID NO 63
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-140-120, variant version
      of SEQ ID42
<220> FEATURE:
<221> NAME/KEY: allele
<222> LOCATION: 24
<223> OTHER INFORMATION: base T ; C in SEQ ID42
<220> FEATURE:
<221> NAME/KEY: primer_bind
<222> LOCATION: 1..23
<223> OTHER INFORMATION: potential microsequencing oligo 5-140-120.mis1
<220> FEATURE:
<221> NAME/KEY: primer_bind
<222> LOCATION: 25..47
<223> OTHER INFORMATION: complement potential microsequencing oligo
      5-140-120.mis2

<400> SEQUENCE: 63
ccttatgata aattacgaca tacttttttt cttaacctag aataaat                    47

<210> SEQ ID NO 64
<211> LENGTH: 48
<212> TYPE: DNA
<213> ORGANISM: Homo Sapiens
<220> FEATURE:
<221> NAME/KEY: allele
<222> LOCATION: 1..48
<223> OTHER INFORMATION: polymorphic fragment 5-140-348, variant version
      of SEQ ID43
<220> FEATURE:
<221> NAME/KEY: allele
<222> LOCATION: 23
<223> OTHER INFORMATION: deletion
<220> FEATURE:
<221> NAME/KEY: primer_bind
<222> LOCATION: 1..22
<223> OTHER INFORMATION: potential microsequencing oligo 5-140-348.mis1

<400> SEQUENCE: 64
ggacttcaag gtaaacataa catcgttctg ttgcatgcaa gtatttga                   48

<210> SEQ ID NO 65
<211> LENGTH: 46
<212> TYPE: DNA
<213> ORGANISM: Homo Sapiens
<220> FEATURE:
<221> NAME/KEY: allele
<222> LOCATION: 1..46
<223> OTHER INFORMATION: polymorphic fragment 5-140-361, variant version
      of SEQ ID44
<220> FEATURE:
<221> NAME/KEY: allele
<222> LOCATION: 23
<223> OTHER INFORMATION: deletion
<220> FEATURE:
<221> NAME/KEY: primer_bind
```

```
<222> LOCATION: 1..22
<223> OTHER INFORMATION: potential microsequencing oligo 5-140-361.mis1

<400> SEQUENCE: 65
aaacataaca atcgttctgt tgtgcaagta tttgatttta atttat                      46

<210> SEQ ID NO 66
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-143-101, variant version
      of SEQ ID45
<220> FEATURE:
<221> NAME/KEY: allele
<222> LOCATION: 24
<223> OTHER INFORMATION: base C ; A in SEQ ID45
<220> FEATURE:
<221> NAME/KEY: primer_bind
<222> LOCATION: 1..23
<223> OTHER INFORMATION: potential microsequencing oligo 5-143-101.mis1
<220> FEATURE:
<221> NAME/KEY: primer_bind
<222> LOCATION: 25..47
<223> OTHER INFORMATION: complement potential microsequencing oligo
      5-143-101.mis2

<400> SEQUENCE: 66 aggaggggt ggcagaggag tcactgcaga ctgtggctga agaggag                      47

<210> SEQ ID NO 67
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-143-84, variant version
      of SEQ ID46
<220> FEATURE:
<221> NAME/KEY: allele
<222> LOCATION: 24
<223> OTHER INFORMATION: base G ; A in SEQ ID46
<220> FEATURE:
<221> NAME/KEY: primer_bind
<222> LOCATION: 1..23
<223> OTHER INFORMATION: potential microsequencing oligo 5-143-84.mis1
<220> FEATURE:
<221> NAME/KEY: primer_bind
<222> LOCATION: 25..47
<223> OTHER INFORMATION: complement potential microsequencing oligo
      5-143-84.mis2

<400> SEQUENCE: 67
accgcatcct gccccagagg aggggtggc agaggagtca ctgcaga                      47

<210> SEQ ID NO 68
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-145-24, variant version
      of SEQ ID47
<220> FEATURE:
<221> NAME/KEY: allele
<222> LOCATION: 24
<223> OTHER INFORMATION: base G ; A in SEQ ID47
<220> FEATURE:
<221> NAME/KEY: primer_bind
```

```
<222> LOCATION: 1..23
<223> OTHER INFORMATION: potential microsequencing oligo 5-145-24.mis1
<220> FEATURE:
<221> NAME/KEY: primer_bind
<222> LOCATION: 25..47
<223> OTHER INFORMATION: complement potential microsequencing oligo
      5-145-24.mis2

<400> SEQUENCE: 68
tagtaagttc tgtgacaact tatgaatgtc ataaagaaca tgtagtt                47

<210> SEQ ID NO 69
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 5-148-352, variant version
      of SEQ ID48
<220> FEATURE:
<221> NAME/KEY: allele
<222> LOCATION: 24
<223> OTHER INFORMATION: base T ; G in SEQ ID48
<220> FEATURE:
<221> NAME/KEY: primer_bind
<222> LOCATION: 1..23
<223> OTHER INFORMATION: potential microsequencing oligo 5-148-352.mis1
<220> FEATURE:
<221> NAME/KEY: primer_bind
<222> LOCATION: 25..47
<223> OTHER INFORMATION: complement potential microsequencing oligo
      5-148-352.mis2

<400> SEQUENCE: 69
tgcttttcct caagcaataa ttgtttccaa cttgtctggg aattgtg                47

<210> SEQ ID NO 70
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1437-325, variant
      version of SEQ ID49
<220> FEATURE:
<221> NAME/KEY: allele
<222> LOCATION: 24
<223> OTHER INFORMATION: base T ; C in SEQ ID49
<220> FEATURE:
<221> NAME/KEY: primer_bind
<222> LOCATION: 1..23
<223> OTHER INFORMATION: potential microsequencing oligo
      99-1437-325.mis1
<220> FEATURE:
<221> NAME/KEY: primer_bind
<222> LOCATION: 25..47
<223> OTHER INFORMATION: complement potential microsequencing oligo
      99-1437-325.mis2

<400> SEQUENCE: 70
caagagctga catttactgc atatttaatt tgtgccgaac actgaac                47

<210> SEQ ID NO 71
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1442-224, variant
      version of SEQ ID50
```

```
<220> FEATURE:
<221> NAME/KEY: allele
<222> LOCATION: 24
<223> OTHER INFORMATION: base T ; G in SEQ ID50
<220> FEATURE:
<221> NAME/KEY: primer_bind
<222> LOCATION: 1..23
<223> OTHER INFORMATION: potential microsequencing oligo
      99-1442-224.mis1
<220> FEATURE:
<221> NAME/KEY: primer_bind
<222> LOCATION: 25..47
<223> OTHER INFORMATION: complement potential microsequencing oligo
      99-1442-224.mis2

<400> SEQUENCE: 71
attaatctca gtcatatttt gggttttttt tcttctctta taattaa                47

<210> SEQ ID NO 72
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: upstream amplification primer for SEQ 30, SEQ
      51

<400> SEQUENCE: 72
aaaagaaaac aaacccagg                                              19

<210> SEQ ID NO 73
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: upstream amplification primer for SEQ 31, SEQ
      52

<400> SEQUENCE: 73
ataagagttt gggaatacc                                              19

<210> SEQ ID NO 74
<211> LENGTH: 18
<212> TYPE: DNA
<213> ORGANISM: Artificial Sequence
<220> FEATURE:
<221> NAME/KEY: primer_bind
<222> LOCATION: 1..18
<223> OTHER INFORMATION: upstream amplification primer for SEQ 32, SEQ
      53

<400> SEQUENCE: 74
tggaaggatg taggatgc                                               18

<210> SEQ ID NO 75
<211> LENGTH: 18
<212> TYPE: DNA
<213> ORGANISM: Artificial Sequence
<220> FEATURE:
<221> NAME/KEY: primer_bind
<222> LOCATION: 1..18
<223> OTHER INFORMATION: upstream amplification primer for SEQ 33, SEQ
      54

<400> SEQUENCE: 75
gctactctgt gtgcaatc                                               18
```

```
<210> SEQ ID NO 76
<211> LENGTH: 20
<212> TYPE: DNA
<213> ORGANISM: Artificial Sequence
<220> FEATURE:
<221> NAME/KEY: primer_bind
<222> LOCATION: 1..20
<223> OTHER INFORMATION: upstream amplification primer for SEQ 34, SEQ
      55, SEQ 35, SEQ 56

<400> SEQUENCE: 76
caaacaataa atgtcagtgg                                                  20

<210> SEQ ID NO 77
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: upstream amplification primer for SEQ 36,
      SEQ 57

<400> SEQUENCE: 77
ggttttgaac agcttagtg                                                   19

<210> SEQ ID NO 78
<211> LENGTH: 18
<212> TYPE: DNA
<213> ORGANISM: Artificial Sequence
<220> FEATURE:
<221> NAME/KEY: primer_bind
<222> LOCATION: 1..18
<223> OTHER INFORMATION: upstream amplification primer for SEQ 37,
      SEQ 58

<400> SEQUENCE: 78
tcttttgagt ctaggacc                                                    18

<210> SEQ ID NO 79
<211> LENGTH: 18
<212> TYPE: DNA
<213> ORGANISM: Artificial Sequence
<220> FEATURE:
<221> NAME/KEY: primer_bind
<222> LOCATION: 1..18
<223> OTHER INFORMATION: upstream amplification primer for SEQ 38, SEQ
      59, SEQ 39, SEQ 60, SEQ 40, SEQ 61

<400> SEQUENCE: 79
aaagatggag gaggagag                                                    18

<210> SEQ ID NO 80
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: upstream amplification primer for SEQ 41, SEQ
      62

<400> SEQUENCE: 80
tgttgctaag agataaacc                                                   19

<210> SEQ ID NO 81
<211> LENGTH: 19
<212> TYPE: DNA
```

```
<213> ORGANISM: Artificial Sequence
<220> FEATURE:
<221> NAME/KEY: primer_bind
<222> LOCATION: 1..19
<223> OTHER INFORMATION: upstream amplification primer for SEQ 42,
      SEQ 63, SEQ 43, SEQ 64, SEQ 44, SEQ 65

<400> SEQUENCE: 81
gggcttctta tgttctttc                                              19

<210> SEQ ID NO 82
<211> LENGTH: 20
<212> TYPE: DNA
<213> ORGANISM: Artificial Sequence
<220> FEATURE:
<221> NAME/KEY: primer_bind
<222> LOCATION: 1..20
<223> OTHER INFORMATION: upstream amplification primer for SEQ 45,
      SEQ 66, SEQ 46, SEQ 67

<400> SEQUENCE: 82
gcctaaaaaa acgctgaaag                                             20

<210> SEQ ID NO 83
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: upstream amplification primer for SEQ 47,
      SEQ 68

<400> SEQUENCE: 83
tagtaagttc tgtgacaac                                              19

<210> SEQ ID NO 84
<211> LENGTH: 18
<212> TYPE: DNA
<213> ORGANISM: Artificial Sequence
<220> FEATURE:
<221> NAME/KEY: primer_bind
<222> LOCATION: 1..18
<223> OTHER INFORMATION: upstream amplification primer for SEQ 48,
      SEQ 69

<400> SEQUENCE: 84
gtttggtctc cctttcc                                                18

<210> SEQ ID NO 85
<211> LENGTH: 20
<212> TYPE: DNA
<213> ORGANISM: Artificial Sequence
<220> FEATURE:
<221> NAME/KEY: primer_bind
<222> LOCATION: 1..20
<223> OTHER INFORMATION: upstream amplification primer for SEQ 49,
      SEQ 70

<400> SEQUENCE: 85
caaaagaaac tcacaaagac                                             20

<210> SEQ ID NO 86
<211> LENGTH: 18
<212> TYPE: DNA
<213> ORGANISM: Artificial Sequence
<220> FEATURE:
<221> NAME/KEY: primer_bind
<222> LOCATION: 1..18
```

```
<223> OTHER INFORMATION: upstream amplification primer for SEQ 50,
      SEQ 71

<400> SEQUENCE: 86
tctggtattt gggaacac                                                18

<210> SEQ ID NO 87
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: downstream amplification primer for SEQ 30,
      SEQ 51

<400> SEQUENCE: 87
gtggaaagat aaaatccag                                               19

<210> SEQ ID NO 88
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: downstream amplification primer for SEQ 31,
      SEQ 52

<400> SEQUENCE: 88
caagattttg cctttcctg                                               19

<210> SEQ ID NO 89
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: downstream amplification primer for SEQ 32,
      SEQ 53

<400> SEQUENCE: 89
gaaaaacagt gactctttg                                               19

<210> SEQ ID NO 90
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: downstream amplification primer for SEQ 33,
      SEQ 54

<400> SEQUENCE: 90
aataaaggtc acaaggaac                                               19

<210> SEQ ID NO 91
<211> LENGTH: 20
<212> TYPE: DNA
<213> ORGANISM: Artificial Sequence
<220> FEATURE:
<221> NAME/KEY: primer_bind
<222> LOCATION: 1..20
<223> OTHER INFORMATION: downstream amplification primer for SEQ 34,
      SEQ 55, SEQ 35, SEQ 56

<400> SEQUENCE: 91
```
atgaggatct caaatacaag                                          20

<210> SEQ ID NO 92
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: downstream amplification primer for SEQ 36,
      SEQ 57

<400> SEQUENCE: 92
gctatcaaat tcctcattc                                           19

<210> SEQ ID NO 93
<211> LENGTH: 20
<212> TYPE: DNA
<213> ORGANISM: Artificial Sequence
<220> FEATURE:
<221> NAME/KEY: primer_bind
<222> LOCATION: 1..20
<223> OTHER INFORMATION: downstream amplification primer for SEQ 37,
      SEQ 58

<400> SEQUENCE: 93
cacaaaaact ttcttcacag                                          20

<210> SEQ ID NO 94
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: downstream amplification primer for SEQ 38,
      SEQ 59, SEQ 39, SEQ 60, SEQ 40, SEQ 61

<400> SEQUENCE: 94
ttccctagaa aaagatcag                                           19

<210> SEQ ID NO 95
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: downstream amplification primer for SEQ 41,
      SEQ 62

<400> SEQUENCE: 95
caaatttcta tcagtaggg                                           19

<210> SEQ ID NO 96
<211> LENGTH: 20
<212> TYPE: DNA
<213> ORGANISM: Artificial Sequence
<220> FEATURE:
<221> NAME/KEY: primer_bind
<222> LOCATION: 1..20
<223> OTHER INFORMATION: downstream amplification primer for SEQ 42,
      SEQ 63, SEQ 43, SEQ 64, SEQ 44, SEQ 65

<400> SEQUENCE: 96
acagtagttg gtaatgtcac                                          20

<210> SEQ ID NO 97
<211> LENGTH: 18
<212> TYPE: DNA
<213> ORGANISM: Artificial Sequence
<220> FEATURE:
<221> NAME/KEY: primer_bind
<222> LOCATION: 1..18
<223> OTHER INFORMATION: downstream amplification primer for SEQ 45,
      SEQ 66, SEQ 46, SEQ 67

<400> SEQUENCE: 97
agcaacacta tccacctc                                                 18

<210> SEQ ID NO 98
<211> LENGTH: 20
<212> TYPE: DNA
<213> ORGANISM: Artificial Sequence
<220> FEATURE:
<221> NAME/KEY: primer_bind
<222> LOCATION: 1..20
<223> OTHER INFORMATION: downstream amplification primer for SEQ 47,
      SEQ 68

<400> SEQUENCE: 98 gtttttaaa gcaagtagcc                                                20

<210> SEQ ID NO 99
<211> LENGTH: 20
<212> TYPE: DNA
<213> ORGANISM: Artificial Sequence
<220> FEATURE:
<221> NAME/KEY: primer_bind
<222> LOCATION: 1..20
<223> OTHER INFORMATION: downstream amplification primer for SEQ 48,
      SEQ 69

<400> SEQUENCE: 99
aaagcctcca tttgccacag                                               20

<210> SEQ ID NO 100
<211> LENGTH: 21
<212> TYPE: DNA
<213> ORGANISM: Artificial Sequence
<220> FEATURE:
<221> NAME/KEY: primer_bind
<222> LOCATION: 1..21
<223> OTHER INFORMATION: downstream amplification primer for SEQ 49,
      SEQ 70

<400> SEQUENCE: 100
attctcattc tctcattttc c                                             21

<210> SEQ ID NO 101
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: downstream amplification primer for SEQ 50,
      SEQ 71

<400> SEQUENCE: 101
aataaaggtc acaaggaac                                                19

<210> SEQ ID NO 102
<211> LENGTH: 19
<212> TYPE: DNA
<213> ORGANISM: Artificial Sequence

```
<220> FEATURE:
<221> NAME/KEY: primer_bind
<222> LOCATION: 1..19
<223> OTHER INFORMATION: microsequencing oligo for 5-124-273.mis1

<400> SEQUENCE: 102
acttcttaat accctagat                                                19

<210> SEQ ID NO 103
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-127-261.mis1

<400> SEQUENCE: 103
gtatacaaga gtttaattt                                                19

<210> SEQ ID NO 104
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-128-60.mis1

<400> SEQUENCE: 104
tgcttgtgtg tgctcccac                                                19

<210> SEQ ID NO 105
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-129-144.mis1

<400> SEQUENCE: 105
ctcttataat taaaaaaaa                                                19

<210> SEQ ID NO 106
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-130-257.mis1

<400> SEQUENCE: 106
gatgaaaaag aaaaggagg                                                19

<210> SEQ ID NO 107
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-130-276.mis1

<400> SEQUENCE: 107
```
ataatagcag tgaagaaga                                                19

<210> SEQ ID NO 108
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-131-395.mis1

<400> SEQUENCE: 108
gcatagcgcc tgtcacgta                                                19

<210> SEQ ID NO 109
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-133-375.mis1

<400> SEQUENCE: 109
tctaaagtgt attctatga                                                19

<210> SEQ ID NO 110
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-135-155.mis1

<400> SEQUENCE: 110
tttccatatc ctctataaa                                                19

<210> SEQ ID NO 111
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-135-198.mis1

<400> SEQUENCE: 111
atattattct ttattattt                                                19

<210> SEQ ID NO 112
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-135-357.mis1

<400> SEQUENCE: 112
gatacctcct gttgctaag                                                19

<210> SEQ ID NO 113
<211> LENGTH: 19
<212> TYPE: DNA

```
<213> ORGANISM: Artificial Sequence
<220> FEATURE:
<221> NAME/KEY: primer_bind
<222> LOCATION: 1..19
<223> OTHER INFORMATION: microsequencing oligo for 5-136-174.mis1

<400> SEQUENCE: 113
aagacaatga aaatctgga                                               19

<210> SEQ ID NO 114
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-140-120.mis1

<400> SEQUENCE: 114
atgataaatt acgacatac                                               19

<210> SEQ ID NO 115
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-140-348.mis1

<400> SEQUENCE: 115
cttcaaggta aacataaca                                               19

<210> SEQ ID NO 116
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-140-361.mis1

<400> SEQUENCE: 116
cataacaatc gttctgttg                                               19

<210> SEQ ID NO 117
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-143-101.mis1

<400> SEQUENCE: 117
gggggtggca gaggagtca                                               19

<210> SEQ ID NO 118
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-143-84.mis1
```

```
<400> SEQUENCE: 118
catcctgccc cagaggagg                                              19

<210> SEQ ID NO 119
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-145-24.mis1

<400> SEQUENCE: 119
aagttctgtg acaacttat                                              19

<210> SEQ ID NO 120
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-148-352.mis1

<400> SEQUENCE: 120
tttcctcaag caataattg                                              19

<210> SEQ ID NO 121
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 99-1437-325.mis1

<400> SEQUENCE: 121
agctgacatt tactgcata                                              19

<210> SEQ ID NO 122
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      99-1442-224.mis1

<400> SEQUENCE: 122
atctcagtca tattttggg                                              19

<210> SEQ ID NO 123
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-124-273.mis2

<400> SEQUENCE: 123
aawccagtaa cagtaataa                                              19

<210> SEQ ID NO 124
```

```
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-127-261.mis2

<400> SEQUENCE: 124
tcataaactt ataaagttt                                                    19

<210> SEQ ID NO 125
<211> LENGTH: 15
<212> TYPE: DNA
<213> ORGANISM: Artificial Sequence
<220> FEATURE:
<221> NAME/KEY: primer_bind
<222> LOCATION: 1..15
<223> OTHER INFORMATION: potential microsequencing oligo for
      5-130-257.mis2

<400> SEQUENCE: 125
tcttcactgc tatta                                                        15

<210> SEQ ID NO 126
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-130-276.mis2

<400> SEQUENCE: 126
atcaactgtt ttcacttac                                                    19

<210> SEQ ID NO 127
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-131-395.mis2

<400> SEQUENCE: 127
aattcctcmr ttctacttg                                                    19

<210> SEQ ID NO 128
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-135-357.mis2

<400> SEQUENCE: 128
cctatatcca tggtttatc                                                    19

<210> SEQ ID NO 129
<211> LENGTH: 19
<212> TYPE: DNA
<213> ORGANISM: Artificial Sequence
<220> FEATURE:
<221> NAME/KEY: primer_bind
<222> LOCATION: 1..19
```

-continued

```
<223> OTHER INFORMATION: potential microsequencing oligo for
      5-136-174.mis2

<400> SEQUENCE: 129
ttgtgtcatc atctttgtc                                                19

<210> SEQ ID NO 130
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-140-120.mis2

<400> SEQUENCE: 130
attctaggtt aagaaaaaa                                                19

<210> SEQ ID NO 131
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-143-101.mis2

<400> SEQUENCE: 131
tcttcagcca cagtctgca                                                19

<210> SEQ ID NO 132
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 5-143-84.mis2

<400> SEQUENCE: 132
cagtgactcc tctgccacc                                                19

<210> SEQ ID NO 133
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-145-24.mis2

<400> SEQUENCE: 133
acatgttctt tatgacatt                                                19

<210> SEQ ID NO 134
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      5-148-352.mis2

<400> SEQUENCE: 134
attcccagac aagttggaa                                                19
```

```
<210> SEQ ID NO 135
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: potential microsequencing oligo for
      99-1437-325.mis2

<400> SEQUENCE: 135
agtgttcggc acaaattaa                                              19

<210> SEQ ID NO 136
<211> LENGTH: 19
<212> TYPE: DNA
<213> ORGANISM: Artificial Sequence
<220> FEATURE:
<221> NAME/KEY: primer_bind
<222> LOCATION: 1..19
<223> OTHER INFORMATION: microsequencing oligo for 99-1442-224.mis2

<400> SEQUENCE: 136
ttataagaga agaaaaaaa                                              19

<210> SEQ ID NO 137
<211> LENGTH: 27
<212> TYPE: DNA
<213> ORGANISM: Artificial Sequence
<220> FEATURE:
<221> NAME/KEY: misc_binding
<222> LOCATION: 1..27
<223> OTHER INFORMATION: amplification oligonucleotide hRBBP1.5

<400> SEQUENCE: 137
cccttgatga gcctccctat ttgacag                                     27

<210> SEQ ID NO 138
<211> LENGTH: 30
<212> TYPE: DNA
<213> ORGANISM: Artificial Sequence
<220> FEATURE:
<221> NAME/KEY: misc_binding
<222> LOCATION: 1..30
<223> OTHER INFORMATION: amplification oligonucleotide hRBBP1.3

<400> SEQUENCE: 138
cgcattgaaa ttcccacgtc gtattgccag                                  30

<210> SEQ ID NO 139
<211> LENGTH: 18
<212> TYPE: DNA
<213> ORGANISM: Artificial Sequence
<220> FEATURE:
<221> NAME/KEY: misc_binding
<222> LOCATION: 1..18
<223> OTHER INFORMATION: sequencing oligonucleotide PrimerPU

<400> SEQUENCE: 139
tgtaaaacga cggccagt                                               18

<210> SEQ ID NO 140
<211> LENGTH: 18
<212> TYPE: DNA
<213> ORGANISM: Artificial Sequence
<220> FEATURE:
<221> NAME/KEY: misc_binding
```

-continued

```
<222> LOCATION: 1..18
<223> OTHER INFORMATION: sequencing oligonucleotide PrimerRP

<400> SEQUENCE: 140
caggaaacag ctatgacc                                                   18
```

NUCLEIC ACID ENCODING A RETINOBLASTOMA BINDING PROTEIN (RBP-7) AND POLYMORPHIC MARKERS ASSOCIATED WITH SAID NUCLEIC ACID

RELATED APPLICATIONS

This application is a continuation of U.S. application Ser. No. 10/071,179, filed Mar. 19, 2002, now U.S. Pat. No. 6,908, 988, which is a divisional of U.S. application Ser. No. 09/345, 882, filed Jun. 30, 1999, now U.S. Pat. No. 6,399,373, which claims priority to U.S. Provisional Patent Application Ser. No. 60/091,315, filed Jun. 30, 1998 and U.S. Provisional Patent Application Ser. No. 60/111,909, filed Dec. 10, 1998, the disclosures of which are incorporated herein by reference in their entireties.

FIELD OF THE INVENTION

The present invention is directed to a polynucleotide comprising open reading frames defining a coding region encoding a retinoblastoma binding protein (RBP-7) as well as regulatory regions located both at the 5' end and the 3' and of said coding region. The present invention also pertains to a polynucleotide carrying the natural regulation signals of the RBP-7 gene which is useful in order to express a heterologous nucleic acid in host cells or host organisms as well as functionally active regulatory polynucleotides derived from said regulatory region. The invention also concerns polypeptides encoded by the coding region of the RBP-7 gene. The invention also deals with antibodies directed specifically against such polypeptides that are useful as diagnostic reagents. The invention includes genetic markers, namely biallelic markers, that are means that may be useful for the diagnosis of diseases related to an alteration in the regulation or in the coding regions of the RBP-7 gene and for the prognosis/diagnosis of an eventual treatment with therapeutic agents, especially agents acting on pathologies involving abnormal cell proliferation and/or abnormal cell differentiation.

BACKGROUND OF THE INVENTION

Among the genetic alterations that have been shown to represent direct or indirect causative agents of proliferative diseases, such as cancers, there may be cited mutations occurring at loci harboring genes that are called tumor suppressor genes.

Tumor suppressor genes are defined as genes involved in the control of abnormal cell proliferation and whose loss or inactivation is associated with the development of malignancy. Tumor suppressor genes encompass ortho-genes, emerogenes, flatogenes, and onco-suppressor genes.

More specifically, tumor suppressor genes are genes whose products inhibit cell growth. Mutant alleles in cancer cells have lost their normal function, and act in the cell in a recessive way in that both copies of the gene must be inactivated in order to change the cell phenotype. The tumor phenotype can be rescued by the wild-type allele, as shown by cell fusion experiments first described by Harris and colleagues (Harris H. et al., 1969). Gemmline mutations of tumor suppressor genes may be transmitted and thus studied in both constitutional and tumor DNA from familial or sporadic cases. The current family of tumor suppressors include DNA-binding transcription factors (i.e. p53, WT1), transcription regulators (i.e., RB, APC) and protein kinase inhibitors (i.e. p16).

The existence of tumor suppressor genes has been particularly shown in cases of hereditary cancers. These are cancer where there is a clear pattern of inheritance, usually autosomal dominant, with a tendency for earlier age of onset than for sporadic tumors.

Tumor suppressor genes are detected in the form of inactivating mutations that are tumorigenic. The two best characterized genes of this class code for the proteins RB (Retinoblastoma protein) and p53.

Retinoblastoma is a human childhood disease, involving a tumor in the retina. It occurs both as an inheritable trait and sporadically (by somatic mutation). Retinoblastoma arises when both copies of the RB gene are inactivated. In the inherited form of the disease, one parental chromosome carries an alteration in this region, usually a deletion. A somatic event in retinal cells that causes the loss of the other copy of the RB gene causes a tumor. Forty percent of cases are hereditary, transmitted as an autosomal dominant trait with 90% penetrance. Of these cases, around 10-15% are transmitted from an affected parent, the remaining arising as de novo germ-line mutations. In the sporadic form of the disease, the parental chromosomes are normal, and both RB alleles are lost by somatic events. The tumor suppressor nature of RB was shown by the introduction of a single copy of RB1 into tumor cell lines lacking the gene, resulting in complete or partial suppression of the tumorigenic phenotype.

The RB protein has a regulatory role in cell proliferation, acting via transcription factors to prevent the transcriptional activation of a variety of genes, the products of which are required for the onset of DNA synthesis, the S phase of the cell cycle.

When investigating on the molecular function of RB, it has been found that the RB protein interacts with a variety of viral proteins, including several tumor antigens, such as SV40 T antigen, adenovirus E1A protein, human papillomavirus E7. These viral proteins have been shown to bind to RB, thereby inactivating it and allowing cell division to occur.

Thus, an important step toward defining a mechanism underlying tumor suppressor activity of the RB gene was the observation that the transforming products of adenovirus (E1A protein), simian virus 40 (large T antigen) and human papillomavirus (E7 protein) could precipitate wild-type RB protein. This, in turn, led to the identification of a family of cellular proteins that can reversibly bind to a discrete domain on the RB protein, referred to as the T/E1A pocket by using the same specificity as the viral products. The subsequent observation that protein binding was inhibited following RB protein phosphorylation in the late $G_1$ phase of the cell cycle suggested the hypothesis that the RB protein, as well as the related product p107, may regulate the functional activity of its binding partners by a cell-cycle dependent pattern of physical association. In particular, the activity of the RB protein has been shown to be regulated through cell cycle-dependent phosphorylation by cyclin-dependent kinases.

The picture of transcription regulation is made even more complex by the finding that a number of RB related proteins (e.g. p107 and p130) also bind members of the E2F family and are therefore involved in regulatory process.

In view of the foregoing, there clearly exists a pressing need to identify and characterize the cellular proteins that interact with the retinoblastoma protein in order to provide diagnostic and therapeutic tools useful to prevent and cure cell differentiation disorders, particularly disorders in which a lack of completion of cell differentiation, particularly in terminal cell differentiation, or in which an abnormal cell proliferation is detected, such as in proliferative diseases like cancer.

For the purpose of the present invention, cells with abnormal proliferation include, but are not limited to, cells characteristic of the following disease states: thyroid hyperplasia, psoriasis, benign prostatic hypertrophy, cancers including breast cancer, sarcomas and other neoplasms, bladder cancer, colon cancer, lung cancer, prostate cancer, various leukemias and lymphomas.

SUMMARY OF THE INVENTION

This invention is based on the discovery of a nucleic acid molecule encoding a novel protein, more particularly a retinoblastoma binding protein (RBP-7).

The present invention pertains to nucleic acid molecules comprising the genomic sequence of the gene encoding RBP-7. The RBP-7 genomic sequence comprises regulatory sequence located upstream (5'-end) and downstream (3'-end) of the transcribed portion of said gene, these regulatory sequences being also part of the invention.

The invention also deals with the complete cDNA sequence encoding the RBP-7 protein, as well as with the corresponding translation product.

Oligonucleotide probes or primers hybridizing specifically with a RBP-7 genomic or cDNA sequence are also part of the present invention, as well as DNA amplification and detection methods using said primers and probes.

A further aspect of the invention is recombinant vectors comprising any of the nucleic acid sequences described above, and in particular of recombinant vectors comprising a RBP-7 regulatory sequence or a sequence encoding a RBP-7 protein, as well as of cell hosts and transgenic non human animals comprising said nucleic acid sequences or recombinant vectors.

Finally, the invention is directed to methods for the screening of substances or molecules that inhibit the expression of RBP-7, as well as with methods for the screening of substances or molecules that interact with a RBP-7 polypeptide or that modulate the activity of a RBP-7 polypeptide.

The invention also concerns biallelic markers of the RBP-7 gene which can be useful for genetic studies, for diagnosis of diseases related to an alteration in the regulation or in the coding regions of the RBP-7 gene and for the prognosis/diagnosis of an eventual treatment with therapeutic agents, especially agents acting on pathologies involving abnormal cell proliferation and/or abnormal cell differentiation

BRIEF DESCRIPTION OF THE SEQUENCES PROVIDED IN THE SEQUENCE LISTING

Figure 1:
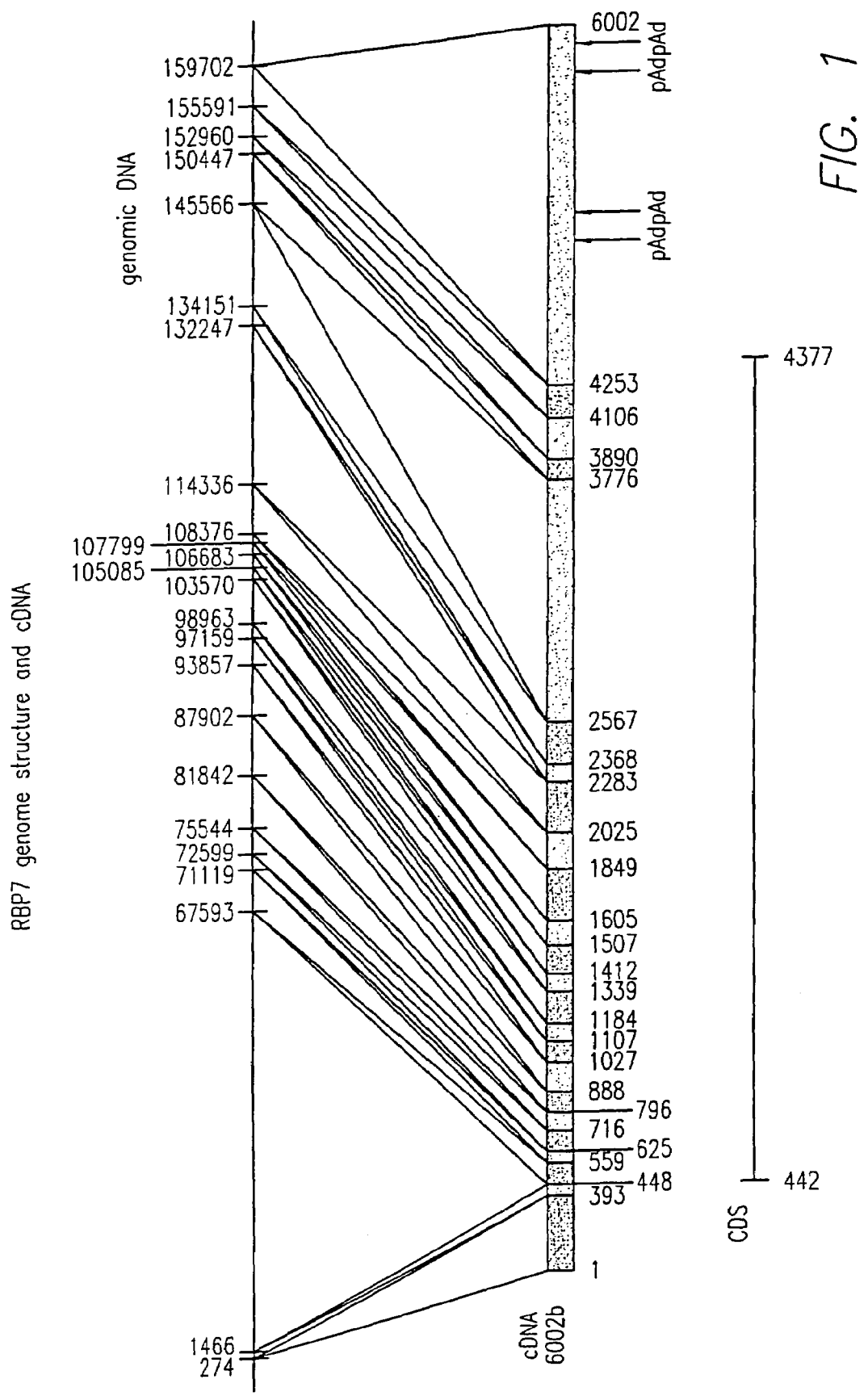
FIG. 1 is a diagram showing a map of the RBP-7 gene.

SEQ ID No. 1 contains a genomic sequence of RBP-7 comprising the 5' regulatory region (upstream untranscribed region), the exons and introns, and the 3' regulatory region (downstream untranscribed region).

SEQ ID No. 2 contains the 5'-regulatory sequence (upstream untrancribed region) of RBP-7.

SEQ ID No. 3 contains the 3'-regulatory sequence (upstream untrancribed region) of RBP-7.

SEQ ID No. 4 contains the RBP-7 cDNA sequence.

SEQ ID Nos 5 to 28 contain the exons 1 to 24 of RBP-7.

SEQ ID No. 29 contains the protein sequence encoded by the nucleotide sequence of SEQ ID No. 4.

SEQ ID Nos 30 to 50 contain the fragments containing a polymorphic base of a biallelic marker (first allele).

SEQ ID Nos 51 to 71 contain the fragments containing a polymorphic base of a biallelic marker (second allele).

SEQ ID Nos 72 to 101 contain the amplification primers.

SEQ ID Nos 102 to 136 contain the microsequencing primers.

SEQ ID Nos 137 and 138 contain cDNA amplification primers.

SEQ ID Nos 139 and 140 respectively contain a primer containing the additional PU 5' sequence and the additional RP 5' sequence described further in Example 3.

In accordance with the regulations relating to Sequence Listings, the following codes have been used in the Sequence Listing to indicate the locations of biallelic markers within the sequences and to identify each of the alleles present at the polymorphic base. The code "r" in the sequences indicates that one allele of the polymorphic base is a guanine, while the other allele is an adenine. The code "y" in the sequences indicates that one allele of the polymorphic base is a thymine, while the other allele is a cytosine. The code "m" in the sequences indicates that one allele of the polymorphic base is an adenine, while the other allele is an cytosine. The code "k" in the sequences indicates that one allele of the polymorphic base is a guanine, while the other allele is a thymine. The code "s" in the sequences indicates that one allele of the polymorphic base is a guanine, while the other allele is a cytosine. The code "w" in the sequences indicates that one allele of the polymorphic base is an adenine, while the other allele is an thymine. The nucleotide code of the original allele for each biallelic marker is the following:

| Biallelic marker | Original allele |
| --- | --- |
| 5-124-273 | A |
| 5-127-261 | C |
| 5-130-257 | A |
| 5-130-276 | A |
| 5-131-395 | A |
| 5-135-357 | A |
| 5-136-174 | T |
| 5-140-120 | T |
| 5-143-101 | C |
| 5-143-84 | G |
| 5-145-24 | A |
| 5-148-352 | T |
| 99-1437-325 | A |
| 99-1442-224 | T |

In some instances, the polymorphic bases of the biallelic markers alter the identity of an amino acids in the encoded polypeptide. This is indicated in the accompanying Sequence Listing by use of the feature VARIANT, placement of an Xaa at the position of the polymorphic amino acid, and definition of Xaa as the two alternative amino acids. For example if one allele of a biallelic marker is the codon CAC, which encodes histidine, while the other allele of the biallelic marker is CAA, which encodes glutamine, the Sequence Listing for the encoded polypeptide will contain an Xaa at the location of the polymorphic amino acid. In this instance, Xaa would be defined as being histidine or glutamine.

In other instances, Xaa may indicate an amino acid whose identity is unknown. In this instance, the feature UNSURE is used, placement of an Xaa at the position of the unknown amino acid and definition of Xaa as being any of the 20 amino acids or being unknown.

DETAILED DESCRIPTION OF THE INVENTION

The aim of the present invention is to provide polynucleotides and polypeptides related to the RBP-7 gene and to a RBP-7 protein, which is potentially involved in the regulation of the differentiation of various cell types in mammals. A deregulation or an alteration of this protein may be involved in the generation of a pathological state in a patient. Such pathological state includes disorders caused by cell apoptosis or in contrast by an abnormal cell proliferation such as in cancers.

The unphosphorylated form of the Retinoblastoma (RB) protein specifically binds several proteins, and these interactions occur only during part of the cell cycle, prior to the S phase. The target proteins of the RB protein include E2F transcription factors and cyclins of the D and E types. Binding to the RB protein inhibits the ability of E2F to activate transcription, which suggests that the RB protein may repress the expression of genes dependent on E2F. Interaction of the RB protein with E2F-1, a member of the E2F transcription factors family, inhibits transcription of genes involved in DNA synthesis and therefore suppresses cell growth. Additionally, it has been found that the complexes formed between E2F and the RB protein are disrupted in the presence of the viral oncoproteins that bind to the RB protein, suggesting a key role of the RB protein in the regulation of E2F activity.

It has been shown that the RB protein forms two types of complexes with E2F. One of these two types involves a binary complex of the RB protein and E2F that does not bind DNA in a gel retardation assay, and the second type of RB protein/E2F complex involves another factor, RBP60, which allows the RB protein/E2F complex to bind DNA and produce a distinct complex in a gel retardation assay. One hypothesis is that RB protein might be regulating the DNA-binding as well as the transcription activation function of E2F. It has also been demonstrated that E2F can bind DNA as an oligomeric complex composed of at least two distinct proteins.

Recent reports indicate that approximately 10 proteins have been identified that bind to the RB protein using the same binding surface as the viral oncoproteins. Several of these cellular proteins, including the E2F transcription factor described above, comprise members of the myc oncogene family, a p46 protein (Rb-AP46), MyoD, Elf-1, protein phosphatase type 1 catalytic subunit and several proteins designated generically as "Retinoblastoma Binding Proteins" (RBBP), some of these latter proteins being defined as E2F-like proteins.

Defeo-Jones et al. (1991) have cloned the cDNA of two members of the RBBP family, namely RBP-1 and RBP-2. RBP-1 and RBP-2 bind specifically to the RB protein in vitro. RBP-2 has been shoxyn to interact noncovalently with RB ptotein via the binding of a consensus amino acid sequence of RBP-2, namely the LXCXE amino acid sequence, to the conserved T/E1A pocket of the RB protein (Kim et al., 1994). This LXCXE consensus amino acid sequence is also present within the adenovirus E1A protein, the SV40 large T antigen as well as within the human papillomavirus E7 protein. RBP-1 and RBP-2 have been hypothesized to function as transcription factors, like E2F. Helin et al. (1992) have cloned a cDNA encoding another member of the RBBP family, namely RBP-3. Sakai et al. (1995) have cloned a novel RBBP protein designated as RBP-6, the locus of which has been mapped on chromosome 16 between p11.2 and p12.

For the E2F family, replicating and differentiating cells need the RB protein or RB protein family members (e.g. p107 or p130) to counterbalance its apoptotic effect. E2F induces apoptosis when over-expressed in cells with the wild type p53 gene, but favors proliferation in p53 −/− cells. E2F-induced apoptosis follows entry of the cell into S-phase. The E2F death-promoting effect can be blocked by co-expression of p105, a RB protein family member. Conversely, by gene knock-out studies, it has been demonstrated that E2F is critical for the normal development of diverse cell types. Mice null for the E2F1 gene show defects at a young age in the terminal differentiation of cell types in which apoptosis play an important role, namely T-cells or epithelial cells of the testis or of other exocrine glands. With increasing age, these animals develop wide-spread tumors. This data indicates that E2F plays a physiological role in normal development, probably by inducing apoptosis in a specific set of developing cells.

The retinoblastoma binding proteins of the E2F type have also been described in PCT Application No. WO 65/24223, PCT Application No. WO 96/25494 and in U.S. Pat. No. 5,650,287, the disclosures of which are incorporated herein by reference in their entireties. Other retinoblastoma binding proteins have been described, notably in PCT Application No. WO 94/12521, in PCT Application No. WO 95/17198, in PCT Application No. 93/23539 and in PCT Application No. WO 93/06168, the disclosures of which are incorporated herein by reference in their entireties.

Definitions

Before describing the invention in greater detail, the following definitions are set forth to illustrate and define the meaning and scope of the terms used to describe the invention herein.

The term "RBP-7 gene", when used herein, encompasses mRNA and cDNA sequences encoding the RBP-7 protein. In the case of a genomic sequence, the RBP-7 gene also includes native regulatory regions which control the expression of the coding sequence of the RBP-7 gene.

The term "functionally active fragment" of the RBP-7 protein is intended to designate a polypeptide carrying at least one of the structural features of the RBP-7 protein involved in at least one of the biological functions and/or activity of the RBP-7 protein. Particularly preferred are peptide fragments carrying either the retinoblastoma protein binding domain and/or the DNA binding domain of the RBP-7 protein.

A "heterologous" or "exogenous" polynucleotide designates a purified or isolated nucleic acid that has been placed, by genetic engineering techniques, in the environment of unrelated nucleotide sequences, such as the final polynucleotide construct does not occur naturally. An illustrative, but not limitatitive, embodiment of such a polynucleotide construct may be represented by a polynucleotide comprising (1) a regulatory polynucleotide derived from the RBP-7 gene sequence and (2) a polynucleotide encoding a cytokine, for example GM-CSF. The polypeptide encoded by the heterologous polynucleotide will be termed an heterologous polypeptide for the purpose of the present invention.

By a "biologically active fragment or variant" of a regulatory polynucleotide according to the present invention is intended a polynucleotide comprising or alternatively consisting of a fragment of said polynucleotide which is functional as a regulatory region for expressing a recombinant polypeptide or a recombinant polynucleotide in a recombinant cell host.

For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operatively linked" to nucleotide sequences which encode the desired polypeptide or the desired polynucleotide. An operable linkage is a linkage in which the regulatory nucleic acid and the DNA sequence sought to be expressed are linked in such a way as to permit gene expression.

As used herein, the term "operably linked" refers to a linkage of polynucleotide elements in a functional relationship. For instance, a promoter or enhancer is operably linked to a coding sequence if it affects the transcription of the coding sequence. More precisely, two DNA molecules (such as a polynucleotide containing a promoter region and a polynucleotide encoding a desired polypeptide or polynucleotide) are said to be "operably linked" if the nature of the linkage between the two polynucleotides does not (1) result in the introduction of a frame-shift mutation or (2) interfere with the ability of the polynucleotide containing the promoter to direct the transcription of the coding polynucleotide. The promoter polynucleotide would be operably linked to a polynucleotide encoding a desired polypeptide or a desired polynucleotide if the promoter is capable of effecting transcription of the polynucleotide of interest.

An "altered copy" of the RBP-7 gene is intended to designate a RBP-7 gene that has undergone at least one substitution, addition or deletion of one or several nucleotides, wherein said nucleotide substitution, addition or deletion preferably causes a change in the amino acid sequence of the resulting translation product or alternatively causes an increase or a decrease in the expression of the RPB-7 gene.

The terms "sample" or "material sample" are used herein to designate a solid or a liquid material suspected to contain a polynucleotide or a polypeptide of the invention. A solid material may be, for example, a tissue slice or biopsy which is searched for the presence of a polynucleotide encoding a RBP-7 protein, either a DNA or RNA molecule or within which is searched for the presence of a native or a mutated RBP-7 protein, or alternatively the presence of a desired protein of interest the expression of which has been placed under the control of a RBP-7 regulatory polynucleotide. A liquid material may be, for example, any body fluid like serum, urine etc., or a liquid solution resulting from the extraction of nucleic acid or protein material of interest from a cell suspension or from cells in a tissue slice or biopsy. The term "biological sample" is also used and is more precisely defined within the Section dealing with DNA extraction.

As used herein, the term "purified" does not require absolute purity; rather, it is intended as a relative definition. Purification if starting material or natural material to at least one order of magnitude, preferably two or three orders, and more preferably four or five orders of magnitude is expressly contemplated. As an example, purification from 0.1% concentration to 10% concentration is two orders of magnitude.

The term "isolated" requires that the material be removed from its original environment (e.g. the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition and still be isolated in that the vector or composition is not part of its natural environment.

Throughout the present specification, the expression "nucleotide sequence" may be employed to designate indifferently a polynucleotide or an oligonucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule.

As used interchangeably herein, the term "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. However, the polynucleotides of the invention are preferably comprised of greater than 50% conventional deoxyribose nucleotides, and most preferably greater than 90% conventional deoxyribose nucleotides. The polynucleotide sequences of the invention may be prepared by any known method, including synthetic, recombinant, ex vivo generation, or a combination thereof, as well as utilizing any purification methods known in the art.

The term "heterozygosity rate" is used herein to refer to the incidence of individuals in a population which are heterozygous at a particular allele. In a biallelic system, the heterozygosity rate is on average equal to $2P_a(1-P_a)$, where $P_a$ is the frequency of the least common allele. In order to be useful in genetic studies, a genetic marker should have an adequate level of heterozygosity to allow a reasonable probability that a randomly selected person will be heterozygous.

The term "genotype" as used herein refers the identity of the alleles present in an individual or a sample. In the context of the present invention a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is a single base pair change. Typically a single nucleotide polymorphism is the replacement of one nucleotide by another nucleotide at the polymorphic site. Deletion of a single nucleotide or insertion of a single nucleotide, also give rise to single nucleotide polymorphisms. In the context of the present invention "single nucleotide polymorphism" preferably refers to a single nucleotide substitution. However, the polymorphism can also involve an insertion or a deletion of at least one nucleotide, preferably between 1 and 5 nucleotides. The nucleotide modification can also involve the presence of several adjacent single base polymorphisms. This type of nucleotide modification is usually called a "variable motif". Generally, a "variable motif" involves the presence of 2 to 10 adjacent single base polymorphisms. In some instances, series of two or more single base polymorphisms can be interrupted by single bases which are not polymorphic. This is also globally considered to be a "variable motif". Typically, between different genomes or between different individuals, the polymorphic site may be occupied by two different nucleotides.

The term "biallelic polymorphism" and "biallelic marker" are used interchangeably herein to refer to a single nucleotide polymorphism having two alleles at a fairly high frequency in the population. A "biallelic marker allele" refers to the nucleotide variants present at a biallelic marker site. Typically, the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker".

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on.

As used herein the terminology "defining a biallelic marker" means that a sequence includes a polymorphic base from a biallelic marker. The sequences defining a biallelic marker may be of any length consistent with their intended use, provided that they contain a polymorphic base from a biallelic marker. The sequence is preferably between 1 and 500 nucleotides in length, more preferably between 5, 10, 15, 20, 25, or 40 and 200 nucleotides and still more preferably between 30 and 50 nucleotides in length. Each biallelic marker therefore corresponds to two forms of a polynucleotide sequence included in a gene, which, when compared with one another, present a nucleotide modification at one position. Preferably, the sequences defining a biallelic marker include a polymorphic base selected from the group consisting of biallelic markers A1 to A21. In some embodiments the sequences defining a biallelic marker comprise one of the sequences selected from the group consisting of SEQ ID Nos 30 to 71. Likewise, the term "marker" or "biallelic marker" requires that the sequence is of sufficient length to practically (although not necessarily unambiguously) identify the polymorphic allele, which usually implies a length of at least 4, 5, 6, 10, 15, 20, 25, or 40 nucleotides.

Variants and Fragments

1. Polynucleotides

The invention also relates to variants and fragments of the polynucleotides described herein, particularly of a RBP-7 gene containing one or more biallelic markers according to the invention.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of polynucleotides according to the invention include, without being limited to, nucleotide sequences that are at least 95% identical to any of SEQ ID Nos 1-28 or the sequences complementary thereto or to any polynucleotide fragment of at least 8 consecutive nucleotides of any of SEQ ID Nos 1-28 or the sequences complementary thereto, and preferably at least 98% identical, more particularly at least 99.5% identical, and most preferably at least 99.9% identical to any of SEQ ID Nos 1-28 or the sequences complementary thereto or to any polynucleotide fragment of at least 8 consecutive nucleotides of any of SEQ ID Nos 1-28 or the sequences complementary thereto.

Changes in the nucleotide of a variant may be silent, which means that they do not alter the amino acids encoded by the polynucleotide.

However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function or activity as the mature RBP-7 protein.

A polynucleotide fragment is a polynucleotide having a sequence that entirely is the same as part but not all of a given nucleotide sequence, preferably the nucleotide sequence of a RBP-7 gene, and variants thereof. The fragment can be a portion of an exon or of an intron of a RBP-7 gene. It can also be a portion of the regulatory sequences of the RBP-7 gene. Preferably, such fragments comprise the polymorphic base of at least one of the biallelic markers of SEQ ID Nos. 30-71.

Such fragments may be "free-standing", i.e. not part of or fused to other polynucleotides, or they may be comprised within a single larger polynucleotide of which they form a part or region. However, several fragments may be comprised within a single larger polynucleotide.

As representative examples of polynucleotide fragments of the invention, there may be mentioned those which are from about 4, 6, 8, 15, 20, 25, 40, 10 to 20, 10 to 30, 30 to 55, 50 to 100, 75 to 100 or 100 to 200 nucleotides in length. Preferred are those fragments which are about 47 nucleotides in length, such as those of SEQ ID Nos 30-71 or the sequences complementary thereto and containing at least one of the biallelic markers of a RBP-7 gene which are described herein. It will of course be understood that the polynucleotides of SEQ ID Nos 30-71 or the sequences complementary thereto can be shorter or longer, although it is preferred that they at least contain the polymorphic base of the biallelic marker which can be located at one end of the fragment or in the internal portion of the fragment.

2. Polypeptides.

The invention also relates to variants, fragments, analogs and derivatives of the polypeptides described herein, including mutated RBP-7 proteins.

The variant may be 1) one in which one or more of the amino acid residues are substituted with a conserved or non-conserved amino acid residue (preferably a conserved amino acid residue) and such substituted amino acid residue may or may not be one encoded by the genetic code, or 2) one in which one or more of the amino acid residues includes a substituent group, or 3) one in which the mutated RBP-7 is fused with another compound, such as a compound to increase the half-life of the polypeptide (for example, polyethylene glycol), or 4) one in which the additional amino acids are fused to the mutated RBP-7, such as a leader or secretory sequence or a sequence which is employed for purification of the mutated RBP-7 or a preprotein sequence. Such variants are deemed to be within the scope of those skilled in the art.

More particularly, a variant RBP-7 polypeptide comprises amino acid changes ranging from 1, 2, 3, 4, 5, 10 to 20 substitutions, additions or deletions of one amino acid, preferably from 1 to 10, more preferably from 1 to 5 and most preferably from 1 to 3 substitutions, additions or deletions of one amino acid. The preferred amino acid changes are those which have little or no influence on the biological activity or the capacity of the variant RBP-7 polypeptide to be recognized by antibodies raised against a native RBP-7 protein.

As illustrative embodiments of variant RBP-7 polypeptides encompassed by the present invention, there are the following polypeptides:

a polypeptide comprising a Glycine residue at the amino acid position 293 of the amino acid sequence of SEQ ID No. 29;
 a polypeptide comprising a Glutamic acid at the amino acid in position 963 of SEQ ID No. 29; and,
 a polypeptide comprising a Methionine residue at the amino acid position 969 of the amino acid sequence of SEQ ID No. 29.

By homologous peptide according to the present invention is meant a polypeptide containing one or several amino acid additions, deletions and/or substitutions in the amino acid sequence of a RBP-7 polypeptide. In the case of an amino acid substitution, one or several-consecutive or non-consecutive-amino acids are replaced by "equivalent" amino acids. The expression "equivalent" amino acid is used herein to designate any amino acid that may substituted for one of the amino acids belonging to the native protein structure without decreasing the binding properties of the corresponding peptides to the retinoblastoma proteins (i.e. RBP, p130, p107 etc.). In other words, the "equivalent" amino acids are those which allow the generation or the synthesis of a polypeptide with a modified sequence when compared to the amino acid sequence of the native RBP-7 protein, said modified polypeptide being able to bind to the retinoblastoma protein and/or to induce antibodies recognizing the parent polypeptide comprising, consisting essentially of, or consisting of a RBP-7 polypeptide.

These equivalent amino acids may be determined either by their structural homology with the initial amino acids to be replaced, by the similarity of their net charge, and optionally by the results of the cross-immunogenicity between the parent peptides and their modified counterparts.

By an equivalent amino acid according to the present invention is also meant the replacement of a residue in the L-form by a residue in the D form or the replacement of a Glutamic acid (E) residue by a Pyro-glutamic acid compound. The synthesis of peptides containing at least one residue in the D-form is, for example, described by Koch (Koch Y., 1977, Biochem. Biophys. Res. Commun., Vol.74:488-491).

A specific, but not restrictive, embodiment of a modified peptide molecule of interest according to the present invention, which comprises, consists essentially of, or consists of a peptide molecule which is resistant to proteolysis, is a peptide in which the —CONH— peptide bond is modified and replaced by a ($CH_2NH$) reduced bond, a (NHCO) retro inverso bond, a ($CH_2$—O) methylene-oxy bond, a ($CH_2$—S) thiomethylene bond, a ($CH_2CH_2$) carba bond, a (CO—$CH_2$) cetomethylene bond, a (CHOH—$CH_2$) hydroxyethylene bond), a (N—N) bound, a E-alcene bond or also a —CH=CH— bond.

A polypeptide fragment is a polypeptide having a sequence that entirely is the same as part but not all of a given polypeptide sequence, preferably a polypeptide encoded by a RBP-7 gene and variants thereof. Preferred fragments include those regions possessing antigenic properties and which can be used to raise antibodies against the RBP-7 protein.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which comprise at least about 5, 6, 7, 8, 9 or 10 to 15, 10 to 20, 15 to 40, or 30 to 55 amino acids of the RBP-7 protein. In some embodiments, the fragments contain at least one amino acid mutation in the RBP-7 protein.

Complementary Polynucleotides

For the purpose of the present invention, a first polynucleotide is deemed to be complementary to a second polynucleotide when each base in the first polynucleotide is paired with its complementary base. Complementary bases are, generally, A and T (or A and U), or C and G.

Identity between Nucleic Acids or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1990; Altschul et al., 1993). In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990, 1993, 1997). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992; Henikoff and Henikoff, 1993). Less preferably, the PAM or PAM250 matrices may also be used (see, e.g., Schwartz and Dayhoff, eds., 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990). The programs listed above may be used with the default parameters or with modified parameters provided by the user.

RBP-7 Gene, Corresponding CDNAS and RBP-7 Coding and Regulatory Sequences

The gene encoding a RBP-7 polypeptide has been found by the inventors to be located on human chromosome 1, more precisely within the Iq43 locus of said chromosome. The RBP-7 gene has a length of about 166 kilobases and contains a 5' regulatory region, 24 exons, and a 3' regulatory region. A 5'-UTR region is spans the whole Exon 1 and the major portion of the 5' end of Exon 2. A 3'-UTR region is spans the major portion of the 3' end of Exon 24.

The present invention first concerns a purified or isolated nucleic acid encoding a Retinoblastoma Binding Protein named RBP-7 as well as a nucleic acid complementary thereto and fragments and variants thereof.

In particular, the invention concerns a purified or isolated nucleic acid comprising at least 8 consecutive nucleotides of a polynucleotide selected from the group consisting of SEQ ID Nos 1 and 4 as well as a nucleic acid sequence complementary thereto and fragments and variants thereof. The length of the fragments described above can range from at least 8, 10, 15, 20 or 30 to 200 nucleotides, preferably from at least 10 to 50 nucleotides, more preferably from at least 40 to 50 nucleotides. In some embodiments, the fragments may comprise more than 200 nucleotides of SEQ ID Nos. 1 and 4 or the sequences complementary thereto.

The invention also pertains to a purified or isolated nucleic acid of at least 8 nucleotides in length that hybridizes under stringent hybridization conditions with a polynucleotide selected from the group consisting of SEQ ID Nos 1 and 4 or the sequences complementary thereto. The length of the nucleic acids described above can range from 8, 10, 15, 20 or 30 to 200 nucleotides, preferably from 10 to 50 nucleotides, more preferably from 40 to 50 nucleotides. Such nucleic acids may be used as probes or primers, such as described in the corresponding section of the present specification.

The invention also encompasses a purified, isolated, or recombinant polynucleotide comprising a nucleotide sequence having at least 70, 75, 80, 85, 90, or 95% nucleotide identity with a nucleotide sequence of SEQ ID Nos 1 and 4 or a complementary sequence thereto or a fragment thereof. Percent identity may be determined using any of the programs and scoring matrices described above. For example, percent identity may be determined using BLASTN with the default parameters. In addition, the scoring matrix may be BLOSUM62

Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No. 1 or the complements thereof, wherein said contiguous span comprises at least 1, 2, 3, 5, or 10 of the following nucleotide positions of SEQ ID No. 1: 1-481, 666-1465, 1521-67592, 67704-71118, 71185-72598, 72690-75543, 75624-81841, 81934-83019, 83406-87901, 88041-93856, 93937-97158, 97236-98962, 99086-103188, 103745-104303, 104654-105084, 105180-106682, 106781-107798, 107897-108392, 108552-114335, 114418-114491, 114594-132246, 132332-134150, 134350-145565, 145842-146332, 146775-150446, 150542-152959, 153176-155590, 155738-159701, 160466-161028, 161453-162450. Additional preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No. 4 or the complements thereof, wherein said contiguous span comprises at least 1, 2, 3, 5, or 10 of the following nucleotide positions of SEQ ID No. 4: 1-208, 1307-1350, 1703-1865, 2107-2180, 2843-3333, 3871-3882, 4222-4276, and 5017-5579. It should be noted that nucleic acid fragments of any size and sequence may also be comprised by the polynucleotides described in this section.

The main structural features of the RBP-7 gene are shown in FIG. 1. The upper line shows a structural map of the polynucleotide of SEQ ID No. 1 including the 24 exons, that are indicated by closed boxes, and the 23 introns, as well the 5'- and 3'-flanking regulatory regions. The position of the first nucleotide at 5' and of each exon is also indicated, the nucleotide at position 1 being the first nucleotide at the 5' end of the polynucleotide of SEQ ID No. 1.

Generally, an intron is defined as a nucleotide sequence that is present both in the genomic DNA and in the unspliced mRNA molecule, and which is absent from the mRNA molecule which has already gone through splicing events.

For the purpose of the present invention and in order to make a clear and unambiguous designation of the different nucleic acids encompassed, it has been postulated that the polynucleotides contained both in the nucleotide sequence of SEQ ID No. 1 and in the nucleotide sequences of SEQ ID No. 4 are considered as exonic sequences. Conversely, the polynucleotides contained in the nucleotide sequence of SEQ ID No. 1 and located between Exon 1 and Exon 24, but which are absent both from the nucleotide sequence of SEQ ID No. 4 are considered as intronic sequences.

More precisely, the structural characteristics of the RBP-7 gene, as represented in FIG. 1 are as follows:

a) a regulatory region, located between the nucleotide at position 1 and the nucleotide at position 273 of SEQ ID No. 1;

b) a "coding" region, located between the nucleotide at position 274 and the nucleotide at position 161451 of SEQ ID No. 1, comprising 24 exons and 23 introns, wherein said region defines the RBP-7 coding region.

c) a regulatory region, beginning at the nucleotide at position 161452 and ending at the nucleotide in position 162450 (the 3'-end nucleotide) of SEQ ID No. 1.

The translation start site ATG is located within the second exon and the translation stop codon is located within Exon 24 of the nucleotide sequence of SEQ ID No. 1.

The middle line of FIG. 1 shows the cDNA corresponding to the longest RBP-7 mRNA including the 24 exons. Each exon is represented by a specific box. The numbers located under the exon boxes indicate the nucleotide position of the 5' end polynucleotide of each exon, it being understood that the nucleotide at position 1 is the 5' end nucleotide of the cDNA. pAd denotes the four potential polyadenylation sites.

The lower line of FIG. 1 shows a map of the RBP-7 coding sequence (CDS), the start codon being located from the nucleotide in position 442 to the nucleotide in position 444 of the RBP-7 cDNA of SEQ ID No. 4 and the stop codon being located from the nucleotide in position 4378 to the nucleotide in position 4380 of the RBP-7 cDNA of SEQ ID No. 4.

The 24 exons included in the RBP-7 gene are represented in FIG. 1 and are described in Table A.

TABLE A

| Exon | SEQ ID No. | Begining position in SEQ ID No. 1 | End position In SEQ ID No. 1 |
| --- | --- | --- | --- |
| 1 | 5 | 274 | 665 |
| 2 | 6 | 1466 | 1520 |
| 3 | 7 | 67593 | 67703 |
| 4 | 8 | 71119 | 71184 |
| 5 | 9 | 72599 | 72689 |
| 6 | 10 | 75544 | 75623 |
| 7 | 11 | 81842 | 81933 |
| 8 | 12 | 87902 | 88040 |
| 9 | 13 | 93857 | 93936 |
| 10 | 14 | 97159 | 97235 |
| 11 | 15 | 98963 | 99117 |
| 12 | 16 | 103570 | 103642 |
| 13 | 17 | 105085 | 105179 |
| 14 | 18 | 106683 | 106780 |
| 15 | 19 | 107799 | 108042 |
| 16 | 20 | 108376 | 108551 |
| 17 | 21 | 114336 | 114593 |
| 18 | 22 | 132247 | 132331 |
| 19 | 23 | 134151 | 134349 |
| 20 | 24 | 145566 | 146774 |
| 21 | 25 | 150447 | 150560 |
| 22 | 26 | 152960 | 153175 |
| 23 | 27 | 155591 | 155737 |
| 24 | 28 | 159702 | 161451 |

The middle line depicts the main structural features of a purified or isolated nucleic acid consisting of the longest cDNA that is obtained after reverse transcribing a mRNA generated after transcription of the RBP-7 gene. The longest mRNA has a nucleotide length of about 6 kilobases.

As it is depicted in FIG. 1, the main characteristics of the longest RBP-7 cDNA are a) A 5'-UTR region extending from the nucleotide at position 1 to the nucleotide at position 441 of SEQ ID No. 4;

b) An open reading frame (ORF) encoding the longest form of RBP-7 protein, wherein said ORF extends from the nucleotide at position 442 to the nucleotide at position 4380 of SEQ ID No. 4. The ATG translation start site is located between the nucleotide at position 442 and the nucleotide at position 444 of SEQ ID No. 4. The stop codon is located between the nucleotide at position 4378 and the nucleotide at position 4380 of SEQ ID No. 4.

c) A 3'-UTR region extending from the nucleotide at position 4381 to the nucleotide at position 6002 of SEQ ID No. 4. This 3'-UTR region contains four potential polyadenylation sites comprising respectively the nucleotides between positions 4878 and 4883, 5116 and 5121, 5896 and 5091 and between positions 5981 and 5986 of SEQ ID No. 4.

Figure 2:
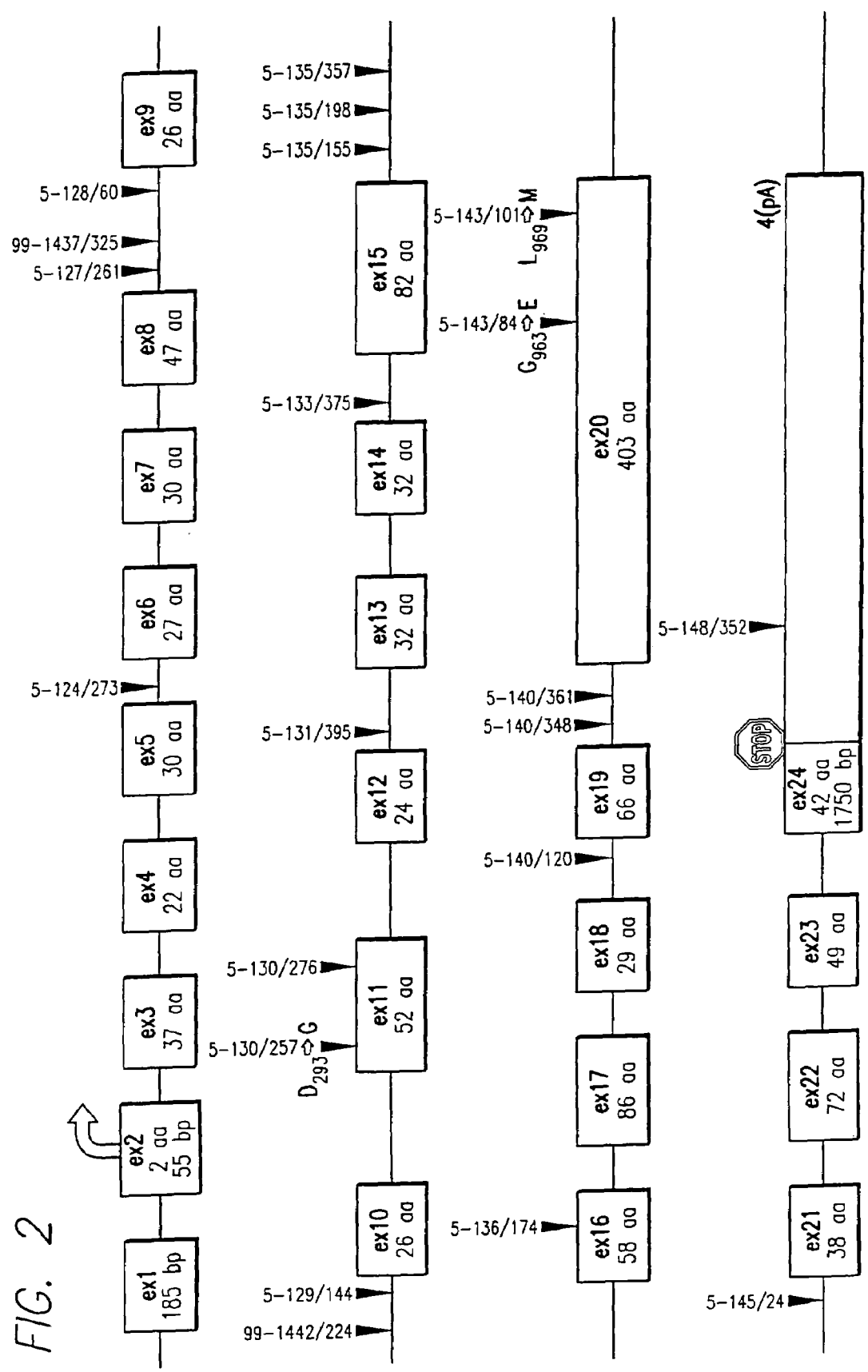
FIG. 2 is a presentation of the RBP-7 gene structure with the amplified fragments and the biallelic markers of the present invention.

FIG. 2 is a representation of the RBP-7 gene in which the 24 exons are shown as closed boxes.

a) In each closed box that represents a given Exon, there are indicated both a number of base pairs corresponding to the non coding sequence eventually present in this Exon, and a number of amino acids. The number of amino acids is calculated as follows, starting from Exon 2: Exon 2 contains two complete codons and the first base of a third codon; only the two complete codons are taken into account and the additional base is taken into account as the first base of the first codon of Exon 3, etc.;

b) The arrows above the Intron lines or above the Exon boxes indicate the localization of the different polymorphic markers of the invention on the RBP-7 gene, as well as their marker names;

c) The bold letters above exons 11 and 20 indicate the effect of the base changes constitutive to these polymorphic markers on the amino acid sequence of the resulting RBP-7 translation product.

The polynucleotide of SEQ ID No. 4 contains, from its 5' end to its 3' end, the sequences resulting from the 24 exons located in Table A on the RBP-7 genomic sequence, said exonic sequences being positioned on the PBP-7 cDNA of SEQ ID No. 4, as detailed in Table B below.

TABLE B

| Exon | SEQ ID No. | Beginning position in SEQ ID No. 4 | End position In SEQ ID No. 4 |
| --- | --- | --- | --- |
| 1 | 5 | 1 | 392 |
| 2 | 6 | 393 | 447 |
| 3 | 7 | 448 | 558 |
| 4 | 8 | 559 | 624 |
| 5 | 9 | 625 | 715 |
| 6 | 10 | 716 | 795 |
| 7 | 11 | 796 | 887 |
| 8 | 12 | 888 | 1026 |
| 9 | 13 | 1027 | 1106 |
| 10 | 14 | 1107 | 1183 |
| 11 | 15 | 1184 | 1338 |
| 12 | 16 | 1339 | 1411 |
| 13 | 17 | 1412 | 1507 |
| 14 | 18 | 1508 | 1604 |
| 15 | 19 | 1605 | 1848 |
| 16 | 20 | 1849 | 2024 |
| 17 | 21 | 2025 | 2282 |
| 18 | 22 | 2283 | 2367 |
| 19 | 23 | 2368 | 2566 |
| 20 | 24 | 2567 | 3775 |
| 21 | 25 | 3776 | 3889 |
| 22 | 26 | 3890 | 4105 |

TABLE B-continued

| Exon | SEQ ID No. | Beginning position in SEQ ID No. 4 | End position In SEQ ID No. 4 |
|---|---|---|---|
| 23 | 27 | 4106 | 4252 |
| 24 | 28 | 4253 | 6002 |

The nucleotide sequence of the RBP-7 cDNA possesses some homologies with a cDNA encoding another human retinoblastoma binding protein, namely hRBP-1. This homology is randomly distributed throughout the whole cDNA sequences, without visible nucleic acid regions that are characteristic of conserved regions between cDNA sequences encoding different retinobastoma binding proteins.

The majority of interrupted genes are transcribed into a RNA that gives rise to a single type of spliced mRNA. But the RNAs of some genes follow patterns of alternative splicing, wherein a single gene gives rise to more than one mRNA species. In some cases, the ultimate pattern of expression is dictated by the primary transcript, because the use of different startpoints or termination sequences alters the splicing pattern. In other cases, a single primary transcript is spliced in more than one way, and internal exons are substituted, added or deleted. In some cases, the multiple products all are made in the same cell, but in others, the process is regulated so that particular splicing patterns occur only under particular conditions.

In the case of retinoblastoma binding proteins, alternative splicing patterns have been observed during the processing of the RBP1 pre-mRNA (Otterson et al., 1993). More precisely, alternative splicing of RBP1 clusters has been observed within a 207-nucleotide internal exon. From the four forms of mRNA detected, three of the predicted RBP1 peptides share amino-terminal and carboxy-terminal domains, while a fourth species encodes a distinct carboxy-terminal domain. Functional analysis of these peptides demonstrated that they are capable of precipitating retinoblastoma protein in vitro from K562 cell lysates, but cannot bind to mutant RB protein.

The inventors have found that a mRNA of about 6 kilobases and containing exon 1 of the RBP-7 gene at its 5' end and exon 24 of the RBP-7 gene at its 3' end, is produced in isolated cells from the prostate tissue, as described in Example 1.

Because the RBP-7 gene contains a large number of exons, it is expected that the corresponding pre-mRNA is processed in a family of mRNA molecules as a result of multiple alternative splicing events.

Additionally, individually combining each polynucleotide molecule defining a specific exon of the RBP-7 gene with at least one polynucleotide molecule defining another exon of the RBP-7 gene will give rise to a family of translation products that may be assayed for their biological functions of interaction with retinoblastoma proteins (i.e. pRb, p107, p130 etc.) or of interaction with DNA sequences of the type recognized by the transcription factors of the E2F family. Such translation products have a shorter size than that of the resulting protein encoded by the longest RBP-7 mRNA and thus may be advantageously used in therapeutics, as compared with the longest polypeptides, due to their weaker immunogenicity, for example.

Consequently, a further aspect of the present invention is a purified or isolated nucleic acid comprising a nucleotide sequence selected from the group consisting of SEQ ID Nos 5-28 or the sequences complementary thereto.

The invention also deals with a purified or isolated nucleic acid comprising a combination of at least two polynucleotides selected from the group consisting of SEQ ID Nos 5-28 or the sequences complementary thereto, wherein the polynucleotides are ordered within the nucleic acid, from the 5' end to the 3' end of said nucleic acid, in the same order as in the SEQ ID No. 1.

In this specific embodiment of a purified or isolated nucleic acid according to the invention, said nucleic acid preferably comprises SEQ ID Nos 5 and 6 at its 5' end and SEQ ID No. 28 at its 3' end.

Regulatory Regions

As already mentioned hereinbefore, the polynucleotide of SEQ ID No. 1 contains regulatory regions both in the non-coding 5'-flanking region (SEQ ID No. 2) and the non-coding 3'-flanking region (SEQ ID No. 3) that border the coding sequences.

The promoter activity of the regulatory region contained in SEQ ID No. 1 can be assessed as described below.

Genomic sequences lying upstream of the RBP-7 gene are cloned into a suitable promoter reporter vector, such as the pSEAP-Basic, pSEAP-Enhancer, pβgal-Basic, pβgal-Enhancer, or pEGFP-1 Promoter Reporter vectors available from Clontech. Briefly, each of these promoter reporter vectors include multiple cloning sites positioned upstream of a reporter gene encoding a readily assayable protein such as secreted alkaline phosphatase, β galactosidase, or green fluorescent protein. The sequences upstream of the RBP-7 coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence.

Promoter sequences within the upstream genomic DNA may be further defined by constructing nested deletions in the upstream DNA using conventional techniques such as Exonuclease III digestion. The resulting deletion fragments can be inserted into the promoter reporter vector to determine whether the deletion has reduced or obliterated promoter activity. In this way, the boundaries of the promoters may be defined. If desired, potential individual regulatory sites within the promoter may be identified using site directed mutagenesis or linker scanning to obliterate potential transcription factor binding sites within the promoter, individually or in combination. The effects of these mutations on transcription levels may be determined by inserting the mutations into the cloning sites in the promoter reporter vectors.

Polynucleotides carrying the regulatory elements located both at the 5' end and at the 3' end of the RBP-7 coding region may be advantageously used to control the transcriptional and translational activity of an heterologous polynucleotide of interest.

A 5' regulatory polynucleotide of the invention may include the 5'-untranslated region (5'-UTR) or the sequence complementary thereto, or a biologically active fragment or variant thereof. The 5'-regulatory polynucleotide harbors a CAAT box from the nucleotide in position 139 to the nucleotide in position 147 of the nucleotide sequence of SEQ ID No. 2. Additionally, the 5'-regulatory polynuceotide of the invention comprises a TATA box from the nucleotide in position 199 to the nucleotide in position 205 of the nucleotide sequence of SEQ ID No. 2.

A 3' regulatory polynucleotide of the invention may include the 3'-untranslated region (3'-UTR) or the sequences complementary thereto, or a biologically active fragment or variant thereof.

Another aspect of the present invention is a purified and/or isolated polynucleotide located at the 5' end of the start codon of the RBP-7 gene, wherein said polynucleotide carries expression and/or regulation signals allowing the expression of the RBP-7 gene. Thus, another art of the present invention is a purified or isolated nucleic acid comprising a nucleotide sequence of SEQ ID No. 2 and functionally active fragments or variants thereof. The fragments may be of any length to facilitate the expression and/or regulation of a gene operably linked thereto. In particular, the fragments may contain one or more binding sites for transcription factors. In some embodiments, the fragments at least 8, 10, 15, 20 or 30 to 200 nucleotides of SEQ ID No. 2. In other embodiments, the fragments may comprise more than 200 nucleotides of SEQ ID No. 2 or the sequence complementary thereto.

The invention further deals with a purified and/or isolated polynucleotide located at the 3' and of the stop codon of the RBP-7 gene, wherein said polynucleotide carries regulation signals involved in the expression of the RBP-7 gene. Thus another part of the present invention is a purified or isolated nucleic acid comprising a nucleotide sequence of SEQ ID No. 3, the sequence complementary thereto, and functionally active fragments or variants thereof. The fragments may be of any length to facilitate the expression and/or regulation of a gene operationally linked thereto. In some embodiments, the fragments may comprise at least 8, 10, 15, 20 or 30 to 200 nucleotides of SEQ ID No. 3 or the sequence complementary thereto. In other embodiments, the fragments may comprise more than 200 nucleotides of SEQ ID No. 3 or the sequence complementary thereto.

Thus, the invention also pertains to a purified or isolated nucleic acid which is selected from the group consisting of:

a) a nucleic acid comprising the nucleotide sequence SEQ ID No. 2 or the sequence complementary thereto;

b) a nucleic acid comprising a biologically active fragment or variant of the nucleic acid of SEQ ID No. 2 or the sequence complementary thereto.

In a specific embodiment of the above nucleic acid, said nucleic acid includes the 5'-untranslated region (5'-UTR) located between the nucleotide at position 1 to the nucleotide at position 441 of SEQ ID No. 4, or the sequences complementary thereto, or a biologically active fragment or variant thereof.

Another aspect of the present invention is a purified or isolated nucleic acid which is selected from the group consisting of:

a) a nucleic acid comprising the nucleotide sequence SEQ ID No. 3 or the sequence complementary thereto;

b) a nucleic acid comprising a biologically active fragment, a variant of the nucleic acid of SEQ ID No. 3 or the sequence complementary thereto.

In a specific embodiment of the above nucleic acid, said nucleic acid includes the 3'-untranslated region (3'-UTR) located between the nucleotide at position 4381 and the nucleotide at position 6002 of SEQ ID No. 4, or the sequences complementary thereto, or a biologically active fragment or variant thereof.

Preferred fragments of the nucleic acid of SEQ ID No. 2 or the sequence complementary thereto have a range of length from 100, 125, 150, 175, 200 to 225, 250, 273 consecutive nucleotides. Preferred fragments will comprise both the CAAT box and the TATA box of the nucleotide sequence of SEQ ID No. 2.

Preferred fragments of the nucleic acid of SEQ ID No. 3 or the sequence complementary thereto have a length of about 600 nucleotides, more particularly of about 300 nucleotides, more preferably of about 200 nucleotides and most preferably about 100 nucleotides.

In order to identify the relevant biologically active polynucleotide derivatives of SEQ ID No. 3, one may follow the procedures described in Sambrook et al. (1989, the disclosure of which is incorporated herein by reference) relating to the use of a recombinant vector carrying a marker gene (i.e. β galactosidase, chloramphenicol acetyl transferase, etc.) the expression of which will be detected when placed under the control of a biologically active derivative polynucleotide of SEQ ID No. 3.

Regulatory polynucleotides of the invention may be prepared from the nucleotide sequence of SEQ ID No. 1 or the sequences complementary thereto by cleavage using the suitable restriction enzymes, as described in Sambrook et al. (1989), supra.

Regulatory polynucleotides may also be prepared by digestion of the nucleotide sequence of SEQ ID No. 1 or the sequences complementary thereto by an exonuclease enzyme, such as Bal31 (Wabiko et al., 1986).

These regulatory polynucleotides can also be prepared by nucleic acid chemical synthesis, as described elsewhere in the specification, when oligonucleotide probes or primers synthesis is disclosed.

The regulatory polynucleotides according to the invention may advantageously be part of a recombinant expression vector that may be used to express a coding sequence in a desired host cell or host organism. The recombinant expression vectors according to the invention are described elsewhere in the specification.

The above defined polynucleotides that carry the expression and/or regulation signals of the RBP-7 gene may be used, for example as part of a recombinant vector, in order to drive the expression of a desired polynucleotide, said desired polynucleotide being either (1) a polynucleotide encoding a RBP-7 protein, or a fragment or variant thereof, or (2) an "heterologous" polynucleotide, such as a polynucleotide encoding a desired "heterologous" polypeptide or a desired RNA in a recombinant cell host.

The invention also encompasses a polynucleotide comprising, consisting essentially of, or consisting of:

a) a nucleic acid comprising a regulatory polynucleotide of SEQ ID No. 2, or the sequence complementary thereto, or a biologically active fragment or variant thereof;

b) a polynucleotide encoding a desired polypeptide or nucleic acid.

c) Optionally, a nucleic acid comprising a regulatory polynucleotide of SEQ ID No. 3, or the sequence complementary thereto, or a biologically active fragment or variant thereof.

In a preferred embodiment, a polynucleotide such as disclosed above comprises the nucleic acid of SEQ ID No. 2, or the sequences complementary thereto, or a fragment, a variant or a biologically active derivative thereof which is located at the 5' and of the polynucleotide encoding the desired polypeptide or polynucleotide.

In another embodiment, a polynucleotide such as that above described comprises the nucleic acid of SEQ ID No. 3, or the sequence complementary thereto, or a fragment, a variant or a biologically active derivative thereof which is located at the 3' end of the polynucleotide encoding the desired polypeptide or nucleic acid. A preferred desired nucleic acid comprises of a ribonucleic acid useful as antisense molecule.

The desired polypeptide encoded by the above described nucleic acid may be of various nature or origin, encompassing proteins of prokaryotic or eukaryotic origin. Among the polypeptides which may be expressed under the control of a RBP-7 regulatory region are bacterial, fungal or viral antigens. Are also encompassed eukaryotic proteins such as intracellular proteins, such as "house keeping" proteins, membrane-bound proteins, such as receptors, and secreted proteins such as the numerous endogenous mediators including cytokines.

The desired nucleic acid encoded by the above described polynucleotide, usually a RNA molecule, may be complementary to a RBP-7 coding sequence and thus useful as an antisense polynucleotide.

Such a polynucleotide may be included in a recombinant expression vector in order to express a desired polypeptide or a desired polynucleotide in host cell or in a host organism. Suitable recombinant vectors that contain a polynucleotide such as described hereinbefore are disclosed elsewhere in the specification.

Coding Regions

As depicted in FIG. 1, the RBP-7 open reading frame is contained in the longest RBP-7 which mRNA has a nucleotide length of about 4 kilobases.

More precisely, the effective RBP-7 coding sequence (CDS) is between the nucleotide at position 442 and the nucleotide at position 4377 of SEQ ID No. 4.

The invention further provides a purified or isolated nucleic acid comprising a polynucleotide selected from the group consisting of a polynucleotide comprising a nucleic acid sequence located between the nucleotide at position 442 and the nucleotide at position 4377 of SEQ ID No. 4, or the sequence complementary thereto, or a variant or fragment thereof or a sequence complementary thereto.

A further object of the present invention comprises polynucleotide fragments of the RBP-7 gene that are useful for the detection of the presence of an unaltered or an altered copy of the RBP-7 gene within the genome of a host organism and also for the detection and/or quantification of the expression of the RBP-7 gene in said host organism.

Thus, another object of the present invention is a purified or isolated nucleic acid encoding a variant or a mutated RBP-7 protein.

A first preferred embodiment of a copy of the RBP-7 gene comprises an allele in which a single base substitution in the codon encoding the Aspartic acid (D) residue in amino acid position 293 of the RBP-7 protein of SEQ ID No. 29 leads to the amino acid replacement for a Glycine (G) residue.

A second preferred embodiment of a copy of the RBP-7 gene comprises an allele in which a single base substitution in the codon encoding the Glycine (G) residue in amino acid position 963 of the RBP-7 protein of SEQ ID No. 29 leads to the amino acid replacement for a Glutamic acid (E) residue.

A third preferred embodiment of a copy of the RBP-7 gene comprises an allele in which a single base substitution in the codon encoding the Leucine (L) residue in amino acid position 969 of the RBP-7 protein of SEQ ID No. 29 leads to the amino acid replacement for a Methionine (M) residue.

Thus, another object of the present invention is a purified or isolated nucleic acid encoding a mutated RBP-7 protein.

The above disclosed polynucleotide that contains only coding sequences derived from the RBP-7 ORF may be expressed in a desired host cell or a desired host organism, when said polynucleotide is placed under the control of suitable expression signals. Such a polynucleotide, when placed under the suitable expression signals, may be inserted in a vector for its expression.

Oligonucleotide Probes and Primers

Polynucleotides derived from the RBP-7 gene described above are useful in order to detect the presence of at least a copy of a nucleotide sequence of SEQ ID No. 1, or a fragment or a variant thereof in a test sample.

The present invention concerns a purified or isolated nucleic acid comprising at least 8 consecutive nucleotides of the nucleotide sequence SEQ ID No. 1 or a sequence complementary thereto or variants thereof. In another embodiment, the present invention relates to nucleic acids comprising at least 8, 10, 15, 20 or 30 to 200 nucleotides, preferably from at least 10 to 50 nucleotides, more preferably from at least 40 to 50 nucleotides of SEQ ID No. 1 or the sequence complementary thereto. In some embodiments, the nucleic acids may comprise more than 200 nucleotides of SEQ ID No. 1 or the sequence complementary thereto.

Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No. 1 or the complements thereof, wherein said contiguous span comprises at least 1, 2, 3, 5, or 10 of the following nucleotide positions of SEQ ID No. 1: 1-481, 666-1465, 1521-67592, 67704-71118, 71185-72598, 72690-75543, 75624-81841, 81934-83019, 83406-87901, 88041-93856, 93937-97158, 97236-98962, 99086-103188, 103745-104303, 104654-105084, 105180-106682, 106781-107798, 107897-108392, 108552-114335, 114418-114491, 114594-132246, 132332-134150, 134350-145565, 145842-146332, 146775-150446, 150542-152959, 153176-155590, 155738-159701, 160466-161028, 161453-162450.

The invention also relates to an oligonucleotide of at least at least 8 nucleotides in length that hybridizes under stringent hybridization conditions with a nucleic acid selected from the group consisting of the nucleotide sequences 1-481, 666-1465, 1521-67592, 67704-71118, 71185-72598, 72690-75543, 75624-81841, 81934-83019, 83406-87901, 88041-93856, 93937-97158, 97236-98962, 99086-103188, 103745-104303, 104654-105084, 105180-106682, 106781-107798, 107897-108392, 108552-114335, 114418-114491, 114594-132246, 132332-134150, 134350-145565, 145842-146332, 146775-150446, 150542-152959, 153176-155590, 155738-159701, 160466-161028, 161453-162450 of SEQ ID No. 1 or a variant thereof or a sequence complementary thereto. In some embodiments, the invention relates to sequences comprising at least 8, 10, 15, 20 or 30 to 200 nucleotides, preferably from at least 10 to 50 nucleotides, more preferably from 40 to 50 nucleotides of SEQ ID No. 1 or the sequence complementary thereto or variants thereof. In some embodiments, the invention relates to sequences comprising more than 200 nucleotides of SEQ ID No. 1 or the sequence complementary thereto.

For the purpose of defining such a hybridizing nucleic acid according to the invention, the stringent hybridization conditions are the following:
   the hybridization step is realized at 65° C. in the presence of 6×SSC buffer, 5× Denhardt's solution, 0,5% SDS and 100 µg/ml of salmon sperm DNA.
   The hybridization step is followed by four washing steps:
      two 5 min washings, preferably at 65° C. in a 2×SSC and 0.1% SDS buffer;

one 30 min washing, preferably at 65° C. in a 2×SSC and 0.1% SDS buffer, one 10 min washing, preferably at 65° C. in a 0.1×SSC and 0.1% SDS buffer, the above hybridization conditions are suitable for a nucleic acid molecule of about 20 nucleotides in length. There is no need to say that the hybridization conditions described above can readily be adapted according to the length of the desired nucleic acid, following techniques well known to the one skilled in the art. The hybridization conditions may for example be adapted according to the teachings disclosed in the book of Hames and Higgins (1985), the disclosure of which is incorporated herein by reference.

Another aspect of the invention is a purified or isolated nucleic acid comprising at least 8 consecutive nucleotides of the nucleotide sequence SEQ ID No. 4 or the sequence complementary thereto or variants thereof. In another embodiment, the nucleic acid comprises from at least 8, 10, 15, 20 or 30 to 200 nucleotides, preferably from at least 10 to 50 nucleotides, more preferably from at least 40 to 50 nucleotides of SEQ ID No. 4 or the sequence complementary thereto or variants thereof. In some embodiments, the fragments may comprise more than 200 nucleotides of SEQ ID No. 4 or the sequence complementary thereto or variants thereof.

Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No. 4 or the complements thereof, wherein said contiguous span comprises at least 1, 2, 3, 5, or 10 of the following nucleotide positions of SEQ ID No. 4: 1-208, 1307-1350, 1703-1865, 2107-2180, 2843-3333, 3871-3882, 4222-4276, and 5017-5579.

Alternatively, the invention also relates to an oligonucleotide of at least 8 nucleotides in length that hybridizes under the stringent hybridization conditions previously defined with a nucleic acid selected from the group consisting of the nucleotide sequences 1-208, 1307-1350, 1703-1865, 2107-2180, 2843-3333, 3871-3882, 4222-4276, and 5017-5579 of SEQ ID No. 1 or a variant thereof or a sequence complementary thereto.

A nucleic probe or primer according to the invention comprises at least 8 consecutive nucleotides of a polynucleotide of SEQ ID Nos 1 or 4 or the sequences complementary thereto, preferably from 8 to 200 consecutive nucleotides, more particularly from 10, 15, 20 or 30 to 100 consecutive nucleotides, more preferably from 10 to 50 nucleotides, and most preferably from 40 to 50 consecutive nucleotides of a polynucleotide of SEQ ID Nos 1 or 4 or the sequences complementary thereto.

In a first preferred embodiment, the probe or primer is suspended in a suitable buffer for performing a hybridization or an amplification reaction.

In a second embodiment, the oligonucleotide probe, which may be immobilized on a support, is capable of hybridizing with a RBP-7 gene, preferably with a region of the RBP-7 gene which comprises a biallelic marker of the present invention. The techniques for immobilizing a nucleotide primer or probe on a solid support are well-known to the skilled artisan and include, but are not limited to, the immobilization techniques described in the present application.

In a third embodiment, the primer is complementary to any nucleotide sequence of the RBP-7 gene and can be used to amplify a region of the RBP-7 gene contained in the nucleic acid sample to be tested which includes a polymorphic base of at least one biallelic marker. Preferably, the amplified region includes a polymorphic base of at least one biallelic marker selected from the group consisting of SEQ ID Nos 30-71 or the sequences complementary thereto. In some embodiments, the primer comprises one of the sequences of SEQ ID Nos 72-101 and 102-136.

When using a polynucleotide probe or primer in a detection method of the invention, the DNA or RNA contained in the sample to be assayed may be subjected to a first extraction step well known to the one skilled in the art, in order to make the DNA or RNA material contained in the initial sample available to a hybridization reaction, prior to the hybridization step itself.

The nucleic acid probes and primers of the invention are also used to detect and/or amplify a portion of the RBP-7 gene within which a polymorphism or a mutation causes a change either in the expression level of the RBP-7 gene or a change in the amino acid sequence of the RBP-7 gene translation product.

The invention further concerns detection or amplification kits containing a pair of oligonucleotide primers or an oligonucleotide probe according to the invention. The kits of the present invention can also comprise optional elements including appropriate amplification reagents such as DNA polymerases when the kit comprises primers, or reagents useful in hybridization between a labeled hybridization probe and a RBP-7 gene containing at least one biallelic marker. In one embodiment, the biallelic marker comprises one of the sequences of SEQ ID Nos 30-71 or the sequences complementary thereto.

In one embodiment the invention encompasses isolated, purified, and recombinant polynucleotides comprising, consisting of, or consisting essentially of a contiguous span of 8 to 50 nucleotides of any one of SEQ ID Nos 1 and 4 and the complement thereof, wherein said span includes a biallelic marker of RBP-7 in said sequence; optionally, wherein said biallelic marker of RBP-7 is selected from the group consisting of A1 to A21, and the complements thereof, or optionally the biallelic markers in linkage disequilibrium therewith; optionally, wherein said contiguous span is 18 to 47 nucleotides in length and said biallelic marker is within 4 nucleotides of the center of said polynucleotide; optionally, wherein said polynucleotide consists of or comprises said contiguous span and said contiguous span is 25 nucleotides in length and said biallelic marker is at the center of said polynucleotide; optionally, wherein the 3' end of said contiguous span is present at the 3' end of said polynucleotide; and optionally, wherein the 3' end of said contiguous span is located at the 3' end of said polynucleotide and said biallelic marker is present at the 3' end of said polynucleotide. In a preferred embodiment, said probes comprises, consists of, or consists essentially of a sequence selected from the sequences SEQ ID Nos 30-71 and the complementary sequences thereto.

In another embodiment the invention encompasses isolated, purified and recombinant polynucleotides comprising, consisting of, or consisting essentially of a contiguous span of 8 to 50 nucleotides of SEQ ID Nos 1 and 4 or the complements thereof, wherein the 3' end of said contiguous span is located at the 3' end of said polynucleotide, and wherein the 3' end of said polynucleotide is located within 20 nucleotides upstream of a biallelic marker of RBP-7 in said sequence; optionally, wherein said biallelic marker of RBP-7 is selected from the group consisting of A1 to A21, and the complements thereof, or optionally the biallelic markers in linkage disequilibrium therewith; optionally, wherein the 3' end of said polynucleotide is located 1 nucleotide upstream of said biallelic marker of RBP-7 in said sequence; and optionally, wherein said polynucleotide comprises, consists of, or consists essentially of a sequence selected from the sequences SEQ ID Nos 102-136.

In a further embodiment, the invention encompasses isolated, purified, or recombinant polynucleotides comprising, consisting of, or consisting essentially of a sequence selected from the sequences SEQ ID Nos 72-101.

In an additional embodiment, the invention encompasses polynucleotides for use in hybridization assays, sequencing assays, and enzyme-based mismatch detection assays for determining the identity of the nucleotide at a biallelic marker of RBP-7 in SEQ ID Nos 1 and 4, or the complements thereof, as well as polynucleotides for use in amplifying segments of nucleotides comprising a biallelic marker of RBP-7 in SEQ ID Nos 1 and 4, or the complements thereof, optionally, wherein said biallelic marker of RBP-7 is selected from the group consisting of A1 to A21, and the complements thereof, or optionally the biallelic markers in linkage disequilibrium therewith.

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the probes and primers of the invention usually ranges between 10 and 75%, preferably between 35 and 60%, and more preferably between 40 and 55%.

The length of these probes and probes can range from 8, 10, 15, 20, or 30 to 100 nucleotides, preferably from 10 to 50, more preferably from 15 to 30 nucleotides. Shorter probes and primers tend to lack specificity for a target nucleic acid sequence and generally require cooler temperatures to form sufficiently stable hybrid complexes with the template. Longer probes and primers are expensive to produce and can sometimes self-hybridize to form hairpin structures. The appropriate length for primers and probes under a particular set of assay conditions may be empirically determined by one of skill in the art.

The primers and probes can be prepared by any suitable method, including, for example, cloning and restriction of appropriate sequences and direct chemical synthesis by a method such as the phosphodiester method of Narang et al. (1979), the phosphodiester method of Brown et al. (1979), the diethylphosphoramidite method of Beaucage et al. (1981) and the solid support method described in EP 0 707 592, the disclosures of which are incorporated herein by reference in their entireties.

Any of the polynucleotides of the present invention can be labeled, if desired, by incorporating a label detectable by spectroscopic, photochemical, biochemical, immunochemical, or chemical means. For example, useful labels include radioactive substances ($^{32}P$, $^{35}S$, $^{3}H$, $^{125}I$), fluorescent dyes (5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in the French Patent No. FR-7810975 or by Urdea et al (1988) or Sanchez-Pescador et al (1988). Advantageously, the probes according to the present invention may have structural characteristics such that they allow the signal amplification, such structural characteristics being, for example, branched DNA probes as those described by Urdea et al. in 1991 or in the European Patent No. EP-0225,807, the disclosure of which is incorporated herein by reference in its entirety (Chiron).

A label can also be used to capture the primer, so as to facilitate the immobilization of either the primer or a primer extension product, such as amplified DNA, on a solid support.

A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the RBP-7 gene or mRNA using other techniques.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the inventions to a single solid support. In addition, polynucleotides other than those of the invention may attached to the same solid support as one or more polynucleotides of the invention.

Consequently, the invention also deals with a method for detecting the presence of a nucleic acid comprising a nucleotide sequence selected from a group consisting of SEQ ID Nos 1, 4, a fragment or a variant thereof or the complementary sequence thereto in a sample, said method comprising the following steps of:

a) bringing into contact a nucleic acid probe or a plurality of nucleic acid probes as described above and the sample to be assayed.

b) detecting the hybrid complex formed between the probe and a nucleic acid in the sample.

In a first preferred embodiment of this detection method, said nucleic acid probe or the plurality of nucleic acid probes are labeled with a detectable molecule.

In a second preferred embodiment of said method, said nucleic acid probe or the plurality of nucleic acid probes has been immobilized on a substrate.

The invention further concerns a kit for detecting the presence of a nucleic acid comprising a nucleotide sequence selected from a group consisting of SEQ ID Nos 1, 4, a fragment or a variant thereof or the complementary sequence thereto in a sample, said kit comprising:

a) a nucleic acid probe or a plurality of nucleic acid probes as described above;

b) optionally, the reagents necessary for performing the hybridization reaction.

In a first preferred embodiment of the detection kit, the nucleic acid probe or the plurality of nucleic acid probes are labeled with a detectable molecule.

In a second preferred embodiment of the detection kit, the nucleic acid probe or the plurality of nucleic acid probes has been immobilized on a substrate.

Oligonucleotide Arrays

A substrate comprising a plurality of oligonucleotide primers or probes of the invention may be used either for detecting or amplifying targeted sequences in the RBP-7 gene and may also be used for detecting mutations in the coding or in the non-coding sequences of the RBP-7 gene.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092, the disclosures of which are incorporated herein by reference in their entireties. These arrays may generally be produced using mechanical synthesis methods or light directed synthesis methods which incorporate a combination of photolithographic methods and solid phase oligonucleotide synthesis (Fodor et al., Science, 251: 767-777, 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ array are provided in U.S. Pat. Nos. 5,143,854 and 5,412,087 and in PCT Publications WO 90/15070, WO 92/10092 and WO 95/11995, the disclosures of which are incorporated herein by reference in their entireties, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated herein by reference in their entireties.

In another embodiment of the oligonucleotide arrays of the invention, an oligonucleotide probe matrix may advantageously be used to detect mutations occurring in the RBP-7 gene and in its regulatory region. For this particular purpose, probes are specifically designed to have a nucleotide sequence allowing their hybridization to the genes that carry known mutations (either by deletion, insertion of substitution of one or several nucleotides). By known mutations is meant mutations on the RBP-7 gene that have been identified according, for example to the technique used by Huang et al. (1996) or Samson et al. (1996).

Another technique that is used to detect mutations in the RBP-7 gene is the use of a high-density DNA array. Each oligonucleotide probe constituting a unit element of the high density DNA array is designed to match a specific subsequence of the RBP-7 genomic DNA or cDNA. Thus, an array comprising, consisting essentially of, or consisting of oligonucleotides complementary to subsequences of the target gene sequence is used to determine the identity of the target sequence with the wild gene sequence, measure its amount, and detect differences between the target sequence and the reference wild gene sequence of the RBP-7 gene. One such design, termed 4L tiled array, uses a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al. in 1996, which is herein incorporated by reference.

Consequently, the invention concerns an array of nucleic acid comprising at least one polynucleotide described above as probes and primers. Preferably, the invention concerns an array of nucleic acid comprising at least two polynucleotides described above as probes and primers.

Amplification of the RBP-7 Gene

1. DNA Extraction

As for the source of the genomic DNA to be subjected to analysis, any test sample can be foreseen without any particular limitation. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the context of the present invention is from peripheral venous blood of each donor.

The techniques of DNA extraction are well-known to the skilled technician. Such techniques are described notably by Lin et al. (1998) and by Mackey et al. (1998).

2. DNA Amplification

DNA amplification techniques are well-known to those skilled in the art. Amplification techniques that can be used in the context of the present invention include, but are not limited to, the ligase chain reaction (LCR) described in EP-A-320 308, WO 9320227 and EP-A-439 182, the disclosures of which are incorporated herein by reference, the polymerase chain reaction (PCR, RT-PCR) and techniques such as the nucleic acid sequence based amplification (NASBA) described in Guatelli JC, et al. (1990) and in Compton J. (1991), Q-beta amplification as described in European Patent Application No. 4544610, strand displacement amplification as described in Walker et al. (1996) and EP A 684 315 and, target mediated amplification as described in PCT Publication WO 9322461, the disclosure of which is incorporated herein by reference.

LCR and Gap LCR are exponential amplification techniques, both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3'hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes, which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227). Gap LCR (GLCR) is a version of LCR where the probes are not adjacent but are separated by 2 to 3 bases.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770 or, to use Asymmetric Gap LCR (RT-AGLCR) as described by Marshall et al., (1994). AGLCR is a modification of GLCR that allows the amplification of RNA.

The PCR technology is the preferred amplification technique used in the present invention. A variety of PCR techniques are familiar to those skilled in the art. For a review of PCR technology, see White (1997) and the publication entitled "PCR Methods and Applications" (1991, Cold Spring Harbor Laboratory Press). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188. Each of these publications is incorporated by reference.

One of the aspects of the present invention is a method for the amplification of the human RBP-7 gene, particularly of the genomic sequences of SEQ ID No. 1 or of the cDNA sequence of SEQ ID No. 4, or a fragment or a variant thereof in a test sample, preferably using the PCR technology. The method comprises the steps of contacting a test sample suspected of containing the target RBP-7 encoding sequence or portion thereof with amplification reaction reagents comprising a pair of amplification primers, and eventually in some instances a detection probe that can hybridize with an internal region of amplicon sequences to confirm that the desired amplification reaction has taken place.

Thus, the present invention also relates to a method for the amplification of a human RBP-7 gene sequence, particularly of a portion of the genomic sequences of SEQ ID No. 1 or of the cDNA sequence of SEQ ID No. 4, or a variant thereof in a test sample, said method comprising the steps of:

a) contacting a test sample suspected of containing the targeted RBP-7 gene sequence comprised in a nucleotide sequence selected from a group consisting of SEQ ID Nos 1 and 4, or fragments or variants thereof with amplification reaction reagents comprising a pair of amplification primers as described above and located on either side of the polynucleotide region to be amplified, and b) optionally detecting the amplification products.

In a preferred embodiment of the above amplification method, the amplification product is detected by hybridization with a labeled probe having a sequence which is complementary to the amplified region.

The primers are more particularly characterized in that they have sufficient complementarity with any sequence of a strand of the genomic sequence close to the region to be amplified, for example with a non-coding sequence adjacent to exons to amplify.

In a particular embodiment of the invention, the primers are selected form the group consisting of the nucleotide sequences detailed in Table C below.

TABLE C

| Forward Primer Name | Position range of amplification primer in SEQ ID No. 1 | Reverse Primer Name | Complementary position range of amplification primer in SEQ ID No. 1 |
|---|---|---|---|
| P1 | 313-330 | P26 | 732-751 |
| P2 | 1282-1299 | P27 | 1682-1699 |
| P3 | 67531-67549 | P28 | 67810-67830 |

TABLE C-continued

| Forward Primer Name | Position range of amplification primer in SEQ ID No. 1 | Reverse Primer Name | Complementary position range of amplification primer in SEQ ID No. 1 |
|---|---|---|---|
| P4 | 70927-70945 | P29 | 71257-71276 |
| P5 | 71613-71631 | P30 | 72043-72060 |
| P6 | 75390-75409 | P31 | 75795-75814 |
| P7 | 77544-77563 | P32 | 77926-77943 |
| P8 | 81708-81726 | P33 | 82108-82127 |
| P9 | 105046-105065 | P34 | 105326-105345 |
| P10 | 104751-104770 | P35 | 105297-105316 |
| P11 | 107691-107710 | P36 | 108091-108110 |
| P12 | 114296-114315 | P37 | 114698-114716 |
| P13 | 114327-114345 | P38 | 114735-114753 |
| P14 | 132101-132118 | P39 | 132504-132521 |
| P15 | 145522-145541 | P40 | 145923-145942 |
| P16 | 145866-145884 | P41 | 146266-146285 |
| P17 | 145956-145976 | P42 | 146399-146418 |
| P18 | 146529-146547 | P43 | 146955-146972 |
| P19 | 152763-152780 | P44 | 153164-153182 |
| P20 | 155404-155422 | P45 | 155706-155726 |
| P21 | 160043-160060 | P46 | 160445-160462 |
| P22 | 160361-160378 | P47 | 160770-160788 |
| P23 | 160742-160759 | P48 | 161147-161165 |
| P24 | 161127-161144 | P49 | 161530-161547 |
| P25 | 161217-161235 | P50 | 161617-161636 |

The invention also concerns a kit for the amplification of a human RBP-7 gene sequence, particularly of a portion of the genomic sequences of SEQ ID No. 1 or of the cDNA sequence of SEQ ID No. 4, or a variant thereof in a test sample, wherein said kit comprises:

a) A pair of oligonucleotide primers located on either side of the RBP-7 region to be amplified;

b) Optionally, the reagents necessary for performing the amplification reaction.

In a preferred embodiment of the amplification kit described above, the primers are selected from the group consisting of the nucleotide sequences of SEQ ID Nos 72-101 and P1-P50.

In another embodiment of the above amplification kit, the amplification product is detected by hybridization with a labeled probe having a sequence which is complementary to the amplified region.

Biallelic Markers of RBP-7

The inventors have discovered nucleotide polymorphisms located within the genomic DNA containing the RBP-7 gene, and among them "Single Nucleotide Polymorphisms" or SNPs that are also termed biallelic markers.

The invention also relates to a nucleotide sequence, preferably a purified and/or isolated polynucleotide comprising a sequence defining a biallelic marker located in the sequence of a RBP-7 gene, a fragment or variant thereof or a sequence complementary thereto. The sequences defining a biallelic marker may be of any length consistent with their intended use, provided that they contain a polymorphic base from a biallelic marker. Preferably, the sequences defining a biallelic marker include the polymorphic base of one of SEQ ID Nos 30-71 or the sequence complementary thereto. In some embodiments the sequences defining a biallelic marker comprise one of the sequences selected from the group consisting of SEQ ID Nos 30-71 or the sequences complementary thereto.

In a preferred embodiment, the invention relates to a set of purified and/or isolated nucleotide sequences, each sequence comprising a sequence defining a biallelic marker located in the sequence of a RBP-7 gene, wherein the set is characterized in that between about 30 and 100%, preferably between about 40 and 60%, more preferably between 50 and 60%, of the sequences defining a biallelic marker are selected from the group consisting of SEQ ID Nos 30-71, the sequences complementary thereto, or a fragment or variant thereof.

The invention further concerns a nucleic acid encoding a RBP-7 protein, wherein said nucleic acid comprises a nucleotide sequence selected from the group consisting of SEQ ID Nos 30-71 or the sequences complementary thereto.

The invention also relates to nucleotide sequence selected from the group consisting of SEQ ID Nos 30-71, the sequences complementary thereto, or a fragment or a variant thereof.

A) Identification of Biallelic Markers

There are two preferred methods through which the biallelic markers of the present invention can be generated.

In a first method, DNA samples from unrelated individuals are pooled together, following which the genomic DNA of interest is amplified and sequenced. The nucleotide sequences thus obtained are then analyzed to identify significant polymorphisms. One of the major advantages of this method resides in the fact that the pooling of the DNA samples substantially reduces the number of DNA amplification reactions and sequencing reactions which must be carried out. Moreover, this method is sufficiently sensitive so that a biallelic marker obtained therewith usually shows a sufficient degree of informativeness for conducting association studies.

In a second method for generating biallelic markers, the DNA samples are not pooled and are therefore amplified and sequenced individually. The resulting nucleotide sequences obtained are then also analyzed to identify significant polymorphisms.

It will readily be appreciated that when this second method is used, a substantially higher number of DNA amplification reactions and sequencing reactions must be carried out. Moreover, a biallelic marker obtained using this method may show a lower degree of informativeness for conducting association studies, e.g. if the frequency of its less frequent allele may be less than about 10%. It will further be appreciated that including such less informative biallelic markers in association studies to identify potential genetic associations with a trait may allow in some cases the direct identification of causal mutations, which may, depending on their penetrance, be rare mutations. This method is usually preferred when biallelic markers need to be identified in order to perform association studies within candidate genes.

The following is a description of the various parameters of a preferred method used by the inventors to generate the markers of the present invention.

1—DNA Extraction

The genomic DNA samples from which the biallelic markers of the present invention are generated are preferably obtained from unrelated individuals corresponding to a heterogeneous population of known ethnic background.

The term "individual" as used herein refers to vertebrates, particularly members of the mammalian species and includes but is not limited to domestic animals, sports animals, laboratory animals, primates and humans. Preferably, the individual is a human.

The number of individuals from whom DNA samples are obtained can vary substantially, preferably from about 10 to about 1000, preferably from about 50 to about 200 individuals. It is usually preferred to collect DNA samples from at least about 100 individuals in order to have sufficient polymorphic diversity in a given population to identify as many markers as possible and to generate statistically significant results.

As for the source of the genomic DNA to be subjected to analysis, any test sample can be foreseen without any particular limitation. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the context of the present invention is from peripheral venous blood of each donor.

The techniques of DNA extraction are well-known to the skilled technician. Details of a preferred embodiment are provided in Example 2.

Once genomic DNA from every individual in the given population has been extracted, it is preferred that a fraction of each DNA sample is separated, after which a pool of DNA is constituted by assembling equivalent amounts of the separated fractions into a single one. However, the person skilled in the art can choose to amplify the pooled or unpooled sequences 2—DNA Amplification The identification of biallelic markers in a sample of genomic DNA may be facilitated through the use of DNA amplification methods. DNA samples can be pooled or unpooled for the amplification step. DNA amplification techniques are well known to those skilled in the art. Various methods to amplify DNA fragments carrying biallelic markers are further described hereinbefore in "Amplification of the RBP-7 gene". The PCR technology is the preferred amplification technique used to identify new biallelic markers. A typical example of a PCR reaction suitable for the purposes of the present invention is provided in Example 3.

In this context, one of the groups of oligonucleotides according to the present invention is a group of primers useful for the amplification of a genomic sequence encoding RBP-7. The primers pairs are characterized in that they have sufficient complementarity with any sequence of a strand of the RBP-7 gene to be amplified, preferably with a sequence of introns adjacent to exons to amplify, with regions of the 3' and 5' ends of the RBP-7 gene, with splice sites or with 5' UTRs or 3' UTRs to hybridize therewith.

These primers focus on exons and splice sites of the RBP-7 gene since an identified biallelic marker as described below presents a higher probability to be an eventual causal mutation if it is located in these functional regions of the gene.

15 pairs of primers were designed with the aim of amplifying each of the 24 exons of the RBP-7 gene (Table 1). To these primers can be added, at either end thereof, a further polynucleotide useful for sequencing such as described in Example 3. Preferred primers include those having the nucleotide sequences disclosed in Example 3. Some of the primers according to the invention allow the amplification of the majority of the RBP-7 Exons shown in FIG. 2.

The primers described above are individually useful as oligonucleotide probes in order to detect the corresponding RBP-7 nucleotide sequence in a sample, and more preferably to detect the presence of a RBP-7 DNA or RNA molecule in a sample suspected to contain it.

3—Sequencing of Amplified Genomic DNA and Identification of Polymorphisms

The amplification products generated as described above with the primers of the invention are then sequenced using methods known and available to the skilled technician. Preferably, the amplified DNA is subjected to automated dideoxy terminator sequencing reactions using a dye-primer cycle sequencing protocol.

Following gel image analysis and DNA sequence extraction, sequence data are automatically processed with adequate software to assess sequence quality The sequence data obtained as described above are transferred to a database, where quality control and validation steps are performed. A base-caller, working using a Unix system automatically flags suspect peaks, taking into account the shape of the peaks, the inter-peak resolution, and the noise level. The base-caller also performs an automatic trimming. Any stretch of 25 or fewer bases having more than 4 suspect peaks is usually considered unreliable and is discarded.

After this first sequence quality analysis, polymorphism analysis software is used to detect the presence of biallelic sites among individual or pooled amplified fragment sequences. The polymorphism search is based on the presence of superimposed peaks in the electrophoresis pattern. These peaks, which present two distinct colors, correspond to two different nucleotides at the same position on the sequence. In order for peaks to be considered significant, peak height has to satisfy conditions of ratio between the peaks and conditions of ratio between a given peak and the surrounding peaks of the same color.

However, since the presence of two peaks can be an artifact due to background noise, two controls are utilized to exclude these artifacts:

the two DNA strands are sequenced and a comparison between the peaks is carried out. The polymorphism has to be detected on both strands for validation.

all the sequencing electrophoresis patterns of the same amplification product provided from distinct pools and/or individuals are compared. The homogeneity and the ratio of homozygous and heterozygous peak height are controlled through these distinct DNAs.

The detection limit for the frequency of biallelic polymorphisms detected by sequencing pools of 100 individuals is about 0.1 for the minor allele, as verified by sequencing pools of known allelic frequencies. However, more than 90% of the biallelic polymorphisms detected by the pooling method have a frequency for the minor allele higher than 0.25. Therefore, the biallelic markers selected by this method have a frequency of at least 0.1 for the minor allele and less than 0.9 for the major allele, preferably at least 0.2 for the minor allele and less than 0.8 for the major allele, more preferably at least 0.3 for the minor allele and less than 0.7 for the major allele, thus a heterozygosity rate higher than 0.18, preferably higher than 0.32, more preferably higher than 0.42.

In a particular embodiment of the invention, the test samples are a pool of 100 individuals and 50 individual samples. This is the methodology used in the preferred embodiment of the present invention, in which 21 biallelic markers have been identified in a genomic region containing the RBP-7 gene. Their location on the genomic RBP-7 DNA is shown in FIG. 2 and their particular sequences are disclosed in example 4. The 24 exons and the intronic sequences surrounding the exons were analyzed. Among the 21 biallelic markers identified within the RBP-7 gene, 6 biallelic markers are located within 4 different exons, and 15 biallelic markers are located within the different intronic regions. The biallelic markers 5-130-257, 5-143-84 and 5-143-101 respectively change asparagine into glycine, glycine into glutamic acid and leucine into methionine in the RBP-7 protein. The amino acid changes caused by the 5-143-84 biallelic marker may be important for the RBP-7 biological activity, since a neutral amino acid is replaced by a positively charged amino acid in a RBP-7 region likely to contain a domain involved in a non-covalent interaction with the retinoblastoma protein or also a pRb related protein such as p107 or p130.

4—Validation of the Biallelic Markers of the Present Invention

The polymorphisms are evaluated for their usefulness as genetic markers by validating that both alleles are present in a population. Validation of the biallelic markers is accomplished by genotyping a group of individuals by a method of the invention and demonstrating that both alleles are present. Microsequencing is a preferred method of genotyping alleles. The validation by genotyping step may be performed on individual samples derived from each individual in the group or by genotyping a pooled sample derived from more than one individual. The group can be as small as one individual if that individual is heterozygous for the allele in question. Preferably the group contains at least three individuals, more preferably the group contains five or six individuals, so that a single validation test will be more likely to result in the validation of more of the biallelic markers that are being tested. It should be noted, however, that when the validation test is performed on a small group it may result in a false negative result if as a result of sampling error none of the individuals tested carries one of the two alleles. Thus, the validation process is less useful in demonstrating that a particular initial result is an artifact, than it is at demonstrating that there is a boiiaficle biallelic marker at a particular position in a sequence. All of the genotyping, haplotyping, and association study methods of the invention may optionally be performed solely with validated biallelic markers.

5—Evaluation of the Frequency of the Biallelic Markers of the Present Invention

The validated biallelic markers are further evaluated for their usefulness as genetic markers by determining the frequency of the least common allele at the biallelic marker site. The higher the frequency of the less common allele the greater the usefulness of the biallelic marker in association and interaction studies. The determination of the least common allele is accomplished by genotyping a group of individuals by a method of the invention and demonstrating that both alleles are present. This determination of frequency by genotyping step may be performed on individual samples derived from each individual in the group or by genotyping a pooled sample derived from more than one individual. The group must be large enough to be representative of the population as a whole. Preferably the group contains at least 20 individuals, more preferably the group contains at least 50 individuals, most preferably the group contains at least 100 individuals. Of course the larger the group the greater the accuracy of the frequency determination because of reduced sampling error. A biallelic marker wherein the frequency of the less common allele is 30% or more is termed a "high quality biallelic marker." All of the genotyping, haplotyping, and association interaction study methods of the invention may optionally be performed solely with high quality biallelic markers.

B—Genotyping an Individual for Biallelic Markers

Methods are provided to genotype a biological sample for one or more biallelic markers of the present invention, all of which may be performed in vitro. Such methods of genotyping comprise determining the identity of a nucleotide at an RBP-7 biallelic marker site by any method known in the art. These methods find use in genotyping case-control populations in association studies as well as individuals in the context of detection of alleles of biallelic markers which are known to be associated with a given trait, in which case both copies of the biallelic marker present in individual's genome are determined so that an individual may be classified as homozygous or heterozygous for a particular allele.

These genotyping methods can be performed nucleic acid samples derived from a single individual or pooled DNA samples.

Genotyping can be performed using similar methods as those described above for the identification of the biallelic markers, or using other genotyping methods such as those further described below. In preferred embodiments, the comparison of sequences of amplified genomic fragments from different individuals is used to identify new biallelic markers whereas microsequencing is used for genotyping known biallelic markers in diagnostic and association study applications.

1—Source of DNA for Genotyping

Any source of nucleic acids, in purified or non-purified form, can be utilized as the starting nucleic acid, provided it contains or is suspected of containing the specific nucleic acid sequence desired. DNA or RNA may be extracted from cells, tissues, body fluids and the like as described above in "DNA extraction". While nucleic acids for use in the genotyping methods of the invention can be derived from any mammalian source, the test subjects and individuals from which nucleic acid samples are taken are generally understood to be human.

2—Amplification of DNA Fragments Comprising Biallelic Markers

Methods and polynucleotides are provided to amplify a segment of nucleotides comprising one or more biallelic marker of the present invention. It will be appreciated that amplification of DNA fragments comprising biallelic markers may be used in various methods and for various purposes and is not restricted to genotyping. Nevertheless, many genotyping methods, although not all, require the previous amplification of the DNA region carrying the biallelic marker of interest. Such methods specifically increase the concentration or total number of sequences that span the biallelic marker or include that site and sequences located either distal or proximal to it. Diagnostic assays may also rely on amplification of DNA segments carrying a biallelic marker of the present invention.

Amplification of DNA may be achieved by any method known in the art. Amplification techniques are described above under the headings "Amplification of the RBP-7 gene".

Some of these amplification methods are particularly suited for the detection of single nucleotide polymorphisms and allow the simultaneous amplification of a target sequence and the identification of the polymorphic nucleotide as it is further described below.

The identification of biallelic markers as described above allows the design of appropriate oligonucleotides, which can be used as primers to amplify DNA fragments comprising the biallelic markers of the present invention. Amplification can be performed using the primers initially used to discover new biallelic markers which are described herein or any set of primers allowing the amplification of a DNA fragment comprising a biallelic marker of the present invention.

In some embodiments the present invention provides primers for amplifying a DNA fragment containing one or more biallelic markers of the present invention. Preferred amplification primers are listed in Example 3. It will be appreciated that the primers listed are merely exemplary and that any other set of primers which produce amplification products containing one or more biallelic markers of the present invention.

The spacing of the primers determines the length of the segment to be amplified. In the context of the present invention amplified segments carrying biallelic markers can range in size from at least about 25 bp to 35 kbp. Amplification fragments from 25-3000 bp are typical, fragments from 50-1000 bp are preferred and fragments from 100-600 bp are highly preferred. It will be appreciated that amplification primers for the biallelic markers may be any sequence which allow the specific amplification of any DNA fragment carrying the markers. Amplification primers may be labeled or immobilized on a solid support as described under the headings entitled "Oligonucleotide probes and primers".

3—Methods of Genotyiing DNA Samples for Biallelic Markers a—Sequencing Assays

The amplification products generated above with the primers of the invention can be sequenced using methods known and available to the skilled technician. Preferably, the amplified DNA is subjected to automated dideoxy terminator sequencing reactions using a dye-primer cycle sequencing protocol. A sequence analysis can allow the identification of the base present at the polymorphic site.

b—Microsequencing Assays

In microsequencing methods, the nucleotide at a polymorphic site in a target DNA is detected by a single nucleotide primer extension reaction. This method involves appropriate microsequencing primers which, hybridize just upstream of the polymorphic base of interest in the target nucleic acid. A polymerase is used to specifically extend the 3' end of the primer with one single ddNTP (chain terminator) complementary to the nucleotide at the polymorphic site. Next the identity of the incorporated nucleotide is determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883, the disclosure of which is incorporated herein by reference in its entirety. Alternatively capillary electrophoresis can be used in order to process a higher number of assays simultaneously. An example of a typical microsequencing procedure that can be used in the context of the present invention is provided in Example 5.

Different approaches can be used for the labeling and detection of ddNTPs. A homogeneous phase detection method based on fluorescence resonance energy transfer has been described by Chen and Kwok (1997) and Chen et al. (1997). In this method amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time.

Microsequencing may be achieved by the established microsequencing method or by developments or derivatives thereof. Alternative methods include several solid-phase microsequencing techniques. The basic microsequencing protocol is the same as described previously, except that the method is conducted as a heterogenous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystyrene particles. In the same manner oligonucleotides or templates may be attached to a solid support in a high-density format. In such solid phase microsequencing reactions, incorporated ddNTPs can be radiolabeled (Syvänen, 1994) or linked to fluorescein (Livak and Hainer, 1994). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate). Other possible reporter-detection pairs include: ddNTP linked to dinitrophenyl (DNP) and anti-DNP alkaline phosphatase conjugate (Harju et al., 1993) or biotinylated ddNTP and horseradish peroxidase-conjugated streptavidin with o-phenylenediamine as a substrate (WO 92/15712, the disclosure of which is incorporated herein by reference in its entirety). As yet another alternative solid-phase microsequencing procedure, Nyren et al. (1993) described a method relying on the detection of DNA polymerase activity by an enzymatic luminometric inorganic pyrophosphate detection assay (ELIDA).

Pastinen et al. (1997) describe a method for multiplex detection of single nucleotide polymorphism in which the solid phase minisequencing principle is applied to an oligonucleotide array format. High-density arrays of DNA probes attached to a solid support (DNA chips) are further described below.

In one aspect the present invention provides polynucleotides and methods to genotype one or more biallelic markers of the present invention by performing a microsequencing assay. Preferred microsequencing primers include those being featured in Example 5. It will be appreciated that the microsequencing primers listed in Example 5 are merely exemplary and that, any primer having a 3' end immediately adjacent to the polymorphic nucleotide may be used. Similarly, it will be appreciated that microsequencing analysis may be performed for any biallelic marker or any combination of biallelic markers of the present invention. One aspect of the present invention is a solid support which includes one or more microsequencing primers listed in Example 5, or fragments comprising at least 8, at least 12, at least 15, or at least 20 consecutive nucleotides thereof and having a 3' terminus immediately upstream of the corresponding biallelic marker, for determining the identity of a nucleotide at a biallelic marker site.

c—Mismatch Detection Assays Based on Polylmerases and Ligases

In one aspect the present invention provides polynucleotides and methods to determine the allele of one or more biallelic markers of the present invention in a biological sample, by allele-specific amplification assays. Methods, primers and various parameters to amplify DNA fragments comprising biallelic markers of the present invention are further described above.

Allele Specific Amplification Primers

Discrimination between the two alleles of a biallelic marker can also be achieved by allele specific amplification, a selective strategy, whereby one of the alleles is amplified without amplification of the other allele. This can be accomplished by placing the polymorphic base at the 3' end of one of the amplification primers. Because the extension forms from the 3' and of the primer, a mismatch at or near this position has an inhibitory effect on amplification. Therefore, under appropriate amplification conditions, these primers only direct amplification on their complementary allele. Determining the precise location of the mismatch and the corresponding assay conditions are well within the ordinary skill in the art.

Ligation/Amplification Based Methods

The "Oligonucleotide Ligation Assay" (OLA) uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al. (1990). In this method, PCR is used to achieve the exponential amplification of target DNA, which is then detected using OLA.

Other amplification methods which are particularly suited for the detection of single nucleotide polymorphism include LCR (ligase chain reaction), Gap LCR (GLCR) which are described above in "Amplification of the RBP-7 gene". LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069, the disclosure of which is incorporated herein by reference in its entirety. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271, the disclosure of which is incorporated herein by reference in its entirety). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

d—Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay may be used including Southern hybridization, Northern hybridization, dot blot hybridization and solid-phase hybridization (see Sambrook et al., 1989).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., 1989). Stringent conditions are sequence dependent and will be different in different circumstances. Generally, stringent conditions are selected to be about 5° C. lower than the thermal melting point (Tm) for the specific sequence at a defined ionic strength and pH. Although such hybridizations can be performed in solution, it is preferred to employ a solid-phase hybridization assay. The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes. Preferably, the hybrids can be bound to a solid phase reagent by virtue of a capture label and detected by virtue of a detection label. In cases where the detection label is directly detectable, the presence of the hybrids on the solid phase can be detected by causing the label to produce a detectable signal, if necessary, and detecting the signal. In cases where the label is not directly detectable, the captured hybrids can be contacted with a conjugate, which generally comprises a binding member attached to a directly detectable label. The conjugate becomes bound to the complexes and the conjugates presence on the complexes can be detected with the directly detectable label. Thus, the presence of the hybrids on the solid phase reagent can be determined.

The polynucleotides provided herein can be used to produce probes which can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. A particularly preferred probe is 25 nucleotides in length. Preferably the polymorphic site of the biallelic marker is within 4 nucleotides of the center of the polynucleotide probe. In particularly preferred probes the polymorphic site of the biallelic marker is at the center of said polynucleotide.

Preferably the probes of the present invention are labeled or immobilized on a solid support. Labels and solid supports are further described in "Oligonucleotide probes and primers". Detection probes are generally nucleic acid sequences or uncharged nucleic acid analogs such as, for example peptide nucleic acids which are disclosed in International Patent Application WO 92/20702, morpholino analogs which are described in U.S. Pat. Nos. 5,185,444; 5,034,506 and 5,142,047, the disclosures of which are incorporated herein by reference in their entireties. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is No. longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

The probes of the present invention are useful for a number of purposes. By assaying the hybridization to an allele specific probe, one can detect the presence or absence of a biallelic marker allele in a given sample.

High-Throughput parallel hybridizations in array format are specifically encompassed within "hybridization assays" and are described below.

e—Hybridization to Addressable Arrays of Oligonucleotides

DNA chips result from the adaptation of computer chips to biology. Efficient access to polymorphism information is obtained through a basic structure comprising high-density arrays of oligonucleotide probes attached to a solid support (the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in S. cerevisiae mutant strains, and in the protease gene of HIV-1 virus (Hacia et al., 1996; Shoemaker et al., 1996; Kozal et al., 1996). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual which, target sequences include a polymorphic marker. EP785280, the disclosure of which is incorporated herein by reference in its entirety, describes a tiling strategy for the detection of single nucleotide polymorphisms. Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of monomers, i.e. nucleotides. Tiling strategies are further described in PCT Application No. WO 95/11995, the disclosure of which is incorporated herein by reference in its entirety. In a particular aspect, arrays are tiled for a number of specific, identified biallelic marker sequences. In particular the array is tiled to include a number of detection blocks, each detection block being specific for a specific biallelic marker or a set of biallelic markers. For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the polymorphic site of the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT Application No. WO 92/10092 and WO 95/11995 and U.S. Pat. No. 5,424,186, the disclosures of which are incorporated herein by reference in their entireties.

Thus, in some embodiments, the chips may comprise an array of nucleic acid sequences of fragments of about 15 nucleotides in length. In further embodiments, the chip may comprise an array including at least one of the sequences selected from the group consisting of the nucleic acids of the sequences set forth as SEQ ID Nos 30-75 and the sequences complementary thereto, or a fragment thereof at least about 8 consecutive nucleotides, preferably 10, 15, 20, more preferably 25, 30, or 40 consecutive nucleotides comprising a biallelic marker of the present invention. In some embodiments, the chip may comprise an array of at least 2, 3, 4, 5, 6, 7, 8 or more of these polynucleotides of the invention. Solid supports and polynucleotides of the present invention attached to solid supports are further described in "Oligonucleotide primers and probes".

f—Integrated Microsequencing and Capillary Electrophoresis Chips

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, the disclosure of which is incorporated herein by reference in its entirety, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts.

For genotyping biallelic markers, the microfluidic system may integrate nucleic acid amplification, microsequencing, capillary electrophoresis and a detection method such as laser-induced fluorescence detection.

Association Studies with the Biallelic Markers of the RBP-7 Gene

The identification of genes involved in suspected heterogeneous, polygenic and multifactorial traits such as cancer can be carried out through two main strategies currently used for genetic mapping: linkage analysis and association studies. Association studies examine the frequency of marker alleles in unrelated trait positive (T+) individuals compared with trait negative (T−) controls, and are generally employed in the detection of polygenic inheritance. Association studies as a method of mapping genetic traits rely on the phenomenon of linkage disequilibrium, which is described below.

If two genetic loci lie on the same chromosome, then sets of alleles of these loci on the same chromosomal segment (called haplotypes) tend to be transmitted as a block from generation to generation. When not broken up by recombination, haplotypes can be tracked not only through pedigrees but also through populations. The resulting phenomenon at the population level is that the occurrence of pairs of specific alleles at different loci on the same chromosome is not random, and the deviation from random is called linkage disequilibrium (LD).

If a specific allele in a given gene is directly involved in causing a particular trait T, its frequency will be statistically increased in a T+ population when compared to the frequency in a T− population. As a consequence of the existence of LD, the frequency of all other alleles present in the haplotype carrying the trait-causing allele (TCA) will also be increased in T+ individuals compared to T− individuals. Therefore, association between the trait and any allele in linkage disequilibrium with the trait-causing allele will suffice to suggest the presence of a trait-related gene in that particular allele's region. Linkage disequilibrium allows the relative frequencies in T+ and T− populations of a limited number of genetic polymorphisms (specifically biallelic markers) to be analyzed as an alternative to screening all possible functional polymorphisms in order to find trait-causing alleles.

The general strategy to perform association studies using biallelic markers derived from a candidate region is to scan two groups of individuals (trait + and trait − control individuals which are characterized by a well defined phenotype as described below) in order to measure and statistically compare the allele frequencies of such biallelic markers in both groups.

If a statistically significant association with a trait is identified for at least one or more of the analyzed biallelic markers, one can assume that: either the associated allele is directly responsible for causing the trait (associated allele is the TCA), or the associated allele is in LD with the TCA. If the evidence indicates that the associated allele within the candidate region is most probably not the TCA but is in LD with the real TCA, then the TCA, and by consequence the gene carrying the TCA, can be found by sequencing the vicinity of the associated marker.

It is another object of the present invention to provide a method for the identification and characterization of an association between alleles for one or several biallelic markers of the human RBP-7 gene and a trait. The method comprises the steps of:

genotyping a marker or a group of biallelic markers according to the invention in trait positive and trait negative individuals; and establishing a statistically significant association between one allele of at least one marker and the trait.

Preferably, the trait positive and trait negative individuals are selected from non-overlapping phenotypes, at opposite ends of the non-bimodal phenotype spectra of the trait under study. In some embodiments, the biallelic marker is one of the biallelic markers of the present invention.

In a preferred embodiment, the trait is a disease and preferably a cancer.

The present invention also provides a method for the identification and characterization of an association between a haplotype comprising alleles for several biallelic markers of the human RBP-7 gene and a trait. The method comprises the steps of:

genotyping a group of biallelic markers according to the invention in trait positive and trait negative individuals; and establishing a statistically significant association between a haplotype and the trait.

In some embodiments, the haplotype comprises two or more biallelic markers defined in SEQ ID Nos 30-71.

The step of testing for and detecting the presence of DNA comprising specific alleles of a biallelic marker or a group of biallelic markers of the present invention can be carried out as described further below.

Vectors for the Expression of a Regulatory or a Coding Polynucleotide According to the Invention Generally, a recombinant vector of the invention may comprise any of the polynucleotides described herein, including regulatory sequences, coding sequences and polynucleotide constructs, as well as any RBP-7 primer or probe as defined above. More particularly, the recombinant vectors of the present invention can comprise any of the polynucleotides described in the "RBP-7 Gene, Corresponding cDNAs And RBP-7 Coding And Regulating Sequences" section, and the "Oligonucleotide Probes And Primers" section.

Any of the regulatory polynucleotides or the coding polynucleotides of the invention may be inserted into recombinant vectors for expression in a recombinant host cell or a recombinant host organism.

Thus, the present invention also encompasses a family of recombinant vectors that contains either a RBP-7 regulatory polynucleotide or a RBP-7 coding polynucleotide or both of them. Preferably, the present invention concerns recombinant vectors that contains either a RBP-7 regulatory polynucleotide or a RBP-7 coding polynucleotide comprising at least one of the biallelic markers of the invention, particularly those of SEQ ID Nos 30-71.

More particularly, the present invention also relates to expression vectors which include nucleic acids encoding a RBP-7 protein under the control of either a RBP-7 regulatory polynucleotide, or an exogenous regulatory sequence.

Another aspect of the present invention is a recombinant expression vector comprising a nucleic acid selected from the group consisting of SEQ ID Nos 1, 4, 5-28 or complementary sequences thereto or fragments or variants thereof.

Another preferred recombinant expression vector according to the invention comprises a nucleic acid comprising a combination of at least two polynucleotides selected from the group consisting of SEQ ID Nos 5-28 or the sequences complementary thereto, wherein the polynucleotides are arranged within the nucleic acid, from the 5' end to the 3' and of said nucleic acid, in the same order than in the SEQ ID No. 1.

Another aspect of the invention is a recombinant expression vector comprising a nucleic acid selected from the group consisting of SEQ ID No. 2 or 3 or the sequences complementary thereto or a biologically active fragment or variant thereof.

A further aspect of the invention is a recombinant expression vector comprising a purified or isolated nucleic acid comprising a) a nucleic acid comprising the nucleotide sequence SEQ ID No. 2, a fragment or variant thereof or a nucleotide sequence complementary thereto;

b) a polynucleotide encoding a protein or a polynucleotide of interest.

The invention also encompasses a recombinant expression vector containing a polynucleotide comprising, consisting essentially of, or consisting of:

a) a nucleic acid comprising a regulatory polynucleotide of SEQ ID No. 2, or the sequence complementary thereto, or a biologically active fragment or variant thereof; and b) a polynucleotide encoding a polypeptide or a polynucleotide of interest.

c) Optionally, the expression vector may further comprise a nucleic acid comprising a regulatory polynucleotide of SEQ ID No. 3, or the sequence complementary thereto, or a biologically active fragment or variant thereof.

The vector containing the appropriate DNA sequence as described above, more preferably a RBP-7 regulatory polynucleotide, a RBP-7 coding polynucleotide or both of them, can be utilized to transform an appropriate host to allow the expression of the desired polypeptide or polynucleotide.

Vectors

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may comprise, consist essentially of, or consist of a chromosomal, non-chromosomal and synthetic DNA. Such a recombinant vector can comprise a transcriptional unit comprising an assembly of (1) a genetic element or elements having a regulatory role in gene expression, for example promoters or enhancers. Enhancers are cis-acting elements of DNA, usually from about 10 to 300 bp that act on the promoter to increase the transcription.

(2) a structural or coding sequence which is transcribed into mRNA and eventually translated into a polypeptide, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The selectable marker genes can be for example dihydrofolate reductase or neomycin resistance for eukaryotic cell culture, TRP1 for *S. cerevisiae* or tetracycline, rifampicine or ampicillin resistance in *E. coli*, or levan saccharase for mycobacteria. The heterologous structural sequence is assembled in appropriate phase with translation initiation and termination sequences, and preferably a leader sequence capable of directing secretion of translated protein into the periplasmic space or extracellular medium.

Useful expression vectors for bacterial use are constructed by inserting a structural DNA sequence encoding a desired polypeptide with suitable translation initiation and termination signals in operable reading phase with a functional promoter. The vector will comprise one or more phenotypic selectable markers and an origin of replication to ensure maintenance of the vector and to, if desirable, provide amplification within the host.

As a representative but non-limiting example, useful expression vectors for bacterial use can comprise a selectable marker and bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

A suitable vector for the expression of the RBP-7 protein above-defined or their peptide fragments is a baculovirus vector that can be propagated in insect cells and in insect cell lines. A specific suitable host vector system is the pVL1392/1393 baculovirus transfer vector (Pharmingen) that is used to transfect the SF9 cell line (ATCC No. CRL 1711) which is derived from *Spodoptera frugiperda*. Other baculovirus vectors are described in Chai et al. (1993), Vlasak et al. (1983) and Lenhardt et al. (1996).

Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example SV40 origin, early promoter, enhancer, splice and polyadenylation sites may be used to provide the required nontranscribed genetic elements.

Large numbers of suitable vectors and promoters are known to those of skill in the art, and commercially available, such as bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); or eukaryotic vectors: pWLNEO, pSV2CAT, pOG44, pXT1, pSG (Stratagene); pSVK3, pBPV, pMSG, pSVL (Pharmacia); baculovirus transfer vector pVL1392/1393 (Pharmingen); pQE-30 (QIAexpress).

Promoters

The suitable promoter regions used in the expression vectors according to the present invention are choosen taking into account of the cell host in which the heterologous gene has to be expressed.

Preferred bacterial promoters are the LacI, LacZ, the T3 or T7 bacteriophage RNA polymerase promoters, the polyhedrin promoter, or the p10 protein promoter from baculovirus (Kit Novagen) (Smith et al., 1983.; O'Reilly et al., 1992), the lambda $P_R$ promoter or also the trc promoter.

Preferred promoters for the expression of the heterologous gene in eukaryotic hosts are the early promoter of CMV, the Herpes simplex virus thymidine kinase promoter, the early or the late promoter from SV40, the LTR regions of certain retroviruses or also the mouse metallothionein I promoter.

Promoter regions can be selected from any desired gene using, for example, CAT (chloramphenicol transferase) vectors and more preferably pKK232-8 and pCM7 vectors. Particularly named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a determined promoter, among the above-described promoters is well in the ability of one skill in the art, guided by his knowledge in the genetic engineering technical field, and by being also guided by the book of Sambrook et al. in 1989 or also by the procedures described by Fuller et al. in 1996.

Other Types of Vectors

The in vivo expression of a RBP-7 polypeptide or a fragment or a variant thereof may be useful in order to study the physiological consequences of a deregulation of its in vivo synthesis on the physiology of the recipient recombinant host organism under study, more particularly on the cell differentiation and on an eventual abnormal proliferation of various kinds of cells, including T cells and epithelial cells.

Consequently, the present invention also relates to recombinant expression vectors mainly designed for the in vivo production of a therapeutic peptide fragment by the introduction of the genetic information in the organism of the patient to be treated. This genetic information may be introduced in vitro in a cell that has been previously extracted from the organism, the modified cell being subsequently reintroduced in the said organism, directly in vivo into the appropriate tissue.

The method for delivering the corresponding protein or peptide to the interior of a cell of a vertebrate in vivo comprises the step of introducing a preparation comprising a physiologically acceptable carrier and a naked polynucleotide operatively coding for the polypeptide into the interstitial space of a tissue comprising the cell, whereby the naked polynucleotide is taken up into the interior of the cell and has a physiological effect.

In a specific embodiment, the invention provides a composition for the in vivo production of a RBP-7 polypeptide containing a naked polynucleotide operatively coding for a RBP-7 polypeptide or a fragment or a variant thereof, in solution in a physiologically acceptable carrier and suitable for introduction into a tissue to cause cells of the tissue to express the said protein or polypeptide.

Advantageously, the composition described above is administered locally, near the site in which the expression of a RBP-7 polypeptide or a fragment or a variant thereof is sought.

The polynucleotide operatively coding for a RBP-7 polypeptide or a fragment or variant thereof may be a vector comprising the genomic DNA or the complementary DNA (cDNA) coding for the corresponding protein or its protein derivative and a promoter sequence allowing the expression of the genomic DNA or the complementary DNA in the desired eukaryotic cells, such as vertebrate cells, specifically mammalian cells.

The promoter contained in such a vector is selected among the group comprising:
- an internal or an endogenous promoter, such as the natural promoter associated with the structural gene coding for the desired RBP-7 polypeptide or the fragment or variant thereof; such a promoter may be completed by a regulatory element derived from the vertebrate host, in particular an activator element;
- a promoter derived from a cytoskeletal protein gene such as the desmin promoter (Bolmont et al., 1990; Zhenlin et al., 1989).

As a general feature, the promoter may be heterologous to the vertebrate host, but it is advantageously homologous to the vertebrate host.

By a promoter heterologous to the vertebrate host is intended a promoter that is not found naturally in the vertebrate host.

Compositions comprising a polynucleotide are described in the PCT Application No. WO 90/11092 and also in the PCT Application No. WO 95/11307 as well as in the articles of Tacson et al. (1996) and of Huygen et al. (1996), the disclosures of which are incorporated herein by reference in their entireties.

In another embodiment, the DNA to be introduced is complexed with DEAE-dextran (Pagano et al., 1967) or with nuclear proteins (Kaneda et al., 1989), with lipids (Felgner et al., 1987) or encapsulated within liposomes (Fraley et al., 1980).

In another embodiment, the polynucleotide encoding a RBP-7 polypeptide or a fragment or a variant thereof may be included in a transfection system comprising polypeptides that promote its penetration within the host cells as it is described in the PCT Application WO 95/10534, the disclosure of which is incorporated herein by reference in its entirety.

The vector according to the present invention may advantageously be administered in the form of a gel that facilitates their transfection into the cells. Such a gel composition may be a complex of poly-L-lysine and lactose, as described by Midoux (1993) or also poloxamer 407 as described by Pastore (1994). Said vector may also be suspended in a buffer solution or be associated with liposomes.

The amount of the vector to be injected to the desired host organism vary according to the site of injection. As an indicative dose, it will be injected between 0,1 and 100 µg of the vector in an animal body, preferably a mammal body, for example a mouse body.

In another embodiment of the vector according to the invention, said vector may be introduced in vitro in a host cell, preferably in a host cell previously harvested from the animal to be treated and more preferably a somatic cell such as a muscle cell. In a subsequent step, the cell that has been transformed with the vector coding for the desired RBP-7 polypeptide or the desired fragment or variant thereof is implanted back into the animal body in order to deliver the recombinant protein within the body either locally or systemically.

Suitable vectors for the in vivo expression of a RBP-7 polypeptide or a fragment or a variant thereof are described hereunder.

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the adenovirus described by Ohwada et al. (1996) or the human adenovirus type 2 or 5 (Ad 2 or Ad 5) or an adenovirus of animal origin (French Patent Application No. FR-93.05954, the disclosure of which is incorporated herein by reference in its entirety).

Among the adenoviruses of animal origin it can be cited the adenoviruses of canine (CAV2, strain Manhattan or A26/61 [ATCC VR-800]), bovine, murine (Mav1, Beard et al., 1980) or simian (SAV). Other adenoviruses are described by Levrero et al. (1991), Graham et al. (1984), in the European Patent Application No. EP-185.573 or in the PCT Application No. WO 95/14785, the disclosures of which are incorporated herein by reference in their entireties.

Retrovirus vectors and adeno-associated virus vectors are generally understood to be the recombinant gene delivery system of choice for the transfer of exogenous polynucleotides in vivo, particularly to mammals, including humans. These vectors provide efficient delivery of genes into cells, and the transferred nucleic acids are stably integrated into the chromosomal DNA of the host. Suitable retroviruses used according to the present invention include those described in the PCT Application No. WO 93/25234, the PCT Application No. WO 94/06920, the PCT Application No. WO 94/24298, Roth et al. (1996), Roux et al. (1989), Julian et al. (1992) and Neda et al. (1991), the disclosures of which are incorporated herein by reference in their entireties. Other preferred retrovirus include Murine Leukemia Viruses such as 4070A and 1504A (Hartley et al., 1976), Abelson (ATCC No. VR-999), Friend (ATCC No. VR-245), Gross (ATCC No. VR-590), Rauscher (ATCC No. VR-998) and Moloney Murine Leukemia Virus (ATCC No. VR-190; PCT Application No. WO 94/24298), the disclosure of which is incorporated herein by reference in its entirety, and also Rous Sarcoma Viruses such as Bryan high titer (ATCC Nos VR-334, VR-657, VR-726, VR-659 and VR-728.

Yet another viral vector system that is contemplated by the invention comprises the adeno-associated virus (AAV). Adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing primary cells relative to transformed cells.

Other compositions containing a vector of the invention comprise advantageously an oligonucleotide fragment of the nucleic sequence of RBP-7 as an antisense tool that inhibits the expression of the corresponding gene and is thus useful to inhibit the expression of the RBP-7 gene in the tagged cells or organs. Preferred methods using antisense polynucleotide according to the present invention are the procedures described by Sczakiel et al. (1995) or also in the PCT Application No. WO 95/24223, the disclosure of which is incorporated herein by reference in its entirety.

Vectors Suitable for Homologous Recombination

Other suitable vectors, particularly for the expression of genes in mammalian cells, may be selected from the group of vectors consisting of P1 bacteriophages, and bacterial artificial chromosomes (BACs). These types of vectors may contain large inserts ranging from about 80-90 kb (P1 bacteriophage) to about 300 kb (BACs).

P1 Bacteriophage.

The construction of P1 bacteriophage vectors such as p158 or p158/neo8 are notably described by Sternberg (1992, 1994). Recombinant P1 clones comprising RBP-7 nucleotide sequences may be designed for inserting large polynucleotides of more than 40 kb (Linton et al., 1993). To generate P1 DNA for transgenic experiments, a preferred protocol is the protocol described by McCormick et al. (1994). Briefly, $E.$ $coli$ (preferably strain NS3529) harboring the P1 plasmid are grown overnight in a suitable broth medium containing 25 µg/ml of kanamycin. The P1 DNA is prepared from the $E. coli$ by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

When the goal is to express a P1 clone comprising RBP-7 nucleotide sequences in a transgenic animal, typically in transgenic mice, it is desirable to remove vector sequences from the P1 DNA fragment, for example by cleaving the P1 DNA at rare-cutting sites within the P1 polylinker (SfiI, NotI or SalI). The P1 insert is then purified from vector sequences on a pulsed-field agarose gel, using methods similar using methods similar to those originally reported for the isolation of DNA from YACs (Schedl et al., 1993a; Peterson et al., 1993). At this stage, the resulting purified insert DNA can be concentrated, if necessary, on a Millipore Ultrafree-MC Filter Unit (Millipore, Bedford, Mass., USA—30,000 molecular weight limit) and then dialyzed against microinjection buffer (10 mM Tris-HCl, pH 7.4; 250 µM EDTA) containing 100 mM NaCl, 30 µM spermine, 70 µM spermidine on a microdyalisis membrane (type VS, 0.025 µM from Millipore). The intactness of the purified P1 DNA insert is assessed by electrophoresis on 1% agarose (Sea Kem GTG; FMC Bio-products) pulse-field gel and staining with ethidium bromide.

Bacterial Artificial Chromosomes (BACs)

The bacterial artificial chromosome (BAC) cloning system (Shizuya et al., 1992) has been developed to stably maintain large fragments of genomic DNA (100-300 kb) in $E. coli$. A preferred BAC vector is the pBeloBAC11 vector that has been described by Kim et al. (1996) BAC libraries are prepared with this vector using size-selected genomic DNA that has been partially digested using enzymes that permit ligation into either the BamHI or HindIII sites in the vector. Flanking these cloning sites are T7 and SP6 RNA polymerase transcription initiation sites that can be used to generate end probes by either RNA transcription or PCR methods. After the construction of a BAC library in $E. coli$, BAC DNA is purified from the host cell as a supercoiled circle. Converting these circular molecules into a linear form precedes both size determination and introduction of the BACs into recipient cells. The cloning site is flanked by two NotI sites, permitting cloned segments to be excised from the vector by NotI digestion. Alternatively, the DNA insert contained in the pBeloBAC11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

Specific DNA Construct Vector for Homologous Recombination

The term "DNA construct" is understood to mean a linear or circular purified or isolated polynucleotide that has been artificially designed and which comprises at least two nucleotide sequences that are not found as contiguous nucleotide sequences in their natural environment.

DNA Construct that Enables Directing Temporal and Spatial Gene Expression in Recombinant Cell Hosts and in Transgenic Animals In order to study the physiological and phenotype consequences of a lack of synthesis of the RBP-7 protein, both at the cell level and at the multi cellular organism level, in particular as regards to disorders related to abnormal cell proliferation, notably cancers, the invention also encompasses DNA constructs and recombinant vectors enabling a conditional expression of a specific allele of the RBP-7 genomic sequence or cDNA and also of a copy of this genomic sequence or cDNA harboring substitutions, deletions, or additions of one or more bases as regards to the RBP-7 nucleotide sequence of SEQ ID Nos 1 or 4, or a fragment thereof, these base substitutions, deletions or additions being located either in an exon, an intron or a regulatory sequence, but preferably in the 5'-regulatory sequence or in an exon of the RBP-7 genomic sequence or within the RBP-7 cDNA of SEQ ID No. 4.

A first preferred DNA construct is based on the tetracycline resistance operon tet from *E. coli* transposon Tn 110 for controlling the RBP-7 gene expression, such as described by Gossen et al. (1992, 1995) and Furth et al. (1994). Such a DNA construct contains seven tet operator sequences from Tn 10 (tetop) that are fused to either a minimal promoter or a 5'-regulatory sequence of the RBP-7 gene, said minimal promoter or said RBP-7 regulatory sequence being operably linked to a polynucleotide of interest that codes either for a sense or an antisense oligonucleotide or for a polypeptide, including a RBP-7 polypeptide or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP16 of herpes simplex virus, placed under the control of a promoter, such as the HCMVIE I enhancer/promoter or the MMTV-LTR. Indeed, a preferred DNA construct of the invention will comprise both the polynucleotide containing the tet operator sequences and the polynucleotide containing a sequence coding for the tTA or the rTA repressor.

In the specific embodiment wherein the conditional expression DNA construct contains the sequence encoding the mutant tetracycline repressor rTA, the expression of the polynucleotide of interest is silent in the absence of tetracycline and induced in its presence.

DNA Constructs Allowing Homologous Recombination: Replacement Vectors

A second preferred DNA construct will comprise, from 5'-end to 3'-end: (a) a first nucleotide sequence that is comprised in the RBP-7 genomic sequence; (b) a nucleotide sequence comprising a positive selection marker, such as the marker for neomycine resistance (neo); and (c) a second nucleotide sequence that is comprised in the RBP-7 genomic sequence, and is located on the genome downstream the first RBP-7 nucleotide sequence (a).

In a preferred embodiment, this DNA construct also comprises a negative selection marker located upstream the nucleotide sequence (a) or downstream the nucleotide sequence (b). Preferably, the negative selection marker is the thymidine kinase (tk) gene (Thomas et al., 1986), the hygromycine beta gene (Te Riele et al., 1990), the hrpt gene (Van der Lugt et al., 1991; Reid et al., 1990) or the Diphteria toxin A fragment (Dt-A) gene (Nada et al., 1993; Yagi et al. 1990). Preferably, the positive selection marker is located within a RBP-7 exon sequence so as to interrupt the sequence encoding a RBP-7 protein.

These replacement vectors are described for example by Thomas et al. (1986; 1987), Mansour et al. (1988) and Koller et al. (1992).

The first and second nucleotide sequences (a) and (c) may be indifferently located within a RBP-7 regulatory sequence, an intronic sequence, an exon sequence or a sequence containing both regulatory and/or intronic and/or exon sequences. The size of the nucleotide sequences (a) and (c) is ranging from 1 to 50 kb, preferably from 1 to 10 kb, more preferably from 2 to 6 kb and most preferably from 2 to 4 kb.

DNA Constructs Allowing Homologous Recombination: Cre-Loxp System

These new DNA constructs make use of the site specific recombination system of the P1 phage. The P1 phage possesses a recombinase called Cre which interacts specifically with a 34 base pairs loxP site. The loxP site is composed of two palindromic sequences of 13 bp separated by a 8 bp conserved sequence (Hoess et al., 1986). The recombination by the Cre enzyme between two loxP sites having an identical orientation leads to the deletion of the DNA fragment.

The Cre-loxP system used in combination with a homologous recombination technique has been first described by Gu et al. (1993, 1994). Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as described by Araki et al. (1995), or by lipofection of the enzyme into the cells, such as described by Baubonis et al. (1993); (b) transfecting the cell host with a vector comprising the Cre coding sequence operably linked to a promoter functional in the recombinant cell host, which promoter being optionally inducible, said vector being introduced in the recombinant cell host, such as described by Gu et al. (1993) and Sauer et al. (1988); (c) introducing in the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. (1994).

In the specific embodiment wherein the vector containing the sequence to be inserted in the RBP-7 gene by homologous recombination is constructed in such a way that selectable markers are flanked by loxP sites of the same orientation, it is possible, by treatment by the Cre enzyme, to eliminate the selectable markers while leaving the RBP-7 sequences of interest that have been inserted by an homologous recombination event. Again, two selectable markers are needed: a positive selection marker to select for the recombination event and a negative selection marker to select for the homologous recombination event. Vectors and methods using the Cre-loxP system are described by Zou et al. (1994).

Thus, a third preferred DNA construct of the invention comprises, from 5'-end to 3'-end: (a) a first nucleotide sequence that is comprised in the RBP-7 genomic sequence; (b) a nucleotide sequence comprising a polynucleotide encoding a positive selection marker, said nucleotide sequence comprising additionally two sequences defining a site recognized by a recombinase, such as a loxP site, the two sites being placed in the same orientation; and (c) a second nucleotide sequence that is comprised in the RBP-7 genomic sequence, and is located on the genome downstream of the first RBP-7 nucleotide sequence (a).

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence, in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant cell host of a sequence encoding the Cre enzyme operably linked to a promoter sequence, preferably an inducible promoter, more preferably a tissue-specific promoter sequence and most preferably a promoter sequence which is both inducible and tissue-specific, such as described by Gu et al. (1994).

The presence of the Cre enzyme within the genome of the recombinant cell host may result of the breeding of two transgenic animals, the first transgenic animal bearing the RBP-7-derived sequence of interest containing the loxP sites as described above and the second transgenic animal bearing the Cre coding sequence operably linked to a suitable promoter sequence, such as described by Gu et al. (1994).

Spatio-temporal control of the Cre enzyme expression may also be achieved with an adenovirus based vector that contains the Cre gene thus allowing infection of cells, or in vivo infection of organs, for delivery of the Cre enzyme, such as described by Anton and Graham (1995) and Kanegae et al. (1995).

The DNA constructs described above may be used to introduce a desired nucleotide sequence of the invention, preferably a RBP-7 genomic sequence or a RBP-7 cDNA sequence, and most preferably an altered copy of a RBP-7 genomic or cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination).

Nuclear Antisense DNA Constructs

Preferably, the antisense polynucleotides of the invention have a 3' polyadenylation signal that has been replaced with a self-cleaving ribozyme sequence, such that RNA polymerase II transcripts are produced without poly(A) at their 3' ends, these antisense polynucleotides being incapable of export from the nucleus, such as described by Liu et al. (1994). In a preferred embodiment, these RBP-7 antisense polynucleotides also comprise, within the ribozyme cassette, a histone stem-loop structure to stabilize cleaved transcripts against 3'-5' exonucleolytic degradation, such as described by Eckner et al. (1991).

Cell Hosts

Another aspect of the invention is a host cell that has been transformed or transfected with one of the polynucleotides described herein, and in particular a polynucleotide either comprising a RBP-7 regulatory polynucleotide or the coding sequence of the RBP-7 polypeptide selected from the group consisting of SEQ ID Nos 1 and 4 or a fragment or a variant thereof. Also included are host cells that are transformed (prokaryotic cells) or that are transfected (eukaryotic cells) with a recombinant vector such as one of those described above. More particularly, the cell hosts of the present invention can comprise any of the polynucleotides described in the "RBP-7 Gene, Corresponding cDNAs And RBP-7 Coding And Regulating Sequences" section, and the "Oligonucleotide Probes And Primers" section.

A further recombinant cell host according to the invention comprises a polynucleotide containing a biallelic marker selected from the group consisting of A1 to A21, and the complements thereof.

An additional recombinant cell host according to the invention comprises any of the vectors described herein, more particularly any of the vectors described in the "Vectors For The Expression Of A Regulatory Or A Coding Polynucleotide According To The Invention" section.

All the above-described vectors are useful to transform or transfect cell hosts in order to express a polynucleotide coding for a RBP-7 polypeptide or their peptide fragments or variants, or a polynucleotide of interest derived from the RBP-7 gene.

Suitable prokaryotic hosts for transformation include *E. coli, Bacillus subtilis*, as well as various species within the genera of *Streptomyces* or *Mycobacterium*). Suitable eukaryotic hosts comprise yeast, insect cells, such as *Drosophila* and Sf9. Various mammalian cell hosts can also be employed to express recombinant protein. Examples of mammalian cell hosts include the COS-7 lines of monkey kidney fibroblasts (Guzman, 1981), and other cell lines capable of expressing a compatible vector, for example the C127, 3T3, CHO, HeLa and BHK cell lines. The selection of an host is within the scope of the one skilled in the art.

A cell host according to the present invention is characterized in that its genome or genetic background (including chromosome, plasmids) is modified by the heterologous nucleic acid coding for a RBP-7 polypeptide or a peptide fragment or variant, or by a polynucleotide of interest derived from the RBP-7 gene.

Preferred cell hosts used as recipients for the expression vectors of the invention are the followings:

a) Prokaryotic cells: *Escherichia coli* strains (I.E. DH5-☐ strain) or *Bacillus slibtilis*.

b) Eukaryotic cell hosts: HeLa cells (ATCC No. CCL2; No. CCL2.1; No. CCL2.2), Cv 1 cells (ATCC No. CCL70), COS cells (ATCC No. CRL1650; No. CRLI651), Sf-9 cells (ATCC No. CRL1711), mammal ES stem cells.

Preferably, the mammal ES stem cells include human (Thomson et al., 1998), mice, rats and rabbits ES stem cells and are preferably used in a process for producing transgenic animals, such as those described below.

The RBP-7 gene expression in human cells may be rendered defective, or alternatively it may be proceeded with the insertion of a RBP-7 genomic or cDNA sequence with the replacement of the RBP-7 gene counterpart in the genome of an animal cell by a RBP-7 polynucleotide according to the invention. These genetic alterations may be generated by homologous recombination events using specific DNA constructs that have been previously described.

One kind of cell hosts that may be used are mammal zygotes, such as murine zygotes. For example, murine zygotes may undergo microinjection with a purified DNA molecule of interest, for example a purified DNA molecule that has previously been adjusted to a concentration range from 1 ng/ml—for BAC inserts—3 ng/µl—for P1 bacteriophage inserts—in 10 mM Tris-HCl, pH 7.4, 250 µM EDTA containing 100 mM NaCl, 30 µM spermine, and 70 µM spermidine. When the DNA to be microinjected has a large size, polyamines and high salt concentrations can be used in order to avoid mechanical breakage of this DNA, as described by Schedl et al (1993b).

Anyone of the polynucleotides of the invention, including the DNA constructs described herein, may be introduced in an embryonic stem (ES) cell line, preferably a mouse ES cell line. ES cell lines are derived from pluripotent, uncommited cells of the inner cell mass of pre-implantation blastocysts. Peferred ES cell lines are the following: ES-E14TG2a (ATCC No. CRL-1821), ES-D3 (ATCC No. CRL1934 and No. CRL-11632), YS001 (ATCC No. CRL-11776), 36.5 (ATCC No. CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells are primary embryonic fibroblasts that are established from tissue of day 13-day 14 embryos of virtually any mouse strain, that are maintained in culture, such as described by Abbondanzo et al. (1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Such methods are well known by the skill artisan.

Transgenic Animals

The terms "transgenic animals" or "host animals" are used herein designate animals that have their genome genetically and artificially manipulated so as to include one of the nucleic acids according to the invention. Preferred animals are non-human mammals and include those belonging to a genus selected from *Mus* (e.g. mice), *Rattus* (e.g. rats) and *Orycto-galus* (e.g. rabbits) which have their genome artificially and genetically altered by the insertion of a nucleic acid according to the invention.

The transgenic animals of the invention all include within a plurality of their cells a cloned recombinant or synthetic DNA sequence, more specifically one of the purified or isolated nucleic acids comprising a RBP-7 coding sequence, a RBP-7 regulatory polynucleotide or a DNA sequence encoding an antisense polynucleotide such as described in the present specification.

Preferred transgenic animals according to the invention contains in their somatic cells and/or in their germ line cells any one of the polynucleotides, the recombinant vectors and the cell hosts described in the present invention. More particularly, the transgenic animals of the present invention can comprise any of the polynucleotides described in the "RBP-7 Gene, Corresponding cDNAs And RBP-7 Coding And Regulating Sequences" section, the "Oligonucleotide Probes And Primers" section, the "Vectors For The Expression Of A Regulatory Or A Coding Polynucleotide According To The Invention" section and the "Cell Hosts" section.

The transgenic animals of the invention thus contain specific sequences of exogenous genetic material such as the nucleotide sequences described above in detail.

In a first preferred embodiment, these transgenic animals may be good experimental models in order to study the diverse pathologies related to cell differentiation, in particular concerning the transgenic animals within the genome of which has been inserted one or several copies of a polynucleotide encoding a native RBP-7 protein, or alternatively a mutant RBP-7 protein.

In a second preferred embodiment, these transgenic animals may express a desired polypeptide of interest under the control of the regulatory polynucleotides of the RBP-7 gene, leading to good yields in the synthesis of this protein of interest, and eventually a tissue specific expression of this protein of interest.

The design of the transgenic animals of the invention may be made according to the conventional techniques well known from the one skilled in the art. For more details regarding the production of transgenic animals, and specifically transgenic mice, it may be referred to Sandou et al. (1994) and also to U.S. Pat. No. 4,873,191, issued Oct. 10, 1989, U.S. Pat. No. 5,464,764 issued Nov. 7, 1995 and U.S. Pat. No. 5,789,215, issued Aug. 4, 1998, these documents being herein incorporated by reference to disclose methods producing transgenic mice.

Transgenic animals of the present invention are produced by the application of procedures which result in an animal with a genome that has incorporated exogenous genetic material. The procedure involves obtaining the genetic material, or a portion thereof, which encodes either a RBP-7 coding sequence, a RBP-7 regulatory polynucleotide or a DNA sequence encoding a RBP-7 antisense polynucleotide such as described in the present specification.

A recombinant polynucleotide of the invention is inserted into an embryonic or ES stem cell line. The insertion is preferably made using electroporation, such as described by Thomas et al. (1987). The cells subjected to electroporation are screened (e.g. by selection via selectable markers, by PCR or by Southern blot analysis) to find positive cells which have integrated the exogenous recombinant polynucleotide into their genome, preferably via an homologous recombination event. An illustrative positive-negative selection procedure that may be used according to the invention is described by Mansour et al. (1988).

Then, the positive cells are isolated, cloned and injected into 3.5 days old blastocysts from mice, such as described by Bradley (1987). The blastocysts are then inserted into a female host animal and allowed to grow to term.

Alternatively, the positive ES cells are brought into contact with embryos at the 2.5 days old 8-16 cell stage (morulae) such as described by Wood et al. (1993) or by Nagy et al.

(1993), the ES cells being internalized to colonize extensively the blastocyst including the cells which will give rise to the germ line.

The offsprings of the female host are tested to determine which animals are transgenic e.g. include the inserted exogenous DNA sequence and which are wild-type.

Thus, the present invention also concerns a transgenic animal containing a nucleic acid, a recombinant expression vector or a recombinant host cell according to the invention.

Recombinant Cell Lines Derived from the Transgenic Animals of the Invention

A further aspect of the invention is recombinant cell hosts obtained from a transgenic animal described herein.

Recombinant cell lines may be established in vitro from cells obtained from any tissue of a transgenic animal according to the invention, for example by transfection of primary cell cultures with vectors expressing onc-genes such as SV40 large T antigen, as described by Chou (1989) and Shay et al. (1991).

RBP-7 Polypeptides

It is now easy to produce proteins in high amounts by genetic engineering techniques through expression vectors such as plasmids, phages or phagemids. The polynucleotide that code for one the polypeptides of the present invention is inserted in an appropriate expression vector in order to produce in vitro the polypeptide of interest.

Thus, the present invention also concerns a method for producing one of the polypeptides described herein, and especially a polypeptide of SEQ ID No. 29 or a fragment or a variant thereof, wherein said method comprises the steps of:

a) Optionally amplifying the nucleic acid coding for a RBP-7 polypeptide, or a fragment or a variant thereof, using a pair of primers according to the invention (by PCR, SDA, TAS, 3SR NASBA, TMA etc.).

b) Inserting the resulting amplified nucleic acid in an appropriate vector;

c) culturing, in an appropriate culture medium, a cell host previously transformed or transfected with the recombinant vector of step b);

d) harvesting the culture medium thus conditioned or lyse the cell host, for example by sonication or by an osmotic shock;

e) separating or purifying, from the said culture medium, or from the pellet of the resultant host cell lysate the thus produced polypeptide of interest.

f) Optionally characterizing the produced polypeptide of interest.

The polypeptides according to the invention may be characterized by binding onto an immunoaffinity chromatography column on which polyclonal or monoclonal antibodies directed to a polypeptide of SEQ ID No. 29, or a fragment or a variant thereof, have previously been immobilized.

Purification of the recombinant proteins or peptides according to the present invention may be carried out by passage onto a Nickel or Cupper affinity chromatography column. The Nickel chromatography column may contain the Ni-NTA resin (Porath et al., 1975).

The polypeptides or peptides thus obtained may be purified, for example by high performance liquid chromatography, such as reverse phase and/or cationic exchange HPLC, as described by Rougeot et al. (1994). The reason to prefer this kind of peptide or protein purification is the lack of byproducts found in the elution samples which renders the resultant purified protein or peptide more suitable for a therapeutic use.

Another aspect of the present invention comprises a purified or isolated RBP-7 polypeptide or a fragment or a variant thereof.

In a preferred embodiment, the RBP-7 polypeptide comprises an amino acid sequence of SEQ ID No. 29 or a fragment or a variant thereof. In a further embodiment, the present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID No. 29.

The RBP-7 polypeptide of the amino acid sequence of SEQ ID No. 29 has 1312 amino acids in length. This 1312 amino acid sequence harbors notably potential sites indicating post-translational modifications such as 8 N-glycosylation sites, 72 phosphorylation sites, 8 N-myristoylation sites and 4 amidation sites. The location of these sites is referred to in the appended Sequence Listing when disclosing the features of the amino acid sequence of SEQ ID No. 29.

The RBP-7 polypeptide shares some homology in amino acid sequence with another retinoblastoma binding protein, namely human RBP-1 (Fattaey et al., 1993). More precisely, a 48% identity has been found between RBP-7 and RBP-1 for the amino acid sequence beginning at position 1 and ending at position 790 of RBP-7. A 30% identity has been found for the amino acid sequence beginning at position 791 and ending at position 1312 of RBP-7.

A further object of the present invention concerns a purified or isolated polypeptide which is encoded by a nucleic acid comprising a nucleotide sequence selected from the group consisting of SEQ ID Nos 1, 4 and 5-28 or fragments or variants thereof. Preferably, the purified or isolated polypeptide comprises at least 10, at least 15, at least 20 or at least 25 consecutive amino acids of the polypeptides encoded by SEQ ID Nos 1, 4 and 5-28.

The invention includes a nucleic acid encoding a RBP-7 polypeptide comprising at least one of the biallelic markers of the present invention, more particularly at least one of the biallelic markers defined in SEQ ID No. 30-71.

More generally, the invention also pertains to a variant RBP-7 polypeptide comprising at least one amino acid substitution, addition or deletion, when compared with the sequence of SEQ ID No. 29. More particularly, the invention encompasses a RBP-7 protein or a fragment thereof comprising a contiguous span of at least 6 amino acids, preferably at least 8 to 10 amino acids, more preferably at least 12, 15, 20, 25, 30, 40, 50, or 100 amino acids of SEQ ID No. 29 comprising at least one of the following amino acids:

a Glycine residue at the amino acid position 293 of SEQ ID No. 29;

a Glutamic acid at the amino acid in position 963 of SEQ ID No. 29;

a Methionine residue at the amino acid position 969 of SEQ ID No. 29.

A variant or mutated RBP-7 polypeptide comprises amino acid changes of at least one amino acid substitution, deletion or addition, preferably from 1 to 10, 20 or 30 amino acid substitutions or additions. The amino acid substitutions are generally non conservative in terms of polarity, charge, hydrophilicity properties of the substitute amino acid when compared with the native amino acid. The amino acid changes occurring in such a mutated RBP-7 polypeptide may be determinant for the biological activity or for the capacity of the mutated RBP-7 polyeptide to be recognized by antibodies raised against a native RBP-7.

Such a variant or mutated RBP-7 protein may be the target of diagnostic tools, such as specific monoclonal or polyclonal antibodies, useful for detecting the mutated RBP-7 protein in a sample.

Are also part of the present invention polypeptides that are homologous to a RBP-7 polypeptide, especially a polypeptide of SEQ ID No. 29, or their fragments or variants.

The invention also encompasses a RBP-7 polypeptide or a fragment or a variant thereof in which at least one peptide bound has been modified as described in "Definitions".

The polypeptides according to the invention may also be prepared by the conventional methods of chemical synthesis, either in a homogenous solution or in solid phase. As an illustrative embodiment of such chemical polypeptide synthesis techniques, it may be cited the homogenous solution technique described by Houbenweyl in 1974.

The RBP-7 polypeptide, or a fragment or a variant thereof may thus be prepared by chemical synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups.

For solid phase synthesis the technique described by Merrifield (1965) may be used in particular.

Antibodies

The polypeptides according to the present invention, especially the polypeptides of SEQ ID No. 29 are allowing the preparation of polyclonal or monoclonal antibodies that recognize the polypeptides of SEQ ID No. 29 or fragments thereof.

The antibodies may be prepared from hybridomas according to the technique described by Kohler and Milstein in 1975. The polyclonal antibodies may be prepared by immunization of a mammal, especially a mouse or a rabbit, with a polypeptide according to the invention that is combined with an adjuvant of immunity, and then by purifying of the specific antibodies contained in the serum of the immunized animal on a affinity chromatography column on which has previously been immobilized the polypeptide that has been used as the antigen.

The invention also concerns a purified or isolated antibody capable of specifically binding to the RBP-7 protein, more particularly to selected peptide fragments thereof, and more preferably polypeptides encoded by nucleic acids comprising one or more biallelic markers of the invention, or a variant thereof. In addition, the invention comprises antibodies capable of specifically binding to a fragment or variant of such a RBP-7 protein comprising an epitope of the RBP-7 protein, preferably an antibody capable of binding to a polypeptide comprising at least 10 consecutive amino acids, at least 15 consecutive amino acids, at least 20 consecutive amino acids, or at least 40 consecutive amino acids of a RBP-7 protein, more preferably an antibody capable of binding specifically to a variant or mutated RBP-7 protein or a fragment thereof and distinguishing between either two variants of RBP-7 or mutated RBP-7 and non-mutated RBP-7 protein.

The proteins expressed from a RBP-7 DNA comprising at least one of the nucleic sequences of SEQ ID Nos 30-71 or a fragment or a variant thereof, preferably the nucleic sequences of the biallelic markers leading to an amino acid substitution, may also be used to generate antibodies capable of specifically binding to the expressed RBP-7 protein or fragments or variants thereof.

In another embodiment, polyclonal or monoclonal antibodies according to the invention are raised against a RBP-7 polypeptide comprising at least one of the following amino acids:

a Glycine residue at the amino acid position 293 of SEQ ID No. 29;

a Glutamic acid at the amino acid in position 963 of SEQ ID No. 29;

a Methionine residue at the amino acid position 969 of SEQ ID No. 29.

Alternatively, the antibodies may be capable of binding fragments of the RBP-7 protein which comprise at least 10 amino acids encoded by the sequences of SEQ ID Nos 1 and 4, preferably comprising at least one of the sequences of SEQ ID Nos 30-71 or a fragment or a variant thereof. In some embodiments, the antibodies may be capable of binding fragments of the RBP-7 protein which comprise at least 15 amino acids encoded by the sequences of SEQ ID Nos 1 and 4, preferably comprising at least one of the sequences of SEQ ID Nos 30-71 or a fragment or a variant thereof. In other embodiments, the antibodies may be capable of binding fragments of the RBP-7 protein which comprise at least 25 amino acids encoded by the sequences of SEQ ID Nos 1 and 4, preferably comprising at least one of the sequences of SEQ ID Nos 30-71 or a fragment or a variant thereof. In further embodiments, the antibodies may be capable of binding fragments of the RBP-7 protein which comprise at least 40 amino acids encoded by the sequences of SEQ ID Nos 1 and 4, preferably comprising at least one of the sequences of SEQ ID Nos 30-71 or a fragment or a variant thereof.

Both monoclonal antibodies and polyclonal antibodies are within the scope of the present invention. Monoclonal or polyclonal antibodies to the protein can then be prepared as follows:

A. Monoclonal Antibody Production by Hybridoma Fusion

Monoclonal antibody to epitopes in the RBP-7 protein or a portion thereof can be prepared from murine hybridomas according to the classical method of Kohler and Milstein, (1975) or derivative methods thereof. Briefly, a mouse is repetitively inoculated with a few micrograms of the RBP-7 protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, (1980), and derivative methods thereof. Selected positive clones can be expanded and their monoclonal antibody product harvested for use. Detailed procedures for monoclonal antibody production are described in Davis, L. et al.

B. Polyclonal Antibody Production by Immunization

Polyclonal antiserum containing antibodies to heterogeneous epitopes in the PBP-7 protein or a portion thereof can be prepared by immunizing suitable animals with the RBP-7 protein or a portion thereof, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, (1971).

Booster injections can be given at regular intervals, and antiserum harvested when antibody titer thereo, as determined semi-quantitatively, for example, by double immunodiffusion in agar against known concentrations of the antigen, begins to fall. See, for example, Ouchterlony, O. et al. (1973). Plateau concentration of antibody is usually in the range of 0.1 to 0.2 mg/ml of serum. Affinity of the antisera for the antigen is determined by preparing competitive binding curves, as described, for example, by Fisher (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

Consequently, the invention is also directed to a method for detecting specifically the presence of a polypeptide according to the invention in a biological sample, said method comprising the following steps:

a) bringing into contact the biological sample with an antibody according to the invention;

b) detecting the antigen-antibody complex formed.

Another aspect of the invention is a diagnostic kit for in vitro detecting the presence of a polypeptide according to the present invention in a biological sample, wherein said kit comprises:

a) a polyclonal or monoclonal antibody as described above, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself Methods for Screening Substances Interacting with a RBP-7 Polypeptide For the purpose of the present invention, a ligand means a molecule, such as a protein, a peptide, an antibody or any synthetic chemical compound capable of binding to the RBP-7 protein or one of its fragments or variants or to modulate the expression of the polynucleotide coding for RBP-7 or a fragment or variant thereof.

In the ligand screening method according to the present invention, a biological sample or a defined molecule to be tested as a putative ligand of the RBP-7 protein is brought into contact with the purified RBP-7 protein, for example the purified recombinant RBP-7 protein produced by a recombinant cell host as described hereinbefore, in order to form a complex between the RBP-7 protein and the putative ligand molecule to be tested.

The present invention pertains to methods for screening substances of interest that interact with a RBP-7 protein or one fragment or variant thereof. By their capacity to bind covalently or non-covalently to a RBP-7 protein or to a fragment or variant thereof, these substances or molecules may be advantageously used both in vitro and in vivo.

In vitro, said interacting molecules may be used as detection means in order to identify the presence of a RBP-7 protein in a sample, preferably a biological sample.

A method for the screening of a candidate substance comprises the following steps:

a) providing a polypeptide comprising, consisting essentially of, or consisting of a RBP-7 protein or a fragment or a variant thereof;

b) obtaining a candidate substance;

c) bringing into contact said polypeptide with said candidate substance;

d) detecting the complexes formed between said polypeptide and said candidate substance.

In one embodiment of the screening method defined above, the complexes formed between the polypeptide and the candidate substance are further incubated in the presence of a polyclonal or a monoclonal antibody that specifically binds to the RBP-7 protein or to said fragment or variant thereof.

Various candidate substances or molecules can be assayed for interaction with a RBP-7 polypeptide. These substances or molecules include, without being limited to, natural or synthetic organic compounds or molecules of biological origin such as polypeptides. When the candidate substance or molecule comprises a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

The invention also pertains to kits useful for performing the hereinbefore described screening method. Preferably, such kits comprise a RBP-7 polypeptide or a fragment or a variant thereof, and optionally means useful to detect the complex formed between the RBP-7 polypeptide or its fragment or variant and the candidate substance. In a preferred embodiment the detection means are monoclonal or polyclonal antibodies directed against the RBP-7 polypeptide or a fragment or a variant thereof.

A. Candidate Ligands Obtained from Random Peptide Libraries

In a particular embodiment of the screening method, the putative ligand is the expression product of a DNA insert contained in a phage vector (Parmley and Smith, 1988). Specifically, random peptide phages libraries are used. The random DNA inserts encode for peptides of 8 to 20 amino acids in length (Oldenburg K. R. et al., 1992.; Valadon P., et al., 1996.; Lucas A. H., 1994; Westerink M. A. J., 1995; Castagnoli L. et al. (Felici F.), 1991). According to this particular embodiment, the recombinant phages expressing a protein that binds to the immobilized RBP-7 protein is retained and the complex formed between the RBP-7 protein and the recombinant phage may be subsequently immunoprecipitated by a polyclonal or a monoclonal antibody directed against the RBP-7 protein.

Once the ligand library in recombinant phages has been constructed, the phage population is brought into contact with the immobilized RBP-7 protein. Then the preparation of complexes is washed in order to remove the non-specifically bound recombinant phages. The phages that bind specifically to the RBP-7 protein are then eluted by a buffer (acid pH) or immunoprecipitated by the monoclonal antibody produced by the hybridoma anti-RBP-7, and this phage population is subsequently amplified by an over-infection of bacteria (for example E. coli). The selection step may be repeated several times, preferably 2-4 times, in order to select the more specific recombinant phage clones. The last step involves characterizing the peptide produced by the selected recombinant phage clones either by expression in infected bacteria and isolation, expressing the phage insert in another host-vector system, or sequencing the insert contained in the selected recombinant phages.

B. Candidate Ligands Obtained through a two-Hybrid Screening Assay

The yeast two-hybrid system is designed to study protein-protein interactions in vivo (Fields and Song, 1989), and relies upon the fusion of a bait protein to the DNA binding domain of the yeast Gal4 protein. This technique is also described in the U.S. Pat. No. 5,667,973 and the U.S. Pat. No. 5,283,173 (Fields et al.) the technical teachings of both patents being herein incorporated by reference.

The general procedure of library screening by the two-hybrid assay may be performed as described by Harper et al. (Harper JW et al., 1993) or as described by Cho et al. (1998) or also Fromont-Racine et al. (1997).

The bait protein or polypeptide comprises, consists essentially of, or consists of a RBP-7 polypeptide or a fragment or variant thereof.

More precisely, the nucleotide sequence encoding the RBP-7 polypeptide or a fragment or variant thereof is fused to a polynucleotide encoding the DNA binding domain of the GAL4 protein, the fused nucleotide sequence being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "pray" polypeptides.

A third vector contains a detectable marker gene, such as β galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non limiting example the two different yeast strains may be the followings:

Y190, the phenotype of which is (MATa, Leu2-3, 112 ura3-12, trp1-901, his3-D200, ade2-101, gal4Dgal180D URA3 GAL-LacZ, LYS GAL-HIS3, cyh$^r$);

Y187, the phenotype of which is (MATα gal4 gal80 his3 trp1-901 ade2-101 ura3-52 leu2-3, -112 URA3 GAL-lac-Zmet$^-$), which is the opposite mating type of Y190.

Briefly, 20 μg of pAS2/RBP-7 and 20 μg of pACT-cDNA library are co-transformed into yeast strain Y190. The transformants are selected for growth on minimal media lacking histidine, leucine and tryptophan, but containing the histidine stnthesis inhibitor 3-AT (50 mM). Positive colonies are screened for beta galactosidase by filter lift assay. The double positive colonies (His$^+$, β-gal$^+$) are then grown on plates lacking histidine, leucine, but containing tryptophan and cycloheximide (10 mg/ml) to select for loss of pAS2/RBP-7 plasmids bu retention of pACT-cDNA library plasmids. The resulting Y190 strains are mated with Y187 strains expressing RBP-7 or non-related control proteins; such as cyclophilin B, lamin, or SNF1, as Gal4 fusions as described by Harper et al. (Harper J W et al., 1993) and by Bram et al. (Bram R J et al., 1993), and screened for β galactosidase by filter lift assay.

Yeast clones that are β gal-after mating with the control Gal4 fusions are considered false positives.

In another embodiment of the two-hybrid method according to the invention, interaction between RBP-7 or a fragment or variant thereof with cellular proteins may be assessed using the Matchmaker Two Hybrid System 2 (Catalog No. K1604-1, Clontech). As described in the manual accompanying the Matchmaker Two Hybrid System 2 (Catalog No. K1604-1, Clontech), the disclosure of which is incorporated herein by reference, nucleic acids encoding the RBP-7 protein or a portion thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain interaction between RBP-7 and the protein or peptide encoded by the initially selected cDNA insert.

C. Candidate Ligand Obtained through Biosensor Assay

Proteins interacting with the RBP-7 protein or portions thereof can also be screened by using an Optical Biosensor as described in Edwards et Leatherbarrow (1997), the disclosure of which is incorporated herein by reference. The main advantage of the method is that it allows the determination of the association rate between the protein and other interacting molecules. Thus, it is possible to specifically select interacting molecules with a high or low association rate. Typically a target molecule is linked to the sensor surface (through a carboxymethl dextran matrix) and a sample of test molecules is placed in contact with the target molecules. The binding of a test molecule to the target molecule causes a change in the refractive index and/or thickness. This change is detected by the Biosensor provided it occurs in the evanescent field (which extend a few hundred nanometers from the sensor surface). In these screening assays, the target molecule can be the RBP-7 protein or a portion thereof and the test sample can be a collection of proteins extracted from tissues or cells, a pool of expressed proteins, combinatorial peptide and/or chemical libraries, or phage displayed peptides. The tissues or cells from which the test proteins are extracted can originate from any species.

Method for Screening Ligands that Modulate the Expression of the RBP-7 Gene

The present invention also concerns a method for screening substances or molecules that are able to increase, or in contrast to decrease, the level of expression of the RBP-7 gene. Such a method may allow the one skilled in the art to select substances exerting a regulating effect on the expression level of the RBP-7 gene and which may be useful as active ingredients included in pharmaceutical compositions for treating patients suffering from deficiencies in the regulation of expression of the RBP-7 gene.

Thus, another aspect of the present invention is a method for the screening of a candidate substance or molecule, said method comprising the following steps:

a) providing a recombinant cell host containing a nucleic acid, wherein said nucleic acid comprises a nucleotide sequence selected from the group consisting of SEQ ID Nos: 1, 4, 30-75 or the sequences complementary thereto or a fragment or a variant thereof;

b) obtaining a candidate substance, and c) determining the ability of the candidate substance to modulate the expression levels of the nucleic acid comprising a nucleotide sequence selected from the group consisting of SEQ ID No: 1, 4, 30-75 or the sequences complementary thereto or a fragment or a variant thereof.

The invention also pertains to kits useful for performing the hereinbefore described screening method. Preferably, such kits comprise a recombinant vector that allows the expression of a nucleic acid comprising a nucleotide sequence selected from the group consisting of SEQ ID No: 1, 4, 30-75 or the sequences complementary thereto or a fragment or a variant thereof or, alternatively, the kit may comprise a recombinant cell host containing such recombinant vectors.

Another subject of the present invention is a method for screening molecules that modulate the expression of the RBP-7 protein. Such a screening method comprises the steps of:

a) cultivating a prokaryotic or an eukaryotic cell that has been transfected with a nucleotide sequence encoding the RBP-7 protein, placed under the control of its own promoter;

b) bringing into contact the cultivated cell with a molecule to be tested;

c) quantifying the expression of the RBP-7 protein.

In another embodiment of a method for screening of a candidate substance or molecule that modulates the expression of the RBP-7 gene, the method comprises the following steps:

a) providing a recombinant cell host containing a nucleic acid, wherein said nucleic acid comprises the nucleotide sequence of SEQ ID No. 2, the sequence complementary thereto, or a biologically active fragment or variant thereof located upstream a polynucleotide encoding a detectable protein;

b) obtaining a candidate substance, and c) determining the ability of the candidate substance to modulate the expression levels of the polynucleotide encoding the detectable protein.

Among the preferred polynucleotides encoding a detectable protein, there may be cited polynucleotides encoding β galactosidase, green fluorescent protein (GFP) and chloramphenicol acetyl transferase (CAT).

The invention also pertains to kits useful for performing the hereinbefore described screening method. Preferably, such kits comprise a recombinant vector that allows the expression of a nucleotide sequence of SEQ ID No. 2 or a biologically active fragment or variant thereof located upstream a polynucleotide encoding a detectable protein.

For the design of suitable recombinant vectors useful for performing the screening methods described above, it will be referred to the section of the present specification wherein the preferred recombinant vectors of the invention are detailed.

Using DNA recombination techniques well known by the one skill in the art, the RBP-7 protein encoding DNA sequence is inserted into an expression vector, downstream from its promoter sequence. As an illustrative example, the promoter sequence of the RBP-7 gene is contained in the nucleic acid of SEQ ID No. 2.

The quantification of the expression of the RBP-7 protein may be realized either at the mRNA level or at the protein level. In the latter case, polyclonal or monoclonal antibodies may be used to quantify the amounts of the RBP-7 protein that have been produced, for example in an ELISA or a RIA assay.

In a preferred embodiment, the quantification of the RBP-7 mRNA is realized by a quantitative PCR amplification of the cDNA obtained by a reverse transcription of the total mRNA of the cultivated RBP-7-transfected host cell, using a pair of primers specific for RBP-7.

Expression levels and patterns of RBP-7 may be analyzed by solution hybridization with long probes as described in International Patent Application No. WO 97/05277, the entire contents of which are incorporated herein by reference. Briefly, the RBP-7 cDNA or the RBP-7 genomic DNA described above, or fragments thereof, is inserted at a cloning site immediately downstream of a bacteriophage (T3, T7 or SP6) RNA polymerase promoter to produce antisense RNA. Preferably, the RBP-7 insert comprises at least 100 or more consecutive nucleotides of the genomic DNA sequence or the cDNA sequences, particularly those comprising at least one of SEQ ID Nos 30-71 or those encoding mutated RBP-7. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40-50° C. for 16 hours in an 80% formamide, 0.4 M NaCl buffer, pH 7-8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Methods for Inhibiting the Expression of a RBP-7 Gene

Other therapeutic compositions according to the present invention comprise advantageously an oligonucleotide fragment of the nucleic sequence of RBP-7 as an antisense tool or a triple helix tool that inhibits the expression of the corresponding RBP-7 gene.

A—Antisense Approach

Preferred methods using antisense polynucleotide according to the present invention are the procedures described by Sczakiel et al. (Sczakiel G. et al., 1995).

Preferably, the antisense tools are choosen among the polynucleotides (15-200 bp long) that are complementary to the 5' and of the RBP-7 mRNA. In another embodiment, a combination of different antisense polynucleotides complementary to different parts of the desired targetted gene are used.

Preferred antisense polynucleotides according to the present invention are complementary to a sequence of the mRNAs of RBP-7 that contains the translation initiation codon ATG.

The antisense nucleic acid molecules to be used in gene therapy may be either DNA or RNA sequences. They comprise a nucleotide sequence complementary to the targeted sequence of the RBP-7 genomic DNA, the sequence of which can be determined using one of the detection methods of the present invention. In a preferred embodiment, the antisense oligonucleotide are able to hybridize with at least one of the splicing sites of the targeted RBP-7 gene, or with the 3'UTR of the 5'UTR. The antisense nucleic acids should have a length and melting temperature sufficient to permit formation of an intracellular duplex having sufficient stability to inhibit the expression of the RBP-7 mRNA in the duplex. Strategies for designing antisense nucleic acids suitable for use in gene therapy are disclosed in Green et al., (1986) and Izant and Weintraub, (1984), the disclosures of which are incorporated herein by reference.

In some strategies, antisense molecules are obtained by reversing the orientation of the RBP-7 coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of RBP-7 antisense nucleic acids in vivo by operably linking DNA containing the antisense sequence to a promoter in a suitable expression vector.

Alternatively, suitable antisense strategies are those described by Rossi et al. (1991), in the International Applications Nos. WO 94/23026, WO 95/04141, WO 92/18522 and in the European Patent Application No. EP 0 572 287 A2, the disclosures of which are incorporated herein by reference in their entireties.

An alternative to the antisense technology that is used according to the present invention involves using ribozymes that will bind to a target sequence via their complementary polynucleotide tail and that will cleave the corresponding RNA by hydrolyzing its target site (namely "hammerhead ribozymes"). Briefly, the simplified cycle of a hammerhead ribozyme involves (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Sczakiel et al. (1995), the specific preparation procedures being referred to in said article being herein incorporated by reference.

B—Triple Helix Approach

The RBP-7 genomic DNA may also be used to inhibit the expression of the RBP-7 gene based on intracellular triple helix formation.

Triple helix oligonucleotides are used to inhibit transcription from a genome. They are particularly useful for studying alterations in cell activity when it is associated with a particular gene.

Similarly, a portion of the RBP-7 genomic DNA can be used to study the effect of inhibiting RBP-7 transcription within a cell. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from the RBP-7 genomic DNA are contemplated within the scope of this invention.

To carry out gene therapy strategies using the triple helix approach, the sequences of the RBP-7 genomic DNA are first scanned to identify 10-mer to 20-mer homopyrimidine or homopurine stretches which could be used in triple-helix based strategies for inhibiting RBP-7 expression. Following identification of candidate homopyrimidine or homopurine stretches, their efficiency in inhibiting RBP-7 expression is assessed by introducing varying amounts of oligonucleotides containing the candidate sequences into tissue culture cells which express the RBP-7 gene.

The oligonucleotides can be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced RBP-7 expression using techniques such as Northern blotting, RNase protection assays, or PCR based strategies to monitor the transcription levels of the RBP-7 gene in cells which have been treated with the oligonucleotide.

The oligonucleotides which are effective in inhibiting gene expression in tissue culture cells may then be introduced in vivo using the techniques described above in the antisense approach at a dosage calculated based on the in vitro results, as described in antisense approach.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (1989), which is hereby incorporated by this reference.

Throughout this application, various references are referred to within parentheses. The disclosures of these publications in their entireties are hereby incorporated by reference into this application to more fully describe the sate of the art to which this invention pertains.

EXAMPLES

Example 1

Analysis of the mRNAs Encoding a RBP-7 Polypeptide Synthesized by the Cells

RBP-7 cDNA was obtained as follows: 4 µl of ethanol suspension containing 1 mg of human prostate total RNA (Clontech laboratories, Inc., Palo Alto, USA; Catalogue N. 64038-1) was centrifuged, and the resulting pellet was air dried for 30 minutes at room temperature.

First strand cDNA synthesis was performed using the Advantage™ RT-for-PCR kit (Clontech laboratories Inc., catalogue N. K1402-1). 1 µl of 20 mM solution of a specific oligo dT primer was added to 12.5 µl of RNA solution in water, heated at 74° C. for 2.5 min and rapidly quenched in an ice bath. 10 µl of 5×RT buffer (50 mM Tris-HCl, pH 8.3, 75 mM KCl, 3 mM $MgCl_2$), 2.5 µl of dNTP mix (10 mM each), 1.25 µl of human recombinant placental RNA inhibitor were mixed with 1 ml of MMLV reverse transcriptase (200 units). 6.5 µl of this solution were added to RNA-primer mix and incubated at 42° C. for one hour. 80 µl of water were added and the solution was incubated at 94° C. for 5 minutes.

5 µl of the resulting solution were used in a Long Range PCR reaction with hot start, in 50 µl final volume, using 2 units of rtTHXL, 20 pmol/µl of each of 5'-CCCTTGAT-GAGCCTCCCTATTTGACAG-3' (SEQ ID No. 137) and 5'-CGCATTGAAATTCCCACGTCGTATTGCCAG-3' (SEQ ID No. 138) primers with 35 cycles of elongation for 6 minutes at 67° C. in thermocycler.

The amplification products corresponding to both cDNA strands are partially sequenced in order to ensure the specificity of the amplification reaction.

Results of Nothem blot analysis of prostate mRNAs support the existence of a major RBP-7 cDNA having about 6 kb in length, which is approximately the size of the longest possible RBP-7 transcript.

Example 2

Detection of RBP-7 Biallelic Markers: DNA Extraction

Donors were unrelated and healthy. They presented a sufficient diversity for being representative of a French heterogeneous population. The DNA from 100 individuals was extracted and tested for the detection of the biallelic markers.

30 ml of peripheral venous blood were taken from each donor in the presence of EDTA. Cells (pellet) were collected after centrifugation for 10 minutes at 2000 rpm. Red cells were lysed by a lysis solution (50 ml final volume: 10 mM Tris pH7.6; 5 mM $MgCl_2$; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:
  3 ml TE 10-2 (Tris-HCl 10 mM, EDTA 2 mM)/NaCl 0.4 M
  200 µl SDS 10%
  500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 µg/ml DNA).

To determine the presence of proteins in the DNA solution, the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

Example 3

Detection of the Biallelic Markers: Amplification of Genomic DNA by PCR

The amplification of specific genomic sequences of the DNA samples of example 2 was carried out on the pool of DNA obtained previously. In addition, 50 individual samples were similarly amplified.

PCR assays were performed using the following protocol:

| | | |
|---|---|---|
| Final volume | 25 | µl |
| DNA | 2 | ng/µl |
| $MgCl_2$ | 2 | mM |
| dNTP (each) | 200 | µM |
| primer (each) | 2.9 | ng/µl |
| Ampli Taq Gold DNA polymerase | 0.05 | unit/µl |
| PCR buffer (10× = 0.1 M TrisHCl pH 8.3 0.5 M KCl | 1× | |

Each pair of primers was designed using the sequence information of the RBP-7 gene disclosed herein and the OSP software (Hillier & Green, 1991). This pair of primers was about 20 nucleotides in length and had the sequences disclosed in Table 1 in the columns labeled PU and RP.

TABLE 1

| Amplicon | Amplification primer PU SEQ ID No. | Amplification primer RP SEQ ID No. |
|---|---|---|
| 5-124 | 72 | 87 |
| 5-127 | 73 | 88 |
| 5-128 | 74 | 89 |
| 5-129 | 75 | 90 |
| 5-130 | 76 | 91 |
| 5-131 | 77 | 92 |
| 5-133 | 78 | 93 |
| 5-135 | 79 | 94 |
| 5-136 | 80 | 95 |
| 5-140 | 81 | 96 |
| 5-143 | 82 | 97 |
| 5-145 | 83 | 98 |
| 5-148 | 84 | 99 |
| 99-1437 | 85 | 100 |
| 99-1442 | 86 | 101 |

Preferably, the primers contained a common oligonucleotide tail upstream of the specific bases targeted for amplification which was useful for sequencing.

Primers PU contain the following additional PU 5' sequence: TGTAAAACGACGGCCAGT (SEQ ID No. 139); primers RP contain the following RP 5' sequence: CAGGAAACAGCTATGACC (SEQ ID No. 140).

The synthesis of these primers was performed following the phosphoramidite method, on a GENSET UFPS 24.1 synthesizer.

DNA amplification was performed on a Genius II thermocycler. After heating at 95° C. for 10 min, 40 cycles were performed. Each cycle comprised: 30 sec at 95° C., 54° C. for 1 min, and 30 sec at 72° C. For final elongation, 10 min at 72° C. ended the amplification. The quantities of the amplification products obtained were determined on 96-well microtiter plates, using a fluorometer and Picogreen as intercalant agent (Molecular Probes).

Example 4

Detection of the Biallelic Markers: Sequencing of Amplified Genomic DNA and Identification of Polymorphisms The sequencing of the amplified DNA obtained in example 3 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis [ABI Prism DNA Sequencing Analysis software (2.1.2 version) and the above mentioned "Trace" basecaller].

The sequence data were further evaluated using the above mentioned polymorphism analysis software designed to detect the presence of biallelic markers among the pooled amplified fragments. The polymorphism search was based on the presence of superimposed peaks in the electrophoresis pattern resulting from different bases occurring at the same position as described previously.

Sixteen fragments of amplification were analyzed. In these segments, 21 biallelic markers were detected. The localization of the biallelic markers is as shown in Table 2.

TABLE 2

| Amplicon | BM | Marker Name | Localization in RBP-7 | BM position in SEQ ID No. 1 | Polymor- phism | SEQ ID No. Allele 1 | SEQ ID No. Allele 2 |
|---|---|---|---|---|---|---|---|
| 5-124 | A1 | 5-124-273 | Intron 5 | 72794 | A*/G | 30 | 51 |
| 5-127 | A2 | 5-127-261 | Intron 8 | 88073 | A/C* | 31 | 52 |
| 5-128 | A3 | 5-128-60 | Intron 8 | 93714 | Del(GT) | 32 | 53 |
| 5-129 | A4 | 5-129-144 | Intron 9 | 97152 | Del(T) | 33 | 54 |
| 5-130 | A5 | 5-130-257 | Exon 11 | 99098 | A*/G | 34 | 55 |
| 5-130 | A6 | 5-130-276 | Exon 11 | 99117 | A/G | 35 | 56 |
| 5-131 | A7 | 5-131-395 | Intron 12 | 103806 | A*/T | 36 | 57 |
| 5-133 | A8 | 5-133-375 | Intron 14 | 106940 | ins(A) | 37 | 58 |
| 5-135 | A9 | 5-135-155 | Intron 15 | 108106 | ins(A) | 38 | 59 |
| 5-135 | A10 | 5-135-198 | Intron 15 | 108149 | ins(GTTT) | 39 | 60 |
| 5-135 | A11 | 5-135-357 | Intron 15 | 108308 | A*/G | 40 | 61 |
| 5-136 | A12 | 5-136-174 | Exon 16 | 108471 | C/T* | 41 | 62 |
| 5-140 | A13 | 5-140-120 | Intron 18 | 134134 | C/T* | 42 | 63 |
| 5-140 | A14 | 5-140-348 | Intron 19 | 134362 | ins(A) | 43 | 64 |
| 5-140 | A15 | 5-140-361 | Intron 19 | 134374 | ins(CA) | 44 | 65 |
| 5-143 | A16 | 5-143-101 | Exon 20 | 146345 | A/C | 45 | 66 |
| 5-143 | A17 | 5-143-84 | Exon 20 | 146328 | A/G* | 46 | 67 |
| 5-145 | A18 | 5-145-24 | Intron 20 | 150329 | A*/G | 47 | 68 |
| 5-148 | A19 | 5-148-352 | Exon 24 | 160031 | G/T | 48 | 69 |
| 99-1437 | A20 | 99-1437-325 | Intron 8 | 90842 | A/G | 49 | 70 |
| 99-1442 | A21 | 99-1442-224 | Intron 9 | 97122 | G/T | 50 | 71 |

*the most frequent allele in the tested Caucasian control population

Example 5

Validation of the Polyynorphisms through Microsequencing

The biallelic markers identified in example 4 were further confirmed and their respective frequencies were determined through microsequencing. Microsequencing was carried out for each individual DNA sample described in Example 2.

Amplification from genomic DNA of individuals was performed by PCR as described above for the detection of the biallelic markers with the same set of PCR primers (Table 1).

The preferred primers used in microsequencing were about 23 nucleotides in length and hybridized just upstream of the considered polymorphic base. According to the invention, the primers used in microsequencing are detailed in Table 3.

TABLE 3

| Marker Name | Mis. 1 in SEQ ID No. | Mis. 2 in SEQ ID No. |
|---|---|---|
| 5-124-273 | 102 | 123 |
| 5-127-261 | 103 | 123 |
| 5-128-60 | 104 | — |
| 5-129-144 | 105 | — |
| 5-130-257 | 106 | 125 |
| 5-130-276 | 107 | 126 |
| 5-131-395 | 108 | 127 |
| 5-133-375 | 109 | — |
| 5-135-155 | 110 | — |
| 5-135-198 | 111 | — |
| 5-135-357 | 112 | 128 |
| 5-136-174 | 113 | 129 |
| 5-140-120 | 114 | 130 |
| 5-140-348 | 115 | — |
| 5-140-361 | 116 | — |
| 5-143-101 | 117 | 131 |
| 5-143-84 | 118 | 132 |
| 5-145-24 | 119 | 133 |
| 5-148-352 | 120 | 134 |
| 99-1437-325 | 121 | 135 |
| 99-1442-224 | 122 | 136 |

The microsequencing reaction was performed as follows:

After purification of the amplification products, the microsequencing reaction mixture was prepared by adding, in a 20 μl final volume: 10 pmol microsequencing oligonucleotide, 1 U Thermosequenase (Amersham E79000G), 1.25 μl Thermosequenase buffer (260 mM Tris HCl pH 9.5, 65 mM $MgCl_2$), and the two appropriate fluorescent ddNTPs (Perkin Elmer, Dye Terminator Set 401095) complementary to the nucleotides at the polymorphic site of each biallelic marker tested, following the manufacturer's recommendations. After 4 minutes at 94° C., 20 PCR cycles of 15 sec at 55° C., 5 sec at 72° C., and 10 sec at 94° C. were carried out in a Tetrad PTC-225 thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized classification as homozygous or heterozygous type based on the height ratio.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

REFERENCES

The disclosures of all of the following publications are incorporated herein by reference in their entireties:

Abbondanzo S J et al., 1993, Methods in Enzymology, Academic Press, New York, pp. 803-823.
Adra et al., 1987, Gene, 60:65-74
Anton M. et al., 1995, J. Virol., 69: 4600-4606.
Araki K. et al., 1995, Proc. Natl. Acad. Sci. USA, 92: 160-164.
Baubonis et al., 1993, Nucleic Acids Res., 21: 2025-2029.
Beard et al., 1980, Virology, Vol. 75:81
Beaucage et al., *Tetrahedron Lett* 1981, 22: 1859-1862
Bolmont et al., J. of Submicroscopic cytology and pathology, 1990, 22:117-122
Bradley A., 1987, Production and analysis of chimaeric mice. In: E. J. Robertson (Ed.), Teratocarcinomas and embryonic stem cells: A practical approach. IRL Press, Oxford, pp. 113.
Bram R J et al., 1993, Mol. Cell Biol., 13: 4760-4769
Brown E L, Belagaje R, Ryan M J, Khorana H G, *Methods Enzymol* 1979;68: 109-151
Castagnoli L. et al. (Felici F.), 1991, J. Mol. Biol., 222:301-310
Chai H. et al., 1993, Biotechnol. Appl. Biochem., 18:259-273
Cho R J et al., 1998, Proc. Natl. Acad. Sci. USA, 95(7): 3752-3757.
Chou J. Y., 1989, Mol. Endocrinol., 3: 1511-1514.
Compton J. *Nature*. 1991 Mar. 7; 350(6313): 91-92.
Current Protocols in Molecular Biology, 1989, Ausubel F M et al. (eds), Greene Publishing Associates, Sections 9.10-9.14.
Davis, L. et al. Basic Methods in Molecular Biology Elsevier, N.Y. Section 21-2
Defeo-Jones et al. Nature, 1991, Vol. 352: 251-254
Eckner R. et al., 1991, EMBO J., 10: 3513-3522.
Edwards et Leatherbarrow, Analytical Biochemistry, 246, 1-6 (1997)
Feldman and Steg, 1996, Medecine/Sciences, synthese, 12:47-55
Felgner et al., 1987, Proc. Natl. Acad. Sci., 84:7413
Fields and Song, 1989, Nature, 340: 245-246
Fisher, D., Chap. 42 in: Manual of Clinical Immunology, 2d Ed. (Rose and Friedman, Eds.) Amer. Soc. For Microbiol., Washington, D.C. (1980).
Flotte et al., 1992, Am. J. Respir. Cell Mol. Biol., 7: 349-356.
Fraley et al., 1980, J. Biol. Chem., 255:10431).
Fromont-Racine M. et al., 1997, Nature Genetics, 16(3): 277-282.
Fuller S. A. et al., 1996, Immunology in Current Protocols in Molecular Biology, Ausubel et al. Eds, John Wiley & Sons, Inc., USA
Furth P. A. et al., 1994, Proc. Natl. Acad. Sci USA, 91: 9302-9306.
Gossen M. et al., 1992, Proc. Natl. Acad. Sci. USA, 89: 5547-5551.
Gossen M. et al., 1995, Science, 268: 1766-1769.
Graham, 1984, EMBO J., 3:2917
Green et al., *Ann. Rev. Biochem.* 55:569-597 (1986)
Griffin et al. *Science* 245:967-971 (1989)
Grompe, M. et al., *Proc. Natl. Acad. Sci. U.S.A* 1989; 86:5855-5892
Grompe, M. *Nature Genetics* 1993; 5:111-117
Gu H. et al., 1993, Cell, 73: 1155-1164.
Gu H. et al., 1994, Science, 265: 103-106.
Guatelli J C et al., 1990, Proc. Natl. Acad. Sci. USA, 87: 1874-1878.
Guzman, 1981, Cell, 23: 175
Hacia J G, Brody L C, Chee M S, Fodor S P, Collins F S, *Nat Genet* 1996;14(4):441-447
Hames B D and Higgins S J, 1985, "Nucleic acid hybridization: a practical approach", Hames and Higgins Ed., IRL Press, Oxford.
Harper J W et al., 1993, Cell, 75: 805-816
Harris H. et al., 1969, Nature, 223: 363-368
Helin et al., 1992, Cell, 70: 337-350
Hillier L. and Green P. *Methods Appl.,* 1991, 1: 124-8.
Hoess et al., 1986, Nucleic Acids Res., 14: 2287-2300.
Houbenweyl, 1974, in Meuthode der Organischen Chemie, E. Wunsch Ed., Volume 15-I et 15-II, Thieme, Stuttgart
Huygen et al., 1996, Nature Medicine, 2(8):893-898
Izant J G, Weintraub H, *Cell* 1984 April; 36(4):1007-15
Julan et al., 1992, J. Gen. Virol., 73: 3251-3255.
Kaneda et al., 1989, Science, 243:375
Kanegae Y. et al., Nucl. Acids Res., 23: 3816-3821.
Kim et al., 1994, Mol. And Cell Biol., 14(11): 7256-7264
Kim U.-J., et al., 1996, Genomics, 34: 213-218.
Koch Y., 1977, Biochem. Biophys. Res. Commun., 74:488-491
Kohler G. and Milstein C., 1975, Nature, 256: 495.
Koller et al., 1992, Annu. Rev. Immunol., 10: 705-30.
Kort et al., 1983, Nucleic Acids Research, 11:8287-8301
Kozal M J, Shah N, Shen N, Yang R, Fucini R, Merigan T C, Richman D D, Morris D, Hubbell E, Chee M, Gingeras T R, *Nat Med* 1996;2(7):753-759
Lenhard T. et al., 1996, Gene, 169:187-190
Levrero et al., 1991, Gene, 101:195
Linton M. F. et al., 1993, J. Clin. Invest., 92: 3029-3037.
Liu Z. et al., 1994, Proc. Natl. Acad. Sci. USA, 91: 4528-4262.
Lucas A. H., 1994, In: Development and Clinical Uses of Haempophilus b Conjugate;
Mansour S. L. et al., 1988, Nature, 336: 348-352.
Mansour S L et al., 1988, Nature, 336: 348-352.
Manz et al., *Adv in Chlromatogr* 1993; 33:1-66
Marshall R. L., et al., *PCR Methods and Applications* 4: 80-84 (1994)
McCormick et al., 1994, Genet. Anal. Tech. Appl., 11: 158-164.

McLaughlin et al., 1989, J. Virol., 62: 1963-1973.
Merrifield R B, 1965, Nature, 207(996): 522-523.
Merrifield R B., 1965, Science, 150(693): 178-185.
Midoux, 1993, Nucleic Acids Research, 21:871-878
Muzyczka et al., 1992, Cuur. Topics in Micro. and Immunol., 158: 97-129.
Nada S. et al., 1993, Cell, 73: 1125-1135.
Nagy A. et al., 1993, Proc. Natl. Acad. Sci. USA, 90: 8424-8428.
Narang S A, Hsiung H M, Brousseau R, *Methods Enzyinol* 1979;68:90-98
Neda et al., 1991, J. Biol. Chem., 266: 14143-14146.
O'Reilly et al., 1992, Baculovirus expression vectors: a Laboratory Manual. W. H. Freeman and Co., New York Adra et al., 1987, Gene, 60:65-74
Ohno et al., 1994, Sciences, 265:781-784
Oldenburg K R. et al., 1992, Proc. Natl. Acad. Sci., 89:5393-5397.
Otterson et al., 1993, Oncogene, 8: 949-957
Ouchterlony, O. et al., Chap. 19 in: Handbook of Experimental Immunology D. Wier (ed) Blackwell (1973)
Pagano et al., 1967, J. Virol., 1:891
Parmley and Smith, Gene, 1988, 73:305-318
Pastore, 1994, Circulation, 90:1-517
PCR Methods and Applications" (1991, Cold Spring Harbor Laboratory Press Pease S. ans William R. S., 1990, Exp. Cell. Res., 190: 209-211.
Peterson et al., 1993, Proc. Natl. Acad. Sci. USA, 90: 7593-7597.
Porath J et al., 1975, Nature, 258(5536): 598-599.
Reid L. H. et al., 1990, Proc. Natl. Acad. Sci. USA, 87: 4299-4303.
Rettlez and Basenga, 1987, Mol. Cell. Biol., 7:1676-1685
Robertson E., 1987, Embryo-derived stem cell lines. In: E. J. Robertson Ed. *Teratocarcinomas and embrionic stem cells: a practical approach*. TRL Press, Oxford, pp. 71.
Rossi et al., *Pharmacol. Ther.* 50:245-254, (1991)
Roth J. A. et al., 1996, Nature Medicine, 2(9):985-991
Rougeot, C. et al.,. *Eur. J. Biochem.* 219 (3): 765-773, 1994
Roux et al., 1989, Proc. Nat] Acad. Sci. USA, 86: 9079-9083.
Sakai et al., 1995, Genomics, 30: 98-101
Sambrook, J. Fritsch, E. F., and T. Maniatis. 1989. Molecular cloning: a laboratory manual. 2ed. Cold Spring Harbor Laboratory, Cold spring Harbor, N.Y.
Samulski et al., 1989, J. Virol., 63: 3822-3828.
Sanchez-Pescador R., 1988, J. Clin. Microbiol., 26(10):1934-1938
Sandou et al., 1994, Science, 265: 1875-1878.
Sauer B. et al., 1988, Proc. Natl. Acad. Sci. USA, 85: 5166-5170.
Schedl A. et al., 1993a, Nature, 362: 258-261.
Schedl et al., 1993b, Nucleic Acids Res., 21: 4783-4787.
Sczakiel G. et al., 1995, Trends Microbiol., 1995, 3(6):213-217
Shay J. W. et al., 1991, Biochem. Biophys. Acta, 1072: 1-7.
Sheffield, V. C. et al, *Proc. Natl. Acad. Sci. U.S.A* 1991; 49:699-706
Shizuya et al., 1992, Porc. Natl. Acad. Sci. USA 89: 8794-8797.
Shoemaker D D, Lashkari D A, Morris D, Mittmann M, Davis R W, *Nat Genet* 1996;14(4):450-456
Smith et al., 1983, Mol. Cell. Biol., 3:2156-2165.
Sosnowski R G, Tu E, Butler W F, O'Connell J P, Heller M J, *Proc Natl Acad Sci USA* 1997;94(4):1119-1123
Sternberg N. L., 1992, Trends Genet., 8: 1-16.
Sternberg N. L., 1994, Mamm. Genome, 5: 397-404.
Tacson et al., 1996, Nature Medicine, 2(8):888-892
Te Riele et al., 1990, Nature, 348: 649-651.
Thomas K. R. et al., 1986, Cell, 44: 419-428.
Thomas K. R. et al., 1987, Cell, 51: 503-512.
Thomson et al., 1998, *Science* 282, 1145-1147
Urdea M. S., 1988, Nucleic Acids Research, 11: 4937-4957
Urdea M S et al., 1991, Nucleic Acids Symp Ser., 24: 197-200.
Vaitukaitis J. et al., 1971, J. Clin. Endocrinol. Metab., 33: 988-991
Valadon P., et al., 1996, J. Mol. Biol., 261:11-22.
Van der Lugt et al., 1991, Gene, 105: 263-267.
Vlasak R. et al., 1983, Eur. J. Biochem., 135:123-126
Wabiko et al., 1986, DNA, 5(4):305-314
Walker G. T. et al., *Clin. Chem.* 42:9-13 [1996]
Westerink M. A. J., 1995, Proc. Natl. Acad. Sci., 92:4021-4025
White, B. A. Molecular Cloning to Genetic Engineering Ed. in Methods in Molecular Biology 67: Humana Press, Totowa 1997
White, M. B. et al., *Genomics* 1992; 12:301-306
Wood S. A. et al., 1993, Proc. Natl. Acad. Sci. USA, 90: 4582-4585.
Yagi T. et al., 1990, Proc. Natl. Acad. Sci. USA, 87: 9918-9922.
Zhenlin et al., Gene, 1989, 78:243-254
Zou Y. R. et al., 1994, Curr. Biol., 4: 1099-1103.

I claim:

1. An isolated, purified, or recombinant polynucleotide consisting essentially of:
   a) a contiguous span of 8 to 50 nucleotides of any one of SEQ ID NOs: 1, 4 or the complements thereof, wherein said span includes a biallelic marker of RBP-7;
   b) a contiguous span of 8 to 50 nucleotides of any one of SEQ ID NOs: 1, 4 or the complements thereof, wherein said span contains a biallelic marker of RBP-7 selected from the group consisting of A1 to A21, and the complements thereof; or
   c) a contiguous span of 8 to 50 nucleotides of any one of SEQ ID NOs: 1, 4 or the complements thereof, wherein the 3' end of said contiguous span is located at the 3' end of said polynucleotide, and wherein the 3' end of said polynucleotide is located within 20 nucleotides upstream of a biallelic marker of RBP-7 in said sequence.

2. The isolated, purified, or recombinant polynucleotide according to claim 1(b), wherein said isolated, purified, or recombinant polynucleotide consists essentially of a contiguous span of 18 to 47 nucleotides of any one of SEQ ID NOs: 1, 4 or the complements thereof, wherein said span contains a biallelic marker of RBP-7 selected from the group consisting of A1 to A21, and the complements thereof, and said biallelic marker is within 4 nucleotides of the center of said polynucleotide.

3. The isolated, purified, or recombinant polynucleotide according to claim 2, wherein said polynucleotide consists of said contiguous span and said contiguous span is 25 nucleotides in length and said biallelic marker is at the center of said polynucleotide.

4. The isolated, purified, or recombinant polynucleotide according to claim 2, wherein said polynucleotide consists essentially of a sequence selected from the sequences SEQ ID NOs: 30-71 and the complementary sequences thereto.

5. The isolated, purified, or recombinant polynucleotide according to claim 1(b), wherein the 3' end of said contiguous span is located at the 3' end of said polynucleotide and said biallelic marker is present at the 3' end of said polynucleotide.

6. The isolated, purified, or recombinant polynucleotide according to claim 1(b), wherein the 3' end of said polynucleotide is located 1 nucleotide upstream of said biallelic marker of RBP-7 in said sequence.

7. The isolated, purified, or recombinant polynucleotide according to claim 6, wherein said polynucleotide consists essentially of a sequence selected from the sequences of SEQ ID NOs: 102-136.

8. An array of polynucleotides comprising at least one polynucleotide attached to a solid support, wherein said polynucleotide consists essentially of:
   a) a contiguous span of 8 to 50 nucleotides of any one of SEQ ID NOs: 1, 4 or the complements thereof, wherein said span includes a biallelic marker of RBP-7;
   b) a contiguous span of 8 to 50 nucleotides of any one of SEQ ID NOs: 1, 4 or the complements thereof, wherein said span contains a biallelic marker of RBP-7 selected from the group consisting of A1 to A21, and the complements thereof; or
   c) a contiguous span of 8 to 50 nucleotides of any one of SEQ ID NOs: 1, 4 or the complements thereof, wherein the 3' end of said contiguous span is located at the 3' end of said polynucleotide, and wherein the 3' end of said polynucleotide is located within 20 nucleotides upstream of a biallelic marker of RBP-7 in said sequence.

9. The array of polynucleotides according to claim 8, wherein said array is addressable.

10. The isolated, purified or recombinant polynucleotide according to claim 1, wherein said polynucleotide consists essentially of a contiguous span of 8 to 50 nucleotides of any one of SEQ ID NOs: 1, 4 or the complements thereof, wherein said span includes a biallelic marker of RBP-7.

11. The isolated, purified or recombinant polynucleotide according to claim 1, wherein said polynucleotide consists essentially of a contiguous span of 8 to 50 nucleotides of any one of SEQ ID NOs: 1, 4 or the complements thereof, wherein said span contains a biallelic marker of RBP-7 selected from the group consisting of A1 to A21, and the complements thereof.

12. The isolated, purified or recombinant polynucleotide according to claim 1, wherein said polynucleotide consists essentially of a contiguous span of 8 to 50 nucleotides of any one of SEQ ID NOs: 1, 4 or the complements thereof, wherein the 3' end of said contiguous span is located at the 3' end of said polynucleotide, and wherein the 3' end of said polynucleotide is located within 20 nucleotides upstream of a biallelic marker of RBP-7 in said sequence.

13. The array of polynucleotides according to claim 8, wherein said at least one polynucleotide consists essentially of a contiguous span of 8 to 50 nucleotides of any one of SEQ ID NOs: 1, 4 or the complements thereof, wherein said span includes a biallelic marker of RBP-7.

14. The array of polynucleotides according to claim 8, wherein said at least one polynucleotide consists essentially of a contiguous span of 8 to 50 nucleotides of any one of SEQ ID NOs: 1, 4 or the complements thereof, wherein said span contains a biallelic marker of RBP-7 selected from the group consisting of A1 to A21, and the complements thereof.

15. The array of polynucleotides according to claim 8, wherein said at least one polynucleotide consists essentially of a contiguous span of 8 to 50 nucleotides of any one of SEQ ID NOs: 1, 4 or the complements thereof, wherein the 3' end of said contiguous span is located at the 3' end of said polynucleotide, and wherein the 3' end of said polynucleotide is located within 20 nucleotides upstream of a biallelic marker of RBP-7 in said sequence.

* * * * *

UNITED STATES PATENT AND TRADEMARK OFFICE
CERTIFICATE OF CORRECTION

PATENT NO. : 7,432,367 B2
APPLICATION NO. : 11/132838
DATED : October 7, 2008
INVENTOR(S) : Lydie Bougueleret It is certified that error appears in the above-identified patent and that said Letters Patent is hereby corrected as shown below:

Column 1,
Line 30, "Gemmline" should read --Germline--.

Column 3,
Line 61, "untrancribed" should read --untranscribed--.
Line 63, "untrancribed" should read --untranscribed--.

Column 4,
Lines 32-33, "an thymine" should read --a thymine--.

Column 5,
Line 51, "shoxyn" should read --shown--.

Column 8,
Lines 18-19, "one modifications" should read --one modification--.

Column 11,
Line 59, "that may substituted" should read --that may substitute--.

Column 13,
Line 52, "Iq43" should read --1q43--.
Line 56, "region is spans" should read --region spans--.
Line 57, "region is spans" should read --region spans--.

Column 14,
Line 58, "5' and" should read --5' end--.

Column 19,
Line 12, "art" should read --part--.
Line 24, "3' and" should read --3' end--.

Column 20,
Line 61, "5' and" should read --5' end--.

UNITED STATES PATENT AND TRADEMARK OFFICE
CERTIFICATE OF CORRECTION

PATENT NO. : 7,432,367 B2
APPLICATION NO. : 11/132838
DATED : October 7, 2008
INVENTOR(S) : Lydie Bougueleret It is certified that error appears in the above-identified patent and that said Letters Patent is hereby corrected as shown below:

Column 21,
Line 2, "comprises of a ribonucleic" should read --comprises a ribonucleic--.

Column 22,
Lines 38-39, "of at least at least 8 nucleotides" should read --of at least 8 nucleotides--.

Column 25,
Line 28, "these probes and probes" should read --these probes and primers--.

Column 30,
Line 56, "selected form the" should read --selected from the--.

Column 35,
Line 32, "boiiaficle" should read --*bona fide*--.

Column 39,
Line 4, "Polylmerases" should read --Polymerases--.

Column 41,
Line 40, "No. longer" should read --no longer--.

Column 45,
Line 28, "comprising" should read --comprising:--.

Column 47,
Line 3, "choosen" should read --chosen--.
Line 6, "Lacl" should read --LacI--.
Line 26, "one skill in the art" should read --one skilled in the art--.

Column 50,
Lines 30-31, "gel, using methods similar using methods similar to those" should read --gel, using methods similar to those--.
Line 38, "spernidine" should read --spermidine--.

UNITED STATES PATENT AND TRADEMARK OFFICE
CERTIFICATE OF CORRECTION

PATENT NO.        : 7,432,367 B2
APPLICATION NO.   : 11/132838
DATED             : October 7, 2008
INVENTOR(S)       : Lydie Bougueleret It is certified that error appears in the above-identified patent and that said Letters Patent is hereby corrected as shown below:

Column 52,
Line 4, "hrpt" should read --hprt--.

Column 54,
Line 55, "*slibtilis*" should read --*subtilis*--.

Column 55,
Line 51, "by the skill artisan" should read --by the skilled artisan--.

Column 57,
Line 26, "code for one the polypeptides" should read
    --codes for one of the polypeptides--.

Column 58,
Line 66, "polyeptide" should read --polypeptide--.

Column 61,
Line 11, "titer thereo" should read --titer thereof--.
Line 45, "itself" should read --itself.--.

Column 63,
Line 57, "stnthesis" should read --synthesis--.
Line 62, "bu retention" should read --by retention--.

Column 65,
Line 58, "one skill in the art" should read --one skilled in the art--.

Column 68,
Line 30, "sate" should read --state--.

UNITED STATES PATENT AND TRADEMARK OFFICE
CERTIFICATE OF CORRECTION

PATENT NO. : 7,432,367 B2
APPLICATION NO. : 11/132838
DATED : October 7, 2008
INVENTOR(S) : Lydie Bougueleret It is certified that error appears in the above-identified patent and that said Letters Patent is hereby corrected as shown below:

Column 71,
Line 39, "Polyynorphisms" should read --Polymorphisms--.

Signed and Sealed this

Sixteenth Day of June, 2009

JOHN DOLL
*Acting Director of the United States Patent and Trademark Office*